US011549101B2

(12) United States Patent
Mueller et al.

(10) Patent No.: US 11,549,101 B2
(45) Date of Patent: *Jan. 10, 2023

(54) ATTENUATED INFLUENZA VIRUSES AND VACCINES

(71) Applicant: The Research Foundation for The State of University New York, Albany, NY (US)

(72) Inventors: Steffen Mueller, Kings Point, NY (US); Eckard Wimmer, East Setauket, NY (US); Bruce Futcher, Setauket, NY (US); Steven Skiena, Setauket, NY (US); Chen Yang, Forest Hills, NY (US)

(73) Assignee: The Research Foundation for State University of New York, Albany, NY (US)

( * ) Notice: Subject to any disclaimer, the term of this patent is extended or adjusted under 35 U.S.C. 154(b) by 110 days.

This patent is subject to a terminal disclaimer.

(21) Appl. No.: 16/436,475

(22) Filed: Jun. 10, 2019

(65) Prior Publication Data

US 2021/0009962 A1 Jan. 14, 2021

Related U.S. Application Data

(63) Continuation of application No. 14/777,204, filed as application No. PCT/US2014/030027 on Mar. 15, 2014, now Pat. No. 10,316,294.

(60) Provisional application No. 61/794,617, filed on Mar. 15, 2013.

(51) Int. Cl.
*C12N 7/00* (2006.01)
*A61K 39/145* (2006.01)

(52) U.S. Cl.
CPC .............. *C12N 7/00* (2013.01); *A61K 39/145* (2013.01); *C12N 2760/16034* (2013.01); *C12N 2760/16061* (2013.01); *C12N 2760/16134* (2013.01); *C12N 2760/16162* (2013.01)

(58) Field of Classification Search
None
See application file for complete search history.

(56) References Cited

U.S. PATENT DOCUMENTS

| | | | |
|---|---|---|---|
| 7,504,109 B2 | 3/2009 | Yang et al. | |
| 7,566,454 B2 | 7/2009 | Lu et al. | |
| 8,039,002 B2 | 10/2011 | Yang et al. | |
| 8,298,820 B2 | 10/2012 | Weiner et al. | |
| 9,017,694 B2 | 4/2015 | Jin et al. | |
| 9,476,032 B2 * | 10/2016 | Wimmer | A61P 31/12 |
| 10,316,294 B2 * | 6/2019 | Mueller | A61P 37/04 |
| 11,371,024 B2 | 6/2022 | Collins et al. | |
| 2008/0118530 A1 * | 5/2008 | Kew | A61K 39/0258 |
| | | | 424/207.1 |
| 2010/0008945 A1 | 1/2010 | Angela et al. | |
| 2011/0184160 A1 | 7/2011 | Weiner et al. | |
| 2012/0269849 A1 | 10/2012 | Wimmer et al. | |
| 2014/0141042 A1 | 5/2014 | Vitelli et al. | |
| 2014/0286992 A1 | 9/2014 | Galarza et al. | |

FOREIGN PATENT DOCUMENTS

| | | |
|---|---|---|
| WO | 2006/042156 A2 | 4/2006 |
| WO | 2008/121992 A2 | 10/2008 |
| WO | 2011044561 A1 | 4/2011 |

OTHER PUBLICATIONS

Belshe, R.B. et al., "Live Attenuated Versus Inactivated Influenza Vaccine in Infants and Young Children" N Engl J. Med (2007); vol. 356(7); pp. 685-696.
Bouvier, N.M. et al., The Biology of Influenza Viruses; Vaccine (2008); 26 Suppl. 4; pp. D49-53.
Cello, J. et al., "Chemical Synthesis of Poliovirus cDNA: Generation of Infectious Virus in the Absence of Natural Template"; Science (2002); vol. 297(5583); pp. 1016-1018.
Coleman, J.R., et al., "Virus Attenuation by Genome-Scale Changes in Codon Pair Bias"; Science (2008) vol. 320 (5884); pp. 1784-1787.
De Jong, J.C. et al., "Haemagglutination-Inhibiting Antibody to Influenza Virus"; Dev Biol (Basel) (2003); vol. 115; pp. 63-73.
Doma, M.K. et al., "Endonucleolytic Cleavage of Eukaryotic mRNAs with Stalls in Translation Elongation"; Nature (2006); vol. 440(7083); pp. 561-564.
Dove, B.K., et al., "A Quantitative Proteomic Analysis of Lung Epithelial (A549) Cells Infected with 2009 Pandemic Influenza A Virus Using Stable Isotope Labelling with Amino Acids in Cell Culture"; Proteomics (2012); vol. 12(9); pp. 1431-1436.
Federov, A. et al., "Regularities of Context-Dependent Condon Bias in Eukaroytic Gene"; NAR (2002); vol. 30:5:' pp. 1192-1197.
Gutman, G.A. et al., "Nonrandom Utilization of Codon Pairs in *Escherichia Coli*"; Proc. Natl. Acad. Sci U. S. A. (1989); vol. 86(10); pp. 3699-3703.
Moura, G. et al., "Large Scale Comparative Codon-Pair Context Analysis Unveils General Rules that Fine-Tune Evolution of mRNA Primary Structure"; PLoS One (2007); vol. 2(9); p. e847.
Simonsen, L., et al. "Impact of Influenza Vaccination on Seasonal Mortality in the U.S. Elderly Population"; Arch. Intem. Med (2005); vol. 165(3); pp. 265-272.
Smith, D.J., et al., "Mapping the Antigenic and Genetic Evolution of Influenza Virus"; Science (2004); vol. 305(5682); pp. 371-376.
Sutejo, R., et al., "Activation of Type I and III Interferon Signalling Pathways Occurs in Lung Epithelial Cells Infected with Low Pathogenic Avian Influenza Viruses"; PLoS One (2012); vol. 7(3); p. e33732.
Mueller, S. et al., "Live Attenuated Influenza VirusVaccines by Computer-Aided Rational Design"; Nat Biotechnol (2010); vol. 28(7); pp. 723-726.

(Continued)

*Primary Examiner* — Shanon A. Foley
*Assistant Examiner* — Myron G Hill
(74) *Attorney, Agent, or Firm* — Fox Rothschild LLP

(57) ABSTRACT

This invention provides highly attenuated influenza viruses and vaccines. The attenuated viruses and vaccines proliferate well and have high safety factors. The attenuated viruses providing protective immunity from challenge by virus of the same subtype, as well as cross protection against heterologous viruses.

11 Claims, 29 Drawing Sheets

Specification includes a Sequence Listing.

(56) References Cited

OTHER PUBLICATIONS

Thompson, W.W. et al. "Epidemiology of Seasonal Influenza: Use of Surveillance Data and Statistical Models to Estimate the Burden of Disease"; J. Infect. Dis. (2006); 194 Suppl 2; pp. S82-91.

Wang, F.P. et al., "Codon-Pair Usage and Genome Evolution" Gene (2009); vol. 433(1-2); pp. 8-15.

Wang, Z. et al., "Live attenuated or Inactivated Influenza Vaccines and Medical Encounters for Respiratory Illnesses Among US Military Personnel"; JAMA (2009); vol. 301(9); pp. 945-953.

World Health Organzation , WHO Manual on Animal Influenza Diagnosis and Surveillance (2002); www.who.int/vaccine_research/diseases/influenza/WHO_manual_on_animaldiagnosis_and_surveillance2002 5.pdf.

Ueda, M. et al., "Maturation Efficiency of Viral Glycoproteins in the ER Impacts the Productions of Influenza A Virus" Virus Research (2008); vol. 136; pp. 91-97.

Tamura, S. et al., "Mechanisms of Brand Cross-Protection Provided by Influenza Virus and their Application to Vaccines"; Jpn J. Infec. Dis (2005); vol. 58:4; pp. 195-207.

Yang, C. et al., "Deliberate Reduction of Hemagglutinin and Neuraminidase Expression of Influenza Virus Leads to an Ultraprotective Live Vaccine in Mice"; PNAS (2013); vol. 110:23; pp. 9481-9486.

\* cited by examiner

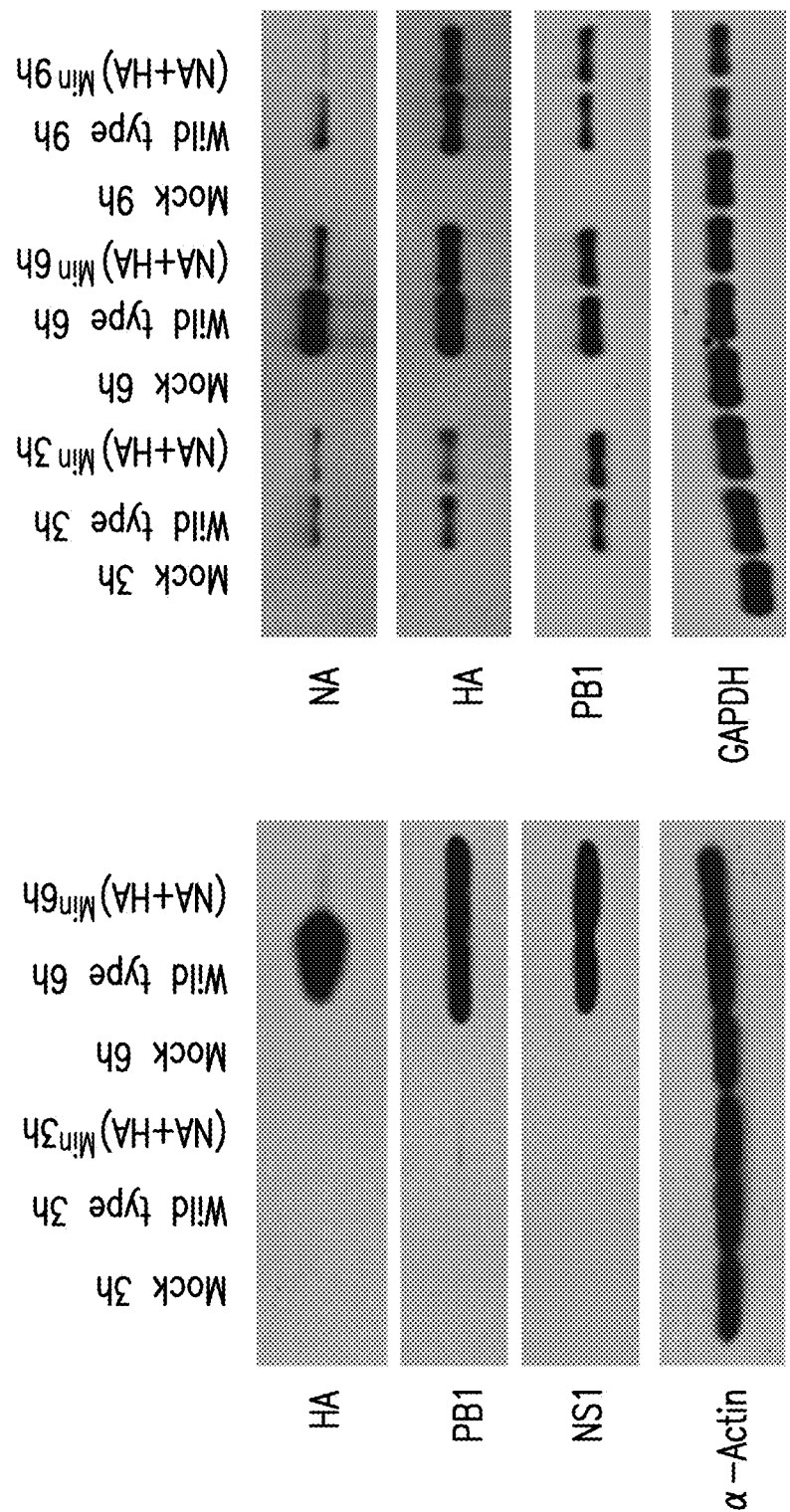

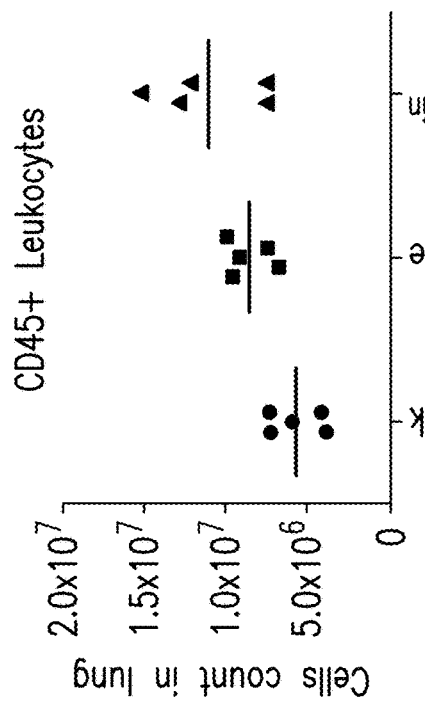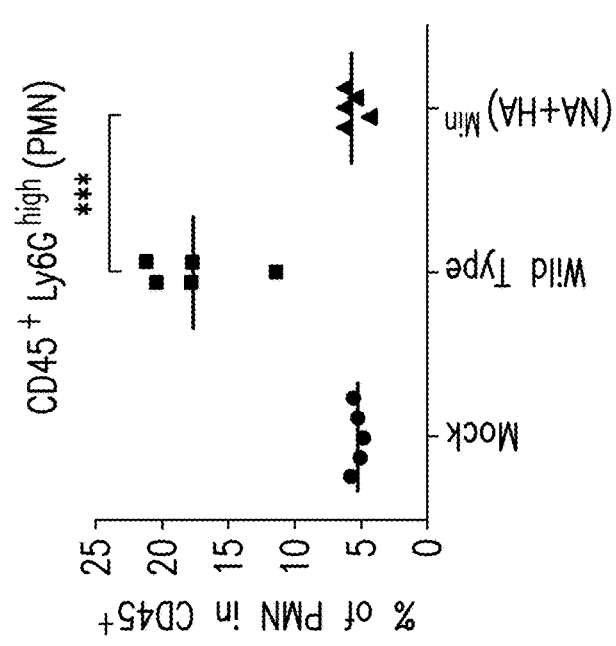
FIG. 19A
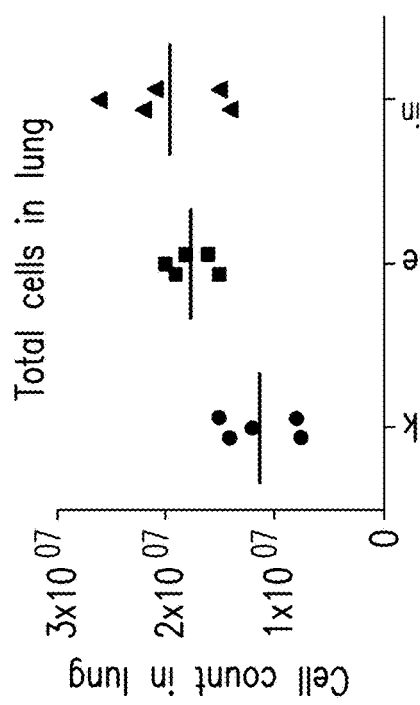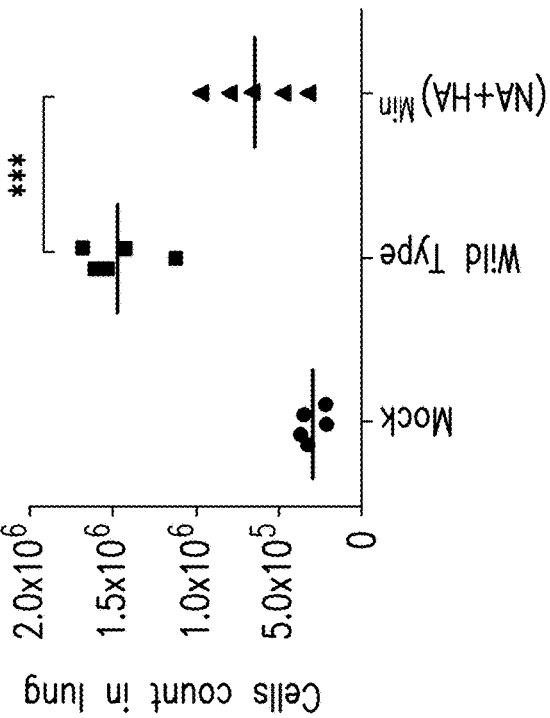
FIG. 19B

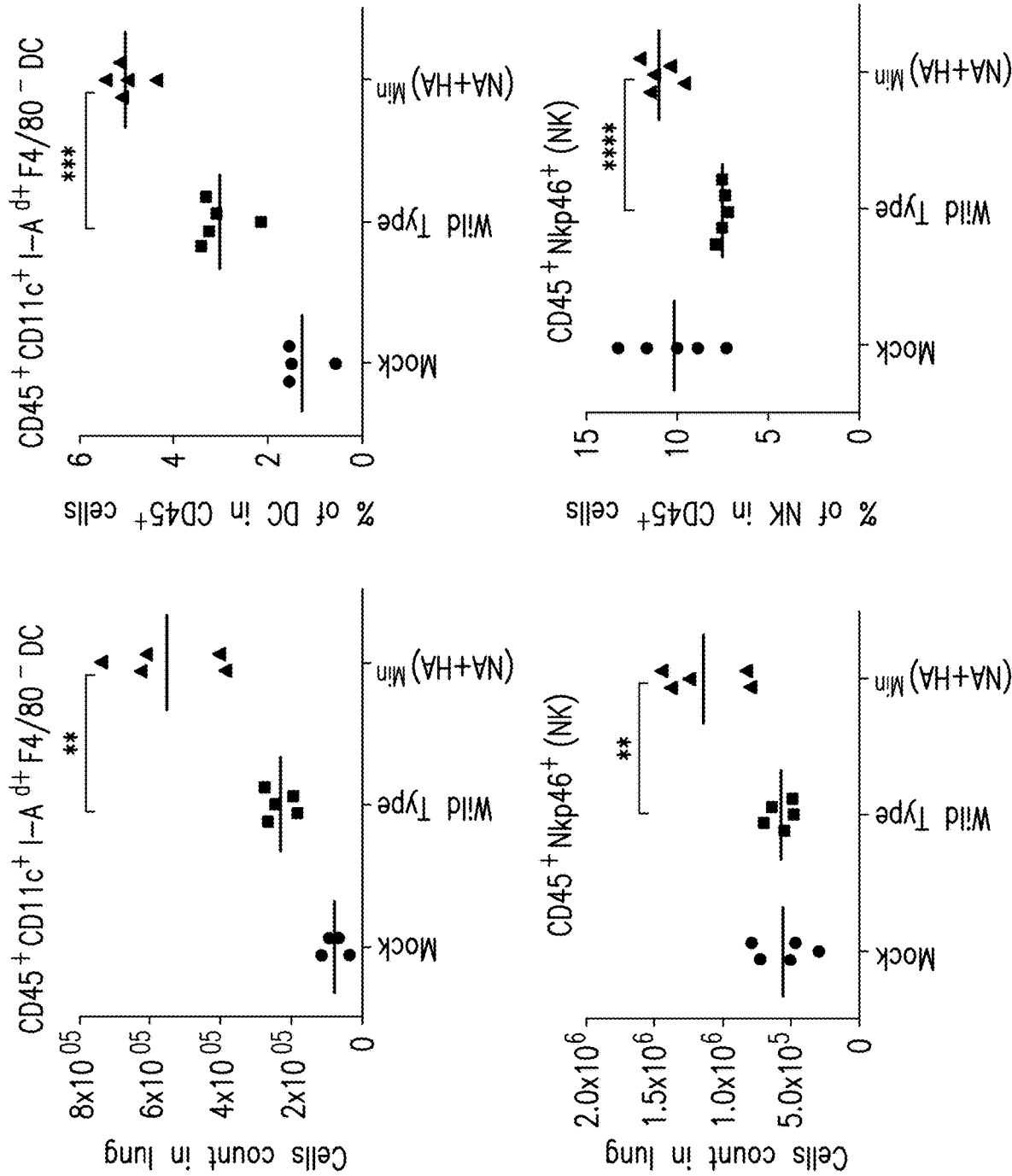

SEQUENCE LISTING

<160> NUMBER OF SEQ ID NOS: 63

<210> SEQ ID NO 1
<211> LENGTH: 1683
<212> TYPE: DNA
<213> ORGANISM: Influenza A Virus

<400> SEQUENCE: 1
atgtacaaaa tagtactagt acttgcgctc cttggagcgg tgcatggtct tgacaaaata 60
tgccttggac atcatgcagt ccccaatggc accatcgtaa agactctcac aaacgaaaag 120
gaagaggtga ccaatgctac tgaaacggtg gaaagtaaaa gcctggacaa actttgcatg 180
aaaagtcgga attacaagga cctaggtaat tgccacccga tagggatggt gatagggact 240
cctgcttgtg acttacacct caccggaaca tgggacactt tgatagagag agacaattcc 300
attgcctact gttacccagg tgccactgtg aatgaagaag cattaaggca gaaaattatg 360
gaaagtggag agattgacaa gataagcacc gggtttacat atgaatcatc catcaatcca 420
gctggaacca ctaaagcatg catgagaaat gggaaaaaca gtttctatgc agagctaaag 480
tggctagtgt cgaaggacaa aggacggaac ttcccacaaa caacaaacac atacaggaat 540
acagattcaa cagaacacct tataatctgg ggaattcatc acccgtcaag cacacaagaa 600
aagaatgatc tgtatggaac acaatcactt tccatttcag tagggagttc tacttatcaa 660
aacaactttg tgcctgtggt gggagcaaga ccacaggtga atggccaaag tgggcggatt 720
gatttccatt gggcgatggt acaaccgggt gataacatca ctttttcgca taacggcgga 780
ctaatagcac ctagtagagt gagtaaacta aagggaagag gccttggcat tcaatcagga 840
gcttcagtag ataatgactg tgaatcaaaa tgtttttgga aaggtggatc catcaacacc 900
aaactccctt ttcagaatct ttccccaaga actgtgggtc aatgccccaa gtatgtgaac 960
aaaaagagcc tgttgcttgc taccggaatg aggaatgtgc cagaggttgt ccaaggaaga 1020
ggcctgttcg gagcaattgc tggattcata gaaaatggat gggaagggat ggtagatggt 1080

```
tggtatggtt tccgacatca aaatgcccaa ggcactggtc aggctgcgga ttacaaaagc      1140
actcaggcag ctatagatca atacccggg aaattgaaca gactgataga aagacaaac       1200 acagagttcg aatccataga atctgagttc agtgaaattg aacatcaaat tggcaatgta     1260
ataaactgga ctaaggattc gataacagac atttggacgt atcaagctga attactggta    1320
gcaatggaaa accagcatac aatcgacatg gctgattcag aaatgctgaa tctatatgag    1380
agagtgagga agcaactgag gcaaaatgca gaagaagatg ggaaagggtg ctttgaaata    1440
tatcacaaat gcgacgacaa ctgcatggaa agcatcagaa caacaccta tgaccataca     1500 caatacagag aagaagcact cttgaacaga ctcaacatta tccggtgaa actctcttct     1560 gggtacaaag atgttatact gtggtttagc ttcgggcgt catgctttgt acttttggct     1620
gtcatcatgg ggcttgtttt cttctgtctg aaaaatggaa acatgcgatg cacaatctgt    1680
att                                                                    1683

<210> SEQ ID NO 2
<211> LENGTH: 1683
<212> TYPE: DNA
<213> ORGANISM: Unknown
<220> FEATURE:
<223> OTHER INFORMATION: deoptimized Influenza A Virus

<400> SEQUENCE: 2
atgtataaga tagtgctcgt actcgcacta ttaggcgcag tgcacggact cgacaaaatt       60
tgcctagggc atcacgcagt gcctaacgga actatcgtta agacacttac taacgaaaaa     120
gaggaagtga ctaacgctac cgaaacagtc gaatcaaaat cactcgacaa attgtgtatg     180
aaaagtcgga attataaaga cctaggcaat tgccatccga tagggatggt gatagggact     240
cccgcttgcg atctgcatct gacagggaca tgggatacac ttatcgaacg ggacaatagt     300
atagcgtatt gttatccagg cgctacagtg aacgaagagg cacttagaca aaaaattatg     360
gaatccggcg aaatcgataa gattagtacc ggattcacat acgaatcctc tattaatccc     420
gcaggaacaa ctaaggcttg tatgcgaaac ggtaagaatt cgttttacgc tgaactgaaa     480
tggcttgtga gtaaggacaa aggtaggaat ttcccacaaa ctactaatac ttataggaat     540
accgattcaa ccgaacatct gattatatgg gggatacacc atccaagttc gacacaagag     600
aaaaacgatc tatacggaac gcaatccctt agcattagcg tagggtctag tacttatcag     660
aataatttcg taccggtagt gggcgctaga ccgcaagtga acggacaatc cggtagaatc     720
gatttccatt gggctatggt gcaaccaggc gataacataa cttttagcca taacggcgga     780
ctgatagcgc ctagtagagt gagtaagctt aagggaaggg ggttggggat acaatccggc     840
gctagcgtag acaacgattg cgaatcaaaa tgcttttgga aagggggtc aattaatact     900 aaattgccat ttcagaatct gtcacctaga acagtgggac aatgccctaa atacgttaat     960
aagaaaagtc tgttactcgc aaccggtatg cgaaacgtac cagaggtagt gcaaggtagg    1020
gggctattcg gagcgatagc gggatttatc gaaaacggat gggagggtat ggtcgacgga    1080
tggtacgggt ttagacacca aaacgcacag ggaaccggac aggcagcaga ctataaatcg    1140
acacaagccg ctatagacca aattaccggt aagcttaaca gactgatcga aaagactaat    1200
accgaattcg aatcaatcga atccgaattt agcgaaatcg aacaccaaat cggaaacgta    1260
attaattgga caaagactc aattaccgat atatggacat atcaagccga actgttagtc    1320
gctatggaga atcagcatac aatcgatatg gccgatagcg aaatgcttaa cctttacgaa    1380
agggtgagaa aacagcttag acaaaacgct gaagaggacg gtaaggggtg tttcgaaata    1440
```

```
taccataaat gcgacgataa ttgtatggag tctatacgga ataacacata cgaccatacg    1500
caatatagag aggaagcact actgaataga cttaacatta atccggttaa gctatctagc    1560
ggatataaag acgtgatatt gtggttctca ttcggagcgt catgtttcgt attgctcgca    1620
gtgattatgg gactcgtatt cttttgcctt aaaaacggta atatgagatg cacaatttgc    1680
ata                                                                   1683

<210> SEQ ID NO 3
<211> LENGTH: 1410
<212> TYPE: DNA
<213> ORGANISM: Influenza A virus

<400> SEQUENCE: 3
atgaatccta atcaaaaatt attcgcactc tctggggtgg ccatagcact gagtatcctc     60
aacctactaa taggaatatc caatgtggga ctgaatgtct cactcacacct gaagggaagc   120 agtgaccagg ataagaattg acatgcacg agtgtaacac aaaccaacac gactttaatc    180
gaaaacacgt atgtcaacaa taccactgtc atcaataagg aaacagggac tacaaagcaa   240
aattatctaa tgctgaacaa gagtttatgc aaagttgaag gatgggtagt ggtggccaag   300
gacaatgcca taagattcgg tgaaagtgaa caaataatag tgacaaggga gccgtatgtg   360
tcatgtgatc cattaggatg taagacgtac gcactgcatc aagggacaac cattagaaac   420
aagcactcaa acggaacaat acacgacagg actgctttca gagggttgat atcaactcct   480
ttggggagcc ccctgtagt cagcaatagt gactttcttt gtgtagggtg gtcaagcacc    540
agttgccatg acggcatcgg gcggatgacc atttgcgtgc aggaaataa taacaacgca    600 acagctacag tgtactatga ccgaaggctc actaccacaa taaaaacatg gcagggaaa    660 atccttagga cgcaagagtc ggaatgtgta tgccacaatg aacatgtgt agtaataatg    720 accgatggat cggcaagcag ccaggcacat acaaaagttc tgtatttcca caaggacta   780 gtaataaaag aggaagccct caaggaatca gccagacaca tagaggagtg ctcatgctat   840
gggcacaatt caaaggtgac ttgtgtatgc agggacaact ggcaaggagc caatagacca   900
gtgattgaaa tagatatgaa tgccatggag catacaagtc agtatctatg tacaggagtt   960
ctcactgaca cgagcagacc atcagacaaa tcaatgggcg actgtaataa tccgatcact  1020
gggagtccgg gagcccctgg ggtcaaagga ttcggcttcc tggatagtga caatacatgg  1080
ttgggccgca caataagtcc tcgttccagg agtggttttg agatgttgaa gataccaat   1140 gctgggacag acccaaattc tagaatcact gagaggcaag aaatagttga aacaacaat  1200 tggtcaggat actcaggaag tttcattgac tattgggatg aaagcagtgt gtgctacaac  1260
ccctgttttt atgttgaatt aataagagga aggcctgaag aagccaagta tgtttggtgg  1320
acgagcaaca gtttagttgc actatgtgga agcccaatct cagttgggtc cggttccttc  1380
cccgatgggg cacaaatcca atactttcg                                    1410

<210> SEQ ID NO 4
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 4
atgaatccta accaaaagct attcgcacta agcggagtcg ccatagccct atcaatactg     60
aatctgttaa tcggaatatc gaacgttggg ttgaacgtta gtttgcacct taagggtca   120
```

| | |
|---|---:|
| tccgaccaag acaaaaattg acatgtact agcgttacgc aaacaaatac gactttgatc | 180 |
| gaaaatacat acgttaacaa tacgacagtg ataaataaag agaccggaac tactaagcaa | 240 |
| aactatctga tgctgaataa gtcactatgt aaggtcgagg gatgggtggt agtcgctaaa | 300 |
| gacaacgcaa taaggttcgg cgaaagcgaa cagataatcg tgacacgcga accatacgtt | 360 |
| agttgcgatc cgttagggtg taagacatac gcattacacc aagggactac gatacggaat | 420 |
| aaacactcta acggaacgat acacgacaga accgcattta gggggttgat atcgacacct | 480 |
| ctcggatcac ctcccgtagt gagtaatagc gatttcttat gcgtggggtg gtcaagtact | 540 |
| agttgtcacg acggaatcgg acgtatgaca atatgcgtac aggggaataa caataacgca | 600 |
| accgcaacag tgtattacga taggagactg actacaacaa ttaagacttg gccggtaag | 660 |
| atactgagaa cacaggaaag cgaatgcgtt tgccataacg gtacatgcgt agtgattatg | 720 |
| acagacggat ccgcaagttc gcaagcccat acgaaagtgc tatattttca caagggctc | 780 |
| gtaatcaaag aggaagccct taagggatcc gctagacata tcgaagagtg tagttgttac | 840 |
| ggacacaata gtaaggttac atgcgtatgt agggacaatt ggcaaggcgc aaatagacca | 900 |
| gtgatagaga tagacatgaa cgctatggag catacgagtc agtatctatg taccggagtg | 960 |
| ttaaccgaca ctagtagacc tagcgataag agtatgggcg attgcaataa tccgataacc | 1020 |
| ggatcacccg gagcaccagg cgttaagggg ttcgggtttc tcgatagcga ataatacatgg | 1080 |
| ttaggtagga caatctcacc taggtcaaga tccggattcg aaatgctcaa atccctaac | 1140 |
| gccggaacag accctaatag taggattacc gaacgacaag agatagtcga caataacaat | 1200 |
| tggtcagggt atagcggatc tttcatagac tattgggacg aatcaagcgt atgttataac | 1260 |
| ccatgtttct atgtcgaact gattagggg agacccgaag aggccaaata tgtgtggtgg | 1320 |
| actagtaata gtctcgtagc cctatgcgga tcaccgataa gcgtagggtc agggtcattc | 1380 |
| ccagacggag cccaaatcca atattttagt | 1410 |

<210> SEQ ID NO 5
<211> LENGTH: 1698
<212> TYPE: DNA
<213> ORGANISM: Influenza A virus

<400> SEQUENCE: 5

| | |
|---|---:|
| atgaaggcaa tactagtagt tctgctatat acatttgcaa ccgcaaatgc agacacatta | 60 |
| tgtataggtt atcatgcgaa caattcaaca gacactgtag acacagtact agaaaagaat | 120 |
| gtaacagtaa cacactctgt taaccttcta agagacaagc ataacgggaa actatgcaaa | 180 |
| ctaagagggg tagccccatt gcatttgggt aaatgtaaca ttgctggctg gatcctggga | 240 |
| aatccagagt gtgaatcact ctccacagca agctcatggt cctacattgt ggaaacatct | 300 |
| agttcagaca atggaacgtg ttacccagga gatttcatcg attatgagga gctaagagag | 360 |
| caattgagct cagtgtcatc atttgaaagg tttgagatat tccccaagac aagttcatgg | 420 |
| cccaatcatg actcgaacaa aggtgtaacg gcagcatgtc ctcatgctgg agcaaaaagc | 480 |
| ttctacaaaa atttaatatg gctagttaaa aaggaaatt cataccccaa gctcagcaaa | 540 |
| tcctacatta tgataaagg aaagaagtc ctcgtgctat gggcattca ccatccatct | 600 |
| actagtgctg accaacaaag tctctatcag aatgcagatg catatgtttt tgtggggaca | 660 |
| tcaagataca gcaagaagtt caagccggaa atagcaataa gacccaaagt gagggatcaa | 720 |
| gaagggagaa tgaactatta ctggacacta gtagagccgg gagacaaaat aacattcgaa | 780 |
| gcaactggaa atctagtggt accgagatat gcattcgcaa tggaaagaaa tgctgggtct | 840 |

| | |
|---|---|
| ggtattatca tttcagatac accagtccac gattgcaata caacttgtca gacacccaag | 900 |
| ggtgctataa acaccagcct cccatttcag aatatacatc cgatcacaat tggaaaatgt | 960 |
| ccaaaatatg taaaaagcac aaaattgaga ctggccacag gattgaggaa tgtcccgtct | 1020 |
| attcaatcta gaggcctatt tggggccatt gccggtttca ttgaaggggg gtggacaggg | 1080 |
| atggtagatg gatggtacgg ttatcaccat caaaatgagc agggggtcagg atatgcagcc | 1140 |
| gacctgaaga gcacacagaa tgccattgac gagattacta caaagtaaa ttctgttatt | 1200 |
| gaaaagatga atacacagtt cacagcagta ggtaaagagt caaccacct ggaaaaaga | 1260 |
| atagagaatt taaataaaaa agttgatgat ggtttcctgg acatttggac ttacaatgcc | 1320 |
| gaactgttgg ttctattgga aaatgaaaga actttggact accacgattc aaatgtgaag | 1380 |
| aacttatatg aaaaggtaag aagccagtta aaaaacaatg ccaaggaaat tggaaacggc | 1440 |
| tgctttgaat tttaccacaa atgcgataac acgtgcatgg aaagtgtcaa aaatgggact | 1500 |
| tatgactacc caaaatactc agaggaagca aaattaaaca gagaagaaat agatggggta | 1560 |
| aagctggaat caacaaggat ttaccagatt ttggcgatct attcaactgt cgccagttca | 1620 |
| ttggtactgg tagtctccct gggggcaatc agtttctgga tgtgctctaa tgggtctcta | 1680 |
| cagtgtagaa tatgtatt | 1698 |

<210> SEQ ID NO 6
<211> LENGTH: 1698
<212> TYPE: DNA
<213> ORGANISM: Unknown
<220> FEATURE:
<223> OTHER INFORMATION: Deoptimized Influenza A virus

<400> SEQUENCE: 6

| | |
|---|---|
| atgaaagcga ttctagtcgt actgctatat acattcgcta ccgctaacgc cgatacacta | 60 |
| tgcatagggt atcacgctaa taatagtaca gacacagtag acacagtact cgaaaaaaac | 120 |
| gttacggtta cacattccgt taatctgtta gaggataagc ataacggtaa gctatgtaaa | 180 |
| ctgagaggcg tagcaccatt gcatttgggt aagtgtaata tagccggatg gatactaggt | 240 |
| aatcccgaat gcgaatcact atcaactgca agttcatggt cttatatagt cgaaactagt | 300 |
| tcaagcgata acggtacatg ttatcccgga gactttatcg attacgaaga gttgagagag | 360 |
| caattgtcta gcgtaagctc attcgaaaga ttcgaaattt ttccgaaaac tagttcatgg | 420 |
| cctaatcacg attcaaataa gggggtaaca gccgcatgcc cacacgcagg cgctaagtca | 480 |
| ttctataaaa atctgatatg gctagtgaaa aagggaatt cttatccgaa actatcaaaa | 540 |
| tcatatatta cgataaggg taaggaggta ctcgtattgt gggggataca ccatccatca | 600 |
| actagcgcag accaacaatc tctgtatcag aatgccgacg catacgtatt cgtagggact | 660 |
| agtaggtact ctaaaaaatt taaacccgaa atcgctatta gaccgaaagt gagagaccag | 720 |
| gagggaagaa tgaattacta ttggacacta gtcgaaccag gcgataagat tacattcgaa | 780 |
| gcgacaggga atctagtggt accgagatac gcattcgcaa tggagagaaa cgccggatcc | 840 |
| ggaattatta ttagcgatac tcccgtacac gattgcaata caacatgtca gacaccaaaa | 900 |
| ggggcaatta atactagcct accatttcag aatatacacc caattacaat cggtaagtgt | 960 |
| ccaaaatacg ttaagtctac gaaacttaga ttggcaacag ggttgagaaa cgtaccatca | 1020 |
| atacagtcta gagggttgtt cggagcaatc gccggattca tagagggggg gtggaccggt | 1080 |
| atggtcgacg gatggtacgg ataccatcat caaaacgaac agggggtccgg atacgcagcc | 1140 |
| gatctgaaat caacacagaa cgcaatcgac gaaattacga ataaagtgaa tagcgtaatc | 1200 |

| | | | | |
|---|---|---|---|---|
| gaaaaaatga | atactcagtt | tacagccgta | ggtaaggaat | ttaatcatct cgaaaaaaga | 1260 |
| attgagaatc | tgaataaaaa | ggtagacgac | gggtttctag | acatttggac atataatgcc | 1320 |
| gaactgttag | tgttactcga | aaacgaaaga | acattagact | atcacgattc taacgttaag | 1380 |
| aatctatacg | aaaagtgag | atcgcaattg | aagaataacg | caaagagat agggaatggg | 1440 |
| tgtttcgaat | tctaccataa | atgcgataat | acatgtatgg | aatccgtaaa aaacggtaca | 1500 |
| tacgattatc | cgaaatatag | cgaagaagca | aaactgaata | gggaagagat tgacggagtt | 1560 |
| aagttggagt | caactaggat | ttaccagata | ctcgcaattt | actctacagt cgcatcaagt | 1620 |
| ctagtgttag | tcgttagctt | aggcgcaatt | agtttttgga | tgtgttcaaa cggatcactg | 1680 |
| caatgtagga | tttgcata | | | | 1698 |

<210> SEQ ID NO 7
<211> LENGTH: 1407
<212> TYPE: DNA
<213> ORGANISM: Influenza A virus

<400> SEQUENCE: 7

| | | | | |
|---|---|---|---|---|
| atgaatccaa | accaaaagat | aataaccatt | ggttcggtct | gtatgacaat tggaatggct | 60 |
| aacttaatat | tacaaattgg | aaacataatc | tcaatatgga | ttagccactc aattcaactt | 120 |
| gggaatcaaa | atcagattga | aacatgcaat | caaagcgtca | ttacttatga aaacaacact | 180 |
| tgggtaaatc | agacatatgt | taacatcagc | aacaccaact | tgctgctgg acagtcagtg | 240 |
| gtttccgtga | aattagcggg | caattcctct | ctctgccctg | ttagtggatg ggctatatac | 300 |
| agtaaagaca | acagtataag | aatcggttcc | aaggggggat | tgtttgtcat aagggaacca | 360 |
| ttcatatcat | gctcccccttt | ggaatgcaga | accttcttct | tgactcaagg ggccttgcta | 420 |
| aatgacaaac | attccaatgg | aaccattaaa | gacaggagcc | catatcgaac cctaatgagc | 480 |
| tgtcctattg | gtgaagttcc | ctctccatac | aactcaagat | ttgagtcagt cgcttggtca | 540 |
| gcaagtgctt | gtcatgatgg | catcaattgg | ctaacaattg | gaatttctgg cccagacaat | 600 |
| ggggcagtgg | ctgtgttaaa | gtacaacggc | ataataacag | acactatcaa gagttggaga | 660 |
| aacaatatat | tgagaacaca | agagtctgaa | tgtgcatgtg | taaatggttc ttgctttact | 720 |
| gtaatgaccg | atggaccaag | tgatggacag | gcctcataca | agatcttcag aatagaaaag | 780 |
| ggaaagatag | tcaaatcagt | cgaaatgaat | gcccctaatt | atcactatga ggaatgctcc | 840 |
| tgttatcctg | attctagtga | aatcacatgt | gtgtgcaggg | ataactggca tggctcgaat | 900 |
| cgaccgtggg | tgtcttttca | ccagaatctg | gaatatcaga | taggatacat atgcagtggg | 960 |
| attttcggag | acaatccacg | ccctaatgat | aagacaggca | gttgtggtcc agtatcgtct | 1020 |
| aatggagcaa | atggagtaaa | aggattttca | ttcaaatacg | gcaatggtgt ttggatagg | 1080 |
| agaactaaaa | gcattagttc | aagaaacggt | tttgagatga | tttgggatcc gaacggatgg | 1140 |
| actgggacag | acaataactt | ctcaataaag | caagatatcg | taggaataaa tgagtggtca | 1200 |
| ggatatagcg | ggagttttgt | tcagcatcca | gaactaacag | gctggattg tataagacct | 1260 |
| tgcttctggg | ttgaactaat | cagagggcga | cccaaagaga | acacaatctg gactagcggg | 1320 |
| agcagcatat | ccttttgtgg | tgtaaacagt | gacactgtgg | gttggtcttg gccagacggt | 1380 |
| gctgagttgc | catttaccat | tgacaag | | | 1407 |

<210> SEQ ID NO 8
<211> LENGTH: 1407
<212> TYPE: DNA
<213> ORGANISM: Unknown

<220> FEATURE:
<223> OTHER INFORMATION: Deoptimized Influenza A virus

<400> SEQUENCE: 8

| | | | | | |
|---|---|---|---|---|---|
| atgaatccta | accaaaaaat | tataacaatc | ggatccgttt | gtatgacaat | cggtatggct | 60 |
| aacctaatac | tgcaaatcgg | taatattata | tcgatttgga | tctcacatag | tatacaattg | 120 |
| ggtaatcaga | atcagataga | gacatgcaat | caatccgtta | ttacatacga | aaataatact | 180 |
| tgggttaatc | agacatacgt | taacatatcg | aatactaatt | tcgctgccgg | acaatccgtc | 240 |
| gttagcgtta | agttagccgg | taatagttca | ctatgccccg | ttagcgggtg | gctatatac | 300 |
| tctaaagaca | attcgattag | aatcggatct | aagggcgacg | tattcgtaat | acgcgaacca | 360 |
| ttcataagtt | gtagtccatt | agagtgtaga | acttttttc | taacacaagg | cgctctattg | 420 |
| aacgataagc | atagtaacgg | tacaattaag | gatagatcac | cttatagaac | attgatgtca | 480 |
| tgtcctatcg | gcgaagtgcc | tagtccatac | aatagtagat | tcgaatccgt | cgcatggtcc | 540 |
| gctagcgcat | gtcacgacgg | gattaattgg | ttgactatag | ggattagcgg | acccgataac | 600 |
| ggcgcagtcg | ctgtgcttaa | gtataacggt | attattaccg | acactataaa | gagttggcga | 660 |
| aataacatac | tgagaacaca | ggaatccgaa | tgcgcatgcg | taaacggttc | atgttttacc | 720 |
| gtaatgactg | acggacctag | cgacggacaa | gcgtcatata | agattttag | aatcgaaaaa | 780 |
| ggtaagatag | tgaaatctgt | cgagatgaac | gctccgaatt | atcattacga | agagtgtagt | 840 |
| tgttatcccg | attctagcga | aattacatgc | gtatgtaggg | acaattggca | cgggtctaat | 900 |
| cgaccatggg | tgtcattcaa | tcagaactta | gagtatcaga | tagggtatat | atgctcaggg | 960 |
| atattcggcg | ataatcctag | accgaacgat | aaaaccggat | catgcggacc | agtgtcatct | 1020 |
| aacggcgcta | acggagtgaa | agggtttagt | ttcaaatacg | gtaacggcgt | atggatcgga | 1080 |
| cgaactaagt | ctatatctag | taggaacgga | ttcgaaatga | tatgggaccc | aaacgggtgg | 1140 |
| accggtaccg | ataataactt | ttcaatcaaa | caggacatag | tcggaattaa | cgaatggtcc | 1200 |
| gggtatagcg | gatcattcgt | gcaacatcca | gagttaaccg | gactcgattg | cataagacca | 1260 |
| tgttttggg | tcgaattgat | taggggagga | ccaaaagaga | atactatatg | gactagcgga | 1320 |
| tctagtatta | gcttttgcgg | agtgaatagc | gataccgtag | ggtggtcatg | gccagacgga | 1380 |
| gccgaactac | catttacaat | cgataag | | | | 1407 |

<210> SEQ ID NO 9
<211> LENGTH: 1698
<212> TYPE: DNA
<213> ORGANISM: Influenza A virus

<400> SEQUENCE: 9

| | | | | | |
|---|---|---|---|---|---|
| atgaaagtaa | aactactgat | cctgttatgt | acatttacag | ctacatatgc | agacacaata | 60 |
| tgtataggct | accatgccaa | caactcaacc | gacactgttg | acacagtact | tgagaagaat | 120 |
| gtgacagtga | cacactctgt | caacctactt | gaggacagtc | acaatggaaa | actgtgccta | 180 |
| ctaaaaggaa | tagcccccct | acaattgggt | aattgcagcg | ttgccggatg | gatcttagga | 240 |
| aacccagaat | gcgaattact | gatttccaag | gaatcatggt | cctacattgt | agaaacacca | 300 |
| aatcctgaga | atggagcatg | ttacccaggg | tatttcgccg | actatgagga | gctaagggag | 360 |
| caattgagtt | cagtatcttc | atttgagaga | ttcgaaatat | tccccaaaga | aagctcatgg | 420 |
| cccaaccaca | ccgtaaccgg | agtatcagca | tcatgctccc | ataatgggaa | aagcagtttt | 480 |
| tacaaaaatt | tgctatggct | gacggggaag | aatggtttgt | acccaaacct | gagcaagtcc | 540 |

```
tatgcaaaca acaaagagaa agaagtcctt atactatggg gtgttcatca cccgcctaac    600
ataggggacc aaaggaccct ctatcacaca gaaatgctt atgtctctgt agtgtcttca    660
cattatagca gaagattcac cccagaaata accaaaaggc ccaaagtaag agatcaggaa    720
ggaagaatca actactactg gactctgctg gaacccgggg atacaataat atttgaggca    780
aatggaaatc taatagcgcc atggtatgct ttcgcactga gtagaggctt tggatcagga    840
atcatcacct caaatgcacc aatggatgaa tgtgatgcta agtgtcaaac acctcaggga    900
gctataaaca gcagtcttcc tttccagaat gtacacccag tcacaatagg agagtgtcca    960
aagtatgtca ggagtgcaaa attaaggatg gttacaggac taaggaacat cccatccatt   1020
caatccagag gtttgtttgg agccattgcc ggtttcattg aaggggggtg gactggaatg   1080
gtagatgggt ggtatggtta tcatcatcag aatgagcaag gatctggcta tgctgcagat   1140
caaaaaagca cacaaaatgc cattaacggg attacaaaca aggtgaattc tgtaattgag   1200
aaaatgaaca ctcaattcac agctgtgggc aaagaattca acaaattgga agaaggatg    1260 gaaaacttaa ataaaaaggt tgatgatggg tttctagaca tttggacata taatgcagaa   1320
ttgttggttc tactggaaaa tgaaaggact ttggatttcc acgactccaa tgtgaagaat   1380
ctgtacgaga agtaaaaag ccaattaaag aataatgcca agaaataggg aaatgggtgt    1440
tttgaattct atcacaagtg taacaatgaa tgcatggaga gtgtgaaaaa tggaacttat   1500
gactatccaa aatattccga agaatcaaag ttaaacaggg aaaaaattga tggagtgaaa   1560
ttggactcaa tgggggtcta tcagattctg cgatctact caactgtcgc cagttccctg    1620
gttcttttgg tctccctggg ggcaatcagc ttctggatgt gttccaatgg gtctttgcag   1680
tgtagaatat gcatctga                                                 1698

<210> SEQ ID NO 10
<211> LENGTH: 1698
<212> TYPE: DNA
<213> ORGANISM: Unknown
<220> FEATURE:
<223> OTHER INFORMATION: Deoptimized Influenza A virus

<400> SEQUENCE: 10
atgaaagtga aactgttaat actgttgtgc acttttaccg ctacatacgc cgatacaatt     60 tgcataggt atcacgctaa taatagtacc gatacagtcg acactgtgtt ggaaaagaac    120
gtaaccgtta cacactccgt taatctgtta gaggattccc ataacggtaa gttgtgtctg    180
ttgaaaggga tcgcaccatt gcaattgggt aattgtagcg tagccggatg gatattgggg    240
aatcccgaat gcgaactatt gattagtaaa gagtcatggt catatatagt cgagacacct    300
aatcccgaaa acggagcatg ctatcccgga tatttcgccg attacgaaga gcttagagag    360
caattgtcta gcgtaagctc attcgaaaga ttcgaaattt ttccaaaaga gtcaagttgg    420
cctaatcata ccgtaacagg cgtatccgca tcatgtagtc ataacggtaa gtcaagcttt    480
tataagaatc tgttatggtt aaccgtgtaa aacggactgt atccaaatct atctaagtca    540
tacgcaaata ataaagagaa agaggtactg attctatggg gggtgcatca cccacctaat    600
ataggcgatc aaagaacatt gtatcatacc gaaaacgcat acgtatccgt cgttagctca    660
cactatagta gaaggtttac acccgaaatt actaagagac ctaaggtaag ggatcaggag    720
ggtaggatta attattattg gactctactg gaaccaggcg atactatcat attcgaagct    780
aacggaaatc taatcgcacc atggtacgca ttcgcactat ctaggggggtt cggatccggg    840 attattactt ctaacgctcc aatggacgaa tgcgacgcaa agtgtcagac accacaggga    900
```

```
gcgattaata gttccctacc attccaaaac gtacaccccg ttacaatcgg cgaatgtccg    960
aaatacgtta gatccgctaa acttagaatg gtgaccggac tgagaaatat accatcaatc   1020
caatctaggg ggctattcgg agccatagcc ggatttatcg aagggggtg  gacagggatg   1080 gtcgacggat ggtatgggta tcaccaccaa aacgaacagg gatccggata cgccgccgat   1140
cagaaatcca cacaaaacgc tattaacgga attacgaata aagtgaatag cgtaatcgaa   1200
aaaatgaata cacaatttac tgccgtaggt aaggaattca ataagttaga gagaaggatg   1260
gagaatctga ataaaaagt  cgacgacgga ttcctagaca tatggacata taacgccgaa   1320
ctgttagtgt tgcttgagaa cgaaaggaca ctagactttc acgattcaaa cgttaaaaat   1380
ctatacgaaa aagtcaaatc ccaattgaaa aataacgcta aagagatagg gaatgggtgt   1440
ttcgaattct atcataagtg taataacgaa tgtatggaat ccgttaaaaa cggaacatac   1500
gattatccaa agtatagcga agagtcaaaa ctgaataggg aaaaaatcga cggagtcaaa   1560
cttgactcaa tggggtgta  tcagatactc gcaatctata gtacagtcgc atctagccta   1620
gtactgttag tgagtctggg agcgataagc ttttggatgt gttctaacgg atcactgcaa   1680
tgtaggatat gcatatga                                                 1698

<210> SEQ ID NO 11
<211> LENGTH: 1410
<212> TYPE: DNA
<213> ORGANISM: Influenza A virus

<400> SEQUENCE: 11
atgaatccaa atcaaaaaat aataacgatt ggctctgttt ctctcaccat tgccacaata     60
tgcttcctta cgcaaattgc catcctggta actactgtaa cattgcattt caagcaatat    120
gaatgcaact cccccccaaa caaccaagtg atgctgtgtg aaccaacaat aatagaaaga    180
aacataacag agatagtgta tctgaccaac accaccatag agaaggaaat atgccccaaa    240
ctagcagaat acagaaattg gtcaaagccg caatgcaaca ttactggatt tgcacctttt    300
tctaaggaca attcgattcg gctttccgct ggtgggaca  tctgggttac aagagaacct    360
tatgtgtcat gcgatcctga caagtgttat caatttgccc ttggacaggg aacaacacta    420
aacaacgggc attcaaatga cacagtacat gataggaccc cttataggac cctattgatg    480
aatgagttgg gtgttccatt tcatttggga accaagcaag tgtgcatagc atggtccagc    540
tcaagttgtc acgatggaaa agcatggctg catgtttgtg taacgggga  tgataaaaat    600 gcaactgcta gcttcattta caatgggagg cttgtagata gtataggttc atggtccaaa    660
aaaatcctca ggacccagga gtcggaatgc gtttgtatca atggaacttg tacagtagta    720
atgactgatg ggagtgcttc aggaaaagct gatactaaaa tactattcat tgaggagggg    780
aaaatcgttc atactagcct attgtcaggg agtgctcagc atgtcgagga gtgctcctgt    840
tatcctcgat atcctggtgt cagatgtgtc tgcagagaca actggaaagg ctccaatagg    900
cccatcgtag atataaatgt aaaggattat agcattgttt ccagttatgt gtgctcagga    960
cttgttggag acacacccag aaaaaacgac agctccagca gtagccattg cttggatcct   1020
aacaatgagg aaggtggtca tggagtgaaa ggctgggcct tgatgatgg  aaatgacgtg   1080 tggatgggaa gaacgatcag cgagaagtta cgctcaggat atgaaacctt caaagtcatt   1140
gaaggctggt ccaaacctaa ctccaaactg cagataaata ggcaagtcat agttgacaga   1200 gataatagg  ccggttattc tggtattttc tctgttgaag gcaaaagctg catcaatcgg   1260
tgcttttatg tggagttgat aaggggaagg aaccaggaaa ctgaagtctt gtggaccctca   1320
```

```
aacagtattg ttgtgttttg tggcacctca ggtacatatg aacaggctc atggcctgat       1380 ggggcggaca tcaatctcat gcctatataa                                       1410

<210> SEQ ID NO 12
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 12 atgaaccta atcaaaaaat aattacaatc ggatccgtta gtctgacaat cgctactata        60
tgttttctga ctcagatagc gatactcgtt acaaccgtta cattgcattt caaacaatac      120
gaatgcaatt ccccccctaa caatcaggta atgttgtgcg aacctacaat aatcgaacgg      180
aatattaccg agatagtgta tctgactaat acgactatcg aaaagagat atgcccaaaa       240 ctagccgaat atcggaattg gtcaaaaccg caatgtaaca taaccggatt cgcaccattt     300
tcgaaagaca attcgattag gttgtccgcc ggaggcgata tttgggttac acgcgaacct     360
tatgtgtcat gcgatcccga taaatgctat caattcgcac tcggacaggg gactacccctt    420 aataacggac attctaacga taccgtacac gatagaactc catatcgaac attgctaatg     480
aacgagttag gcgtaccatt ccatttgggc actaaacagg tatgtatcgc atggtctagc    540
tctagttgcc atgacggtaa ggcttggttg catgtgtgcg ttaccggcga cgataagaac    600
gcaaccgcta gctttatata aacggtagg ttggtcgact caatcgggtc atggtcaaaa     660
aaaatactta gaacgcaaga gtccgaatgc gtatgcataa acggtacatg caccgtagtg    720
atgaccgacg gatccgctag cggtaaggcc gatacgaaaa tactgtttat cgaagagggt   780
aagatagtgc atacgagtct actatccgga tccgctcaac atgtcgaaga gtgttcatgt    840
tatcctaggt atcccggcgt tagatgcgta tgtagggata attggaaagg gagtaataga    900
cctatagtcg atattaacgt taaggattat tcaatcgtaa gtagttatgt gtgtagcgga    960
ctcgtaggcg atacacctag aaaaaacgat agctctagta gctcacattg cctagaccct   1020
aataacgaag agggggggca tggcgttaag ggatgggcat tcgacgacgg taacgacgtt   1080
tggatgggta ggactattag cgaaaagctt agatccgggt atgagacatt caaagtgata   1140
gagggatggt ctaaacctaa ttcaaaactg caaattaata ggcaagtgat agtcgatagg   1200
gataatagat ccgggtattc cggaattttt agcgttgagg gtaagtcatg tattaatagg   1260 tgttttatg tcgagcttat taggggggaga aatcaggaaa ccgaagtgtt gtggacatcc    1320
aattcaatcg tcgttttttg cggaactagc ggaacatacg gtaccggatc atggcccgac   1380
ggagccgata ttaaccttat gcctatataa                                       1410

<210> SEQ ID NO 13
<211> LENGTH: 1689
<212> TYPE: DNA
<213> ORGANISM: Influenza A virus

<400> SEQUENCE: 13
atggccatca tttatctcat tctcctgttc acagcagtga gagggacca gatatgcatt        60 ggataccatg ccaataattc cacagagaag gtcgacacaa ttctagagcg gaacgtcact      120
gtgactcatg ccaaggacat tcttgagaag acccataacg gaaagttatg caaactaaac      180
ggaatccctc cacttgaact aggggactgt agcattgccg gatggctcct tggaaatcca    240
gaatgtgata ggcttctaag tgtgccagaa tggtcctata taatgggaga agaaaacccg      300
```

```
agagacggtt tgtgttatcc aggcagcttc aatgattatg aagaattgaa acatctcctc    360
agcagcgtga acatttcga gaaagtaaag attctgccca agatagatg gacacagcat     420 acaacaactg gaggttcacg ggcctgcgcg gtgtctggta atccatcatt cttcaggaac    480
atggtctggc tgacaaagaa aggatcaaat tatccggttg ccaaggatc gtacaacaat    540 acaagcggag aacaaatgct aataatttgg ggggtgcacc atcccaatga tgagacagaa    600
caaagaacat tgtaccagaa tgtgggaacc tatgtttccg taggcacacc aacattgaac    660
aaaaggtcaa ccccagacat agcaacaagg cctaaagtga atggacaagg aggtagaatg    720
gaattctctt ggacccctat tggatatgtgg gacaccataa attttgagag tactggtaat    780
ctaattgcac cagagtatgg attcaaaata tcgaaaagag gtagttcagg gatcatgaaa    840
acagaaggaa cacttgggaa ctgtgagacc aaatgccaaa ctccctttgg agcaataaat    900
acaacattgc cttttcacaa tgtccaccca ctgacaatag gtgagtgccc caaatatgta    960
aaatcggaga agttggtctt agcaacagga ctaaggaatg ttccccagat tgaatcaaga   1020
ggattgtttg gggcaatagc tggttttata gaaggaggat ggcaaggaat ggttgatggt   1080
tggtatggat accatcacag caatgaccag ggatcagggt atgcagcaga caaagaatcc   1140
actcaaaagg catttgatgg aatcaccaac aaggtaaatt ctgtgattga aaagatgaat   1200
acccaatttg aagctgttgg gaaagaattc agtaacttag agagaagact ggagaacttg   1260
aacaaaaaga tggaagacgg gtttctagat gtgtggacac aatgctgaa gcttctagtt   1320 ctgatggaaa atgagaggac acttgacttt catgattcta atgtcaagaa tctgtatgat   1380
aaagtcagaa tgcagctgag agacaacgtc aagaactag gaaatggatg ttttgaattt   1440
tatcacaaat gtgatgatga atgcatgaat agtgtgaaaa acgggacgta tgattatccc   1500
aagtatgaag aagagtctaa actaaataga atgaaatca aaggggtaaa attgagcagc   1560
atgggggttt atcaaatcct tgccatttat gctacagtag caggttctct gtcactggca   1620
atcatgatgg ctgggatctc tttctggatg tgctccaacg ggtctctgca gtgcaggatc   1680
tgcatatga                                                           1689
```

<210> SEQ ID NO 14
<211> LENGTH: 1689
<212> TYPE: DNA
<213> ORGANISM: Unknown
<220> FEATURE:
<223> OTHER INFORMATION: Deoptimized Influenza A virus

<400> SEQUENCE: 14

```
atggcaataa tctatctgat actgttgttt acagccgtta ggggcgatca gatatgcata     60
gggtatcacg ctaataatag taccgaaaaa gtcgatacaa tactcgaaag aaacgtaacc    120
gttacacacg ctaaagatat actcgaaaag acacataacg gtaagctatg caaacttaac    180
ggtataccac cacttgagtt aggcgattgc tcaatcgcag gatggttgtt ggggaatccc    240
gaatgcgata ggctattgag cgtacccgaa tggtcttata ttatgggaaaa agagaatcct    300 agagacggat tgtgttatcc cggatctttt aacgattacg aagagcttaa acatctgcta    360
tctagcgtta acatttcga aaaagtgaaa attctgccaa agataggtg gacacagcat     420 acgactaccg gaggatctag ggcatgcgcc gttagcggta atccgtcatt ctttagaaat    480
atggtatggt tgacaaaaaa ggggtctaat tatccagtcg ctaagggatc gtataataat    540
acaagcggag agcaaatgtt gattatatgg ggagtgcatc accctaacga cgaaaccgaa    600
caacggacac tgtatcaaaa cgtcggaaca tacgttagcg tcggtacacc aactctgaat    660
```

| | | |
|---|---|---|
| aaaagatcga ctcccgatat cgcaactaga ccaaaagtga acggacaggg ggggagaatg | 720 | |
| gagtttagtt ggacactact cgatatgtgg gatacaatta atttcgaatc aaccggtaat | 780 | |
| ctgatcgcac ccgaatacgg gtttaagatt agtaaaaggg ggtcatccgg tattatgaaa | 840 | |
| accgaaggta cactagggaa ttgcgaaact aagtgtcaga caccactagg ggctattaat | 900 | |
| acaacactac catttcataa tgtgcatcca ttgacaatcg gagagtgtcc taagtatgtg | 960 | |
| aaatccgaaa aactagtgct tgcaaccgga ctgagaaacg taccgcaaat cgaatccaga | 1020 | |
| gggttgttcg gagcaatcgc agggtttatc gaaggggggt ggcagggaat ggtcgacgga | 1080 | |
| tggtatgggt atcatcactc taacgatcag ggatccggat acgcagccga taaggagtca | 1140 | |
| acccaaaaag cattcgacgg aattactaat aaggtgaata gcgtaatcga aaaaatgaat | 1200 | |
| acacaattcg aagccgtcgg taaagagttt cgaatctcg aaaggagact tgagaatctg | 1260 | |
| aataaaaaaa tggaggacgg attcttagac gtatggacat ataatgccga actgttagtc | 1320 | |
| cttatggaga cgaacggac actagacttt cacgatagta acgttaagaa tctgtatgac | 1380 | |
| aaagtgagaa tgcaattgag agacaatgtg aaagagctag gtaacggatg tttcgaattc | 1440 | |
| tatcataaat gcgacgacga gtgtatgaat agcgttaaaa acggtacata tgactatcct | 1500 | |
| aagtatgagg aagagtcaaa gcttaataga acgagattaa agggagtgaa actatctagt | 1560 | |
| atgggagtgt atcagatact cgcaatatac gctacagtcg ccggatccct atcacttgcg | 1620 | |
| attatgatgg ccggaattag cttttggatg tgctctaacg gatcattgca atgtaggatt | 1680 | |
| tgcatatga | 1689 | |

<210> SEQ ID NO 15
<211> LENGTH: 1410
<212> TYPE: DNA
<213> ORGANISM: Influenza A virus

<400> SEQUENCE: 15

| | | |
|---|---|---|
| atgaatccaa atcaaaagat aataacaatt ggctctgtct ctctcaccat tgcaacagta | 60 | |
| tgcttcatca tgcagattgc catcctggca actactgtga cattgcattt taaacaacat | 120 | |
| gagtgcgact cccccgcgag caaccaagta atgccatgtg aaccaataat aatagaaagg | 180 | |
| aacataacag agatagtgta tttgaataac accaccatag agaaagagat tgccccgaa | 240 | |
| gcagtggaat acagaaattg gtcaaagccg caatgtcaaa ttacaggatt tgcaccttt | 300 | |
| tctaaggaca attcaatccg gctttctgct ggtgggggaca tttgggtgac gagagaacct | 360 | |
| tatgtgtcat gcgatcctgg caagtgttat caatttgcac tcgggcaggg gaccacacta | 420 | |
| gacaacaaac attcaaatgg cacaatacat gatagaatcc ctcaccgaac cctattaatg | 480 | |
| aatgagttgg gtgttccatt tcatttagga accaaacaag tgtgtgtagc atggtccagc | 540 | |
| tcaagttgtc acgatggaaa agcatggttg catgtttgtg tcactgggga tgatagaaat | 600 | |
| gcgactgcta gcttcattta tgacgggagg cttgtggaca gtattggttc atggtctcaa | 660 | |
| aatatcctca ggacccagga gtcggaatgc gtttgtatca atgggacttg cacagtagta | 720 | |
| atgactgatg gaagtgcatc aggaagagcc gatactagaa tactattcat aaagagggg | 780 | |
| aaaattgtcc atattagccc attgtcagga agtgctcagc atatagagga gtgttcctgt | 840 | |
| taccctcgat atcctgacgt cagatgtatc tgcagagaca actggaaagg ctctaatagg | 900 | |
| cccgttatag acataaatat ggaagattat agcattgatt ccagttatgt gtgctcaggg | 960 | |
| cttgttggcg acacacccag gaacgacgac agctctagca atagcaattg cagggatcct | 1020 | |
| aacaatgaga gagggaatcc aggagtgaaa ggctgggcct ttgacaatgg agatgatgta | 1080 | |

-continued

| | |
|---|---|
| tggatgggaa gaacaatcaa caaagattca cgctcaggtt atgaaacttt caaagtcatt | 1140 |
| ggtggttggt ccacacctaa ttccaaatcg caggtcaata gacaggtcat agttgacaac | 1200 |
| aataattggt ctggttactc tggtattttc tctgttgagg gcaaaagctg catcaatagg | 1260 |
| tgcttttatg tggagttgat aaggggaagg ccacaggaga ctagagtatg gtggacctca | 1320 |
| aacagtattg ttgtgttttg tggcacttca ggtacttatg aacaggctc atggcctgat | 1380 |
| ggggcgaaca tcaatttcat gcctatataa | 1410 |

<210> SEQ ID NO 16
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 16

| | |
|---|---|
| atgaatccta accagaaaat tattactata gggtcagtgt cattgactat cgcaaccgta | 60 |
| tgctttatta tgcaaatagc gatactcgca actaccgtaa cattgcattt taaacaacac | 120 |
| gaatgcgata gtcccgctag caatcaggta atgccatgcg aacctattat aatcgaacgg | 180 |
| aatattaccg agatagtgta tcttaacaat actactatcg aaaagagat atgcccagag | 240 |
| gccgtcgagt atagaaattg gtctaaacct caatgtcaga ttaccggatt cgcaccattc | 300 |
| tctaaagaca attcgattag attgtccgcc ggaggcgata tatgggtgac acgcgaacct | 360 |
| tatgtgtcat gcgatcccgg taagtgttat caattcgcac tcggacaggg gactacactc | 420 |
| gataataaac attctaacgg tacgatacac gataggattc cacataggac actattgatg | 480 |
| aacgagttag gcgtaccgtt tcatctaggc actaaacagg tatgcgttgc gtggtctagc | 540 |
| tcatcatgtc atgacggtaa ggcatggttg catgtgtgcg taaccggcga cgatagaaac | 600 |
| gctaccgcta gttttatata cgacggtagg ctagtcgatt caatcggatc atggtcacag | 660 |
| aatatactta gaacacagga atccgaatgc gtttgtatta acggtacatg tacagtcgtt | 720 |
| atgaccgacg gatccgcatc cggtagggcc gatactagga tactgtttat aaaagagggc | 780 |
| aaaatcgtgc atattagccc acttagcgga tccgcacaac atatcgaaga gtgtagttgc | 840 |
| tatcctaggt atcctgacgt tagatgtatt tgcagagaca attggaaagg gtctaataga | 900 |
| cccgtaatcg atatcaatat ggaggattat tcaatcgata gctcttatgt gtgtagcgga | 960 |
| ttagtcggcg atacacctag aaacgacgat agctctagta attcgaattg tagggaccct | 1020 |
| aataacgaga gaggcaatcc cggcgttaaa gggtgggcat cgataacgg cgacgacgtt | 1080 |
| tggatgggc gaacaattaa taaggactct agatccgggt atgagacatt caaagtgata | 1140 |
| ggggggtggt ctacacctaa ctcaaaatct caagtgaata ggcaagtgat agtcgacaat | 1200 |
| aacaattggt cagggtatag cggtatattc tcagtcgagg gtaagtcatg tattaataga | 1260 |
| tgttttacg ttgagttgat tagggggcga ccacaagaga ctagagtgtg gtggactagt | 1320 |
| aatagtatag tcgttttttg cggaactagc ggtacatacg gaaccggatc atggcctgac | 1380 |
| ggagcgaata ttaattttat gccaatctaa | 1410 |

<210> SEQ ID NO 17
<211> LENGTH: 1701
<212> TYPE: DNA
<213> ORGANISM: Influenza A virus

<400> SEQUENCE: 17

```
atgaagacta tcattgcttt gagctacatt ctatgtctgg ttttcgctca aaaacttccc      60
ggaaatgaca acagcacggc aacgctgtgc cttgggcacc atgcagtacc aaacggaacg     120
atagtgaaaa caatcacgaa tgaccaaatt gaagttacta atgctactga gctggttcag     180
agttcctcaa caggtgaaat atgcgacagt cctcatcaga tccttgatgg agaaaactgc     240
acactaatag atgctctatt gggagaccct cagtgtgatg cttccaaaa taagaaatgg     300
gaccttttg ttgaacgcag caaagcctac agcaactgtt acccttatga tgtgccggat     360
tatgcctccc ttaggtcact agttgcctca tccggcacac tggagtttaa caatgaaagc     420
ttcaattgga ctggagtcac tcaaaatgga acaagctctg cttgcaaaag agatctaat     480
aacagtttct ttagtagact gaattggttg acccacttaa aattcaaata cccagcattg     540
aacgtgacta tgccaaacaa tgaaaaattt gacaaattgt acatttgggg ggttcaccac     600
ccgggtacgg acaatgacca aatcttcttg tatgctcaag catcaggaag aatcacagtc     660
tctaccaaaa gaagccaaca aactgtaatc ccgaatatcg gatccagacc tagagtaagg     720
ratatccccca gcagaataag catctattgg acaatagtaa aaccgggaga catacttttg     780
attaacagca cagggaatct aattgctcct aggggttact tcaaaatacg aagtgggaaa     840
agctcaataa tgagatcaga tgcacccatt ggcaaatgca attctgaatg catcactcca     900
aatggaagca ttcccaatga caaaccattt caaaatgtaa acagaatcac atatgggcc     960
tgtcccagat atgttaagca aaacactctg aaattggcaa cagggatgag aaatgtacca    1020
gagaaacaaa ctagaggcat atttggcgca atcgcgggtt tcatagaaaa tggttgggag    1080
ggaatggtgg atggttggta cggtttcagg catcaaaatt ctgagggaat aggacaagca    1140
gcagatctca aaagcactca agcagcaatc aatcaaatca atgggaagct gaataggttg    1200
atcgggaaaa ccaacgagaa attccatcag attgaaaaag aattctcaga agtagaaggg    1260
agaattcagg acctcgagaa atatgttgag gacactaaaa tagatctctg gtcatacaac    1320
gcggagcttc ttgttgcct ggagaaccaa catacaattg atctaactga ctcagaaatg    1380
aacaaactgt ttgaaagaac aaagaagcaa ctgagggaaa atgctgagga tatgggcaat    1440
ggttgtttca aaatatacca caaatgtgac aatgcctgca taggatcaat cagaaatgga    1500
acttatgacc atgatgtata cagagatgaa gcattaaaca accggttcca gatcaaaggc    1560
gttgagctga agtcaggata caaagattgg atcctatgga tttcctttgc catatcatgt    1620
ttttttgcttt gtgttgtttt gttggggttc atcatgtggg cctgccaaaa aggcaacatt    1680
aggtgcaaca tttgcatttg a                                              1701
```

<210> SEQ ID NO 18
<211> LENGTH: 1701
<212> TYPE: DNA
<213> ORGANISM: Unknown
<220> FEATURE:
<223> OTHER INFORMATION: Deoptimized Influenza A virus

<400> SEQUENCE: 18

```
atgaaaacaa ttatcgcact gtcatacata ctgtgtctgg tattcgctca aaaattgccc      60
ggtaacgaca attcaaccgc tacattgtgc ttagggcatc acgccgtacc gaacggaact     120
atcgttaaga caattactaa cgaccaaatc gaagtgacta acgctacaga gttggtgcaa     180
tcctctagta caggcgaaat atgcgattca ccacaccaaa tccttgacgg agagaattgt     240
acacttatcg acgcactatt aggcgatcca caatgcgacg gatttcagaa taaaaaatgg     300
```

| | |
|---|---|
| gatctattcg ttgagagatc caaagcttat tcaaattgtt atccatacga cgtaccggat | 360 |
| tacgctagcc ttaggtcact cgttgcgtca agcggtactc tcgaattcaa taacgagtca | 420 |
| ttcaattgga ctggcgttac gcaaaacgga actagtagcg catgtaaaag acggtctaat | 480 |
| aatagctttt ttagcagact gaattggttg actcatctga aattcaaata tcccgcactt | 540 |
| aacgttacta tgcctaataa cgaaaaattc gataagctat atatatgggg cgtacaccat | 600 |
| cccggaacgg ataacgatca gatattcttg tacgctcaag ctagcggtag gattaccgtt | 660 |
| agtactaaaa gatcccaaca accgtaatt ccgaatatcg gatctagacc tagggtgaga | 720 |
| ratataccgt ctaggattag catatattgg actatcgtta aacccggaga catactgttg | 780 |
| atcaatagta caggcaatct gatcgcacct agggggtatt tcaaaattag atccggtaag | 840 |
| tctagcatta tgagatccga cgcaccaatc ggtaaatgta atagcgaatg cattacacca | 900 |
| aacggatcaa tccctaacga taagccattc caaaacgtaa ataggattac atacggcgca | 960 |
| tgccctagat acgttaaaca gaatacgctt aaacttgcga caggtatgcg aaacgtaccc | 1020 |
| gaaaaacaga ctagggggat attcggcgca atcgccggat ttatcgaaaa cggatgggag | 1080 |
| ggtatggtcg acgatggta cggatttaga catcaaaata gcgaagggat agggcaagcc | 1140 |
| gccgatctga aatcaacgca agccgctatt aatcaaatta acgaaaaact gaatagattg | 1200 |
| atcggtaaga ctaacgaaaa atttcaccaa atcgaaaaag agtttagcga agttgaggga | 1260 |
| aggatacaag accttgagaa atacgttgag gatactaaga tcgacctatg gtcatataat | 1320 |
| gccgagttgc tagtcgcact cgagaatcag catacaatcg atctgactga tagcgaaatg | 1380 |
| aataaattgt tcgaaagaac gaaaaaacaa ttgcgcgaaa acgccgaaga catggggaat | 1440 |
| gggtgtttta agatatacca taaatgcgat aacgcatgca tagggtcaat cagaaacgga | 1500 |
| acatacgatc acgacgtata tagagacgaa gcccttaata atagattcca aattaaaggc | 1560 |
| gttgagctta aaagcggata caaagactgg atactgtgga ttagtttcgc aatctcatgc | 1620 |
| tttctattgt gcgttgtgct attggggttc ataatgtggg catgtcagaa agggaatatt | 1680 |
| agatgcaata tttgtatatg a | 1701 |

<210> SEQ ID NO 19
<211> LENGTH: 1410
<212> TYPE: DNA
<213> ORGANISM: Influenza A virus

<400> SEQUENCE: 19

| | |
|---|---|
| atgaatccaa atcaaaagat aataacgatt ggctctgttt ctctcaccat ttccacaata | 60 |
| tgcttcttca tgcaaattgc catcttgata actactgtaa cattgcattt caagcaatat | 120 |
| gaattcaact cccccccaaa caaccaagtg atgctgtgtg aaccaacaat aatagaaaga | 180 |
| aacataacag agatagtgta tctgaccaac accaccatag agaaggaaat atgccccaaa | 240 |
| ctagcagaat acagaaattg gtcaaagccg caatgtgaca ttacaggatt tgcacctttt | 300 |
| tctaaggaca attcgattag ctttccgct ggtgggggaca tctgggtgac aagagaacct | 360 |
| tatgtgtcat gcgatcctga caagtgttat caatttgccc ttggacaggg aacaacacta | 420 |
| aacaacgtgc attcaaacga cacagtacat gataggaccc cttatcggac cctattgatg | 480 |
| aatgagttag gtgttccatt tcatctgggg accaagcaag tgtgcatagc atggtccagc | 540 |
| tcaagttgtc acgatggaaa agcatggctg catgtttgtg taacggggga tgataaaaat | 600 |
| gcaactgcta gcttcattta caatgggagg cttgtagata gtgttgtttc atggtccaaa | 660 |
| gatatcctca ggacccagga gtcagaatgc gtttgtatca atggaacttg tacagtagta | 720 |

```
atgactgatg ggagtgcttc aggaaaagct gatactaaaa tactattcat tgaggagggg      780
aaaatcgttc atactagcac attgtcagga agtgctcagc atgtcgagga gtgctcctgc      840
tatcctcgat atcctggtgt cagatgtgtc tgcagagaca actggaaagg ctccaatagg      900
cccattgtag atataaacat aaagaattat agcattgttt ccagttatgt gtgctcagga      960
cttgttggag acacacccag aaaaaccgac agctccagca gtagccattg cttggatcct     1020
aacaatgaag aaggtggtca tggagtgaaa ggctgggcct ttgatgatgg aaatgacgtg     1080
tggatgggaa gaacgatcag cgagaagtta cgcttaggat atgaaacctt caaagtcatt     1140
gaaggctggt ccaaccctaa ttccaaattg cagataaata ggcaagtcat agttgacaga     1200
ggtaataggt ccggttattc tggtattttc tctgttgaag gcaaaagctg catcaatcgg     1260
tgcttttatg tggagttgat aaggggaaga aaagaggaaa ctgaagtctt gtggacctca     1320
aacagtattg ttgtattttg tggaacctca ggtacatatg aacaggctc atggcctgat     1380 ggggcggaca tcaatctcat gcctatataa                                      1410
```

<210> SEQ ID NO 20
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 20

```
atgaatccta accaaaagat tattacaatc ggatccgtta gccttactat atccacaatt       60 tgtttttta tgcaaatagc gatactgata actaccgtta cattgcattt caaacaatac      120
gaattcaatt caccccctaa taatcaggtt atgttgtgcg aacctactat tatcgaacgg      180
aatataaccg agatagtgta tctaacgaac actacaatcg aaaagagat atgccctaag      240 ctcgcagagt atagaaattg gtcaaaaccc caatgcgata taccggatt cgcaccattt      300 agtaaggata atagtattag gttgtccgcc ggaggcgata tatgggttac acgcgaacca      360
tacgtgtcat gcgatcccga taatgctat caattcgctc tcggacaggg aacgacattg      420
aataacgtac attcaaacga taccgtacac gataggacac cttatagaac actattgatg      480
aacgaactag gcgtaccttt ccatctcgga actaaacagg tttgtatcgc ttggtctagt      540
agctcatgcc atgacggtaa ggcatggttg catgtgtgcg ttaccggcga cgataaaaac      600
gcaaccgcta gtttcatata taacggtagg ttagtcgata gcgtagtgag ttggtctaaa      660
gacatactgc gaacacagga atccgagtgc gtatgcataa acggtacatg taccgtagtg      720
atgaccgacg gatccgctag cggtaaggcc gatacgaaaa tattgttcat agaggagggt      780
aagatagtgc atacaagtac actatccgga tccgctcaac atgtcgaaga gtgctcatgt      840
tatcctagat atcccggcgt tagatgcgta tgtagagaca attggaaagg gtctaataga      900
ccgatagtcg acattaatat taaaaactat tcaatcgtta gctcatatgt gtgttccgga      960
ttagtcggcg atacccctag aaaaaccgat agctctagct catcccattg tcttgaccct     1020
aataacgaag agggggggca tggcgttaag ggatgggcat cgacgacgg taacgacgtt     1080 tggatgggac ggacaattag cgaaaaactt agattggggt atgagacttt taaggtaatc     1140
gaagggtggt ctaatcctaa ttcgaaactg caaattaata ggcaagtgat agtcgatagg     1200
gggaataggt ccggatatag cggaatcttt tccgttgagg gtaagtcatg tattaatagg     1260 tgttttatg tcgaactgat tagggggaga aaagaggaaa ccgaagtgtt atggactagt     1320
```
aactcaatcg ttgtgttttg cggtacatcc ggtacttatg gaaccggatc atggccagac    1380
ggagccgata taaaccttat gccaatttaa                                    1410

<210> SEQ ID NO 21
<211> LENGTH: 1704
<212> TYPE: DNA
<213> ORGANISM: Influenza A virus

<400> SEQUENCE: 21
atggagaaaa tagtgcttct tcttgcaata gtcagccttg ttaaaagtga tcagatttgc      60
atcggttacc atgcaaacaa ctcgacagag caggttgaca caataatgga aaagaacgtt     120
actgttacac atgcccaaga catactggag aagacacata acgggaaact ctgcgatcta     180
gatggagtga agcctctgat tctacgagat tgtagtgtag ctggatggct cctcggaaac     240
ccaatgtgtg acgaattcat caatgtgccg gaatggtctt acatagtgga aaggccaac      300 ccagccaatg acctctgtta cccagggaat tcaacgact atgaagaact gaaacaccta      360
ttgagcagaa taaccattt tgagaaaatt cagatcatcc ccaaaagttc ttggtccgat      420
catgaagcct catcaggggt gagctcagca tgtccatacc agggaacgcc ctcctttttc     480
agaaatgtgg tatggcttat caaaaagaac aatacatacc caacaataaa gagaagctac     540
aataatacca accaggaaaa tcttttgata ctgtggggga ttcatcattc taatgatgca     600
gcagagcaga taaagctcta tcaaaaccca accacctata tttccgttgg gacatcaaca     660
ctaaaccaga gattggtacc aaaaatagcc actagatcca agtaaacgg gcaaagtgga     720 aggatggatt tcttctggac aattttaaaa ccgaatgatg caatcaactt cgagagtaat     780
ggaaatttca ttgctccaga atatgcatac aaaattgtca aggaaggaga ctcagcaatt     840
atgaaaagtg aagtggaata tggtaactgc aacaccaagt gtcaaactcc aatagggcg     900 ataaactcta gtatgccatt ccacaacata caccctctca ccatcgggga atgccccaaa     960
tatgtgaaat caaacaaatt agtccttgct actgggctca gaaatagtcc tctaagagaa    1020
agaagaagaa aaagaggact atttggagct atagcaggt ttatagaggg aggatggcag    1080
ggaatggtag atggttggta tgggtaccac atagcaatg agcaggggag tgggtacgct    1140
gcagacaaag aatccactca aaaggcaata gatggagtca ccaataaggt caactcgatc    1200
attgacaaaa tgaacactca gtttgaggcc gttggaaggg aatttaataa cttggaaagg    1260
agaatagaga acttaaacaa gaaaatggaa gacggattcc tagatgtctg gacttataat    1320
gctgaacttc tggttctcat ggaaaatgag agaactctag acttccatga ctcaaatgtc    1380
aagaaccttt acgacagggt ccgactacag cttagggata tgcaaagga gctgggtaac    1440 ggttgtttcg agttctatca caaatgtgat aatgaatgta tggaaagtgt aagaaacgga    1500
acgtatgact acccgcagta ttcagaagaa gcaagattaa aaagagagga ataagtgga    1560 gtaaaattgg aatcaatggg aacttaccaa atactgtcaa tttattcaac agttgcgagt    1620
tctctagcac tggcaatcat ggtggctggt ctatctttgt ggatgtgctc caatgggtcg    1680
ttacaatgca gaatttgcat ttaa                                          1704

<210> SEQ ID NO 22
<211> LENGTH: 1704
<212> TYPE: DNA
<213> ORGANISM: Unknown
<220> FEATURE:
<223> OTHER INFORMATION: Deoptimized Influenza A virus

<400> SEQUENCE: 22

```
atggagaaaa tagtgctact actcgcaatc gttagtctgg ttaagtccga tcagatatgc    60
ataqggtatc acgctaacaa tagtaccgaa caggtcgaca ctattatgga aaaaaacgtt   120
accgttacac acgcacagga catactcgaa aaacccata acggtaagtt atgcgattta   180
gacggagtta agccactgat acttagggat tgttcagtcg ccggatggtt gttagggaat   240
ccaatgtgcg acgaattcat taacgtaccc gaatggtcat acatagtcga aaagcgaat   300
cccgctaacg atctatgtta ccagggaat tttaacgatt acgaagagct taagcatcta   360
ctatctagaa taaaccattt cgaaaagatt cagataatac cgaaatcgag ttggtccgat   420
cacgaagcgt caagcggagt gagtagcgca tgcccatacc aaggaacacc atcattcttt   480
agaaacgtcg tttggttgat taaaaaaaat aatacatatc cgactattaa gagatcatat   540
aataatacaa accaagagaa tctactgata ctatgggga tacaccatag taacgacgca   600
gccgaacaga ttaagctata tcagaatcca actacataca ttagcgtagg gactagtaca   660
cttaatcaga gactcgtacc taaaatcgct actagatcga aggtaaacgg acaatccggt   720
agaatggact ttttttggac tatactgaaa cctaacgacg caattaattt cgaatctaac   780
ggaaattta tcgctcccga atacgcatat aagatagtaa agagggggga tagcgcaatt   840
atgaaatccg aagtcgaata cggaaattgc aatactaagt gtcagacacc aatcggagca   900
attaactcta gtatgccatt ccataacata catccactta caatcggaga atgccctaaa   960
tacgttaagt ctaacaaact cgtactcgca accggactta ggaatagtcc acttagagag  1020
agacgaagaa agagagggtt gttcggagca atcgcagggt tcatagaggg ggggtggcag  1080
ggtatggtcg acggatggta cgggtatcat cattctaacg aacagggatc cggatacgca  1140
gccgataaag agagtactca gaaagcaatc gacgagtga cgaataaagt gaattcgata  1200
atcgataaga tgaatacgca attcgaagcc gtaggtaggg aattcaataa tctcgagaga  1260
cgaatcgaaa accttaacaa aaaaatggaa acggattcc tagacgtatg gacttataac  1320
gccgaactgt tagtgcttat ggagaacgaa agaacccttg actttcacga ttctaacgtt  1380
aagaatctat acgatagagt gagactgcaa ttgagggata cgctaaaga gttagggaac  1440
gggtgtttcg aattctatca taaatgcgat aacgaatgta tggagtcagt gagaaacggt  1500
acatacgact atccgcaata ttccgaagag gctagattga aaagagagga gattagcgga  1560
gtgaaacttg agtcaatggg gacatatcag atattgtcaa tatactcaac cgtcgctagt  1620
agtctcgcac tcgcaattat ggtcgccgga ctgtcactat ggatgtgttc aaacggtagt  1680
ctgcaatgta ggatttgtat ataa                                         1704
```

<210> SEQ ID NO 23
<211> LENGTH: 1350
<212> TYPE: DNA
<213> ORGANISM: Influenza A virus

<400> SEQUENCE: 23

```
atgaatccaa atcagaagat aataaccatt gggtcaatct gtatggtaat tggaatagtt    60
agcttaatgt tacaaattgg gaacataatc tcaatatggg tcagtcattc aattcaaaca   120
gggaatcaac accaagatga accaatcaga atgctaatt tcttactga aacgctgtg   180
gcttcagtaa cattagcggg caattcatct ctttgcccg ttagaggatg ggctgtacac   240
agtaaagaca cagtataag gattggttcc aaggggggat tgtttgttat tagagagccg   300
ttcatctcat gctcccactt ggaatgcaga acttcttttt tgactcaggg agccttactg   360
```

| | |
|---|---|
| aatgacaagc actccaatgg gactgtcaaa gacagaagcc ctcacagaac attaatgagt | 420 |
| tgtcctgtgg gtgaggctcc ctccccatat aactcaaggt ttgagtctgt tgcttggtca | 480 |
| gcaagtgctt gccatgatgg caccagttgg ttgacaattg gaatttctgg cccagacaat | 540 |
| ggggctgtgg ctgtattgaa atacaatggc ataataacag acaccatcaa gagttggagg | 600 |
| aacaacatac tgagaactca agagtctgaa tgtgcatgtg taaatggctc ttgctttact | 660 |
| gtaatgactg atggaccaag taatgggcag gcatcatata agatcttcaa aatggaaaaa | 720 |
| ggaaaagtgg ttaaatcagt cgaattgaat gcccctaatt atcactatga ggaatgctcc | 780 |
| tgttatcctg atgctggcga aatcacatgt gtgtgcaggg ataattggca tggctcaaat | 840 |
| aggccatggg tatcttttca tcagaatttg gagtatcaaa taggatatat atgtagtgga | 900 |
| gttttcggag acaatccacg ccccaatgat ggaacaggta gttgtgatcc agtgtcccct | 960 |
| aacgggcat atgggataaa agggttttca tttaaatacg gcaatggtgt ttggatcgga | 1020 |
| agaaccaaaa gcactaattc caggagtggt tttgaaatga tttgggatcc aaatgggtgg | 1080 |
| actgaaacgg acagtagctt ttcagtgaaa caagatatag tagcaataac tgattggtca | 1140 |
| gggtatagcg ggagttttgt tcagcatcca gaactgacag gattagattg cataagacct | 1200 |
| tgcttctggg ttgagttaat cagagggcgg cccaaagaga gcacaatttg gactagtggg | 1260 |
| agcagcatat cttttttgtgg tgtaaatagc gacactgtga gttggtcttg gccagacggt | 1320 |
| gctgagttgc cattcaccat tgacaagtag | 1350 |

<210> SEQ ID NO 24
<211> LENGTH: 1350
<212> TYPE: DNA
<213> ORGANISM: Unknown
<220> FEATURE:
<223> OTHER INFORMATION: Deoptimized Influenza A virus

<400> SEQUENCE: 24

| | |
|---|---|
| atgaatccga atcaaaaaat tataacaata gggtcaatct gtatggtaat cggtatagtg | 60 |
| tcacttatgt tacaaatcgg gaatattata tctatttggg tgtcacactc aatccaaacc | 120 |
| ggtaatcaac accaagacga acctatacgg aatgcgaatt tcttaacaga gaatgccgta | 180 |
| gctagcgtta cgttagccgg taatagttca ttgtgtcccg ttaggggtg ggctgtgcat | 240 |
| agtaaggata atagtattag gatagggtct aaaggcgacg tattcgtgat acgcgaacct | 300 |
| tttatctctt gctcacactt agagtgtaga acatttttc tgactcaagg cgcactgtta | 360 |
| aacgataaac actctaacgg tacagttaag gataggtcac cacataggac attgatgtca | 420 |
| tgtcccgtag gcgaagctcc tagtccatat aatagtagat cgaaagcgt tgcatggtcc | 480 |
| gctagcgctt gtcacgacgg aactagttgg ttgacaatcg ggatatccgg acccgataat | 540 |
| ggcgcagtcg cagtgttgaa gtataatggg attataaccg atactatcaa atcatggaga | 600 |
| aataatatac tgagaacaca ggagtccgaa tgcgcttgcg ttaacggatc atgctttacc | 660 |
| gttatgactg acgaccatc taacgggcaa gctagttata aaattttcaa aatggagaaa | 720 |
| ggtaaggtag tgaaatccgt tgagcttaac gctccaaatt atcattacga agagtgtagt | 780 |
| tgctatccag acgctggcga aattacttgc gtatgtagag acaattggca cggatctaat | 840 |
| agaccatggg ttagctttaa tcagaattta gagtatcaga tagggtatat atgttccgga | 900 |
| gtgttcggcg ataatcctag acctaacgac ggtacagggt catgcgatcc agtgagtcca | 960 |
| aacgcgcat acggaattaa agggtttagc tttaagtatg gaatggcgt atggatcggt | 1020 |
| aggactaagt ctactaatag tagatccgga ttcgaaatga tatgggaccc taatgggtgg | 1080 |

```
actgagactg atagtagttt tagcgtaaaa caggatatag tcgctataac cgattggagc    1140
gggtatagcg gatcattcgt acagcatccc gaattgactg ggttagactg tattagacca    1200
tgcttttggg tcgaattgat taggggggaga ccaaaagagt caactatatg gactagcgga    1260
tctagtatta gtttttgcgg agtgaattcc gataccgtta gttggtcatg ccagacgga     1320 gctgagttgc catttacaat cgataaatag                                     1350

<210> SEQ ID NO 25
<211> LENGTH: 1659
<212> TYPE: DNA
<213> ORGANISM: Influenza A virus

<400> SEQUENCE: 25
atgaacattc aaattctggc attcattgct tgtgtgctga ctggagctaa aggagacaaa      60
atatgtcttg gcaccatgc tgtggcaaat ggaacaaaag tgaacacatt aacagagagg     120
gggattgaag tagtgaatgc cacagagaca gttgaaactg cgaatatcaa gaaaatatgt     180
actcaaggga aagaccaac agatctggga caatgtggac ttctagggac cctaatagga     240 cctcccccaat gtgatcaatt cctggagttt tcctctgatt tgataattga gcgaagagaa    300
ggaaccgatg tatgctatcc cggtaaaattc acaaatgaag aatcactgag acagatcctt    360
cgaagatcag aggaattgg taaggagtca atgggcttca cctatagtgg aataaggacc      420
aatggagcga caagtgcctg cacaagatca ggttcttctt tctatgcaga gatgaagtgg     480
ttgctgtcga attcagacaa tgcagcattc ccacagatga caaaatcgta tagaaatccc    540
agaaacaaac cagctctgat aatttgggga gttcatcact ctgaatcggt tagcgagcag     600
accaaactct atggaagtgg aaacaagttg ataaaagtaa gaagctcaaa ataccaacaa    660
tcatttaccc caaatcctgg agcacggaga atcgatttcc actggctact cctggatccc    720
aatgacacag tgaccttcac tttcaatggg gcattcatag cccctgacag gcaagttttc    780
tttagaggag aatcaatagg agtccagagt gatgctcctt ggattctag ttgtggaggg      840 aattgctttc acagtggggg tacgatagtc agttccctgc cattccaaaa catcaaccct    900
agaactgtgg gaaaatgccc tcggtatgtc aaacagaaaa gcctccttct ggctacagga    960
atgagaaatg ttccagagaa accaagaaa agaggccttt ttggagcaat tgctggattc    1020
atagagaacg gatgggaggg tctcatcaat ggatggtatg gtttcagaca tcaaaatgca    1080
caaggagagg gaactgcagc tgactacaaa agcacccagt ctgcaataga tcagatcaca    1140
ggcaaattga atcgtctaat tgcaaaaaca aatcagcagt ttgggctgat agacaatgag    1200
ttcaatgagg tagaacaaca ataggaaat gtcattaatt ggacacaaga cgcaatgact    1260
gagatatggt cgtataatgc tgagctgttg gtggcaatgg aaaatcaaca tacaatagat    1320
cttacggatt cagaaatgag caaactttat gagcgtgtca gaaacaact gagggagaat    1380 gctgaagaag atgggactgg atgtttcgaa atattccata gtgtgatga tcattgtatg    1440 gagagcataa gaaacaacac ttatgaccat actcaataca gaacagagtc actgcagaat    1500
agaatacaga tagacccagt gaaattgagt agtggataca aagacataat cttatggttt    1560
agcttcgggg catcatgttt tcttcttcta gccattgcaa tgggattggt tttcatttgc    1620
ataaaaaatg gaaacatgca gtgcactatt tgtatatag                           1659

<210> SEQ ID NO 26
<211> LENGTH: 1659
<212> TYPE: DNA
<213> ORGANISM: Unknown
```

```
<220> FEATURE:
<223> OTHER INFORMATION: Deoptimized Influenza A virus

<400> SEQUENCE: 26
atgaatatac agatactcgc attcatagct tgcgtactta ccggagctaa aggcgataag      60
atatgtctag ggcatcacgc agtcgcaaac ggaacgaaag tgaatacact tacagagaga     120
gggatagagg tcgttaacgc tacagagaca gtcgaaaccg caaatattaa aaaaatttgt     180
acacaaggaa aacgaccaac cgatctggga caatgcggac tgttagggac actgatagga     240
ccaccacaat gcgatcaatt ccttgagttt agtagcgatc tgataatcga acgaagagag     300
ggaactgacg tttgttatcc cggtaagttc actaacgaag agagtcttag acagatactg     360
agacggtcag ggggaatcgg aaaagagtca atggggttta cgtattctgg gattaggact     420
aatggcgcaa ctagcgcatg tactagaagc ggatcatcat tctatgccga aatgaaatgg     480
ttgttgtcga attccgataa cgctgcattc ccacaaatga ctaaatcgta tagaaatcct     540
aggaataaac ccgcactgat aatatgggga gtgcatcata cgaatccgt aagtgaacag     600
actaaattgt acggatcagg taataaactg attaaagtga gatctagtaa gtatcagcaa     660
tcgtttacac ctaatcccgg agctagacgt atcgatttcc attggctatt gctcgaccct     720
aacgataccg ttacattcac attcaatggc gcattcatag cgccagatag ggcaagtttt     780
tttagaggcg aatcaatcgg agtgcaatca gacgcaccac ttgactcaag ttgcggaggg     840
aattgtttcc atagcggagg gactatagtg agtagtctgc cattccaaaa tattaatcct     900
agaacagtgg gtaagtgtcc tagatacgtt aaacagaaaa gtctgttact cgcaaccgga     960
atgcgtaacg tacccgaaaa acctaaaaaa aggggattgt tcggagcgat agccggattc    1020
atagagaatg gatgggaggg actgattaac ggatggtacg gatttagaca ccaaaacgct    1080
cagggagagg gaaccgcagc cgattataaa tcgacacaat ctgcaatcga tcagattacc    1140
ggtaagctta atagattgat tggtaagact aatcagcaat tcggactgat agacaatgag    1200
tttaacgaag tcgagcaaca gataggaat gtgattaatt ggacacaaga cgctatgact    1260
gagatttggt cttataatgc cgaactgcta gtcgctatgg agaatcaaca cacaatcgat    1320
ctaaccgata gcgaaatgtc aaaattgtat gagagagtga aaaacagct agagagaat    1380
gcagaggaag acggaactgg gtgtttcgag atattccata aatgcgacga tcactgtatg    1440
gaatctatta gaaataatac atacgatcat acacagtata aacagagtc acttcaaaat    1500
cggatacaga tagacccagt taaactatct agcggatata aagacataat actgtggttc    1560
tcattcggag ctagttgttt tctgttgctc gcaatcgcta tgggacttgt attcatatgt    1620
attaaaaacg gtaatatgca atgtacaatt tgcatatag                           1659

<210> SEQ ID NO 27
<211> LENGTH: 1362
<212> TYPE: DNA
<213> ORGANISM: Influenza A virus

<400> SEQUENCE: 27
atgaatccaa atcagaagat aataacaatt ggctccgtct ctctaaccat tgcaacagta      60
tgtttcctca tgcagattgc cattctagca atgactgtaa cactgcattt caggcaaaat     120
gaatgcagca tttccgcgaa cagtcaggta gtgccgtgtg aaccaactac agaaaagag     180
gtctgttcga acgtagtaga ctatagaagc tggtcaaagc cgcagtgtca aattacagga     240
tttgcccctt tttccaagga caactcaatt cgactttctg ctggtggaga catttggata     300
```

| | |
|---|---|
| acaagagagc cttatgtgtc gtgtgacacc agcaaatgtt accaatttgc acttgggcag | 360 |
| gggaccacac tggataacaa acattcaaac ggaacaatac atgatagaat ctcccatcgg | 420 |
| acccttttga tgaatgaact gggtgttcca tttcacttgg gaaccaaaca agtttgcata | 480 |
| gcatggtcca gctcaagttg ccatgatggg aaagcatggt tgcacgtttg tgtcactggg | 540 |
| gatgatagaa atgcaactgc tagtttcatt tacaatggga tgcttgttga cagtattggt | 600 |
| tcatggtctc aaaatatcct caggacccag gagtcagaat gcgtttgcat caatgggtct | 660 |
| tgtacagtag tgatgactga tggaagtgcc tcagggaagg ccgatactag gatattattc | 720 |
| gtcaaagaag gaaagattgt tcacattagc ccattgtcag gaagtgctca gcatatagag | 780 |
| gaatgttcct gttatcccg atacccaaac gtcagatgtg tctgcaggga caactggaag | 840 |
| ggctctaata ggcctgttat agacataaac atggcagatt atagcatcga ctccagttat | 900 |
| gtgtgctcag gactcgttgg ggacacacca aggaatgagg atagttctag cagcagcaac | 960 |
| tgtagggatc ccaatgaaga gaggggaaac ccaggagtga aggatgggc ctttgacagt | 1020 |
| ggagatgatg tttggatggg tagaacaatc agtagggatt cgcggtcagg ctatgagaca | 1080 |
| tttaaggtca ttggtggttg gaccactgcc aattccaaat cacagaccag cagacaagtc | 1140 |
| atagttgata ataacaattg gtctggttat tctggtattt tctctgttga acacaaaagc | 1200 |
| tgtatcaata ggtgttttta tgtggagtta ataagaggaa ggccgaaaga aactagagta | 1260 |
| tggtggacct caaacagtat tgtcgtgttt tgtggcactt ctggcactta tggaacaggc | 1320 |
| tcatggcctg atggggcgaa catcaatttc atgcctatat aa | 1362 |

<210> SEQ ID NO 28
<211> LENGTH: 1362
<212> TYPE: DNA
<213> ORGANISM: Unknown
<220> FEATURE:
<223> OTHER INFORMATION: Deoptimized Influenza A virus

<400> SEQUENCE: 28

| | |
|---|---|
| atgaatccga atcagaaaat cattactatc ggatccgtta gcttgacaat cgcaaccgta | 60 |
| tgttttctta tgcagattgc gatactcgca atgaccgtta cattgcattt tagacaaaac | 120 |
| gagtgttcta ttagcgctaa ctctcaggtc gtgccatgcg aacctacaac cgaaaaagag | 180 |
| gtttgttcaa acgtagtcga ttataggtca tggtctaaac cgcaatgtca gattaccgga | 240 |
| ttcgcaccat tttcgaaaga caattcgatt agactatccg ccggaggcga tatttggata | 300 |
| actagggaac catacgtgtc atgcgataca agtaagtgtt atcaattcgc actcggccaa | 360 |
| gggactacac tcgataacaa acactctaac ggtacaatac acgataggat tagtcatagg | 420 |
| acactgctta tgaacgagtt aggcgtacca ttccatctgg gaactaaaca ggtatgcata | 480 |
| gcctggtcat ctagttcatg tcacgacggt aaggcatggt tgcacgtatg cgtaaccggc | 540 |
| gacgatagaa acgctaccgc ctcattcata tataacggta tgctagtcga ctcaatcggg | 600 |
| tcatggtcac aaaatatact taggacacag gaatccgaat gcgtatgtat taacggatca | 660 |
| tgtacagtcg ttatgaccga cggatccgct agcggtaagg ccgatacacg gatactgttc | 720 |
| gttaaagagg gtaagatagt gcatattagc ccacttagcg gatccgccca catatcgaa | 780 |
| gagtgttcat gttatcctag atatccgaac gttaggtgcg tttgtaggga taattggaaa | 840 |
| gggtctaatc gacccgttat cgatattaat atggccgatt atagtatcga tagttcatac | 900 |
| gtttgttccg gattagtcgg cgatactcct agaaacgaag atagttctag ctctagtaat | 960 |
| tgtagagacc caaacgaaga gagagggaat cccggagtga agggtgggc attcgatagc | 1020 |

| | |
|---|---|
| ggtgacgacg tttggatggg taggacaatt agtagggact ctagatccgg gtatgagact | 1080 |
| tttagggtga taggcggatg gacaaccgca aactctaaga gtcagactag tagacaggtg | 1140 |
| atagtcgata ataataattg gtccgggtat agcgggattt ttagcgtcga gcataagtca | 1200 |
| tgtattaatc ggtgttttta tgtcgaattg attaggggge gacctaaaga gactagggtg | 1260 |
| tggtggacta gcaattcgat agtcgttttt tgcggtacta gcggaacata cggaaccgga | 1320 |
| agttggccag acggagcgaa tattaatttt atgcctatat aa | 1362 |

<210> SEQ ID NO 29
<211> LENGTH: 1704
<212> TYPE: DNA
<213> ORGANISM: Influenza A virus

<400> SEQUENCE: 29

| | |
|---|---|
| atgaatactc aaattttggc attcattgct tgtatgctga ttggaactaa aggagacaaa | 60 |
| atatgtcttg gcaccatgc tgtggcaaat gggacaaaag tgaacacact aacagagagg | 120 |
| ggaattgaag tagtcaatgc cacgagacg gtggaaactg taaatattaa gaaaatatgc | 180 |
| actcaaggaa aaaggccaac agatctggga caatgtggac ttctaggaac cctaatagga | 240 |
| cctccccaat gcgatcaatt tctggagttt gacgctaatt tgataattga acgaagagaa | 300 |
| ggaaccgatg tgtgctatcc cgggaagttc acaaatgaag aatcactgag gcagatcctt | 360 |
| cgagggtcag gaggaattga taaagagtca atgggtttca cctatagtgg aataagaacc | 420 |
| aatgggggcga cgagtgcctg cagaagatca ggttcttctt tctatgcgga gatgaaatgg | 480 |
| ttactgtcga attcagacaa tgcggcatt ccccaaatga ctaagtcgta taggaatccc | 540 |
| aggaacaaac cagctctgat aatctgggga gtgcatcact ctggatcagc tactgagcag | 600 |
| accaaactct atggaagtgg aaacaagttg ataacagtag gaagctcgaa ataccagcaa | 660 |
| tcattcactc caagtccggg agcacggcca caagtgaatg gacaatcagg aaggattgat | 720 |
| tttcattggc tactccttga ccccaatgac acagtgacct tcactttcaa tggggcattc | 780 |
| atagcccctg acagggcaag tttctttaga ggagaatcgc taggagtcca gagtgatgtt | 840 |
| cctttggatt ctggttgtga aggggattgc ttccacagtg ggggtacgat agtcagttcc | 900 |
| ctgccattcc aaaacatcaa ccctagaaca gtggggaaat gccctcgata tgtcaaacag | 960 |
| acaagcctcc ttttggctac aggaatgaga acgtcccag agaacccaa gcaggcctac | 1020 |
| cagaaacgga tgaccagagg ccttttttga gcgattgctg gattcataga gaatggatgg | 1080 |
| gaaggtctca tcgatggatg gtatggtttc agacatcaaa atgcacaagg agaaggaact | 1140 |
| gcagctgact acaaaagcac ccaatctgca atagatcaga tcacaggcaa attgaatcgt | 1200 |
| ctgattgaca aaacaaacca gcagtttgaa ctgatagaca atgaattcag tgagatagaa | 1260 |
| caacaaatcg gaatgtcat taactggaca cgagactcaa tgactgaggt atggtcgtat | 1320 |
| aatgctgagc tgttggtggc aatggagaat cagcatacaa tagatcttgc agactcagaa | 1380 |
| atgaacaaac tttacgaacg cgtcagaaaa caactaaggg aaaatgctga agaagatgga | 1440 |
| actggatgct ttgagatatt ccataagtgt gatgatcagt gtatggagag cataaggaac | 1500 |
| aacacttatg accataccca atacaggaca gagtcattgc agaatagaat acagatagac | 1560 |
| ccagtgaaat tgagtagtgg atacaaagac ataatcttat ggtttagctt cggggcatca | 1620 |
| tgttttcttc ttctagccat tgcaatggga ttggttttca tttgcataaa gaatggaaac | 1680 |
| atgcggtgca ctatttgtat atag | 1704 |

<210> SEQ ID NO 30
<211> LENGTH: 1704
<212> TYPE: DNA
<213> ORGANISM: Unknown
<220> FEATURE:
<223> OTHER INFORMATION: Deoptimized Influenza A virus

<400> SEQUENCE: 30

| | | | | | |
|---|---|---|---|---|---|
| atgaatacac | agatactcgc | attcatagcg | tgtatgctta | tcggaactaa | aggcgataaa | 60 |
| atttgcttag | ggcatcacgc | agtcgctaac | ggaactaaag | tgaatacgct | taccgaacgc | 120 |
| ggaatagagg | tcgtgaacgc | taccgagaca | gtcgaaacag | tcaatataaa | aaaaatttgt | 180 |
| acacagggaa | aaagaccaac | cgatctggga | caatgcggac | tgttagggac | actaatcgga | 240 |
| ccaccacaat | gcgatcaatt | cctcgaattc | gacgctaatc | tgataatcga | acggagagag | 300 |
| ggaactgacg | tatgctatcc | cggtaagttt | acgaacgaag | agtcacttag | acagatactt | 360 |
| aggggggtcag | gggggataga | caaagagtct | atggggttta | catatagcgg | aatacggact | 420 |
| aacgagcta | caagtgcatg | tagacgatcc | ggatcatcgt | tttacgccga | aatgaaatgg | 480 |
| ttgttgtcta | atagcgataa | cgctgcattc | ccacaaatga | ctaagtctta | taggaatcct | 540 |
| agaaataaac | ccgcactgat | tatttgggga | gtgcatcata | gtggatcagc | aaccgaacag | 600 |
| actaagttgt | acggatcagg | taataaactg | attacagtcg | gatcgagtaa | atatcagcaa | 660 |
| tcgttcacac | ctagtcccgg | agctagacca | caagtgaacg | gacaatctgg | taggattgac | 720 |
| tttcattggt | tgcttctaga | cccaaacgat | acagtgacat | tcactttaa | cggagcattt | 780 |
| atcgcacccg | atagggctag | tttctttagg | ggagagtcac | tcggagtgca | atcagacgta | 840 |
| ccacttgata | gcggatgcga | aggcgattgt | tttcactcag | ggggaactat | agtgagtagt | 900 |
| ctgccattcc | aaaatattaa | tcctagaacc | gtcggtaagt | gtcctaggta | cgttaaacag | 960 |
| actagtctat | tgctcgcaac | cggaatgcgt | aacgtacccg | aaaatcctaa | acaggcatat | 1020 |
| cagaaacgga | tgactagggg | gctattcgga | gcgattgccg | gattcataga | gaatgggtgg | 1080 |
| gagggactga | tagacggatg | gtacgggttc | agacaccaaa | acgctcaggg | agagggaaca | 1140 |
| gccgcagact | ataagtctac | gcaatcggca | atcgatcaga | ttaccggtaa | gcttaataga | 1200 |
| ctgatagaca | aaactaatca | gcaattcgaa | ctgatagaca | acgaatttag | tgagatagag | 1260 |
| caacagatag | ggaatgtgat | aaattggact | agagactcaa | tgactgaggt | atggtcatat | 1320 |
| aacgccgaac | tgttggtcgc | aatggagaat | cagcatacaa | tcgatctagc | cgatagcgaa | 1380 |
| atgaataaac | tttacgaaag | ggtgcgaaaa | caattgcgag | agaatgcgga | agaggacgga | 1440 |
| accggatgtt | tcgaaatttt | ccataaatgc | gacgatcaat | gtatggaatc | gattaggaat | 1500 |
| aatacatacg | atcatacaca | atatagaacc | gaatcacttc | agaataggat | tcaaatcgat | 1560 |
| cccgttaagt | tgagtagcgg | atataaagac | attatactat | ggttctcatt | cggagctagt | 1620 |
| tgctttctat | tgcttgcgat | agctatggga | ttggtgttca | tatgcataaa | aaacggtaat | 1680 |
| atgcgatgta | cgatttgcat | atag | | | | 1704 |

<210> SEQ ID NO 31
<211> LENGTH: 1410
<212> TYPE: DNA
<213> ORGANISM: Influenza A virus

<400> SEQUENCE: 31

| | | | | | |
|---|---|---|---|---|---|
| atgaatccga | atcagaagat | aataacaatc | ggggtagtga | ataccactct | gtcaacaata | 60 |
| gcccttctca | ttggagtggg | aaacttagtt | ttcaacacag | tcatacatga | gaaaatagga | 120 |

```
gaccatcaaa tagtgaccca tccaacaata atgaccCctg aagtaccgaa ctgcagtgac    180
actataataa catacaataa cactgttata acaacataa caacaacaat aataactgaa    240
gcagaaaggc cttTcaagtc tccactaccg ctgtgcccct tcagaggatt cttccctttt    300
cacaaggaca atgcaatacg actgggtgaa acaaagacg tcatagtcac aagggagcct    360
tatgttagct gcgataatga caactgctgg tcctttgctc tcgcacaagg agcattgcta    420
gggactaaac atagcaatgg gaccattaaa gacagaacac catataggtc tctaattcgt    480
ttcccaatag gaacagctcc agtactagga aattacaaag agatatgcat tgcttggtcg    540
agcagcagtt gctttgacgg gaaagagtgg atgcatgtgt gcatgacagg gaatgataat    600
gatgcaagtg cccagataat atatggagga agaatgacag actccattaa atcatggagg    660
aaagacatac taagaaccca ggagtctgaa tgtcaatgca ttgacgggac ttgtgttgtt    720
gctgtcacag atggccctgc tgctaatagt gcagatcaca gggtttactg gatacgggag    780
ggaagaataa taaagtatga aaatgttccc aaaacaaaga tacaacactt agaagaatgt    840
tcctgctatg tggacattga tgtttactgt atatgtaggg acaattggaa gggctctaac    900
agaccttgga tgagaatcaa caacgagact atactggaaa caggatatgt atgtagtaaa    960
tttcactcag acacccccag gccagctgac ccttcaataa tgtcatgtga ctccccaagc    1020
aatgtcaatg gaggacccgg agtgaagggg tttggtttca agctggcaa tgatgtatgg    1080 ttaggtagaa cagtgtcaac tagtggtaga tcgggctttg aaattatcaa agttacagaa    1140
gggtggatca actctcctaa ccatgtcaaa tcaattacac aaacactagt gtccaacaat    1200
gactggtcag gctattcagg tagcttcatt gtcaaagcca aggactgttt tcagccctgt    1260
ttttatgttg agcttatacg agggaggccc aacaagaatg atgacgtctc ttggacaagt    1320
aatagtatag ttactttctg tggactagac aatgaacctg gatcgggaaa ttggccagat    1380
ggttctaaca ttgggtttat gcccaagtaa                                     1410

<210> SEQ ID NO 32
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 32
atgaatccta atcagaaaat aattactata ggggtcgtta atactacact atctacaatc     60
gctctactaa tcggagtcgg taatctagtc tttaatacag tgatacacga aaagataggc    120
gaccatcaga tagtgacaca tcctacaatt atgacacccg aagtgcctaa ttgtagcgat    180
acaataatta catataacaa taccgttata acaatatta caacaacaat tataaccgaa    240
gccgaacgac cattcaaaag tccactaccc ctatgtccat ttaggggtt ttttccgttt    300 cataaggata cgctatacg gttaggcgaa aataaagacg taatcgttac tagggagcca    360
tacgttagtt gcgataacga taattgttgg tcattcgcac tcgctcaagg cgcactgtta    420
gggactaaac actctaacgg aacaattaaa gacagaacac cttataggtc actgataaga    480
ttccctatcg gaaccgctcc cgtactaggc aattataaag agatatgcat agcatggtca    540
agttcgtcat gtttcgacgg taaagagtgg atgcacgtat gtatgaccgg taacgataac    600
gacgctagcg cacagataat atacggaggg cgaatgacag actcaattaa gagttggcgt    660
aaagacatac tgagaacaca agagtccgaa tgccaatgca tagacggaac ttgcgtagtc    720
gccgttacag acggacccgc agctaactcc gctgaccata gagtgtattg gattagggag    780
```

```
ggaaggataa taaagtatga gaacgtgcct aagactaaga tacaacatct tgaagagtgt    840
tcatgttatg tcgacataga cgtgtattgc atatgtagag acaattggaa agggtctaat    900
aggccatgga tgagaataaa taacgaaact atactcgaaa ccggatacgt atgttctaag    960
ttccatagcg atacacctag acccgcagac ccatctatta tgtcatgcga tagcccatct   1020
aacgttaacg gcggacccgg agtcaaaggg ttcggattca aagccggtaa cgacgtttgg   1080
ttagggagaa ccgttagtac tagcggtagg tccggattcg aaattataaa ggttacagag   1140
gggtggataa atagtccgaa tcacgttaag tcaattacac aaacacttgt gtctaataac   1200
gattggtccg gatatagcgg atcattcata gtcaaagcta aggattgctt tcagccatgt   1260
ttttacgtcg aactgataag ggggagaccg aataaaaacg acgacgttag ttggactagt   1320
aattcgatag tgacattttg cggattggac aacgaacccg gatccggtaa ttggcctgac   1380
ggatcgaata tagggtttat gcctaaataa                                    1410

<210> SEQ ID NO 33
<211> LENGTH: 1710
<212> TYPE: DNA
<213> ORGANISM: Influenza A virus

<400> SEQUENCE: 33
agcaaaagca ggggatacaa aatgaacact caaatcctgg tattcgctct ggtggcgagc     60
attccgacaa atgcagacaa gatctgcctt gggcatcatg ccgtgtcaaa cgggactaaa    120
gtaaacacat taactgagag aggagtggaa gtcgttaatg caactgaaac ggtggaacga    180
acaaacgttc ccaggatctg ctcaaaaggg aaaaggacag ttgacctcgg tcaatgtgga    240
cttctgggaa caatcactgg gccaccccaa tgtgaccaat tcctagaatt ttcggccgac    300
ttaattattg agaggcgaga aggaagtgat gtctgttatc ctgggaaatt cgtgaatgaa    360
gaagctctga ggcaaattct cagagagtca ggcggaattg acaaggagac aatgggattc    420
acctacagcg gaataagaac taatggaaca accagtgcat gtaggagatc aggatcttca    480
ttctatgcag agatgaaatg gctcctgtca aacacagaca atgctgcttt cccgcaaatg    540
actaagtcat acaagaacac aaggaaagac ccagctctga taatatgggg gatccaccat    600
tccggatcaa ctacagaaca gaccaagcta tatgggagtg aaacaaaact gataacagtt    660
gggagttcta attaccaaca gtcctttgta ccgagtccag agcgagacc acaagtgaat    720 ggccaatctg aagaattga cttcattgg ctgatactaa accctaatga cacggtcact    780
ttcagtttca atggggcctt catagctcca gaccgtgcaa gctttctgag agggaagtcc    840
atgggaattc agagtgaagt acaggttgat gccaattgtg aaggagattg ctatcatagt    900
ggagggacaa taataagtaa tttgcccttt cagaacataa atagcagggc agtaggaaaa    960
tgtccgagat atgttaagca agagagtctg ctgttggcaa caggaatgaa gaatgttccc   1020
gaaatcccaa agaggaggag gagaggccta tttggtgcta tagcgggttt cattgaaaat   1080
ggatgggaag gtttgattga tgggtggtat ggcttcaggc atcaaaatgc acaagggag   1140 ggaactgctg cagattacaa aagcacccaa tcagcaattg atcaaataac agggaaatta   1200
aatcggctta tagaaaaaac taaccaacag tttgagttaa tagacaacga attcactgag   1260
gttgaaaggc aaattggcaa tgtgataaac tggaccagag attccatgac agaagtgtgg   1320
tcctataacg ctgaactctt agtagcaatg gagaatcagc acacaattga tctggccgac   1380
tcagaaatga acaaactgta cgaacgagtg aagagacaac tgagagagaa tgccgaagaa   1440
gatggcactg gttgcttcga aatatttcac aagtgtgatg acgactgcat ggccagtatt   1500
```

| | |
|---|---:|
| agaaacaaca cctatgatca cagcaagtac agggaagaag caatacaaaa tagaatacag | 1560 |
| attgacccag tcaaactaag cagcggctac aaagatgtga tactttggtt tagcttcggg | 1620 |
| gcatcatgtt tcatacttct ggccattgca atgggccttg tcttcatatg tgtgaagaat | 1680 |
| ggaaacatgc ggtgcactat ttgtatataa | 1710 |

<210> SEQ ID NO 34
<211> LENGTH: 1710
<212> TYPE: DNA
<213> ORGANISM: Unknown
<220> FEATURE:
<223> OTHER INFORMATION: Deoptimized Influenza A virus

<400> SEQUENCE: 34

| | |
|---|---:|
| agtaagagta gggggtataa aatgaataca cagatactcg tattcgcact cgttgcgtca | 60 |
| ataccgacaa acgccgataa gatttgccta gggcatcacg cagtgtcaaa cggaactaaa | 120 |
| gtgaatacac ttaccgaaag gggcgttgag gtagtgaacg ctacagagac tgtcgaacgg | 180 |
| actaacgtac ctaggatttg tagtaagggt aaaagaacag tcgacctagg caatgcgga | 240 |
| ctgttaggca caattaccgg accaccacaa tgcgaccaat ttctcgaatt tagcgctgat | 300 |
| ctgattatcg aacggagaga gggatccgac gtttgttatc ccggtaaatt cgttaacgaa | 360 |
| gaggcactga gacagatact tagagaatcc ggagggtag acaaagagac aatggggttt | 420 |
| acatatagcg gaattagaac taacggaact actagcgcat gtaggagatc cggatctagc | 480 |
| ttttacgccg aaatgaaatg gttactgtca aataccgata cgccgcatt tccgcaaatg | 540 |
| actaagtcat ataagaatac taggaaagac cccgcactga taatttgggg gatacaccat | 600 |
| agcggatcga ctaccgaaca gacaaagcta tacggtagcg gaataaact gataacagtg | 660 |
| ggatcaagta attaccaaca gtcattcgta ccgagtccag cgctagacc acaagtgaac | 720 |
| ggacaatccg gacgtataga tttccattgg ttgatactga atccgaacga tacagtgaca | 780 |
| tttagctta acgcgcatt catagcaccc gatagggcat cattccttag ggtaagagt | 840 |
| atggggatac aaagcgaagt gcaagtcgac gctaattgcg aaggcgattg ttatcatagc | 900 |
| gggggactaa ttattagtaa tctgccattc caaaatatta atagtagggc agtgggaaag | 960 |
| tgtccaaggt acgttaaaca ggaatcactg ttactcgcaa ccggaatgaa aaacgtacca | 1020 |
| gagataccta agagacgaag aagggggttg ttcggcgcta tagccggatt catagagaac | 1080 |
| ggatgggagg gactgataga cggatggtac gggttcagac accaaaacgc tcaaggcgaa | 1140 |
| gggacagccg cagactataa gagtacacaa tccgctatcg atcaaattac cggtaagctt | 1200 |
| aatagactga tcgaaaaaac taatcaacaa ttcgaactaa tcgataacga atttacggaa | 1260 |
| gtcgaaagac agattggcaa tgtgataaat tggactagaa actctatgac tgaggtttgg | 1320 |
| tcatataacg ccgaactgtt agtcgcaatg gaaaatcagc atacgataga ccttgccgat | 1380 |
| agcgaaatga ataagctata cgaaagggtg aaacgacaat tgaggggaaaa cgccgaagag | 1440 |
| gacgaacag ggtgtttcga aattttttcac aaatgcgacg acgattgtat ggctagtatt | 1500 |
| aggaataata catacgacca tagtaagtat agagaggaag cgatacagaa taggattcaa | 1560 |
| atcgatcccg taaaactgtc tagcggatac aaagacgtta tactgtggtt ctcattcgga | 1620 |
| gcgtcatgtt tcatactgct tgcaatcgct atggggttag tgttcatatg cgttaaaaac | 1680 |
| ggaaatatgc gatgtactat ttgtatttaa | 1710 |

<210> SEQ ID NO 35
<211> LENGTH: 1416
<212> TYPE: DNA
<213> ORGANISM: Influenza A virus

<400> SEQUENCE: 35

| | | | | | |
|---|---|---|---|---|---|
| atgaatccaa | atcagaaact | atttgcatta | tctggagtgg | caatagcact | tagtgtactg | 60 |
| aacttattga | taggaatctc | aaacgtcgga | ttgaacgtat | ctctacatct | aaaggaaaaa | 120 |
| ggacccaaac | aggaggagaa | tttaacatgc | acgaccatta | tcaaaacaa | cactactgta | 180 |
| gtagaaaaca | catatgtaaa | taatacaaca | ataattacca | agggaactga | tttgaaaaca | 240 |
| ccaagctatc | tgctgttgaa | caagagcctg | tgcaatgttg | aagggtgggt | cgtgatagca | 300 |
| aaagacaatg | cagtaagatt | tggggaaagt | gaacaaatca | ttgttaccag | ggagccatat | 360 |
| gtatcatgcg | acccaacagg | atgcaaaatg | tatgccttgc | accaagggac | taccattagg | 420 |
| aacaaacatt | caaatggaac | gattcatgac | agaacagctt | tcagaggtct | catctccact | 480 |
| ccattgggca | ctccaccaac | cgtaagtaac | agtgacttta | tgtgtgttgg | atggtcaagc | 540 |
| acaacttgcc | atgatgggat | tgctaggatg | actatctgta | tacaaggaaa | taatgacaat | 600 |
| gctacagcaa | cggtttatta | caacagaagg | ctgaccacta | ccattaagac | ctgggccaga | 660 |
| aacattctga | ggactcaaga | atcagaatgt | gtgtgccaca | atggcacatg | tgcagttgta | 720 |
| atgaccgacg | gatcggctag | tagtcaagcc | tatacaaaag | taatgtatt | ccacaaggga | 780 |
| ttagtagtta | aggaggagga | gttaagggga | tcagccagac | atattgagga | atgctcctgt | 840 |
| tatggacaca | tcaaaaggt | gacctgtgtg | tgcagagata | ctggcaggg | agcaaacagg | 900 |
| cctattatag | aaattgatat | gagcacattg | gagcacacaa | gtagatacgt | gtgcactgga | 960 |
| attctcacag | acaccagcag | acctgggac | aaatctagtg | gtgattgttc | caatccaata | 1020 |
| actgggagtc | ccggcgttcc | gggagtgaag | ggattcgggt | ttctaaatgg | gataacaca | 1080 |
| tggcttggta | ggaccatcag | ccccagatca | agaagtggat | cgaaatgtt | gaaaatacct | 1140 |
| aatgcaggta | ctgatcccaa | ttctagaata | gcagaacgac | aggaaattgt | cgacaataac | 1200 |
| aattggtcag | ctattccgg | aagctttatt | gactattgga | atgataacag | tgaatgctac | 1260 |
| aatccatgct | tttacgtaga | gttaattaga | ggaagacccg | aagaggctaa | atacgtatgg | 1320 |
| tgggcaagta | acagtctaat | tgccctatgt | ggaagcccat | tcccagttgg | gtctggttcc | 1380 |
| ttccccgatg | gggcacaaat | ccaatacttt | tcgtaa | | | 1416 |

<210> SEQ ID NO 36
<211> LENGTH: 1416
<212> TYPE: DNA
<213> ORGANISM: Unknown
<220> FEATURE:
<223> OTHER INFORMATION: Deoptimized Influenza A virus

<400> SEQUENCE: 36

| | | | | | |
|---|---|---|---|---|---|
| atgaatccga | accaaaaatt | gttcgcatta | agcggagtcg | caatcgcact | aagcgtactg | 60 |
| aatctgttga | tagggataag | taacgtaggg | ttgaacgtat | cactacattt | gaaagagaaa | 120 |
| gggcctaaac | aggaagagaa | tttgacatgt | actacaatta | tcagaataa | tactaccgta | 180 |
| gtcgaaaata | catacgttaa | caatacaaca | attattacta | agggaaccga | tctgaaaact | 240 |
| ccaagttatc | tgttactgaa | taatctcta | tgtaacgttg | agggatgggt | agtgatcgca | 300 |
| aaggataacg | ccgttagatt | cggcgaaagc | gaacagatta | tagtgactag | agagccatac | 360 |
| gtatcatgcg | atccaaccgg | atgcaaaatg | tacgcattac | accaagggac | aactattagg | 420 |

| | |
|---|---|
| aataaacact ctaacggtac gatacacgat agaaccgcat ttaggggtt gattagtaca | 480 |
| ccactcggta caccaccaac cgtttcgaat agcgacttta tgtgcgtagg gtggtctagt | 540 |
| actacatgtc acgacggaat cgctagaatg acaatttgca tacaggggaa taacgataac | 600 |
| gctaccgcaa ccgtatatta taatagaaga ctaactacta ctattaagac atgggctagg | 660 |
| aatatactga gaacgcaaga atccgaatgc gtttgtcata acggtacatg cgccgtagtg | 720 |
| atgaccgacg gatccgctag ttcgcaagca tatactaagg taatgtattt tcacaaaggg | 780 |
| ttagtagtga aagaggaaga gttgagggg tccgctagac atattgagga atgctcatgt | 840 |
| tacggacata atcaaaaggt gacatgcgta tgtagagaca attggcaagg cgcaaataga | 900 |
| cccattatcg aaatcgatat gagtacactc gaacatacta gtagatatgt gtgtaccgga | 960 |
| atactaaccg atacgagtag acccggcgat aagtctagcg gagattgctc aaacccaatt | 1020 |
| accggatcac ccggagtgcc aggcgttaag ggattcggat tccttaacgg agacaataca | 1080 |
| tggttaggga gaactattag tcctaggagt aggtccggat tcgaaatgct taagatacct | 1140 |
| aacgccggaa ccgacccaaa tagtaggatt gccgaacgac aagagattgt cgacaataac | 1200 |
| aattggtccg gatatagcgg atcattcata gactattgga acgacaatag cgaatgctat | 1260 |
| aacccatgtt tttacgttga gttgattagg ggtagacccg aagaggcaaa atacgtttgg | 1320 |
| tgggcatcta acagtctaat cgcattatgc ggatcaccat ttcccgtagg tagcggatca | 1380 |
| tttcccgacg gagcccaaat tcaatatttt agttaa | 1416 |

<210> SEQ ID NO 37
<211> LENGTH: 1683
<212> TYPE: DNA
<213> ORGANISM: Influenza A virus

<400> SEQUENCE: 37

| | |
|---|---|
| atggaaacaa tatcactaat aactatacta ctagtagtaa cagcaagcaa tgcagataaa | 60 |
| atctgcatcg gccaccagtc aacaaactcc acagaaactg tggacacgct aacagaaacc | 120 |
| aatgttcctg tgacacatgc caaagaattg ctccacacag agcataatgg aatgctgtgt | 180 |
| gcaacaagcc tgggacatcc cctcattcta gacacatgca ctattgaagg actagtctat | 240 |
| ggcaaccctt cttgtgacct gctgttggga ggaagagaat ggtcctacat cgtcgaaaga | 300 |
| tcatcagctg taaatggaac gtgttaccct gggaatgtag aaaacctaga ggaactcagg | 360 |
| acactttta gttccgctag ttcctaccaa agaatccaaa tcttcccaga cacaacctgg | 420 |
| aatgtgactt acactggaac aagcagagca tgttcaggtt cattctacag gagtatgaga | 480 |
| tggctgactc aaaagagcgg ttttttaccct gttcaagacg cccaatacac aaataacagg | 540 |
| ggaaagagca ttcttttcgt gtggggcata catcacccac ccacctatac cgagcaaaca | 600 |
| aatttgtaca taagaaacga cacaacaaca agcgtgacaa cagaagattt gaataggacc | 660 |
| ttcaaaccag tgatagggcc aaggcccctt gtcaatggtc tgcagggaag aattgattat | 720 |
| tattggtcgg tactaaaacc aggccaaaca ttgcgagtac gatccaatgg gaatctaatt | 780 |
| gctccatggt atggacacgt tctttcagga gggagccatg gaagaatcct gaagactgat | 840 |
| ttaaaaggtg gtaattgtgt agtgcaatgt cagactgaaa aaggtggctt aaacagtaca | 900 |
| ttgccattcc acaatatcag taaatatgca tttggaacct gccccaaata tgtaagagtt | 960 |
| aatagtctca aactggcagt cggtctgagg aacgtgcctg ctagatcaag tagaggacta | 1020 |
| tttggagcca tagctggatt catagaagga ggttggccag gactagtcgc tggctggtat | 1080 |
| ggtttccagc attcaaatga tcaaggggtt ggtatggctg cagatagga ttcaactcaa | 1140 |

| | |
|---|---|
| aaggcaattg ataaaataac atccaaggtg aataatatag tcgacaagat gaacaagcaa | 1200 |
| tatgaaataa ttgatcatga attcagtgag gttgaaacta gactcaatat gatcaataat | 1260 |
| aagattgatg accaaataca agacgtatgg gcatataatg cagaattgct agtactactt | 1320 |
| gaaaatcaaa aaacactcga tgagcatgat gcgaacgtga acaatctata taacaaggtg | 1380 |
| aagagggcac tgggctccaa tgctatggaa gatgggaaag gctgtttcga gctataccat | 1440 |
| aaatgtgatg atcagtgcat ggaaacaatt cggaacggga cctataatag gagaaagtat | 1500 |
| agagaggaat caagactaga aaggcagaaa atagaggggg ttaagctgga atctgaggga | 1560 |
| acttacaaaa tcctcaccat ttattcgact gtcgcctcat ctcttgtgct tgcaatgggg | 1620 |
| tttgctgcct tcctgttctg ggccatgtcc aatggatctt gcagatgcaa catttgtata | 1680 |
| taa | 1683 |

<210> SEQ ID NO 38
<211> LENGTH: 1683
<212> TYPE: DNA
<213> ORGANISM: Unknown
<220> FEATURE:
<223> OTHER INFORMATION: Deoptimized Influenza A virus

<400> SEQUENCE: 38

| | |
|---|---|
| atggagacaa ttagtctgat tactatacta ttggtcgtta cagcgtcaaa cgctgacaaa | 60 |
| atatgtatag gccatcaatc cactaattca accgaaacag tcgatacact aaccgaaacg | 120 |
| aatgtgccag tgacacacgc taaagagcta ctgcataccg aacataacgg aatgctatgc | 180 |
| gctactagcc tagggcatcc actgatactc gatacatgta ctatcgaggg actcgtatac | 240 |
| ggtaatccta gttgcgatct actgttaggc ggtagggaat ggtcatacat agtcgaacga | 300 |
| tcatccgccg taaacggaac atgttatccc ggtaatgtcg agaatctcga gagcttaggg | 360 |
| acactattct catccgctag ctcataccaa cgaatacaga ttttttcccga tactacatgg | 420 |
| aatgtgacat ataccggaac tagtagggca tgttccggat cattctatag atcaatgaga | 480 |
| tggttgacac aaaaaatccgg cttttaccct gtgcaagacg cacaatatac gaataatagg | 540 |
| ggtaaatcta ctattcgt atggggtata catcatccac ctactatac cgaacagact | 600 |
| aatctgtata ttagaaacga tacaactaca tccgttacaa ccgaagactt gaataggaca | 660 |
| ttcaaacccg taatcggacc tagaccacta gtgaacggat tgcagggtag aatcgattac | 720 |
| tattggtccg tacttaagcc agggcaaaca cttagagtga atctaacgg taatctaatc | 780 |
| gcaccatggt acggacacgt acttagcgga gggtcacacg taggatact taagaccgat | 840 |
| ctgaaagggg ggaattgcgt agtgcaatgc caaaccgaaa aaggcggact gaattcgaca | 900 |
| ctaccattcc ataatattag caaatacgca ttcggaacat gtcctaagta cgttagggtg | 960 |
| aatagtctga aactcgcagt gggattgaga aacgtacccg ctagatcgag taggggggcta | 1020 |
| ttcggcgcaa tcgcagggtt tatcgaaggc ggatggccag gactagttgc cggatggtac | 1080 |
| ggattccaac atagtaacga tcaaggcgta gggatggccg ccgatagga tagcacacaa | 1140 |
| aaagcaatcg ataagattac tagtaaggtt aataatatag tcgataagat gaataagcaa | 1200 |
| tacgaaatta tcgatcacga attagcgaa gtcgaaacta gactgaatat gataaataat | 1260 |
| aagatagacg atcagataca agacgtatgg gcatataacg ccgaactgtt agtgttgctt | 1320 |
| gagaatcaga gacactcga cgaacacgac gcaaacgtta ataatctgta taataaagtg | 1380 |
| aaaagagcac tagggtctaa cgctatggag gacggtaagg gatgtttcga actatatcat | 1440 |
| aaatgcgacg atcaatgcat ggagacaatt agaaacggta catataatcg gagaaagtat | 1500 |

| | |
|---|---|
| agagaggaat ctagactcga aagacagaaa atcgaaggcg ttaaactcga atccgaagga | 1560 |
| acatataaga tactgactat ttatagtaca gtcgctagct cactagtgct tgctatggga | 1620 |
| ttcgccgcat tcttgttttg gctatgtca aacggatcat gtaggtgtaa tatttgtatt | 1680 |
| taa | 1683 |

<210> SEQ ID NO 39
<211> LENGTH: 1404
<212> TYPE: DNA
<213> ORGANISM: Influenza A virus

<400> SEQUENCE: 39

| | |
|---|---|
| atgaatccaa atcaaaagat aatagcactt ggctctgttt ctataactat tgcgacaata | 60 |
| tgtttactca tgcagattgc catcttagca acgactatga cactcacttt caatgaatgt | 120 |
| accaacccat cgaacaatca agcagtgcca tgtgaaccaa tcataataga aaggaacata | 180 |
| acagagatag tgcatttgaa taatactacc atagagaagg aaagttgtcc taaagtagca | 240 |
| gaatacaaga attggtcaaa accgcaatgt caaattacag ggttcgcccc tttctccaag | 300 |
| gacaactcaa ttaggctttc tgcaggcggg gatatttggg tgacaagaga accttatgta | 360 |
| tcgtgcggtc ttggtaaatg ttaccaattt gcacttgggc agggaaccac tttgaacaac | 420 |
| aaacactcaa atggcacaat acatgatagg agtccccata gaaccctttt aatgaacgag | 480 |
| ttgggtgttc catttcattt gggaaccaaa caagtgtgca tagcatggtc cagctcaagc | 540 |
| tgccatgatg ggaaggcatg gttacatgtt tgtgtcactg gggatgatag aaatgcgact | 600 |
| gctagcatca tttatgatgg gatgcttacc gacagtattg gttcatggtc taagaacatc | 660 |
| ctcagaactc aggagtcaga atgcgtttgc atcaatggaa cttgtacagt agtaatgact | 720 |
| gatggaagtg catccaggaag ggctgatact aaaatactat tcattagaga agggaaaatt | 780 |
| gtccacattg gtccactgtc aggaagtgct cagcatgtgg aggaatgctc ctgttacccc | 840 |
| cggtatccag aagttagatg tgtttgcaga gacaattgga agggctccaa tagacccgtg | 900 |
| ctatatataa atgtggcaga ttatagtgtt gattctagtt atgtgtgctc aggacttgtt | 960 |
| ggcgacacac caagaaatga cgatagctcc agcagcagta actgcaggga tcctaataac | 1020 |
| gagagagggg gcccaggagt gaaagggtgg gcctttgaca atggaaatga tgtttggatg | 1080 |
| ggacgaacaa tcaagaaaga ttcgcgctct ggttatgaga ctttcagggt cgttggtggt | 1140 |
| tggactacgg ctaattccaa gtcacaaata aataggcaag tcatagttga cagtgataac | 1200 |
| tggtctgggt attctggtat attctctgtt gaaggaaaaa cctgcatcaa caggtgtttt | 1260 |
| tatgtggagt tgataagagg gagaccacag gagaccagag tatggtggac ttcaaatagc | 1320 |
| atcattgtat tttgtggaac ttcaggtacc tatggaacag ctcatggcc tgatggagcg | 1380 |
| aatatcaatt tcatgtctat ataa | 1404 |

<210> SEQ ID NO 40
<211> LENGTH: 1404
<212> TYPE: DNA
<213> ORGANISM: Unknown
<220> FEATURE:
<223> OTHER INFORMATION: Deoptimized Influenza A virus

<400> SEQUENCE: 40

| | |
|---|---|
| atgaatccga atcagaaaat aatcgcatta gggtccgttt cgattactat agcgactata | 60 |
| tgcctattga tgcaaatcgc aatactcgca acgactatga cattgcattt taacgaatgc | 120 |
| actaatccct ctaataatca ggccgttcca tgcgaaccaa tcataatcga acggaatatt | 180 |

-continued

```
accgagatag tgcatcttaa caatacgact atcgaaaaag agtcatgccc taaggtagcg    240
gaatataaaa attggtctaa gcctcaatgt cagattaccg gattcgcacc attctctaaa    300
gataattcaa ttaggcttag cgcaggcgga gatatatggg tgactagaga gccatacgta    360
agttgcggac tcgtaagtg ttatcaattc gcattaggcc aagggacaac ccttaataat     420
aagcatagta acggtactat acacgatagg agtccacata ggactcttct tatgaacgag    480
ttaggcgtac cattccatt agggactaaa caggtttgta tcgcatggtc tagtagttca     540
tgtcatgacg gtaaggcatg gttgcatgtt tgcgttaccg gcgacgatag aaacgctacc    600
gcttcaatca tatacgacgg tatgcttacc gattcaatcg gatcatggtc taaaaatata    660
cttagaaccc aagagtccga atgcgtatgt attaacggta catgtacagt cgttatgaca    720
gacggatccg ctagcggtag ggccgataca aagatactat tcatacgcga aggtaagata    780
gtgcatatcg gaccattgtc cggatccgca caacacgttg aggaatgctc atgttatcct    840
agatatcccg aagtgagatg cgtatgtaga gataattgga aagggtcaaa tagacccgta    900
ctgtatataa acgttgccga ttatagcgtc gatagttcat atgtgtgtag cggactagtg    960
ggcgatacac ctagaaacga cgattcatct agtagttcga attgtaggga tcctaataac    1020
gaaagaggcg gaccaggcgt taaagggtgg gcattcgata acggtaacga cgtttggatg    1080
gggagaacta ttaaaaaaga ttctagatca gggtatgaga cattcagagt ggtgggggggg   1140 tggactaccg ctaactctaa gtctcaaatt aatagacagg tgatagtcga tagcgataat    1200
tggtcagggt attccggtat ttttagcgtt gagggtaaga catgtattaa taggtgtttt    1260
tatgtcgaat tgattagggg gcgaccacaa gagactaggg tttggtggac tagtaattcg    1320
attatagtgt tttgcggaac tagcggaaca tacggaaccg gatcatggcc agacggagcg    1380
aatataaatt ttatgtctat ataa                                           1404
```

<210> SEQ ID NO 41
<211> LENGTH: 2341
<212> TYPE: DNA
<213> ORGANISM: Influenza virus
<220> FEATURE:
<221> NAME/KEY: CDS
<222> LOCATION: (25)..(2298)

<400> SEQUENCE: 41

```
agcgaaagca ggcaaaccat ttga atg gat gtc aat ccg acc tta ctt ttc        51
                         Met Asp Val Asn Pro Thr Leu Leu Phe
                          1               5 tta aaa gtg cca gca caa aat gct ata agc aca act ttc cct tat act       99
Leu Lys Val Pro Ala Gln Asn Ala Ile Ser Thr Thr Phe Pro Tyr Thr
 10              15                  20                  25 gga gac cct cct tac agc cat ggg aca gga aca gga tac acc atg gat      147
Gly Asp Pro Pro Tyr Ser His Gly Thr Gly Thr Gly Tyr Thr Met Asp
                 30                  35                  40 act gtc aac agg aca cat cag tac tca gaa aag gga aga tgg aca aca      195
Thr Val Asn Arg Thr His Gln Tyr Ser Glu Lys Gly Arg Trp Thr Thr
             45                  50                  55 aac acc gaa act gga gca ccg caa ctc aac ccg att gat ggg cca ctg      243
Asn Thr Glu Thr Gly Ala Pro Gln Leu Asn Pro Ile Asp Gly Pro Leu
         60                  65                  70 cca gaa gac aat gaa cca agt ggt tat gcc caa aca gat tgt gta ttg      291
Pro Glu Asp Asn Glu Pro Ser Gly Tyr Ala Gln Thr Asp Cys Val Leu
     75                  80                  85
```

| | | |
|---|---|---|
| gaa gca atg gct ttc ctt gag gaa tcc cat cct ggt att ttt gaa aac<br>Glu Ala Met Ala Phe Leu Glu Glu Ser His Pro Gly Ile Phe Glu Asn<br>90                      95                    100                 105 | 339 |
| tcg tgt att gaa acg atg gag gtt gtt cag caa aca cga gta gac aag<br>Ser Cys Ile Glu Thr Met Glu Val Val Gln Gln Thr Arg Val Asp Lys<br>                110                    115                    120 | 387 |
| ctg aca caa ggc cga cag acc tat gac tgg act cta aat aga aac caa<br>Leu Thr Gln Gly Arg Gln Thr Tyr Asp Trp Thr Leu Asn Arg Asn Gln<br>                      125                    130                    135 | 435 |
| cct gct gca aca gca ttg gcc aac aca ata gaa gtg ttc aga tca aat<br>Pro Ala Ala Thr Ala Leu Ala Asn Thr Ile Glu Val Phe Arg Ser Asn<br>          140                    145                    150 | 483 |
| ggc ctc acg gcc aat gag tct gga agg ctc ata gac ttc ctt aag gat<br>Gly Leu Thr Ala Asn Glu Ser Gly Arg Leu Ile Asp Phe Leu Lys Asp<br>       155                    160                    165 | 531 |
| gta atg gag tca atg aaa aaa gaa gaa atg ggg atc aca act cat ttt<br>Val Met Glu Ser Met Lys Lys Glu Glu Met Gly Ile Thr Thr His Phe<br>170                      175                    180                 185 | 579 |
| cag aga aag aga cgg gtg aga gac aat atg act aag aaa atg ata aca<br>Gln Arg Lys Arg Arg Val Arg Asp Asn Met Thr Lys Lys Met Ile Thr<br>                190                    195                    200 | 627 |
| cag aga aca ata ggt aaa aag aag cag aga ttg aac aaa agg agt tat<br>Gln Arg Thr Ile Gly Lys Lys Lys Gln Arg Leu Asn Lys Arg Ser Tyr<br>              205                    210                    215 | 675 |
| cta att aga gca ttg acc ctg aac aca atg acc aaa gat gct gag aga<br>Leu Ile Arg Ala Leu Thr Leu Asn Thr Met Thr Lys Asp Ala Glu Arg<br>          220                    225                    230 | 723 |
| ggg aag cta aaa cgg aga gca att gca acc cca ggg atg caa ata agg<br>Gly Lys Leu Lys Arg Arg Ala Ile Ala Thr Pro Gly Met Gln Ile Arg<br>      235                    240                    245 | 771 |
| ggg ttt gta tac ttt gtt gag aca ctg gca agg agt ata tgt gag aaa<br>Gly Phe Val Tyr Phe Val Glu Thr Leu Ala Arg Ser Ile Cys Glu Lys<br>250                      255                    260               265 | 819 |
| ctt gaa caa tca ggg ttg cca gtt gga ggc aat gag aag aaa gca aag<br>Leu Glu Gln Ser Gly Leu Pro Val Gly Gly Asn Glu Lys Lys Ala Lys<br>                270                    275                    280 | 867 |
| ttg gca aat gtt gta agg aag atg atg acc aat tct cag gac acc gaa<br>Leu Ala Asn Val Val Arg Lys Met Met Thr Asn Ser Gln Asp Thr Glu<br>          285                    290                    295 | 915 |
| ctt tct ttc acc atc act gga gat aac acc aaa tgg aac gaa aat cag<br>Leu Ser Phe Thr Ile Thr Gly Asp Asn Thr Lys Trp Asn Glu Asn Gln<br>      300                    305                    310 | 963 |
| aat cct cgg atg ttt ttg gcc atg atc aca tat atg aca aga aat cag<br>Asn Pro Arg Met Phe Leu Ala Met Ile Thr Tyr Met Thr Arg Asn Gln<br>315                      320                    325 | 1011 |
| ccc gaa tgg ttc aga aat gtt cta agt att gct cca ata atg ttc tca<br>Pro Glu Trp Phe Arg Asn Val Leu Ser Ile Ala Pro Ile Met Phe Ser<br>330                      335                    340               345 | 1059 |
| aac aaa atg gcg aga ctg gga aaa ggg tat atg ttt gag agc aag agt<br>Asn Lys Met Ala Arg Leu Gly Lys Gly Tyr Met Phe Glu Ser Lys Ser<br>                350                    355                    360 | 1107 |
| atg aaa ctt aga act caa ata cct gca gaa atg cta gca agc atc gat<br>Met Lys Leu Arg Thr Gln Ile Pro Ala Glu Met Leu Ala Ser Ile Asp<br>          365                    370                    375 | 1155 |
| ttg aaa tat ttc aat gat tca aca aga aag aag att gaa aaa atc cga<br>Leu Lys Tyr Phe Asn Asp Ser Thr Arg Lys Lys Ile Glu Lys Ile Arg<br>      380                    385                    390 | 1203 |
| ccg ctc tta ata gag ggg act gca tca ttg agc cct gga atg atg atg<br>Pro Leu Leu Ile Glu Gly Thr Ala Ser Leu Ser Pro Gly Met Met Met<br>395                      400                    405 | 1251 |

-continued

| | |
|---|---|
| ggc atg ttc aat atg tta agc act gta tta ggc gtc tcc atc ctg aat<br>Gly Met Phe Asn Met Leu Ser Thr Val Leu Gly Val Ser Ile Leu Asn<br>410               415               420               425 | 1299 |
| ctt gga caa aag aga tac acc aag act act tac tgg tgg gat ggt ctt<br>Leu Gly Gln Lys Arg Tyr Thr Lys Thr Thr Tyr Trp Trp Asp Gly Leu<br>               430               435               440 | 1347 |
| caa tcc tct gac gat ttt gct ctg att gtg aat gca ccc aat cat gaa<br>Gln Ser Ser Asp Asp Phe Ala Leu Ile Val Asn Ala Pro Asn His Glu<br>               445               450               455 | 1395 |
| ggg att caa gcc gga gtc gac agg ttt tat cga acc tgt aag cta ctt<br>Gly Ile Gln Ala Gly Val Asp Arg Phe Tyr Arg Thr Cys Lys Leu Leu<br>460               465               470 | 1443 |
| gga atc aat atg agc aag aaa aag tct tac ata aac aga aca ggt aca<br>Gly Ile Asn Met Ser Lys Lys Lys Ser Tyr Ile Asn Arg Thr Gly Thr<br>475               480               485 | 1491 |
| ttt gaa ttc aca agt ttt ttc tat cgt tat ggg ttt gtt gcc aat ttc<br>Phe Glu Phe Thr Ser Phe Phe Tyr Arg Tyr Gly Phe Val Ala Asn Phe<br>490               495               500               505 | 1539 |
| agc atg gag ctc ccc agt ttt ggg gtg tct ggg atc aac gag tca gcg<br>Ser Met Glu Leu Pro Ser Phe Gly Val Ser Gly Ile Asn Glu Ser Ala<br>               510               515               520 | 1587 |
| gac atg agt att gga gtt act gtc atc aaa aac aat atg ata aac aat<br>Asp Met Ser Ile Gly Val Thr Val Ile Lys Asn Asn Met Ile Asn Asn<br>               525               530               535 | 1635 |
| gat ctt ggt cca gca aca gct caa atg gcc ctt cag ttg ttc atc aaa<br>Asp Leu Gly Pro Ala Thr Ala Gln Met Ala Leu Gln Leu Phe Ile Lys<br>540               545               550 | 1683 |
| gat tac agg tac acg tac cga tgc cat aga ggt gac aca caa ata caa<br>Asp Tyr Arg Tyr Thr Tyr Arg Cys His Arg Gly Asp Thr Gln Ile Gln<br>555               560               565 | 1731 |
| acc cga aga tca ttt gaa ata aag aaa ctg tgg gag caa acc cgt tcc<br>Thr Arg Arg Ser Phe Glu Ile Lys Lys Leu Trp Glu Gln Thr Arg Ser<br>570               575               580               585 | 1779 |
| aaa gct gga ctg ctg gtc tcc gac gga ggc cca aat tta tac aac att<br>Lys Ala Gly Leu Leu Val Ser Asp Gly Gly Pro Asn Leu Tyr Asn Ile<br>               590               595               600 | 1827 |
| aga aat ctc cac att cct gaa gtc tgc cta aaa tgg gaa ttg atg gat<br>Arg Asn Leu His Ile Pro Glu Val Cys Leu Lys Trp Glu Leu Met Asp<br>               605               610               615 | 1875 |
| gag gat tac cag ggg cgt tta tgc aac cca ctg aac cca ttt gtc agc<br>Glu Asp Tyr Gln Gly Arg Leu Cys Asn Pro Leu Asn Pro Phe Val Ser<br>620               625               630 | 1923 |
| cat aaa gaa att gaa tca atg aac aat gca gtg atg atg cca gca cat<br>His Lys Glu Ile Glu Ser Met Asn Asn Ala Val Met Met Pro Ala His<br>635               640               645 | 1971 |
| ggt cca gcc aaa aac atg gag tat gat gct gtt gca aca aca cac tcc<br>Gly Pro Ala Lys Asn Met Glu Tyr Asp Ala Val Ala Thr Thr His Ser<br>650               655               660               665 | 2019 |
| tgg atc ccc aaa aga aat cga tcc atc ttg aat aca agt caa aga gga<br>Trp Ile Pro Lys Arg Asn Arg Ser Ile Leu Asn Thr Ser Gln Arg Gly<br>               670               675               680 | 2067 |
| gta ctt gaa gat gaa caa atg tac caa agg tgc tgc aat tta ttt gaa<br>Val Leu Glu Asp Glu Gln Met Tyr Gln Arg Cys Cys Asn Leu Phe Glu<br>685               690               695 | 2115 |
| aaa ttc ttc ccc agc agt tca tac aga aga cca gtc ggg ata tcc agt<br>Lys Phe Phe Pro Ser Ser Ser Tyr Arg Arg Pro Val Gly Ile Ser Ser<br>700               705               710 | 2163 |
| atg gtg gag gct atg gtt tcc aga gcc cga att gat gca cgg att gat<br>Met Val Glu Ala Met Val Ser Arg Ala Arg Ile Asp Ala Arg Ile Asp<br>               715               720               725 | 2211 |

-continued

```
ttc gaa tct gga agg ata aag aaa gaa gag ttc act gag atc atg aag      2259
Phe Glu Ser Gly Arg Ile Lys Lys Glu Glu Phe Thr Glu Ile Met Lys
730                 735                 740                 745 atc tgt tcc acc att gaa gag ctc aga cgg caa aaa tag tgaatttagc       2308
Ile Cys Ser Thr Ile Glu Glu Leu Arg Arg Gln Lys
                750                 755 ttgtccttca tgaaaaaatg ccttgtttct act                                  2341
```

<210> SEQ ID NO 42
<211> LENGTH: 757
<212> TYPE: PRT
<213> ORGANISM: Influenza virus

<400> SEQUENCE: 42

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320
```

-continued

```
Met Ile Thr Tyr Met Thr Arg Asn Gln Pro Glu Trp Phe Arg Asn Val
            325                 330                 335
Leu Ser Ile Ala Pro Ile Met Phe Ser Asn Lys Met Ala Arg Leu Gly
        340                 345                 350
Lys Gly Tyr Met Phe Glu Ser Lys Ser Met Lys Leu Arg Thr Gln Ile
            355                 360                 365
Pro Ala Glu Met Leu Ala Ser Ile Asp Leu Lys Tyr Phe Asn Asp Ser
370                 375                 380
Thr Arg Lys Lys Ile Glu Lys Ile Arg Pro Leu Leu Ile Glu Gly Thr
385                 390                 395                 400
Ala Ser Leu Ser Pro Gly Met Met Met Gly Met Phe Asn Met Leu Ser
                405                 410                 415
Thr Val Leu Gly Val Ser Ile Leu Asn Leu Gly Gln Lys Arg Tyr Thr
                420                 425                 430
Lys Thr Thr Tyr Trp Trp Asp Gly Leu Gln Ser Ser Asp Asp Phe Ala
            435                 440                 445
Leu Ile Val Asn Ala Pro Asn His Glu Gly Ile Gln Ala Gly Val Asp
        450                 455                 460
Arg Phe Tyr Arg Thr Cys Lys Leu Leu Gly Ile Asn Met Ser Lys Lys
465                 470                 475                 480
Lys Ser Tyr Ile Asn Arg Thr Gly Thr Phe Glu Phe Thr Ser Phe Phe
                485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Val Thr
        515                 520                 525
Val Ile Lys Asn Asn Met Ile Asn Asn Asp Leu Gly Pro Ala Thr Ala
530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Ile
                565                 570                 575
Lys Lys Leu Trp Glu Gln Thr Arg Ser Lys Ala Gly Leu Leu Val Ser
            580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Gln Gly Arg Leu
610                 615                 620
Cys Asn Pro Leu Asn Pro Phe Val Ser His Lys Glu Ile Glu Ser Met
625                 630                 635                 640
Asn Asn Ala Val Met Met Pro Ala His Gly Pro Ala Lys Asn Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Val Leu Glu Asp Glu Gln Met
        675                 680                 685
Tyr Gln Arg Cys Cys Asn Leu Phe Glu Lys Phe Phe Pro Ser Ser Ser
690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
```

```
Lys Glu Glu Phe Thr Glu Ile Met Lys Ile Cys Ser Thr Ile Glu Glu
                740                 745                 750

Leu Arg Arg Gln Lys
        755

<210> SEQ ID NO 43
<211> LENGTH: 2341
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (25)..(2298)
<220> FEATURE:
<221> NAME/KEY: misc_difference
<222> LOCATION: (531)..(2143)

<400> SEQUENCE: 43
agcgaaagca ggcaaaccat ttga atg gat gtc aat ccg acc tta ctt ttc          51
                          Met Asp Val Asn Pro Thr Leu Leu Phe
                           1               5 tta aaa gtg cca gca caa aat gct ata agc aca act ttc cct tat act         99
Leu Lys Val Pro Ala Gln Asn Ala Ile Ser Thr Thr Phe Pro Tyr Thr
 10              15                  20                  25 gga gac cct cct tac agc cat ggg aca gga aca gga tac acc atg gat        147
Gly Asp Pro Pro Tyr Ser His Gly Thr Gly Thr Gly Tyr Thr Met Asp
                 30                  35                  40 act gtc aac agg aca cat cag tac tca gaa aag gga aga tgg aca aca        195
Thr Val Asn Arg Thr His Gln Tyr Ser Glu Lys Gly Arg Trp Thr Thr
             45                  50                  55 aac acc gaa act gga gca ccg caa ctc aac ccg att gat ggg cca ctg        243
Asn Thr Glu Thr Gly Ala Pro Gln Leu Asn Pro Ile Asp Gly Pro Leu
         60                  65                  70 cca gaa gac aat gaa cca agt ggt tat gcc caa aca gat tgt gta ttg        291
Pro Glu Asp Asn Glu Pro Ser Gly Tyr Ala Gln Thr Asp Cys Val Leu
     75                  80                  85 gaa gca atg gct ttc ctt gag gaa tcc cat cct ggt att ttt gaa aac        339
Glu Ala Met Ala Phe Leu Glu Glu Ser His Pro Gly Ile Phe Glu Asn
 90                  95                 100                 105 tcg tgt att gaa acg atg gag gtt gtt cag caa aca cga gta gac aag        387
Ser Cys Ile Glu Thr Met Glu Val Val Gln Gln Thr Arg Val Asp Lys
                110                 115                 120 ctg aca caa ggc cga cag acc tat gac tgg act cta aat aga aac caa        435
Leu Thr Gln Gly Arg Gln Thr Tyr Asp Trp Thr Leu Asn Arg Asn Gln
            125                 130                 135 cct gct gca aca gca ttg gcc aac aca ata gaa gtg ttc aga tca aat        483
Pro Ala Ala Thr Ala Leu Ala Asn Thr Ile Glu Val Phe Arg Ser Asn
        140                 145                 150 ggc ctc acg gcc aat gag tct gga agg ctc ata gac ttc ctt aag gac        531
Gly Leu Thr Ala Asn Glu Ser Gly Arg Leu Ile Asp Phe Leu Lys Asp
    155                 160                 165 gtt atg gag tct atg aaa aaa gag gaa atg ggg att acg aca cat ttt        579
Val Met Glu Ser Met Lys Lys Glu Glu Met Gly Ile Thr Thr His Phe
170                 175                 180                 185 caa cga aaa aga cgg gtt agg gat aat atg aca aaa aaa atg att acg        627
Gln Arg Lys Arg Arg Val Arg Asp Asn Met Thr Lys Lys Met Ile Thr
                190                 195                 200 caa cga aca atc gga aag aaa aaa cag aga ctg aat aag cga tca tac        675
Gln Arg Thr Ile Gly Lys Lys Lys Gln Arg Leu Asn Lys Arg Ser Tyr
            205                 210                 215
```

-continued

| | |
|---|---|
| ttg att agg gca ctt aca ctt aac act atg act aag gac gcc gaa agg<br>Leu Ile Arg Ala Leu Thr Leu Asn Thr Met Thr Lys Asp Ala Glu Arg<br>220 225 230 | 723 |
| gga aag cta aag cgt aga gca att gca aca ccc gga atg caa att agg<br>Gly Lys Leu Lys Arg Arg Ala Ile Ala Thr Pro Gly Met Gln Ile Arg<br>235 240 245 | 771 |
| ggg ttc gta tac ttc gtc gag aca ctc gct aga tcc ata tgc gaa aag<br>Gly Phe Val Tyr Phe Val Glu Thr Leu Ala Arg Ser Ile Cys Glu Lys<br>250 255 260 265 | 819 |
| tta gag caa tcc gga ctg cca gtc ggg ggg aac gaa aaa aaa gcg aaa<br>Leu Glu Gln Ser Gly Leu Pro Val Gly Gly Asn Glu Lys Lys Ala Lys<br>270 275 280 | 867 |
| ctc gct aac gtc gtt aga aaa atg atg act aat agt cag gat acc gaa<br>Leu Ala Asn Val Val Arg Lys Met Met Thr Asn Ser Gln Asp Thr Glu<br>285 290 295 | 915 |
| ctg tca ttt acg att acc ggc gat aat act aag tgg aac gag aat cag<br>Leu Ser Phe Thr Ile Thr Gly Asp Asn Thr Lys Trp Asn Glu Asn Gln<br>300 305 310 | 963 |
| aat cct aga atg ttt ctc gca atg atc aca tat atg aca cgt aac caa<br>Asn Pro Arg Met Phe Leu Ala Met Ile Thr Tyr Met Thr Arg Asn Gln<br>315 320 325 | 1011 |
| ccc gaa tgg ttt aga aac gta ctg tca atc gca cca att atg ttt agc<br>Pro Glu Trp Phe Arg Asn Val Leu Ser Ile Ala Pro Ile Met Phe Ser<br>330 335 340 345 | 1059 |
| aat aag atg gct aga ttg ggc aag ggg tat atg ttt gaa tct aag agt<br>Asn Lys Met Ala Arg Leu Gly Lys Gly Tyr Met Phe Glu Ser Lys Ser<br>350 355 360 | 1107 |
| atg aaa ttg cga aca cag ata cct gcc gaa atg cta gca tca atc gat<br>Met Lys Leu Arg Thr Gln Ile Pro Ala Glu Met Leu Ala Ser Ile Asp<br>365 370 375 | 1155 |
| cta aag tac ttt aac gat agt aca cga aaa aaa atc gaa aag att aga<br>Leu Lys Tyr Phe Asn Asp Ser Thr Arg Lys Lys Ile Glu Lys Ile Arg<br>380 385 390 | 1203 |
| ccg tta ctg ata gag gga acc gcc agc cta tcc ccc gga atg atg atg<br>Pro Leu Leu Ile Glu Gly Thr Ala Ser Leu Ser Pro Gly Met Met Met<br>395 400 405 | 1251 |
| ggg atg ttt aat atg ctt agt acc gtg tta ggc gtt agc ata ctt aac<br>Gly Met Phe Asn Met Leu Ser Thr Val Leu Gly Val Ser Ile Leu Asn<br>410 415 420 425 | 1299 |
| tta ggg caa aaa cgt tat act aag act aca tat tgg tgg gac gga ctg<br>Leu Gly Gln Lys Arg Tyr Thr Lys Thr Thr Tyr Trp Trp Asp Gly Leu<br>430 435 440 | 1347 |
| caa tct agc gac gat ttc gca cta atc gtt aac gca cct aac cat gag<br>Gln Ser Ser Asp Asp Phe Ala Leu Ile Val Asn Ala Pro Asn His Glu<br>445 450 455 | 1395 |
| ggg ata caa gcc gga gtc gat aga ttc tat aga aca tgc aaa ctg tta<br>Gly Ile Gln Ala Gly Val Asp Arg Phe Tyr Arg Thr Cys Lys Leu Leu<br>460 465 470 | 1443 |
| ggg att aat atg tct aaa aaa aag tca tac ata aat aga acc gga aca<br>Gly Ile Asn Met Ser Lys Lys Lys Ser Tyr Ile Asn Arg Thr Gly Thr<br>475 480 485 | 1491 |
| ttt gaa ttc act agc ttt ttt tac aga tac gga ttc gtt gct aat ttt<br>Phe Glu Phe Thr Ser Phe Phe Tyr Arg Tyr Gly Phe Val Ala Asn Phe<br>490 495 500 505 | 1539 |
| agt atg gag tta cct agt ttc gga gtt agc gga att aac gaa tcc gcc<br>Ser Met Glu Leu Pro Ser Phe Gly Val Ser Gly Ile Asn Glu Ser Ala<br>510 515 520 | 1587 |
| gat atg tca atc ggc gta acc gtt att aag aat aat atg att aat aac<br>Asp Met Ser Ile Gly Val Thr Val Ile Lys Asn Asn Met Ile Asn Asn<br>525 530 535 | 1635 |

| | | |
|---|---|---|
| gat cta ggg cca gca acc gca caa atg gca ttg cag ttg ttc ata aag<br>Asp Leu Gly Pro Ala Thr Ala Gln Met Ala Leu Gln Leu Phe Ile Lys<br>540 545 550 | 1683 | |
| gat tat cgt tat aca tat aga tgt cat aga ggc gat aca cag ata cag<br>Asp Tyr Arg Tyr Thr Tyr Arg Cys His Arg Gly Asp Thr Gln Ile Gln<br>555 560 565 | 1731 | |
| act aga cga tca ttt gaa atc aaa aaa ttg tgg gag caa act agg tct<br>Thr Arg Arg Ser Phe Glu Ile Lys Lys Leu Trp Glu Gln Thr Arg Ser<br>570 575 580 585 | 1779 | |
| aaa gcc gga ctg tta gtg tcc gac gga ggg cct aat cta tac aat att<br>Lys Ala Gly Leu Leu Val Ser Asp Gly Gly Pro Asn Leu Tyr Asn Ile<br>590 595 600 | 1827 | |
| agg aat ctg cat ata ccc gaa gtg tgt cta aag tgg gag ctt atg gac<br>Arg Asn Leu His Ile Pro Glu Val Cys Leu Lys Trp Glu Leu Met Asp<br>605 610 615 | 1875 | |
| gaa gac tat cag ggg aga ttg tgc aat ccg ctt aac cca ttc gtt agc<br>Glu Asp Tyr Gln Gly Arg Leu Cys Asn Pro Leu Asn Pro Phe Val Ser<br>620 625 630 | 1923 | |
| cat aaa gag ata gag tca atg aat aac gcc gtt atg atg cca gca cac<br>His Lys Glu Ile Glu Ser Met Asn Asn Ala Val Met Met Pro Ala His<br>635 640 645 | 1971 | |
| gga ccc gct aag aat atg gaa tac gac gca gtc gca act aca cat agt<br>Gly Pro Ala Lys Asn Met Glu Tyr Asp Ala Val Ala Thr Thr His Ser<br>650 655 660 665 | 2019 | |
| tgg ata ccg aaa cgg aat cga tcc ata ctg aat aca tcc caa aga ggc<br>Trp Ile Pro Lys Arg Asn Arg Ser Ile Leu Asn Thr Ser Gln Arg Gly<br>670 675 680 | 2067 | |
| gta ctc gaa gac gaa caa atg tac caa cgg tgt tgc aat cta ttt gaa<br>Val Leu Glu Asp Glu Gln Met Tyr Gln Arg Cys Cys Asn Leu Phe Glu<br>685 690 695 | 2115 | |
| aaa ttt ttt cct agt agt agc tat aga cga cca gtc ggg ata tcc agt<br>Lys Phe Phe Pro Ser Ser Ser Tyr Arg Arg Pro Val Gly Ile Ser Ser<br>700 705 710 | 2163 | |
| atg gtg gag gct atg gtt tcc aga gcc cga att gat gca cgg att gat<br>Met Val Glu Ala Met Val Ser Arg Ala Arg Ile Asp Ala Arg Ile Asp<br>715 720 725 | 2211 | |
| ttc gaa tct gga agg ata aag aaa gaa gag ttc act gag atc atg aag<br>Phe Glu Ser Gly Arg Ile Lys Lys Glu Glu Phe Thr Glu Ile Met Lys<br>730 735 740 745 | 2259 | |
| atc tgt tcc acc att gaa gag ctc aga cgg caa aaa tag tgaatttagc<br>Ile Cys Ser Thr Ile Glu Glu Leu Arg Arg Gln Lys<br>750 755 | 2308 | |
| ttgtccttca tgaaaaaatg ccttgtttct act | 2341 | |

<210> SEQ ID NO 44
<211> LENGTH: 757
<212> TYPE: PRT
<213> ORGANISM: unknown
<220> FEATURE:
<223> OTHER INFORMATION: Synthetic Construct

<400> SEQUENCE: 44

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

```
Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480
```

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
            755

<210> SEQ ID NO 45
<211> LENGTH: 2341
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (25)..(2298)
<220> FEATURE:
<221> NAME/KEY: misc_difference
<222> LOCATION: (531)..(1488)

<400> SEQUENCE: 45
agcgaaagca ggcaaaccat ttga atg gat gtc aat ccg acc tta ctt ttc        51
                         Met Asp Val Asn Pro Thr Leu Leu Phe
                          1               5 tta aaa gtg cca gca caa aat gct ata agc aca act ttc cct tat act        99
Leu Lys Val Pro Ala Gln Asn Ala Ile Ser Thr Thr Phe Pro Tyr Thr
10                  15                  20                  25

| | | |
|---|---|---|
| gga gac cct cct tac agc cat ggg aca gga aca gga tac acc atg gat<br>Gly Asp Pro Pro Tyr Ser His Gly Thr Gly Thr Gly Tyr Thr Met Asp<br>                              30                     35                 40 | | 147 |
| act gtc aac agg aca cat cag tac tca gaa aag gga aga tgg aca aca<br>Thr Val Asn Arg Thr His Gln Tyr Ser Glu Lys Gly Arg Trp Thr Thr<br>                45                     50                     55 | | 195 |
| aac acc gaa act gga gca ccg caa ctc aac ccg att gat ggg cca ctg<br>Asn Thr Glu Thr Gly Ala Pro Gln Leu Asn Pro Ile Asp Gly Pro Leu<br>         60                     65                     70 | | 243 |
| cca gaa gac aat gaa cca agt ggt tat gcc caa aca gat tgt gta ttg<br>Pro Glu Asp Asn Glu Pro Ser Gly Tyr Ala Gln Thr Asp Cys Val Leu<br>75                     80                     85 | | 291 |
| gaa gca atg gct ttc ctt gag gaa tcc cat cct ggt att ttt gaa aac<br>Glu Ala Met Ala Phe Leu Glu Glu Ser His Pro Gly Ile Phe Glu Asn<br>90                     95                   100               105 | | 339 |
| tcg tgt att gaa acg atg gag gtt gtt cag caa aca cga gta gac aag<br>Ser Cys Ile Glu Thr Met Glu Val Val Gln Gln Thr Arg Val Asp Lys<br>                   110                   115               120 | | 387 |
| ctg aca caa ggc cga cag acc tat gac tgg act cta aat aga aac caa<br>Leu Thr Gln Gly Arg Gln Thr Tyr Asp Trp Thr Leu Asn Arg Asn Gln<br>                 125                   130               135 | | 435 |
| cct gct gca aca gca ttg gcc aac aca ata gaa gtg ttc aga tca aat<br>Pro Ala Ala Thr Ala Leu Ala Asn Thr Ile Glu Val Phe Arg Ser Asn<br>            140                     145               150 | | 483 |
| ggc ctc acg gcc aat gag tct gga agg ctc ata gac ttc ctt aag gac<br>Gly Leu Thr Ala Asn Glu Ser Gly Arg Leu Ile Asp Phe Leu Lys Asp<br>155                   160                   165 | | 531 |
| gtt atg gag tct atg aaa aaa gag gaa atg ggg att acg aca cat ttt<br>Val Met Glu Ser Met Lys Lys Glu Glu Met Gly Ile Thr Thr His Phe<br>170                   175                   180               185 | | 579 |
| caa cga aaa aga cgg gtt agg gat aat atg aca aaa aaa atg att acg<br>Gln Arg Lys Arg Arg Val Arg Asp Asn Met Thr Lys Lys Met Ile Thr<br>                 190                   195               200 | | 627 |
| caa cga aca atc gga aag aaa aaa cag aga ctg aat aag cga tca tac<br>Gln Arg Thr Ile Gly Lys Lys Lys Gln Arg Leu Asn Lys Arg Ser Tyr<br>            205                     210               215 | | 675 |
| ttg att agg gca ctt aca ctt aac act atg act aag gac gcc gaa agg<br>Leu Ile Arg Ala Leu Thr Leu Asn Thr Met Thr Lys Asp Ala Glu Arg<br>220                   225                   230 | | 723 |
| gga aag cta aag cgt aga gca att gca aca ccc gga atg caa att agg<br>Gly Lys Leu Lys Arg Arg Ala Ile Ala Thr Pro Gly Met Gln Ile Arg<br>235                   240                   245 | | 771 |
| ggg ttc gta tac ttc gtc gag aca ctc gct aga tcc ata tgc gaa aag<br>Gly Phe Val Tyr Phe Val Glu Thr Leu Ala Arg Ser Ile Cys Glu Lys<br>250                   255                   260               265 | | 819 |
| tta gag caa tcc gga ctg cca gtc ggg ggg aac gaa aaa aaa gcg aaa<br>Leu Glu Gln Ser Gly Leu Pro Val Gly Gly Asn Glu Lys Lys Ala Lys<br>                 270                   275               280 | | 867 |
| ctc gct aac gtc gtt aga aaa atg atg act aat agt cag gat acc gaa<br>Leu Ala Asn Val Val Arg Lys Met Met Thr Asn Ser Gln Asp Thr Glu<br>            285                     290               295 | | 915 |
| ctg tca ttt acg att acc ggc gat aat act aag tgg aac gag aat cag<br>Leu Ser Phe Thr Ile Thr Gly Asp Asn Thr Lys Trp Asn Glu Asn Gln<br>300                   305                   310 | | 963 |
| aat cct aga atg ttt ctc gca atg atc aca tat atg aca cgt aac caa<br>Asn Pro Arg Met Phe Leu Ala Met Ile Thr Tyr Met Thr Arg Asn Gln<br>                 315                   320               325 | | 1011 |
| ccc gaa tgg ttt aga aac gta ctg tca atc gca cca att atg ttt agc<br>Pro Glu Trp Phe Arg Asn Val Leu Ser Ile Ala Pro Ile Met Phe Ser<br>330                   335                   340               345 | | 1059 |

```
aat aag atg gct aga ttg ggc aag ggg tat atg ttt gaa tct aag agt      1107
Asn Lys Met Ala Arg Leu Gly Lys Gly Tyr Met Phe Glu Ser Lys Ser
                350                 355                 360 atg aaa ttg cga aca cag ata cct gcc gaa atg cta gca tca atc gat      1155
Met Lys Leu Arg Thr Gln Ile Pro Ala Glu Met Leu Ala Ser Ile Asp
            365                 370                 375 cta aag tac ttt aac gat agt aca cga aaa aaa atc gaa aag att aga      1203
Leu Lys Tyr Phe Asn Asp Ser Thr Arg Lys Lys Ile Glu Lys Ile Arg
        380                 385                 390 ccg tta ctg ata gag gga acc gcc agc cta tcc ccc gga atg atg atg      1251
Pro Leu Leu Ile Glu Gly Thr Ala Ser Leu Ser Pro Gly Met Met Met
    395                 400                 405 ggg atg ttt aat atg ctt agt acc gtg tta ggc gtt agc ata ctt aac      1299
Gly Met Phe Asn Met Leu Ser Thr Val Leu Gly Val Ser Ile Leu Asn
410                 415                 420                 425 tta ggg caa aaa cgt tat act aag act aca tat tgg tgg gac gga ctg      1347
Leu Gly Gln Lys Arg Tyr Thr Lys Thr Thr Tyr Trp Trp Asp Gly Leu
                430                 435                 440 caa tct agc gac gat ttc gca cta atc gtt aac gca cct aac cat gag      1395
Gln Ser Ser Asp Asp Phe Ala Leu Ile Val Asn Ala Pro Asn His Glu
                445                 450                 455 ggg ata caa gcc gga gtc gat aga ttc tat aga aca tgc aaa ctg tta      1443
Gly Ile Gln Ala Gly Val Asp Arg Phe Tyr Arg Thr Cys Lys Leu Leu
            460                 465                 470 ggg att aat atg tct aaa aaa aag tca tac ata aat aga acc gga aca      1491
Gly Ile Asn Met Ser Lys Lys Lys Ser Tyr Ile Asn Arg Thr Gly Thr
        475                 480                 485 ttt gaa ttc aca agt ttt ttc tat cgt tat ggg ttt gtt gcc aat ttc      1539
Phe Glu Phe Thr Ser Phe Phe Tyr Arg Tyr Gly Phe Val Ala Asn Phe
490                 495                 500                 505 agc atg gag ctc ccc agt ttt ggg gtg tct ggg atc aac gag tca gcg      1587
Ser Met Glu Leu Pro Ser Phe Gly Val Ser Gly Ile Asn Glu Ser Ala
                510                 515                 520 gac atg agt att gga gtt act gtc atc aaa aac aat atg ata aac aat      1635
Asp Met Ser Ile Gly Val Thr Val Ile Lys Asn Asn Met Ile Asn Asn
                525                 530                 535 gat ctt ggt cca gca aca gct caa atg gcc ctt cag ttg ttc atc aaa      1683
Asp Leu Gly Pro Ala Thr Ala Gln Met Ala Leu Gln Leu Phe Ile Lys
            540                 545                 550 gat tac agg tac acg tac cga tgc cat aga ggt gac aca caa ata caa      1731
Asp Tyr Arg Tyr Thr Tyr Arg Cys His Arg Gly Asp Thr Gln Ile Gln
        555                 560                 565 acc cga aga tca ttt gaa ata aag aaa ctg tgg gag caa acc cgt tcc      1779
Thr Arg Arg Ser Phe Glu Ile Lys Lys Leu Trp Glu Gln Thr Arg Ser
570                 575                 580                 585 aaa gct gga ctg ctg gtc tcc gac gga ggc cca aat tta tac aac att      1827
Lys Ala Gly Leu Leu Val Ser Asp Gly Gly Pro Asn Leu Tyr Asn Ile
                590                 595                 600 aga aat ctc cac att cct gaa gtc tgc cta aaa tgg gaa ttg atg gat      1875
Arg Asn Leu His Ile Pro Glu Val Cys Leu Lys Trp Glu Leu Met Asp
                605                 610                 615 gag gat tac cag ggg cgt tta tgc aac cca ctg aac cca ttt gtc agc      1923
Glu Asp Tyr Gln Gly Arg Leu Cys Asn Pro Leu Asn Pro Phe Val Ser
            620                 625                 630 cat aaa gaa att gaa tca atg aac aat gca gtg atg atg cca gca cat      1971
His Lys Glu Ile Glu Ser Met Asn Asn Ala Val Met Met Pro Ala His
        635                 640                 645 ggt cca gcc aaa aac atg gag tat gat gct gtt gca aca aca cac tcc      2019
Gly Pro Ala Lys Asn Met Glu Tyr Asp Ala Val Ala Thr Thr His Ser
650                 655                 660                 665
```

```
tgg atc ccc aaa aga aat cga tcc atc ttg aat aca agt caa aga gga    2067
Trp Ile Pro Lys Arg Asn Arg Ser Ile Leu Asn Thr Ser Gln Arg Gly
                670                 675                 680 gta ctt gaa gat gaa caa atg tac caa agg tgc tgc aat tta ttt gaa    2115
Val Leu Glu Asp Glu Gln Met Tyr Gln Arg Cys Cys Asn Leu Phe Glu
                685                 690                 695 aaa ttc ttc ccc agc agt tca tac aga aga cca gtc ggg ata tcc agt    2163
Lys Phe Phe Pro Ser Ser Ser Tyr Arg Arg Pro Val Gly Ile Ser Ser
                700                 705                 710 atg gtg gag gct atg gtt tcc aga gcc cga att gat gca cgg att gat    2211
Met Val Glu Ala Met Val Ser Arg Ala Arg Ile Asp Ala Arg Ile Asp
                715                 720                 725 ttc gaa tct gga agg ata aag aaa gaa gag ttc act gag atc atg aag    2259
Phe Glu Ser Gly Arg Ile Lys Lys Glu Glu Phe Thr Glu Ile Met Lys
730                 735                 740                 745 atc tgt tcc acc att gaa gag ctc aga cgg caa aaa tag tgaatttagc    2308
Ile Cys Ser Thr Ile Glu Glu Leu Arg Arg Gln Lys
                750                 755 ttgtccttca tgaaaaaatg ccttgtttct act                               2341
```

<210> SEQ ID NO 46
<211> LENGTH: 757
<212> TYPE: PRT
<213> ORGANISM: unknown
<220> FEATURE:
<223> OTHER INFORMATION: Synthetic Construct

<400> SEQUENCE: 46

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
                100                 105                 110

Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
        130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
                180                 185                 190

Asp Asn Met Thr Lys Lys Met Ile Thr Gln Arg Thr Ile Gly Lys Lys
            195                 200                 205

Lys Gln Arg Leu Asn Lys Arg Ser Tyr Leu Ile Arg Ala Leu Thr Leu
        210                 215                 220
```

-continued

```
Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
            245                 250                 255

Thr Leu Ala Arg Ser Ile Cys Glu Lys Leu Glu Gln Ser Gly Leu Pro
        260                 265                 270

Val Gly Gly Asn Glu Lys Lys Ala Lys Leu Ala Asn Val Val Arg Lys
    275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
            325                 330                 335

Leu Ser Ile Ala Pro Ile Met Phe Ser Asn Lys Met Ala Arg Leu Gly
        340                 345                 350

Lys Gly Tyr Met Phe Glu Ser Lys Ser Met Lys Leu Arg Thr Gln Ile
    355                 360                 365

Pro Ala Glu Met Leu Ala Ser Ile Asp Leu Lys Tyr Phe Asn Asp Ser
370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
            405                 410                 415

Thr Val Leu Gly Val Ser Ile Leu Asn Leu Gly Gln Lys Arg Tyr Thr
        420                 425                 430

Lys Thr Thr Tyr Trp Trp Asp Gly Leu Gln Ser Ser Asp Asp Phe Ala
    435                 440                 445

Leu Ile Val Asn Ala Pro Asn His Glu Gly Ile Gln Ala Gly Val Asp
450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
            485                 490                 495

Tyr Arg Tyr Gly Phe Val Ala Asn Phe Ser Met Glu Leu Pro Ser Phe
        500                 505                 510

Gly Val Ser Gly Ile Asn Glu Ser Ala Asp Met Ser Ile Gly Val Thr
    515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
            565                 570                 575

Lys Lys Leu Trp Glu Gln Thr Arg Ser Lys Ala Gly Leu Leu Val Ser
        580                 585                 590

Asp Gly Gly Pro Asn Leu Tyr Asn Ile Arg Asn Leu His Ile Pro Glu
    595                 600                 605

Val Cys Leu Lys Trp Glu Leu Met Asp Glu Asp Tyr Gln Gly Arg Leu
610                 615                 620

Cys Asn Pro Leu Asn Pro Phe Val Ser His Lys Glu Ile Glu Ser Met
625                 630                 635                 640
```

```
                    Asn Asn Ala Val Met Met Pro Ala His Gly Pro Ala Lys Asn Met Glu
                                    645                 650                 655

Tyr Asp Ala Val Ala Thr Thr His Ser Trp Ile Pro Lys Arg Asn Arg
                                660                 665                 670

Ser Ile Leu Asn Thr Ser Gln Arg Gly Val Leu Glu Asp Glu Gln Met
                                675                 680             685

Tyr Gln Arg Cys Cys Asn Leu Phe Glu Lys Phe Phe Pro Ser Ser Ser
                                690                 695             700

Tyr Arg Arg Pro Val Gly Ile Ser Ser Met Val Glu Ala Met Val Ser
                    705                 710                 715                 720

Arg Ala Arg Ile Asp Ala Arg Ile Asp Phe Glu Ser Gly Arg Ile Lys
                                    725                 730                 735

Lys Glu Glu Phe Thr Glu Ile Met Lys Ile Cys Ser Thr Ile Glu Glu
                                740                 745             750

Leu Arg Arg Gln Lys
                            755

<210> SEQ ID NO 47
<211> LENGTH: 2341
<212> TYPE: DNA
<213> ORGANISM: Influenza virus

<400> SEQUENCE: 47
agcgaaagca ggtcaattat attcaatatg gaaagaataa agaactaag aaatctaatg        60 tcgcagtctc gcacccgcga gatactcaca aaaccaccg tggaccatat ggccataatc       120
aagaagtaca catcaggaag acaggagaag aacccagcac ttaggatgaa atggatgatg       180
gcaatgaaat atccaattac agcagacaag aggataacgg aaatgattcc tgagagaaat       240
gagcaaggac aaactttatg gagtaaaatg aatgatgcag atcagaccg agtgatggta       300 tcacctctgg ctgtgacatg gtggaatagg aatggaccaa taacaaatac agttcattat       360
ccaaaaatct acaaaactta ttttgaaaga gtcgaaaggc taaagcatgg aaccttggc       420 cctgtccatt ttagaaacca agtcaaaata cgtcggagag ttgacataaa tcctggtcat       480
gcagatctca gtgccaagga ggcacaggat gtaatcatgg aagttgtttt ccctaacgaa       540
gtgggagcca ggatactaac atcggaatcg caactaacga taaccaaaga gaagaaagaa       600
gaactccagg attgcaaaat ttctcctttg atggttgcat acatgttgga gagaactg       660 gtccgcaaaa cgagattcct cccagtggct ggtggaacaa gcagtgtgta cattgaagtg       720
ttgcatttga ctcaaggaac atgctgggaa cagatgtata ctccaggagg ggaagtgagg       780
aatgatgatg ttgatcaaag cttgattatt gctgctagga catagtgag aagagctgca       840 gtatcagcag atcccactagc atctttattg gagatgtgcc acagcacaca gattggtgga       900
attaggatgg tagacatcct taggcagaac ccaacagaag agcaagccgt ggatatatgc       960
aaggctgcaa tgggactgag aattagctca tccttcagtt ttggtggatt cacatttaag      1020
agaacaagcg gatcatcagt caagagagag gaagaggtgc ttacgggcaa tcttcaaaca      1080
ttgaagataa gagtgcatga gggatatgaa gagttcacaa tggttgggag aagagcaaca      1140
gccatactca gaaaagcaac caggagattg attcagctga tagtgagtgg gagagacgaa      1200
cagtcgattg ccgaagcaat aattgtggcc atggtatttt cacaagagga ttgtatgata      1260
aaagcagtca gaggtgatct gaatttcgtc aatagggcga atcagcgatt gaatcctatg      1320
catcaacttt taagcatttt tcagaaggat gcgaaagtgc ttttttcaaaa ttggggagtt      1380 gaacctatcg acaatgtgat gggaatgatt gggatattgc cagacatgac tccaagcatc      1440
```

```
gagatgtcaa tgagaggagt gagaatcagc aaaatgggtg tagatgagta ctccagcacg    1500
gagagggtag tggtgagcat tgaccgtttt ttgagaatcc gggaccaacg aggaaatgta    1560
ctactgtctc ccgaggaggt cagtgaaaca cagggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca agtagaatg     1920 cagttctcct catttactgt gaatgtgagg ggatcaggaa tgagaatact tgtaaggggc    1980
aattctcctg tattcaacta taacaaggcc acgaagagac tcacagttct cggaaaggat   2040
gctggcactt taactgaaga cccagatgaa ggcacagctg gagtggagtc cgctgttctg    2100 agggattcc tcattctggg caaagaagac aagagatatg gccagcact aagcatcaat      2160 gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341

<210> SEQ ID NO 48
<211> LENGTH: 2341
<212> TYPE: DNA
<213> ORGANISM: unknown
<220> FEATURE:
<223> OTHER INFORMATION: synthetic

<400> SEQUENCE: 48
agcgaaagca ggtcaattat attcaatatg gagagaatca aagagcttag gaatcttatg      60
tcacaatcta gaactagaga gatactgact aagactacag tcgatcatat ggctataatc     120
aaaaaatata ctagcggaag acaggaaaaa atcccgcac ttagaatgaa atggatgatg      180
gctatgaaat accctattac agccgataag cgaattaccg aaatgatacc agagagaaac    240
gaacagggac agacattgtg gtctaaaatg aacgacgccg gatccgatag agtgatggtt     300
tcgccactag ccgtaacatg gtggaataga acggaccta ttacgaatac agtgcattac     360
cctaagatat acaaaacata tttcgaaaga gtcgagagac tgaaacacgg aacattcgga   420
ccagtgcatt ttcggaatca ggttaagatt agacgtagag tcgatattaa tccagggcat   480
gcagatctct ccgctaaaga ggcacaagac gttattatgg aggtcgtgtt tcctaacgag   540
gtcggcgcta ggatactgac tagcgaatcg caattgacaa ttacgaaaga gaaaaaagag   600
gaactccagg attgcaaaat tagcccactt atggtcgcat atatgctcga acgcgaattg   660
gttagaaaga ctagattcct accagtcgca ggcggaacgt ctagcgtgta tatcgaagtg   720
ttgcatctaa cacagggaac atgttgggag caaatgtata ctccaggagg cgaagtgaga   780
aacgacgacg ttgatcaatc gctaatcata gccgctagga atatagtgag aagggcagcc   840
gttagcgcag acccacttgc gtcactactc gaaatgtgcc atagtacgca aatcggaggg   900
attagaatgg tcgatatcct taggcagaat cctacagagg aacaggccgt agacatatgc   960
aaagccgcaa tgggattgcg aattagctca tcattctcat cggagggtt tacgtttaaa    1020 cggactagcg gatctagcgt aaaacgcgaa gaggaagtgc ttactggcaa tctgcaaaca   1080
ctaaagatta gggtgcatga gggatacgaa gagtttacaa tggtcggacg tagagcaacc   1140
```

```
gctatactta gaaaagcgac taggagactg atacaattga tcgttagcgg aagggacgaa    1200
cagtcaatcg ccgaagcgat aatagtcgca atggtgtttt cgcaagagga ttgcatgatt    1260
aaggccgtta ggggggatct gaatttcgtt aatagggcta atcagagact gaatcctatg    1320
catcaattgc ttagacattt tcagaaagac gctaaagtgt tgtttcagaa ttggggagtc    1380
gaacctatcg ataacgttat gggtatgata gggatactgc cagatatgac accatcaatc    1440
gaaatgtcaa tgagaggcgt taggattagt aagatgggcg tagacgaata ctccagcact    1500
gagagagtgg tagtgtcaat cgatagattt cttaggatta gggatcagag aggcaacgta    1560
ctgctatcac ccgaagaagt tagcgaaaca cagggaaccg aaaaattgac aattacgtat    1620
agtagtagta tgatgtggga gattaacgga ccagagtcag tgttagtgaa tacatatcaa    1680
tggataatac ggaattggga gacagtgaaa atacaatggt cacagaatcc tacaatgcta    1740
tacaataaga tggagttcga acctttcaa tcgttagtgc ctaaggccat aagaggccaa    1800
tatagtgggt tcgttagaac attgtttcag caaatgagag acgtactcgg aacattcgat    1860
accgcacaga taattaagct attgccattc gcagccgcac cacctaagca atctagaatg    1920
caattttcta gctttaccgt taacgttagg ggatccggaa tgcgaatact cgttaggggg    1980
aatagtccag tgtttaatta caataaggca actaagagat tgacagtgtt aggcaaggac    2040
gcaggaacat tgaccgaaga cccagacgag ggaccgctg gagtggaatc cgcagtgctt    2100
agggggtttc tgatactcgg aaaggaggat aagagatacg gacctgcact atcgattaac    2160
gaactatcta atctcgctaa aggcgaaaaa gcgaatgtgt taatcggaca gggagacgta    2220
gtgttagtga tgaaacggaa acgcgatagc tcaatactga cagactcaca aaccgctact    2280
aagagaattc ggatggcaat taattagtgt cgaatagttt aaaaacgacc ttgtttctac    2340
t                                                                    2341

<210> SEQ ID NO 49
<211> LENGTH: 2233
<212> TYPE: DNA
<213> ORGANISM: Influenza virus

<400> SEQUENCE: 49
agcgaaagca ggtactgatc caaaatggaa gattttgtgc gacaatgctt caatccgatg      60
attgtcgagc ttgcggaaaa aacaatgaaa gagtatgggg aggacctgaa atcgaaaaca    120
aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggagaata gattcatcga aattggagta acaaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg gccagcagag gcctctggga ttccttttcgt    600 cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
```

```
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg ctagcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaagggg gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa cttttgtgagc atggagtttt ctctcactga cccaagactt   1620
gaaccacata aatgggagaa gtactgtgtt cttgagatag agatatgct tataagaagt   1680
gccataggcc aggtttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aaggagtgga ggaaagttcc   1920
attgggaagg tctgcaggac tttattagca aagtcggtat tcaacagctt gtatgcatct   1980
ccacaactag aaggattttc agctgaatca agaaaaactgc ttcttatcgt tcaggctctt   2040
agggacaacc ttgaacctgg gacctttgat cttgggggc tatatgaagc aattgaggag   2100
tgcctgatta atgatccctg ggtttttgctt aatgcttctt ggttcaactc cttccttaca   2160
catgcattga gttagttgtg gcagtgctac tatttgctat ccatactgtc aaaaaagta   2220
ccttgttttct act                                                    2233

<210> SEQ ID NO 50
<211> LENGTH: 2233
<212> TYPE: DNA
<213> ORGANISM: unknown
<220> FEATURE:
<223> OTHER INFORMATION: synthetic

<400> SEQUENCE: 50
agcgaaagca ggtactgatc caaaatggag gatttcgtta ggcaatgctt taatccaatg     60
atagtcgagt tagccgaaaa gactatgaaa gagtatggcg aagacctaaa gattgagact    120
aataaattcg ccgcaatttg cacacacctt gaggtttgct ttatgtattc cgattttcac    180
tttattaacg aacagggaga gtcaattata gtcgagttag gcgatccgaa cgcattgcta    240
aagcatagat ttgaaattat agagggacgc gataggacaa tggcatggac cgtagttaat    300
tcgatttgca atacaaccgg agccgaaaaa ccgaaattct acccgatcct atacgattat    360
aaagagaata ggtttatcga aatcggagtg actagacgcg aagtgcatat ttattatctc    420
gaaaaagcga ataagattaa gtccgaaaag acacacatac acatttttag ctttaccgga    480
gaggaaatgg caacaaaagc cgattataca cttgacgaag agtctagggc taggattaag    540
actagactgt ttacaattag acaggaaatg gctagtaggg ggttgtggga tagctttaga    600
caatccgaaa gaggcgaaga gacaatcgaa gagagatttg aaattaccgg aacaatgcga    660
aagcttgccg atcaatccct accccccaat ttctctagcc ttgagaattt tagggcatac    720
```

```
gttgacggat tcgaacctaa cggatatata gagggaaagc tatcgcaaat gtctaaagag    780
gttaacgcta gaatcgaacc attcctaaag acaacaccta gaccacttag actgccaaac    840
ggaccaccat gctcacagcg atctaagttt ctgcttatgg acgcactaaa gttgtcaatc    900
gaagacccat cacacgaggg agaggggata ccattgtacg acgcaattaa gtgtatgcga    960
acatttttcg gatggaaaga gcctaacgta gtgaaaccac acgaaaaagg gattaatccg    1020
aattatctgc ttagttggaa acaggtgtta gccgaattgc aggatatcga aaacgaagag    1080
aaaattccga aaactaagaa tatgaaaaaa actagccaac tgaaatgggc acttggcgag    1140
aatatggcac ccgaaaaagt cgatttcgac gattgcaaag acgtcggcga tctaaagcaa    1200
tacgatagcg acgaacccga acttagatca ctcgctagtt ggatacagaa cgagttcaat    1260
aaggcatgcg aattgaccga tagctcatgg atagagcttg acgagatagg cgaagacgta    1320
gcaccaatcg aacacatagc ctctatgaga cggaattatt ttacatccga agtgtcacat    1380
tgtagggcaa cagagtatat tatgaaaggg gtgtatatta ataccgcatt gcttaacgct    1440
agttgcgccg caatggacga tttccaactg ataccgatga tctcgaagtg tagaacaaaa    1500
gagggacgta gaaagactaa tctgtatggg ttcattatta agggaaggtc tcatttaagg    1560
aacgatacag acgtagtgaa tttcgttagt atggagttta gccttaccga tccgagactc    1620
gaaccacaca aatgggaaaa gtattgcgta ctagagatag gggatatgtt gattagatcc    1680
gcaatcggac aggtttcgag accaatgttt ttgtacgtta ggactaacgg aacctcgaag    1740
attaaaatga aatggggaat ggagatgcgt agatgcctat tgcaatccct tcagcaaatc    1800
gaatctatga tagaggccga atctagcgtt aaagagaaag atatgacaaa agagttttt    1860 gaaaataagt ccgaaacatg gccaatcgga gagtcaccaa aagggggtga ggaatcctca    1920
atcggaaaag tttgtagaac attgctcgca aaatccgtat tcaatagtct atacgccagc    1980
ccacaactag agggattctc tgctgagtca cgaaaactgt tactgatagt gcaagccctt    2040
agggataatc tcgaacccgg aacattcgat ctagggggg tgtacgaagc aatcgaagag    2100
tgtctgatta acgatccatg ggtactgctt aacgctagtt ggtttaattc gttccttaca    2160
cacgcactat cttagttgtg gcagtgctac tatttgctat ccatactgtc caaaaagta    2220 ccttgtttct act                                                       2233

<210> SEQ ID NO 51
<211> LENGTH: 1775
<212> TYPE: DNA
<213> ORGANISM: Influenza virus
<220> FEATURE:
<221> NAME/KEY: CDS
<222> LOCATION: (33)..(1730)

<400> SEQUENCE: 51
agcaaaagca ggggaaaata aaacaaccca aa atg aag gca aac cta ctg gtc    53
                                    Met Lys Ala Asn Leu Leu Val
                                     1               5 ctg tta agt gca ctt gca gct gca gat gca gac aca ata tgt ata ggc    101
Leu Leu Ser Ala Leu Ala Ala Ala Asp Ala Asp Thr Ile Cys Ile Gly
         10                  15                  20 tac cat gcg aac aat tca acc gac act gtt gac aca gta ctc gag aag    149
Tyr His Ala Asn Asn Ser Thr Asp Thr Val Asp Thr Val Leu Glu Lys
     25                  30                  35 aat gtg aca gtg aca cac tct gtt aac ctg ctc gaa gac agc cac aac    197
Asn Val Thr Val Thr His Ser Val Asn Leu Leu Glu Asp Ser His Asn
40                  45                  50                  55
```

```
gga aaa cta tgt aga tta aaa gga ata gcc cca cta caa ttg ggg aaa        245
Gly Lys Leu Cys Arg Leu Lys Gly Ile Ala Pro Leu Gln Leu Gly Lys
             60                  65                  70 tgt aac atc gcc gga tgg ctc ttg gga aac cca gaa tgc gac cca ctg        293
Cys Asn Ile Ala Gly Trp Leu Leu Gly Asn Pro Glu Cys Asp Pro Leu
         75                  80                  85 ctt cca gtg aga tca tgg tcc tac att gta gaa aca cca aac tct gag        341
Leu Pro Val Arg Ser Trp Ser Tyr Ile Val Glu Thr Pro Asn Ser Glu
         90                  95                 100 aat gga ata tgt tat cca gga gat ttc atc gac tat gag gag ctg agg        389
Asn Gly Ile Cys Tyr Pro Gly Asp Phe Ile Asp Tyr Glu Glu Leu Arg
        105                 110                 115 gag caa ttg agc tca gtg tca tca ttc gaa aga ttc gaa ata ttt ccc        437
Glu Gln Leu Ser Ser Val Ser Ser Phe Glu Arg Phe Glu Ile Phe Pro
120             125                 130                 135 aaa gaa agc tca tgg ccc aac cac aac aca aac gga gta acg gca gca        485
Lys Glu Ser Ser Trp Pro Asn His Asn Thr Asn Gly Val Thr Ala Ala
                140                 145                 150 tgc tcc cat gag ggg aaa agc agt ttt tac aga aat ttg cta tgg ctg        533
Cys Ser His Glu Gly Lys Ser Ser Phe Tyr Arg Asn Leu Leu Trp Leu
            155                 160                 165 acg gag aag gag ggc tca tac cca aag ctg aaa aat tct tat gtg aac        581
Thr Glu Lys Glu Gly Ser Tyr Pro Lys Leu Lys Asn Ser Tyr Val Asn
        170                 175                 180 aaa aaa ggg aaa gaa gtc ctt gta ctg tgg ggt att cat cac ccg cct        629
Lys Lys Gly Lys Glu Val Leu Val Leu Trp Gly Ile His His Pro Pro
185                 190                 195 aac agt aag gaa caa cag aat atc tat cag aat gaa aat gct tat gtc        677
Asn Ser Lys Glu Gln Gln Asn Ile Tyr Gln Asn Glu Asn Ala Tyr Val
200                 205                 210                 215 tct gta gtg act tca aat tat aac agg aga ttt acc ccg gaa ata gca        725
Ser Val Val Thr Ser Asn Tyr Asn Arg Arg Phe Thr Pro Glu Ile Ala
                220                 225                 230 gaa aga ccc aaa gta aga gat caa gct ggg agg atg aac tat tac tgg        773
Glu Arg Pro Lys Val Arg Asp Gln Ala Gly Arg Met Asn Tyr Tyr Trp
            235                 240                 245 acc ttg cta aaa ccc gga gac aca ata ata ttt gag gca aat gga aat        821
Thr Leu Leu Lys Pro Gly Asp Thr Ile Ile Phe Glu Ala Asn Gly Asn
        250                 255                 260 cta ata gca cca atg tat gct ttc gca ctg agt aga ggc ttt ggg tcc        869
Leu Ile Ala Pro Met Tyr Ala Phe Ala Leu Ser Arg Gly Phe Gly Ser
265                 270                 275 ggc atc atc acc tca aac gca tca atg cat gag tgt aac acg aag tgt        917
Gly Ile Ile Thr Ser Asn Ala Ser Met His Glu Cys Asn Thr Lys Cys
280                 285                 290                 295 caa aca ccc ctg gga gct ata aac agc agt ctc cct tac cag aat ata        965
Gln Thr Pro Leu Gly Ala Ile Asn Ser Ser Leu Pro Tyr Gln Asn Ile
                300                 305                 310 cac cca gtc aca ata gga gag tgc cca aaa tac gtc agg agt gcc aaa       1013
His Pro Val Thr Ile Gly Glu Cys Pro Lys Tyr Val Arg Ser Ala Lys
            315                 320                 325 ttg agg atg gtt aca gga cta agg aac act ccg tcc att caa tcc aga       1061
Leu Arg Met Val Thr Gly Leu Arg Asn Thr Pro Ser Ile Gln Ser Arg
        330                 335                 340 ggt cta ttt gga gcc att gcc ggt ttt att gaa ggg gga tgg act gga       1109
Gly Leu Phe Gly Ala Ile Ala Gly Phe Ile Glu Gly Gly Trp Thr Gly
345                 350                 355 atg ata gat gga tgg tat ggt tat cat cat cag aat gaa cag gga tca       1157
Met Ile Asp Gly Trp Tyr Gly Tyr His His Gln Asn Glu Gln Gly Ser
360                 365                 370                 375
```

```
ggc tat gca gcg gat caa aaa agc aca caa aat gcc att aac ggg att    1205
Gly Tyr Ala Ala Asp Gln Lys Ser Thr Gln Asn Ala Ile Asn Gly Ile
            380                 385                 390 aca aac aag gtg aac act gtt atc gag aaa atg aac att caa ttc aca    1253
Thr Asn Lys Val Asn Thr Val Ile Glu Lys Met Asn Ile Gln Phe Thr
        395                 400                 405 gct gtg ggt aaa gaa ttc aac aaa tta gaa aaa agg atg gaa aat tta    1301
Ala Val Gly Lys Glu Phe Asn Lys Leu Glu Lys Arg Met Glu Asn Leu
            410                 415                 420 aat aaa aaa gtt gat gat gga ttt ctg gac att tgg aca tat aat gca    1349
Asn Lys Lys Val Asp Asp Gly Phe Leu Asp Ile Trp Thr Tyr Asn Ala
        425                 430                 435 gaa ttg tta gtt cta ctg gaa aat gaa agg act ctg gat ttc cat gac    1397
Glu Leu Leu Val Leu Leu Glu Asn Glu Arg Thr Leu Asp Phe His Asp
440                 445                 450                 455 tca aat gtg aag aat ctg tat gag aaa gta aaa agc caa tta aag aat    1445
Ser Asn Val Lys Asn Leu Tyr Glu Lys Val Lys Ser Gln Leu Lys Asn
            460                 465                 470 aat gcc aaa gaa atc gga aat gga tgt ttt gag ttc tac cac aag tgt    1493
Asn Ala Lys Glu Ile Gly Asn Gly Cys Phe Glu Phe Tyr His Lys Cys
        475                 480                 485 gac aat gaa tgc atg gaa agt gta aga aat ggg act tat gat tat ccc    1541
Asp Asn Glu Cys Met Glu Ser Val Arg Asn Gly Thr Tyr Asp Tyr Pro
            490                 495                 500 aaa tat tca gaa gag tca aag ttg aac agg gaa aag gta gat gga gtg    1589
Lys Tyr Ser Glu Glu Ser Lys Leu Asn Arg Glu Lys Val Asp Gly Val
        505                 510                 515 aaa ttg gaa tca atg ggg atc tat cag att ctg gcg atc tac tca act    1637
Lys Leu Glu Ser Met Gly Ile Tyr Gln Ile Leu Ala Ile Tyr Ser Thr
520                 525                 530                 535 gtc gcc agt tca ctg gtg ctt ttg gtc tcc ctg ggg gca atc agt ttc    1685
Val Ala Ser Ser Leu Val Leu Leu Val Ser Leu Gly Ala Ile Ser Phe
            540                 545                 550 tgg atg tgt tct aat gga tct ttg cag tgc aga ata tgc atc tga        1730
Trp Met Cys Ser Asn Gly Ser Leu Gln Cys Arg Ile Cys Ile
        555                 560                 565 gattagaatt tcagaaatat gaggaaaaac acccttgttt ctact              1775

<210> SEQ ID NO 52
<211> LENGTH: 565
<212> TYPE: PRT
<213> ORGANISM: Influenza virus

<400> SEQUENCE: 52

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110
```

```
Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
        130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
        290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525
```

```
Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 53
<211> LENGTH: 1775
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (33)..(1730)
<220> FEATURE:
<221> NAME/KEY: misc_difference
<222> LOCATION: (180)..(1655)

<400> SEQUENCE: 53
```

| | | |
|---|---|---|
| agcaaaagca ggggaaaata aaaacaacca aa atg aag gca aac cta ctg gtc<br>                                                         Met Lys Ala Asn Leu Leu Val<br>                                                         1                 5 | | 53 |

```
ctg tta agt gca ctt gca gct gca gat gca gac aca ata tgt ata ggc    101
Leu Leu Ser Ala Leu Ala Ala Ala Asp Ala Asp Thr Ile Cys Ile Gly
         10                  15                  20 tac cat gcg aac aat tca acc gac act gtt gac aca gta ctc gag aag    149
Tyr His Ala Asn Asn Ser Thr Asp Thr Val Asp Thr Val Leu Glu Lys
     25                  30                  35 aat gtg aca gtg aca cac tct gtt aac ctg tta gag gac tca cat aac    197
Asn Val Thr Val Thr His Ser Val Asn Leu Leu Glu Asp Ser His Asn
 40                  45                  50                  55 gga aag cta tgt agg ctt aag gga atc gca cca ctg caa ttg ggc aag    245
Gly Lys Leu Cys Arg Leu Lys Gly Ile Ala Pro Leu Gln Leu Gly Lys
                 60                  65                  70 tgt aat ata gcc gga tgg ttg ttg ggg aat ccc gaa tgc gat cca ctg    293
Cys Asn Ile Ala Gly Trp Leu Leu Gly Asn Pro Glu Cys Asp Pro Leu
             75                  80                  85 tta ccc gtt agg tca tgg tca tat ata gtc gag aca cct aat agc gaa    341
Leu Pro Val Arg Ser Trp Ser Tyr Ile Val Glu Thr Pro Asn Ser Glu
         90                  95                 100 aac gga att tgt tat ccc ggc gat ttt atc gat tac gaa gag ctt aga    389
Asn Gly Ile Cys Tyr Pro Gly Asp Phe Ile Asp Tyr Glu Glu Leu Arg
    105                 110                 115 gag caa ttg tct agc gtt agt tca ttc gaa aga ttc gaa att ttt ccg    437
Glu Gln Leu Ser Ser Val Ser Ser Phe Glu Arg Phe Glu Ile Phe Pro
120                 125                 130                 135 aaa gag tct agt tgg cca aat cat aat act aac gga gtg act gcc gca    485
Lys Glu Ser Ser Trp Pro Asn His Asn Thr Asn Gly Val Thr Ala Ala
                140                 145                 150 tgc tca cac gaa ggc aag tct agc ttt tat agg aat ctg ttg tgg ttg    533
Cys Ser His Glu Gly Lys Ser Ser Phe Tyr Arg Asn Leu Leu Trp Leu
            155                 160                 165 act gag aaa gag gga tca tat ccg aaa ctg aaa aac tca tac gtg aac    581
Thr Glu Lys Glu Gly Ser Tyr Pro Lys Leu Lys Asn Ser Tyr Val Asn
        170                 175                 180 aaa aag gga aag gaa gtg tta gtg ttg tgg ggg ata cac cat cca cca    629
Lys Lys Gly Lys Glu Val Leu Val Leu Trp Gly Ile His His Pro Pro
    185                 190                 195
```

| | | |
|---|---|---|
| aat agt aaa gag caa cag aat ata tat cag aac gaa aac gca tac gtt<br>Asn Ser Lys Glu Gln Gln Asn Ile Tyr Gln Asn Glu Asn Ala Tyr Val<br>200                         205                     210                   215 | 677 | |
| agc gtc gta act agt aat tat aat aga agg ttt aca ccc gaa atc gca<br>Ser Val Val Thr Ser Asn Tyr Asn Arg Arg Phe Thr Pro Glu Ile Ala<br>                    220                    225                 230 | 725 | |
| gag aga ccg aaa gtt aga gac caa gcc gga aga atg aat tat tat tgg<br>Glu Arg Pro Lys Val Arg Asp Gln Ala Gly Arg Met Asn Tyr Tyr Trp<br>             235                    240                   245 | 773 | |
| aca cta ctg aaa ccc ggc gat aca att ata ttc gaa gcg aac gga aat<br>Thr Leu Leu Lys Pro Gly Asp Thr Ile Ile Phe Glu Ala Asn Gly Asn<br>        250                   255                   260 | 821 | |
| ctg atc gca ccg atg tat gca ttc gca cta tct agg ggg ttc gga tcc<br>Leu Ile Ala Pro Met Tyr Ala Phe Ala Leu Ser Arg Gly Phe Gly Ser<br>265                         270                     275 | 869 | |
| gga att att act agt aac gct agt atg cac gaa tgt aac acg aag tgt<br>Gly Ile Ile Thr Ser Asn Ala Ser Met His Glu Cys Asn Thr Lys Cys<br>280                         285                    290                 295 | 917 | |
| cag act cca cta ggc gca att aac tct agt ctg cca tat cag aat ata<br>Gln Thr Pro Leu Gly Ala Ile Asn Ser Ser Leu Pro Tyr Gln Asn Ile<br>                    300                    305                 310 | 965 | |
| cat ccc gta aca atc ggc gaa tgc cca aaa tac gtt aga tcc gct aag<br>His Pro Val Thr Ile Gly Glu Cys Pro Lys Tyr Val Arg Ser Ala Lys<br>             315                    320                   325 | 1013 | |
| ctt aga atg gtt acc gga ctg aga aat aca cca tca atc caa tct agg<br>Leu Arg Met Val Thr Gly Leu Arg Asn Thr Pro Ser Ile Gln Ser Arg<br>        330                   335                   340 | 1061 | |
| ggg ttg ttc gga gcg ata gcc gga ttt atc gaa ggg ggg tgg aca ggg<br>Gly Leu Phe Gly Ala Ile Ala Gly Phe Ile Glu Gly Gly Trp Thr Gly<br>345                         350                     355 | 1109 | |
| atg ata gac ggt tgg tac gga tat cat cac caa aac gaa cag gga tcc<br>Met Ile Asp Gly Trp Tyr Gly Tyr His His Gln Asn Glu Gln Gly Ser<br>360                         365                    370                 375 | 1157 | |
| gga tac gca gcc gat cag aaa tcg acg caa aac gct att aac gga att<br>Gly Tyr Ala Ala Asp Gln Lys Ser Thr Gln Asn Ala Ile Asn Gly Ile<br>                    380                    385                 390 | 1205 | |
| act aat aaa gtg aat acc gta atc gaa aaa atg aat atc caa ttt acc<br>Thr Asn Lys Val Asn Thr Val Ile Glu Lys Met Asn Ile Gln Phe Thr<br>             395                    400                   405 | 1253 | |
| gca gtc gga aag gaa ttc aat aag ctt gag aaa aga atg gag aat ctg<br>Ala Val Gly Lys Glu Phe Asn Lys Leu Glu Lys Arg Met Glu Asn Leu<br>        410                   415                   420 | 1301 | |
| aat aaa aaa gtc gac gac gga ttt cta gac ata tgg act tat aac gcc<br>Asn Lys Lys Val Asp Asp Gly Phe Leu Asp Ile Trp Thr Tyr Asn Ala<br>425                         430                     435 | 1349 | |
| gaa ctg tta gtg ttg ctc gaa aac gaa aga aca cta gac ttt cac gac<br>Glu Leu Leu Val Leu Leu Glu Asn Glu Arg Thr Leu Asp Phe His Asp<br>440                         445                    450                 455 | 1397 | |
| tca aac gtt aag aat cta tac gaa aaa gtg aaa tcc caa ttg aaa aat<br>Ser Asn Val Lys Asn Leu Tyr Glu Lys Val Lys Ser Gln Leu Lys Asn<br>                    460                    465                 470 | 1445 | |
| aac gct aaa gag ata ggg aac gga tgt ttc gag ttc tat cat aaa tgc<br>Asn Ala Lys Glu Ile Gly Asn Gly Cys Phe Glu Phe Tyr His Lys Cys<br>             475                    480                   485 | 1493 | |
| gat aac gaa tgt atg gaa tcc gtt agg aac gga aca tac gat tat cct<br>Asp Asn Glu Cys Met Glu Ser Val Arg Asn Gly Thr Tyr Asp Tyr Pro<br>        490                   495                   500 | 1541 | |
| aag tat agc gaa gag tca aaa ctg aat agg gag aaa gtc gac gga gtg<br>Lys Tyr Ser Glu Glu Ser Lys Leu Asn Arg Glu Lys Val Asp Gly Val<br>505                         510                    515 | 1589 | |

```
aaa ctc gaa tca atg ggg ata tat cag ata ctg gca atc tat agt aca    1637
Lys Leu Glu Ser Met Gly Ile Tyr Gln Ile Leu Ala Ile Tyr Ser Thr
520             525                 530                 535 gtc gcc agc tca ctg gtt ctt ttg gtc tcc ctg ggg gca atc agt ttc    1685
Val Ala Ser Ser Leu Val Leu Leu Val Ser Leu Gly Ala Ile Ser Phe
                540                 545                 550 tgg atg tgt tct aat gga tct ttg cag tgc aga ata tgc atc tga        1730
Trp Met Cys Ser Asn Gly Ser Leu Gln Cys Arg Ile Cys Ile
                555                 560                 565 gattagaatt tcagaaatat gaggaaaaac acccttgttt ctact                  1775

<210> SEQ ID NO 54
<211> LENGTH: 565
<212> TYPE: PRT
<213> ORGANISM: unknown
<220> FEATURE:
<223> OTHER INFORMATION: Synthetic Construct

<400> SEQUENCE: 54

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Gly Ser Tyr Pro Lys Leu
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285
```

```
His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 55
<211> LENGTH: 1565
<212> TYPE: DNA
<213> ORGANISM: Influenza virus
<220> FEATURE:
<221> NAME/KEY: CDS
<222> LOCATION: (46)..(1542)

<400> SEQUENCE: 55
agcaaaagca gggtagataa tcactcactg agtgacatca aaatc atg gcg tcc caa      57
                                                 Met Ala Ser Gln
                                                 1 ggc acc aaa cgg tct tac gaa cag atg gag act gat gga gaa cgc cag       105
Gly Thr Lys Arg Ser Tyr Glu Gln Met Glu Thr Asp Gly Glu Arg Gln
5                   10                  15                  20 aat gcc act gaa atc aga gca tcc gtc gga aaa atg att ggt gga att       153
Asn Ala Thr Glu Ile Arg Ala Ser Val Gly Lys Met Ile Gly Gly Ile
                25                  30                  35
```

| | | |
|---|---|---|
| gga cga ttc tac atc caa atg tgc acc gaa ctc aaa ctc agt gat tat<br>Gly Arg Phe Tyr Ile Gln Met Cys Thr Glu Leu Lys Leu Ser Asp Tyr<br>          40                        45                        50 | | 201 |
| gag gga cgg ttg atc caa aac agc tta aca ata gag aga atg gtg ctc<br>Glu Gly Arg Leu Ile Gln Asn Ser Leu Thr Ile Glu Arg Met Val Leu<br>          55                        60                        65 | | 249 |
| tct gct ttt gac gaa agg aga aat aaa tac ctg gaa gaa cat ccc agt<br>Ser Ala Phe Asp Glu Arg Arg Asn Lys Tyr Leu Glu Glu His Pro Ser<br>70                        75                        80 | | 297 |
| gcg ggg aaa gat cct aag aaa act gga gga cct ata tac agg aga gta<br>Ala Gly Lys Asp Pro Lys Lys Thr Gly Gly Pro Ile Tyr Arg Arg Val<br>85                        90                        95                        100 | | 345 |
| aac gga aag tgg atg aga gaa ctc atc ctt tat gac aaa gaa gaa ata<br>Asn Gly Lys Trp Met Arg Glu Leu Ile Leu Tyr Asp Lys Glu Glu Ile<br>                        105                       110                       115 | | 393 |
| agg cga atc tgg cgc caa gct aat aat ggt gac gat gca acg gct ggt<br>Arg Arg Ile Trp Arg Gln Ala Asn Asn Gly Asp Asp Ala Thr Ala Gly<br>          120                       125                       130 | | 441 |
| ctg act cac atg atg atc tgg cat tcc aat ttg aat gat gca act tat<br>Leu Thr His Met Met Ile Trp His Ser Asn Leu Asn Asp Ala Thr Tyr<br>             135                     140                       145 | | 489 |
| cag agg aca aga gct ctt gtt cgc acc gga atg gat ccc agg atg tgc<br>Gln Arg Thr Arg Ala Leu Val Arg Thr Gly Met Asp Pro Arg Met Cys<br>150                      155                       160 | | 537 |
| tct ctg atg caa ggt tca act ctc cct agg agg tct gga gcc gca ggt<br>Ser Leu Met Gln Gly Ser Thr Leu Pro Arg Arg Ser Gly Ala Ala Gly<br>165                      170                       175                       180 | | 585 |
| gct gca gtc aaa gga gtt gga aca atg gtg atg gaa ttg gtc agg atg<br>Ala Ala Val Lys Gly Val Gly Thr Met Val Met Glu Leu Val Arg Met<br>                       185                       190                       195 | | 633 |
| atc aaa cgt ggg atc aat gat cgg aac ttc tgg agg ggt gag aat gga<br>Ile Lys Arg Gly Ile Asn Asp Arg Asn Phe Trp Arg Gly Glu Asn Gly<br>200                      205                       210 | | 681 |
| cga aaa aca aga att gct tat gaa aga atg tgc aac att ctc aaa ggg<br>Arg Lys Thr Arg Ile Ala Tyr Glu Arg Met Cys Asn Ile Leu Lys Gly<br>          215                       220                       225 | | 729 |
| aaa ttt caa act gct gca caa aaa gca atg atg gat caa gtg aga gag<br>Lys Phe Gln Thr Ala Ala Gln Lys Ala Met Met Asp Gln Val Arg Glu<br>230                      235                       240 | | 777 |
| agc cgg aac cca ggg aat gct gag ttc gaa gat ctc act ttt cta gca<br>Ser Arg Asn Pro Gly Asn Ala Glu Phe Glu Asp Leu Thr Phe Leu Ala<br>245                      250                       255                       260 | | 825 |
| cgg tct gca ctc ata ttg aga ggg tcg gtt gct cac aag tcc tgc ctg<br>Arg Ser Ala Leu Ile Leu Arg Gly Ser Val Ala His Lys Ser Cys Leu<br>                       265                       270                       275 | | 873 |
| cct gcc tgt gtg tat gga cct gcc gta gcc agt ggg tac gac ttt gaa<br>Pro Ala Cys Val Tyr Gly Pro Ala Val Ala Ser Gly Tyr Asp Phe Glu<br>                     280                       285                       290 | | 921 |
| aga gag gga tac tct cta gtc gga ata gac cct ttc aga ctg ctt caa<br>Arg Glu Gly Tyr Ser Leu Val Gly Ile Asp Pro Phe Arg Leu Leu Gln<br>          295                       300                       305 | | 969 |
| aac agc caa gtg tac agc cta atc aga cca aat gag aat cca gca cac<br>Asn Ser Gln Val Tyr Ser Leu Ile Arg Pro Asn Glu Asn Pro Ala His<br>310                      315                       320 | | 1017 |
| aag agt caa ctg gtg tgg atg gca tgc cat tct gcc gca ttt gaa gat<br>Lys Ser Gln Leu Val Trp Met Ala Cys His Ser Ala Ala Phe Glu Asp<br>325                      330                       335                       340 | | 1065 |
| cta aga gta tta agc ttc atc aaa ggg acg aag gtg ctc cca aga ggg<br>Leu Arg Val Leu Ser Phe Ile Lys Gly Thr Lys Val Leu Pro Arg Gly<br>          345                       350                       355 | | 1113 |

| | | | | | | | | | | | | | | |
|---|---|---|---|---|---|---|---|---|---|---|---|---|---|---|
| aag | ctt | tcc | act | aga | gga | gtt | caa | att | gct | tcc | aat | gaa | aat | atg | gag | 1161 |
| Lys | Leu | Ser | Thr | Arg | Gly | Val | Gln | Ile | Ala | Ser | Asn | Glu | Asn | Met | Glu |
| | | | 360 | | | | 365 | | | | 370 | | | | act atg gaa tca agt aca ctt gaa ctg aga agc agg tac tgg gcc ata 1209
Thr Met Glu Ser Ser Thr Leu Glu Leu Arg Ser Arg Tyr Trp Ala Ile
        375             380             385 agg acc aga agt gga gga aac acc aat caa cag agg gca tct gcg ggc 1257
Arg Thr Arg Ser Gly Gly Asn Thr Asn Gln Gln Arg Ala Ser Ala Gly
        390             395             400 caa atc agc ata caa cct acg ttc tca gta cag aga aat ctc cct ttt 1305
Gln Ile Ser Ile Gln Pro Thr Phe Ser Val Gln Arg Asn Leu Pro Phe
405             410             415             420 gac aga aca acc att atg gca gca ttc aat ggg aat aca gag gga aga 1353
Asp Arg Thr Thr Ile Met Ala Ala Phe Asn Gly Asn Thr Glu Gly Arg
        425             430             435 aca tct gac atg agg acc gaa atc ata agg atg atg gaa agt gca aga 1401
Thr Ser Asp Met Arg Thr Glu Ile Ile Arg Met Met Glu Ser Ala Arg
        440             445             450 cca gaa gat gtg tct ttc cag ggg cgg gga gtc ttc gag ctc tcg gac 1449
Pro Glu Asp Val Ser Phe Gln Gly Arg Gly Val Phe Glu Leu Ser Asp
        455             460             465 gaa aag gca gcg agc ccg atc gtg cct tcc ttt gac atg agt aat gaa 1497
Glu Lys Ala Ala Ser Pro Ile Val Pro Ser Phe Asp Met Ser Asn Glu
470             475             480 gga tct tat ttc ttc gga gac aat gca gag gag tac gac aat taa 1542
Gly Ser Tyr Phe Phe Gly Asp Asn Ala Glu Glu Tyr Asp Asn
485             490             495 agaaaaatac ccttgtttct act                                          1565

<210> SEQ ID NO 56
<211> LENGTH: 498
<212> TYPE: PRT
<213> ORGANISM: Influenza virus

<400> SEQUENCE: 56

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

-continued

```
Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 57
<211> LENGTH: 1565
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (46)..(1542)
<220> FEATURE:
<221> NAME/KEY: misc_difference
<222> LOCATION: (126)..(1425)
```

-continued

<400> SEQUENCE: 57

```
agcaaaagca gggtagataa tcactcactg agtgacatca aaatc atg gcg tcc caa        57
                                                  Met Ala Ser Gln
                                                   1 ggc acc aaa cgg tct tac gaa cag atg gag act gat gga gaa cgc cag         105
Gly Thr Lys Arg Ser Tyr Glu Gln Met Glu Thr Asp Gly Glu Arg Gln
  5              10                  15                  20 aat gcc act gaa atc aga gct agc gtc gga aaa atg ata ggg gga atc         153
Asn Ala Thr Glu Ile Arg Ala Ser Val Gly Lys Met Ile Gly Gly Ile
             25                  30                  35 gga agg ttt tac ata caa atg tgt acc gaa ctc aaa ttg tcc gat tac         201
Gly Arg Phe Tyr Ile Gln Met Cys Thr Glu Leu Lys Leu Ser Asp Tyr
         40                  45                  50 gaa ggg aga ttg atc caa aat agt ctg aca atc gaa aga atg gtg tta         249
Glu Gly Arg Leu Ile Gln Asn Ser Leu Thr Ile Glu Arg Met Val Leu
     55                  60                  65 agc gca ttc gac gaa aga cgg aat aag tat ctc gaa gag cat cct agc         297
Ser Ala Phe Asp Glu Arg Arg Asn Lys Tyr Leu Glu Glu His Pro Ser
 70                  75                  80 gca ggc aag gat cca aaa aaa acc gga ggg cca atc tat agg aga gtg         345
Ala Gly Lys Asp Pro Lys Lys Thr Gly Gly Pro Ile Tyr Arg Arg Val
 85                  90                  95                 100 aac gga aag tgg atg cgc gaa ctg ata ctg tac gat aaa gag gag att         393
Asn Gly Lys Trp Met Arg Glu Leu Ile Leu Tyr Asp Lys Glu Glu Ile
                105                 110                 115 aga cgg ata tgg cga caa gcg aat aac gga gac gac gct act gcc gga         441
Arg Arg Ile Trp Arg Gln Ala Asn Asn Gly Asp Asp Ala Thr Ala Gly
                120                 125                 130 ctg aca cat atg atg ata tgg cac tct aat ctt aac gac gct aca tac         489
Leu Thr His Met Met Ile Trp His Ser Asn Leu Asn Asp Ala Thr Tyr
            135                 140                 145 caa cgg act agg gca ctc gtt aga acc gga atg gat cct aga atg tgc         537
Gln Arg Thr Arg Ala Leu Val Arg Thr Gly Met Asp Pro Arg Met Cys
        150                 155                 160 tca ctt atg cag gga tct aca ctc cct aga cga tcc gga gcc gca gga         585
Ser Leu Met Gln Gly Ser Thr Leu Pro Arg Arg Ser Gly Ala Ala Gly
165                 170                 175                 180 gca gcc gtt aag gga gtc gga act atg gtt atg gaa ctc gtt aga atg         633
Ala Ala Val Lys Gly Val Gly Thr Met Val Met Glu Leu Val Arg Met
                185                 190                 195 ata aaa agg ggg att aac gat agg aat ttt tgg aga ggc gaa aac gga         681
Ile Lys Arg Gly Ile Asn Asp Arg Asn Phe Trp Arg Gly Glu Asn Gly
                200                 205                 210 cgt aaa act aga atc gca tac gaa aga atg tgc aat ata ctc aaa ggg         729
Arg Lys Thr Arg Ile Ala Tyr Glu Arg Met Cys Asn Ile Leu Lys Gly
                215                 220                 225 aaa ttc caa acc gca gcg caa aaa gct atg atg gat caa gtt agg gag         777
Lys Phe Gln Thr Ala Ala Gln Lys Ala Met Met Asp Gln Val Arg Glu
            230                 235                 240 tct agg aat cca gga aat gcc gaa ttc gaa gac ctt aca ttt ctc gct         825
Ser Arg Asn Pro Gly Asn Ala Glu Phe Glu Asp Leu Thr Phe Leu Ala
245                 250                 255                 260 cgg tcc gca cta atc ctt cgc gga tca gtc gca cac aaa tct tgc tta         873
Arg Ser Ala Leu Ile Leu Arg Gly Ser Val Ala His Lys Ser Cys Leu
                265                 270                 275 ccc gca tgc gta tac gga cct gca gtc gct agc gga tac gat ttc gaa         921
Pro Ala Cys Val Tyr Gly Pro Ala Val Ala Ser Gly Tyr Asp Phe Glu
            280                 285                 290
```

```
cgc gaa ggg tat agt cta gta gga att gat cca ttt aga ttg ctc caa      969
Arg Glu Gly Tyr Ser Leu Val Gly Ile Asp Pro Phe Arg Leu Leu Gln
            295                 300                 305 aat tcg caa gtg tat agt ctg att aga cct aac gag aat cct gca cac     1017
Asn Ser Gln Val Tyr Ser Leu Ile Arg Pro Asn Glu Asn Pro Ala His
        310                 315                 320 aaa tct caa ctc gta tgg atg gca tgc cat agt gcc gca ttc gaa gac     1065
Lys Ser Gln Leu Val Trp Met Ala Cys His Ser Ala Ala Phe Glu Asp
325                 330                 335                 340 ctt aga gtg cta tct ttc ata aag gga acg aaa gtg ttg cct agg gga     1113
Leu Arg Val Leu Ser Phe Ile Lys Gly Thr Lys Val Leu Pro Arg Gly
                345                 350                 355 aag cta tct act agg gga gtg caa atc gct agt aac gag aat atg gag     1161
Lys Leu Ser Thr Arg Gly Val Gln Ile Ala Ser Asn Glu Asn Met Glu
            360                 365                 370 act atg gag tct agt aca ctc gaa ctg aga tct aga tat tgg gct att     1209
Thr Met Glu Ser Ser Thr Leu Glu Leu Arg Ser Arg Tyr Trp Ala Ile
        375                 380                 385 agg act aga tcc gga ggg aat acg aat cag caa cga gct agc gcc ggg     1257
Arg Thr Arg Ser Gly Gly Asn Thr Asn Gln Gln Arg Ala Ser Ala Gly
390                 395                 400 caa atc tca atc caa cct aca ttt tcc gtg caa cgg aat ctg cca ttc     1305
Gln Ile Ser Ile Gln Pro Thr Phe Ser Val Gln Arg Asn Leu Pro Phe
405                 410                 415                 420 gat cgg aca acg att atg gcc gca ttc aat ggg aat acc gag gga cgg     1353
Asp Arg Thr Thr Ile Met Ala Ala Phe Asn Gly Asn Thr Glu Gly Arg
                425                 430                 435 act agc gat atg aga acc gaa att atc aga atg atg gaa tcc gct aga     1401
Thr Ser Asp Met Arg Thr Glu Ile Ile Arg Met Met Glu Ser Ala Arg
            440                 445                 450 cca gag gac gtt tcg ttt caa gga cgg gga gtc ttc gag ctc tcg gac     1449
Pro Glu Asp Val Ser Phe Gln Gly Arg Gly Val Phe Glu Leu Ser Asp
        455                 460                 465 gaa aag gca gcg agc ccg atc gtg cct tcc ttt gac atg agt aat gaa     1497
Glu Lys Ala Ala Ser Pro Ile Val Pro Ser Phe Asp Met Ser Asn Glu
470                 475                 480 gga tct tat ttc ttc gga gac aat gca gag gag tac gac aat taa        1542
Gly Ser Tyr Phe Phe Gly Asp Asn Ala Glu Glu Tyr Asp Asn
485                 490                 495 agaaaaatac ccttgtttct act                                           1565

<210> SEQ ID NO 58
<211> LENGTH: 498
<212> TYPE: PRT
<213> ORGANISM: unknown
<220> FEATURE:
<223> OTHER INFORMATION: Synthetic Construct

<400> SEQUENCE: 58

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
                20                  25                  30

Ile Gly Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
        50                  55                  60

Arg Met Val Leu Ser Ala Phe Asp Glu Arg Arg Asn Lys Tyr Leu Glu
65                  70                  75                  80
```

```
Glu His Pro Ser Ala Gly Lys Asp Pro Lys Thr Gly Gly Pro Ile
                 85                  90                  95
Tyr Arg Arg Val Asn Gly Lys Trp Met Arg Glu Leu Ile Leu Tyr Asp
            100                 105                 110
Lys Glu Glu Ile Arg Arg Ile Trp Arg Gln Ala Asn Asn Gly Asp Asp
            115                 120                 125
Ala Thr Ala Gly Leu Thr His Met Met Ile Trp His Ser Asn Leu Asn
130                 135                 140
Asp Ala Thr Tyr Gln Arg Thr Arg Ala Leu Val Arg Thr Gly Met Asp
145                 150                 155                 160
Pro Arg Met Cys Ser Leu Met Gln Gly Ser Thr Leu Pro Arg Arg Ser
                165                 170                 175
Gly Ala Ala Gly Ala Ala Val Lys Gly Val Gly Thr Met Val Met Glu
                180                 185                 190
Leu Val Arg Met Ile Lys Arg Gly Ile Asn Asp Arg Asn Phe Trp Arg
            195                 200                 205
Gly Glu Asn Gly Arg Lys Thr Arg Ile Ala Tyr Glu Arg Met Cys Asn
            210                 215                 220
Ile Leu Lys Gly Lys Phe Gln Thr Ala Ala Gln Lys Ala Met Met Asp
225                 230                 235                 240
Gln Val Arg Glu Ser Arg Asn Pro Gly Asn Ala Glu Phe Glu Asp Leu
                245                 250                 255
Thr Phe Leu Ala Arg Ser Ala Leu Ile Leu Arg Gly Ser Val Ala His
                260                 265                 270
Lys Ser Cys Leu Pro Ala Cys Val Tyr Gly Pro Ala Val Ala Ser Gly
            275                 280                 285
Tyr Asp Phe Glu Arg Glu Gly Tyr Ser Leu Val Gly Ile Asp Pro Phe
            290                 295                 300
Arg Leu Leu Gln Asn Ser Gln Val Tyr Ser Leu Ile Arg Pro Asn Glu
305                 310                 315                 320
Asn Pro Ala His Lys Ser Gln Leu Val Trp Met Ala Cys His Ser Ala
                325                 330                 335
Ala Phe Glu Asp Leu Arg Val Leu Ser Phe Ile Lys Gly Thr Lys Val
                340                 345                 350
Leu Pro Arg Gly Lys Leu Ser Thr Arg Gly Val Gln Ile Ala Ser Asn
            355                 360                 365
Glu Asn Met Glu Thr Met Glu Ser Ser Thr Leu Glu Leu Arg Ser Arg
            370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Ile Gln Pro Thr Phe Ser Val Gln Arg
                405                 410                 415
Asn Leu Pro Phe Asp Arg Thr Thr Ile Met Ala Ala Phe Asn Gly Asn
                420                 425                 430
Thr Glu Gly Arg Thr Ser Asp Met Arg Thr Glu Ile Ile Arg Met Met
            435                 440                 445
Glu Ser Ala Arg Pro Glu Asp Val Ser Phe Gln Gly Arg Gly Val Phe
450                 455                 460
Glu Leu Ser Asp Glu Lys Ala Ala Ser Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn
```

<210> SEQ ID NO 59
<211> LENGTH: 1413
<212> TYPE: DNA
<213> ORGANISM: Influenza virus

<400> SEQUENCE: 59

```
agcgaaagca ggggtttaaa atgaatccaa atcagaaaat aacaaccatt ggatcaatct     60
gtctggtagt cggactaatt agcctaatat tgcaaatagg gaatataatc tcaatatgga    120
ttagccattc aattcaaact ggaagtcaaa accatactgg aatatgcaac caaaacatca    180
ttacctataa aaatagcacc tgggtaaagg acacaacttc agtgatatta accggcaatt    240
catctctttg tcccatccgt gggtgggcta tatacagcaa agacaatagc ataagaattg    300
gttccaaagg agacgttttt gtcataagag agccctttat ttcatgttct cacttggaat    360
gcaggacctt ttttctgacc caaggtgcct tactgaatga caagcattca aatgggactg    420
ttaaggacag aagcccttat agggccttaa tgagctgccc tgtcggtgaa gctccgtccc    480
cgtacaattc aagatttgaa tcggttgctt ggtcagcaag tgcatgtcat gatggcatgg    540
gctggctaac aatcggaatt tcaggtccag ataatggagc agtggctgta ttaaaataca    600
acggcataat aactgaaacc ataaaaagtt ggaggaagaa aatattgagg acacaagagt    660
ctgaatgtgc ctgtgtaaat ggttcatgtt ttactataat gactgatggc ccgagtgatg    720
ggctggcctc gtacaaaatt ttcaagatcg aaaaggggaa ggttactaaa tcaatagagt    780
tgaatgcacc taattctcac tatgaggaat gttcctgtta ccctgatacc ggcaaagtga    840
tgtgtgtgtg cagagacaac tggcatggtt cgaaccggcc atgggtgtct ttcgatcaaa    900
acctggatta tcaaatagga tacatctgca gtggggtttt cggtgacaac ccgcgtcccg    960
aagatggaac aggcagctgt ggtccagtgt atgttgatgg agcaaacgga gtaaagggat   1020
tttcatatag gtatggtaat ggtgtttgga taggaaggac caaaagtcac agttccagac   1080
atgggtttga gatgatttgg gatcctaatg gatggacaga gactgatagt aagttctctg   1140
ttaggcaaga tgttgtggca atgactgatt ggtcagggta tagcggaagt ttcgttcaac   1200
atcctgagct aacagggcta gactgtatga ggccgtgctt ctgggttgaa ttaatcaggg   1260
gacgacctaa agaaaaaaca atctggacta gtgcgagcag catttctttt tgtggcgtga   1320
atagtgatac tgtagattgg tcttggccag acggtgctga gttgccattc agcattgaca   1380
agtagtctgt tcaaaaaact ccttgtttct act                                1413
```

<210> SEQ ID NO 60
<211> LENGTH: 1413
<212> TYPE: DNA
<213> ORGANISM: unknown
<220> FEATURE:
<223> OTHER INFORMATION: synthetic

<400> SEQUENCE: 60

```
agcgaaagca ggggtttaaa atgaatccaa atcagaaaat aacaaccatt ggatcaatct     60
gtctggtagt cggactaatt agcctaatat tgcaaatagg gaatataatc tcaatatgga    120
tttcgcattc aatccaaacc ggatcacaaa atcatacagg catatgcaat cagaatataa    180
ttacttataa aaatagtaca tgggtgaaag atactactag cgtgatacta accggcaatt    240
ctagtctatg tccgattagg gggtgggcta tatactctaa agacaatagt atacggatag    300
ggtctaaggg agacgttttc gtaattaggg aaccgtttat aagttgttca catctagagt    360
gtaggacctt ttttctgaca caaggcgcac tattaaacga taagcattct aacggtacag    420
```

```
ttaaggatag gtcaccttat agggcactta tgtcatgtcc cgtaggcgaa gcccctagtc    480
catacaatag tagatttgaa tccgttgcat ggtccgctag cgcatgtcac gacggaatgg    540
ggtggttgac tatagggatt agcggacccg ataacggagc cgttgccgta ctgaaatata    600
acggtataat taccgaaact attaagagtt ggcgtaaaaa aatattgcgt acacaagagt    660
ccgaatgcgc atgcgttaac ggatcatgtt ttacaattat gactgacgga cctagcgacg    720
ggttagcgtc atacaaaatt tttaaaatcg aaaaaggcaa ggttactaag tcaatcgagt    780
taaacgcacc taattcgcat tacgaagagt gttcatgtta tcccgatacc ggaaaggtta    840
tgtgcgtttg tagggataat tggcacggtt cgaacagacc ttgggtgtca ttcgatcaaa    900
atctagacta tcaaatcgga tatatatgta gcggagtgtt cggcgataat cctagaccag    960
aggacggtac aggcagctgt ggaccggttt acgttgacgg cgctaacggc gttaaggggt   1020
ttagttatag atacggcaat ggcgtatgga tcggtaggac taagtcacat agttctagac   1080
acggatttga aatgatatgg gatcctaacg gatggaccga aaccgactcg aagtttagcg   1140
ttaggcaaga cgtagtcgct atgaccgatt ggtccgggta tagcggatca ttcgtgcaac   1200
atccagagtt aaccggattg gattgtatgc gaccatgttt ttgggttgag ttgattaggg   1260
ggagaccgaa agagaaaact atatggacta gcgcgagcga catttctttt tgtggcgtga   1320
atagtgatac tgtagattgg tcttggccag acggtgctga gttgccattc agcattgaca   1380
agtagtctgt tcaaaaaact ccttgtttct act                                1413
```

<210> SEQ ID NO 61
<211> LENGTH: 1026
<212> TYPE: DNA
<213> ORGANISM: Influenza virus

<400> SEQUENCE: 61

```
agcgaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
tgcagggaag aacactgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cgctattgcc gcaaatatca ttgggatctt gcacttgaca ttgtggattc    840
ttgatcgtct tttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt catttttgtca gcatagagct ggagtaaaaa actaccttgt   1020
ttctac                                                              1026
```

<210> SEQ ID NO 62
<211> LENGTH: 890
<212> TYPE: DNA
<213> ORGANISM: Influenza virus

<400> SEQUENCE: 62

| | | | | | |
|---|---|---|---|---|---|
| agcaaaagca | gggtgacaaa | gacataatgg | atccaaacac | tgtgtcaagc | tttcaggtag | 60 |
| attgctttct | ttggcatgtc | cgcaaacgag | ttgcagacca | agaactaggt | gatgccccat | 120 |
| tccttgatcg | gcttcgccga | gatcagaaat | ccctaagagg | aagggcagc | accctcggtc | 180 |
| tggacatcga | gacagccaca | cgtgctggaa | agcagatagt | ggagcggatt | ctgaaagaag | 240 |
| aatccgatga | ggcacttaaa | atgaccatgc | cctctgtacc | tgcgtcgcgt | tacctaactg | 300 |
| acatgactct | tgaggaaatg | tcaagggact | ggtccatgct | catacccaag | cagaaagtgg | 360 |
| caggccctct | ttgtatcaga | atggaccagg | cgatcatgga | taagaacatc | atactgaaag | 420 |
| cgaacttcag | tgtgattttt | gaccggctgg | agactctaat | attgctaagg | gctttcaccg | 480 |
| aagagggagc | aattgttggc | gaaatttcac | cattgccttc | tcttccagga | catactgctg | 540 |
| aggatgtcaa | aaatgcagtt | ggagtcctca | tcggggact | tgaatggaat | gataacacag | 600 |
| ttcgagtctc | tgaaactcta | cagagattcg | cttggagaag | cagtaatgag | aatgggagac | 660 |
| ctccactcac | tccaaaacag | aaacgagaaa | tggcgggaac | aattaggtca | gaagtttgaa | 720 |
| gaaataagat | ggttgattga | agaagtgaga | cacaaactga | agataacaga | gaatagtttt | 780 |
| gagcaaataa | catttatgca | agccttacat | ctattgcttg | aagtggagca | agagataaga | 840 |
| actttctcgt | ttcagcttat | ttaataataa | aaaacaccct | tgtttctact | | 890 |

<210> SEQ ID NO 63
<211> LENGTH: 890
<212> TYPE: DNA
<213> ORGANISM: unknown
<220> FEATURE:
<223> OTHER INFORMATION: synthetic

<400> SEQUENCE: 63

| | | | | | |
|---|---|---|---|---|---|
| agcaaaagca | gggtgacaaa | gacataatgg | atccaaacac | tgtgtcaagc | tttcaggtag | 60 |
| attgctttct | ttggcatgtc | cgcaaacgag | ttgcagacca | agaactaggt | gatgccccat | 120 |
| tccttgaccg | actgagacgg | gatcagaaat | ccctaggggg | caggggatcg | accctaggcc | 180 |
| tagacatcga | aaccgcaact | agggccggaa | agcagatcgt | ggagcgtata | ctgaaagagg | 240 |
| agtccgacga | agcgcttaag | atgactatgg | ccagcgtacc | cgctagtcgg | taccttaccg | 300 |
| atatgacact | cgaagagatg | tcacgcgatt | ggtctatgct | aatccctaag | cagaaagtgg | 360 |
| ccggacctct | atgtatacgg | atggaccagg | cgattatgga | caaaaacatt | atccttaaag | 420 |
| cgaacttttc | cgtgatattc | gatcgcctag | agactctgat | actgttgcgt | gcattcacag | 480 |
| aagagggagc | aattgttggc | gaaatttcac | cattgccttc | tcttccagga | catactgctg | 540 |
| aggatgtcaa | aaatgcagtt | ggagtcctca | tcggggact | tgaatggaat | gataacacag | 600 |
| ttcgagtctc | tgaaactcta | cagagattcg | cttggagaag | cagtaatgag | aatgggagac | 660 |
| ctccactcac | tccaaaacag | aaacgagaaa | tggcgggaac | aattaggtca | gaagtttgaa | 720 |
| gaaataagat | ggttgattga | agaagtgaga | cacaaactga | agataacaga | gaatagtttt | 780 |
| gagcaaataa | catttatgca | agccttacat | ctattgcttg | aagtggagca | agagataaga | 840 |
| actttctcgt | ttcagcttat | ttaataataa | aaaacaccct | tgtttctact | | 890 |

ATTENUATED INFLUENZA VIRUSES AND VACCINES

CROSS-REFERENCE TO RELATED APPLICATIONS

This application is a continuation of U.S. application Ser. No. 14/777,204, filed Sep. 15, 2015, which is a 371 of PCT/US2014/030027, filed Mar. 15, 2014, which claims the benefit of priority to U.S. Application No. 61/794,617, filed Mar. 15, 2013, all of which are incorporated herein by reference in their entireties.

FEDERAL FUNDING

This invention was made with government support under AI015122 and AI075219 awarded the National Institutes of Health. The government has certain rights in the invention.

FIELD OF THE INVENTION

This invention provides highly attenuated influenza viruses and vaccines. The attenuated viruses and vaccines proliferate well and have high safety factors. The attenuated viruses providing protective immunity from challenge by virus of the same subtype, as well as cross protection against heterologous viruses.

BACKGROUND OF THE INVENTION

Influenza is a human disease that leads every year to >30,000 deaths in the US and several hundred thousand deaths globally (1). Major neutralization antigenic proteins, hemagglutinin (HA) and neuraminidase (NA) on the virion surface, provide protecting immunity, but undergo yearly genetic variation by point mutations (genetic drift). This renders the viruses resistant to population immunity and set the stage for seasonal epidemics. Further, influenza virus may acquire a new antigenic make-up (reassortment of heterologous genes, referred to as genetic shift) leading to pandemics. Because the flu is seasonal and variable, new vaccines must be produced every year. This is made more complex since more than one type or strain of influenza virus co-circulates in any flu season, a phenomenon demanding that more than one new vaccine may have to be developed every year.

Currently, only two major types of vaccines are licensed, the intramuscularly administered inactivated vaccines ("Flu shot"), and the live attenuated vaccine (LAIV), given intranasally ("FluMist®"). The efficacy of the two vaccines is suboptimal. The injectable inactivated vaccines that requires a large quantity of starting material (the equivalent of approximately $10^{10}$ plaque-forming units, PFU, per dose), are incapable of inducing significant cell-mediated immunity, which is being recognized as an important determinant of protection (4). Moreover, the overall efficacy of the inactivated vaccine in the U.S. adult population aged 18-65 years is only 59% (5). The LAIV "FluMist," on the other hand, induces both humoral and cellular immunity but it is restricted in use to people 2 to 49 yr of age (6, 7). Moreover, recurrent administration of LAIV, which always uses the same attenuating viral backbone, could result in tolerance in repeat recipients (8).

Influenza viruses that have been classified as type A, B, and C, are enveloped, negative-strand RNA viruses of Orthomyxoviridae of which subtypes of type A are the major culprit of human disease (3). The viruses transcribe and replicate their multipartite genome in the cell nucleus, each segment encoding one or two polypeptides. Of these the most important antigenic molecules are the glycoproteins hemagglutinin (HA) and neuraminidase (NA).

SUMMARY OF THE INVENTION

A long-held dogma posits that strong presentation to the immune system of the dominant influenza virus glycoprotein antigens hemagglutinin (HA) and neuraminidase (NA) is paramount for inducing protective immunity against influenza virus infection. It has now been discovered that attenuated viruses in which expression of the two dominant influenza virus glycoprotein antigens, HA and NA, is reduced, are highly effective in providing long lasting protective immunity against lethal wild type challenge and cross protection against diverse subtypes. Further, the viruses have exceptional safety profiles. Accordingly, the invention provides an attenuated influenza virus in which expression of hemagglutinin (HA) and neuraminidase (NA) is reduced. In certain embodiments, HA and NA are the only the only virus proteins having reduced expression. In other embodiments of the invention, the expression of one or more other virus proteins may also be reduced, such as, for example, PA, PB1, PB2, NP, NS, Ml, or M2. In certain embodiments, when the expression of a virus proteins other than HA and NA is reduced, the reduction is small compared to the reduction of HA and NA. According to the invention, reduction in expression of virus proteins of the invention is accomplished by changes in protein encoding sequence, for example by lowering the codon pair bias of the protein-encoding sequence, substituting rare codons, modifying G+C content, modifying CG and/or TA (or UA) dinucleotide content, or combinations. Reduced expression can also be accomplished by modifications to the regulatory sequences of the proteins.

In one such embodiment, reducing the codon-pair bias comprises identifying a codon pair in the parent protein-encoding sequence having a codon-pair score that can be reduced, and reducing the codon-pair bias by substituting the codon pair with a codon pair that has a lower codon-pair score. In another such embodiment, reducing the codon-pair bias comprises rearranging the codons of a parent protein-encoding sequence. In certain embodiments, the reduced-expression HA protein-encoding sequence and the reduced-expression NA protein-encoding sequence individually have a codon pair bias less than −0.1, or less than −0.2, or less than −0.3, or less than −0.4. Codon pair bias of a protein-encoding sequence (i.e., an open reading frame) is calculated as described in Coleman et al., 2000 (ref 12) and herein.

In an embodiment of the invention, expression of one or both of the HA protein-encoding sequence and the NA protein-encoding sequence is reduced by replacing one or more codons with synonymous codons that are less frequent in the host.

The invention further provides an influenza vaccine composition for inducing a protective immune response in a subject, wherein the vaccine composition comprises virus in which expression of HA is reduced and expression of NA is reduced. In certain embodiments, only expression of HA and NA is reduced. In some embodiments, expression of another virus protein is also reduced.

The invention also provides a method of eliciting a protective immune response in a subject comprising administering to the subject a prophylactically or therapeutically effective dose of a vaccine composition comprising an attenuated influenza virus, wherein expression of HA is reduced and expression of NA is reduced. In certain embodiments, only expression of HA and NA is reduced. In some embodiments, expression of another virus protein is also reduced. In an embodiment of the invention, an immune response is elicited that is effective against influenza of the same subtype as the attenuated virus of the vaccine. In another embodiment, an immune response is elicited that is effective against a heterologous influenza virus.

The invention also provides a method of making an attenuated influenza virus genome comprising a) obtaining the nucleotide sequence encoding the hemagglutinin protein of an influenza virus and the nucleotide sequence encoding the neuraminidase protein of an influenza virus, b) recoding the hemagglutinin-encoding nucleotide sequence to reduce expression and recoding the neuraminidase-encoding nucleotide sequence to reduce expression, and substituting the recoded nucleotide sequences into an influenza virus genome to make an attenuated influenza virus genome. In certain embodiments, only expression of HA and NA is reduced. In some embodiments, expression of another virus protein is also reduced.

DESCRIPTION OF THE FIGURES

(FIG. 1A) $NA^{Min}$ and $HA^{Min}$ were designed (leaving 120-200 nt long wt sequences at 5' and 3' ends) and constructed by chemical synthesis. They were then used to replace by reverse genetics (13) one or two corresponding genes of wt PR8. The number of synonymous mutations is shown. (FIG. 1B) Recovered viruses were analyzed for plaque size phenotypes on MDCK monolayers. (FIG. 1C) Growth kinetics of wt PR8 and reduced codon-pair bias variants were analyzed on MDCK cells after infections at an MOI of 0.01. Every three hours post-infection, cell supernatants were collected and analyzed for virus titers by plaque assays. (FIG. 1D) Growth kinetics of wt PR8 and $(NA+HA)^{Min}$ virus in A549 cells. Cells were infected at an MOI of 1.

FIGS. 2A-2B. Protein expression and mRNA levels in $(NA+HA)^{Min}$-infected in tissue culture cells. MDCK cells were infected with $(NA+HA)^{Min}$ or wt PR8 at a MOI of 5. (FIG. 2A) Western blot analyses were performed to determine the viral protein expression the infected cells at 3 h and 6 h p.i. (FIG. 2B) Northern blot analyses were performed to determine mRNA levels of HA, NA, PB1 and GAPDH in $(NA+HA)^{Min}$ or wt PR8-infected MDCK cells. At 3, 6, and 9 h p.i., cytoplasmic mRNA were collected and analyzed. For $HA^{Min}$ and $HA^{WT}$ transcript probes, the same 150 nt that recognized the common 3' end of the respective genes was used. Similarly, the probes for $NA^{Min}$ and $NA^{WT}$ have the same 150 nt sequence corresponding to the common 3' end of the NA genes.

(FIGS. 3A and 3B) Measurement of the median lethal dose ($LD_{50}$). Groups of five male Balb/C mice were intranasally infected with the $(NA+HA)^{Min}$ variant at $10^4$, $10^5$, or $10^6$ PFU and the relative body weight and survival rate were monitored for 14 days p.i. Mice that lost 25% of their body weight were euthanized. $LD_{50}$ was calculated based on the method of Reed-Muench (24). (FIGS. 3C and 3D) Measurement of the median protective dose ($PD_{50}$). Groups of five male Balb/C mice were vaccinated with $10^2$, $10^1$, or $10^0$ PFU of $(NA+HA)^{Min}$ on day 0. On day 28 post vaccination, all mice were challenged with $10^5$ PFU wt PR8 virus. The relative body weight and survival rate after challenge were monitored. $PD_{50}$ was calculated based on the method of Reed-Muench (24). (FIGS. 3E and 3F) Safe and effective vaccine range of the $(NA+HA)^{Min}$ (open box) and wt PR8 virus (gray zone) were plotted. Any vaccine dose within this region warranted survival of the animals, and also completely protected them from lethal homogeneous challenge. Error bars represent SD.

(FIG. 4A) Groups of three male Balb/C mice were infected with $10^4$ PFU of wt PR8 or $(NA+HA)^{Min}$. On day 1, 3, 5, 7, 9 and 11 p.i., the mice were euthanized and their lungs harvested and homogenized. Viral titers in the homogenates were determined by plaque assays on MDCK cells. * All wt PR8-infected mice were dead on day 5. ‡ The virus titers in $(NA+HA)^{Min}$-infected mice after day 9 were undetectable (less than 4 PFU). (FIG. 4B) Comparison of virus titers in lungs of three mice each infected with wt PR8 or $(NA+HA)^{Min}$ at a dose from $10^1$ to $10^4$ PFU. The lungs of the animals were harvest on day 3, and plaque assays were performed to determine virus titers. Error bars represent SD.

(FIGS. 5C and 5D) Mice vaccinated with $(NA+HA)^{Min}$ virus were also challenged with 100 $LD_{50}$ A/Victoria/3/75 (H3N2) virus (=$3.2 \times 10^4$ PFU). Survival rate and relative body weights were monitored for 14 days. All mice vaccinated with at least $10^3$ PFU of $(NA+HA)^{Min}$(H1N1) survived the lethal challenge. The cross protection $PD_{50}$ against H3N2 Victoria virus calculated is 147 PFU based on the method of Reed-Muench (24). Error bars represent SD.

(FIGS. 7A and 7B) Groups of five male Balb/c mice were infected intranasally with different doses of $NA^{Min}$ variant. The relative body weight and survival rate were monitored for 14 days. The $LD_{50}$ calculated was $2.4 \times 10^5$ PFU. (C and D) Groups of five males were vaccinated with different dose of $NA^{Min}$ variant, 28 days p.i., mice were challenged with $10^5$ PFU wt influenza A/PR/8/34 (PR8). The relative body weight and survival rate were monitored for 14 days. Error bars represent SD.

(FIG. 9A) Commassie stain. (FIGS. 9B and 9C) silver stain. (FIG. 9D) Western blot.

(FIG. 10A) $^{35}$S labeled proteins in infected MDCK cells. (FIG. 10B) Northern analysis of viral mRNAs expressed in infected MDCK.

FIG. 11 shows mice passively immunized with PR8-(NA+HA)$^{Min}$ sera survived and remained healthy upon challenge with WT virus.

FIG. 11 shows mice passively immunized with PR8-(NA+HA)$^{Min}$ sera maintained weight (Panel A) and had improved survival (Panel B) when challenged with H3N2 virus.

(FIG. 13A) Inhibition of hemagglutination by sera from PR8-(NA+HA)$^{Min}$ immunized mice. (FIG. 13B) Neutralization of virus infection of MDCK cells by sera from PR8-(NA+HA)$^{Min}$ immunized mice.

FIGS. 19A-19I. Immune cell infiltration of lung tissue 3 days post-infection. (FIG. 19A) CD45$^+$ leukocytes, (FIG. 19B) CD45$^+$ Ly6G$^{high}$ polymorphonuclear leukocytes (PMN), (FIG. 19C) CD45$^+$CD11c$^+$ I-A$^{d+}$ F4/80$^-$ dendritic cells, (FIG. 19D) CD45$^+$ NKp46+ natural killer cells, (FIG. 19E) CD45$^+$CD11b$^+$Ly6C$^{high}$Ly6G$^-$ inflammatory monocytes, (FIG. 19F) CD45$^+$ I-A$^{d+}$ F4/80$^+$ macrophages, (G) CD45$^+$CD3$^+$CD4$^+$ T helper cells, (FIG. 19H) CD45$^+$ CD19$^+$ B cells, and (FIG. 19I) CD45$^+$CD19$^+$IgM$^+$ B cells.

DETAILED DESCRIPTION

Figure 1A:
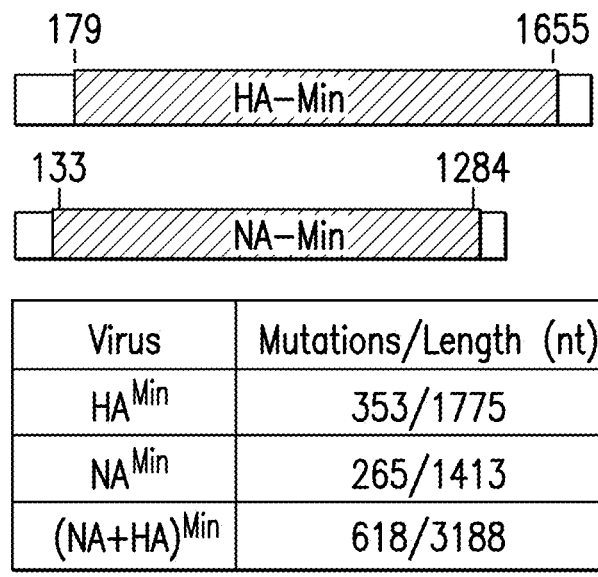
FIGS. 1A-1D. Construction of variants having reduced codon pair bias and phenotypes in tissue cultures.

The present invention relates to the production of attenuated influenza viruses that can be used to protect against viral infection and disease. A basic premise in flu vaccination is adequate delivery of HA and NA to vaccine recipients assuming that a very high dose ("Flu shot") or a dose corresponding to live viral infection ("FluMist") of these traditionally dominant antigenic polypeptides alone are sufficient for adequate vaccine efficacy. Those expectations aside, the present invention benefits from a contrary approach. The invention provides attenuated influenza viruses in which expression of HA and NA is reduced, which have excellent growth properties useful to vaccine production, yet possess an extraordinary safety profile and enhanced protective characteristics. The attenuated viruses proliferate nearly as well as wild type virus, have highly attenuated phenotypes, as revealed by LD$_{50}$ values, are unusually effective in providing protective immunity against challenge by influenza virus of the same subtype, and also provide protective immunity against challenge by influenza virus of other subtypes.

In certain attenuated viruses of the invention, the expression of one or more other virus proteins may also be reduced, such as, for example, PA, PB1, PB2, NP, NS, M1, or M2. In certain embodiments, when the expression of a virus proteins other than HA and NA is reduced, the reduction is small compared to the reduction of HA and NA.

In certain attenuated influenza viruses of the invention, expression of hemagglutinin (HA) and neuraminidase (NA) is reduced, and expression of other influenza proteins (i.e., NP, M (including M1 and M2), NS, PA, PB1, and PB2 protein is not substantially changed (i.e., substantially reduced or increased). In an embodiment of the invention, expression of NP, PA, PB1, and PB2 is not substantially reduced. That expression of the NP, M (including M1 and M2), NS, PA, PB1, and PB2 protein encoding sequences is not substantially reduced means that in embodiments where there is a small change in expression of one or more of those proteins (e.g., NP, PA, PB1, PB2, M, and or M), the change in expression of those proteins has little or no effect on attenuation. Little or no effect on attenuation includes one or both of the following: 1) Any reduced expression of NP, M (including M1 and M2), NS, PA, PB1, or PB2 does not reduce viral replication or viral infectivity more than 20% when the NP, M (including M1 and M2), NS, PA, PB1, or PB2 is expressed at the reduced level in a test influenza virus in which only the level of that protein is reduced; 2) The level of expression of NP, M (including M1 and M2), NS, PA, PB1, or PB2 is reduced by less than 20% in the attenuated virus in which expression of HA and NA is reduced.

In certain embodiments of the invention, the attenuated influenza viruses of the invention comprise a recoded hemagglutinin (HA) nucleic acid and a recoded neuraminidase (NA) nucleic acid. In certain of these embodiments, another virus protein, such as NP, M (including M1 and M2), NS, PA, PB1, or PB2, is recoded. In others of these embodiments, other protein encoding sequences (i.e., NP, M (including M1 and M2), NS, PA, PB1, and PB2 protein encoding sequences are not recoded. That the NP, M (including M1 and M2), NS, PA, PB1, and PB2 protein encoding sequences are not recoded does not exclude mutations and other variations in those sequences, but only means that any mutations or variations made in those sequences have little or no effect on attenuation. Little or no effect on attenuation includes one or both of the following: 1) The mutations or variations in the NP, M (including M1 and M2), NS, PA, PB1, or PB2 sequence do not reduce viral replication or viral infectivity more than 20% when the variant NP, M (including M1 and M2), NS, PA, PB1, or PB2 nucleic acid sequence is the only variant in a test influenza virus; 2) Mutations or variations in any of the NP, M (including M1 and M2), NS, PA, PB1, or PB2 nucleic acid represent fewer than 10% of the nucleotides in that coding sequence.

The viruses of the invention are highly attenuated. In embodiments of the invention, compared to wild type, the viruses are at least 5,000 fold attenuated, or at least 10,000 fold attenuated, or at least 20,000 fold attenuated, or at least 33,000 fold attenuated, or at least 50,000 fold attenuated, of at least 100,000 fold attenuated in the BALB/c mouse model compared to a wild type virus having proteins of the same sequence but encoded by a different nucleotide sequence.

The attenuated viruses are also highly protective against wild type virus of the same subtype. In embodiments of the invention, the protective dose (PD$_{50}$) of the viruses is less than 100 PFU, or less than 50 PFU, or less than 20 PFU, or less than 10 PFU, or less than 5 PFU, when measured by a mouse model, such as exemplified herein.

The attenuated viruses of the invention also exhibit a large margin of safety (i.e., the difference between $LD_{50}$ and $PD_{50}$), thus have high safety factors, defined herein as the ratio of $LD_{50}/PD_{50}$. In certain embodiments of the invention, the safety factor is at least $10^2$, or at least $10^3$, or at least $10^4$, or at least $10^5$, or at least $2\times10^5$, or at least $5\times10^5$, or at least $10^6$, or at least $2\times10^6$, or at least $5\times10^6$. In certain embodiments, the safety factor is from $10^2$ to $10^3$, or from $10^3$ to $10^4$, or from $10^4$ to $10^5$, or from $10^5$ to $10^6$.

The attenuated viruses of the invention are also highly protective against heterologous viruses. In certain embodiments of the invention, the protective dose ($PD_{50}$) of an attenuated virus of the invention is less than 1000 PFU, or less than 500 PFU, or less than 200 PFU, or less than 100 PFU, when measured by a mouse model, such as exemplified herein The recoding of HA and NA protein encoding sequences of the attenuated viruses of the invention can have been made utilizing any algorithm or procedure known in the art or newly devised for recoding a protein encoding sequence. According to the invention, nucleotide substitutions are engineered in multiple locations in the HA and NA coding sequences, wherein the substitutions introduce a plurality of synonymous codons into the genome. In certain embodiments, the synonymous codon substitutions alter codon bias, codon pair bias, the density of infrequent codons or infrequently occurring codon pairs, RNA secondary structure, CG and/or TA (or UA) dinucleotide content, C+G content, translation frameshift sites, translation pause sites, the presence or absence microRNA recognition sequences or any combination thereof, in the genome. The codon substitutions may be engineered in multiple locations distributed throughout the HA and NA coding sequences, or in the multiple locations restricted to a portion of the HA and NA coding sequences. Because of the large number of defects (i.e., nucleotide substitutions) involved, the invention provides a means of producing stably attenuated viruses and live vaccines.

As discussed further below, in some embodiments, a virus coding sequence is recoded by substituting one or more codon with synonymous codons used less frequently in the influenza host (e.g., humans, birds, pigs). In some embodiments, a virus coding sequence is recoded by substituting one or more codons with synonymous codons used less frequently in the influenza virus. In certain embodiments, the number of codons substituted with synonymous codons is at least 5. In some embodiments, at least 10, or at least 20 codons are substituted with synonymous codons.

In some embodiments, virus codon pairs are recoded to reduce (i.e., lower the value of) codon-pair bias. In certain embodiments, codon-pair bias is reduced by identifying a codon pair in an HA or NA coding sequence having a codon-pair score that can be reduced and reducing the codon-pair bias by substituting the codon pair with a codon pair that has a lower codon-pair score. In some embodiments, this substitution of codon pairs takes the form of rearranging existing codons of a sequence. In some such embodiments, a subset of codon pairs is substituted by rearranging a subset of synonymous codons. In other embodiments, codon pairs are substituted by maximizing the number of rearranged synonymous codons. It is noted that while rearrangement of codons leads to codon-pair bias that is reduced (made more negative) for the virus coding sequence overall, and the rearrangement results in a decreased CPS at many locations, there may accompanying CPS increases at other locations, but on average, the codon pair scores, and thus the CPB of the modified sequence, is reduced. In some embodiments, recoding of codons or codon-pairs can take into account altering the G+C content of the HA and NA coding sequences. In some embodiments, recoding of codons or codon-pairs can take into account altering the frequency of CG and/or TA dinucleotides in the HA and NA coding sequences.

In certain embodiments, the recoded (i.e., reduced-expression) HA protein-encoding sequence has a codon pair bias less than −0.1, or less than −0.2, or less than −0.3, or less than −0.4. In certain embodiments, the recoded (i.e., reduced-expression) NA protein-encoding sequence has a codon pair bias less than −0.1, or less than −0.2, or less than −0.3, or less than −0.4. In certain embodiments, the codon pair bias of the recoded HA protein encoding sequence is reduced by at least 0.1, or at least 0.2, or at least 0.3, or at least 0.4, compared to the parent HA protein encoding sequence from which it is derived. In certain embodiments, the codon pair bias of the recoded NA protein encoding sequence is reduced by at least 0.1, or at least 0.2, or at least 0.3, or at least 0.4, compared to the parent NA protein encoding sequence from which it is derived. In certain embodiments, rearrangement of synonymous codons of the HA protein-encoding sequence provides a codon-pair bias reduction of at least 0.1, or at least 0.2, or at least 0.3, or at least 0.4, parent HA protein encoding sequence from which it is derived. In certain embodiments, rearrangement of synonymous codons of the NA protein-encoding sequence provides a codon-pair bias reduction of at least 0.1, or at least 0.2, or at least 0.3, or at least 0.4, parent NA protein encoding sequence from which it is derived.

Usually, these substitutions and alterations are made and reduce expression of the encoded virus proteins without altering the amino acid sequence of the encoded protein. In certain embodiments, the invention also includes alterations in the HA and/or NA coding sequences that result in substitution of non-synonymous codons an amino acid substitutions in the encoded protein, which may or may not be conservative.

Most amino acids are encoded by more than one codon. See the genetic code in Table 1. For instance, alanine is encoded by GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy.

TABLE 1

| | Genetic Code[a] | | | | |
|---|---|---|---|---|---|
| | U | C | A | G | |
| U | Phe | Ser | Tyr | Cys | U |
| | Phe | Ser | Tyr | Cys | C |
| | Leu | Ser | STOP | STOP | A |
| | Leu | Ser | STOP | Trp | G |

TABLE 1-continued

Genetic Code[a]

|   | U | C | A | G |   |
|---|---|---|---|---|---|
| C | Leu | Pro | His | Arg | U |
|   | Leu | Pro | His | Arg | C |
|   | Leu | Pro | Gln | Arg | A |
|   | Leu | Pro | Gln | Arg | G |
| A | Ile | Thr | Asn | Ser | U |
|   | Ile | Thr | Asn | Ser | C |
|   | Ile | Thr | Lys | Arg | A |
|   | Met | Thr | Lys | Arg | G |
| G | Val | Ala | Asp | Gly | U |
|   | Val | Ala | Asp | Gly | C |
|   | Val | Ala | Glu | Gly | A |
|   | Val | Ala | Glu | Gly | G |

[a]The first nucleotide in each codon encoding a particular amino acid is shown in the left-most column; the second nucleotide is shown in the top row; and the third nucleotide is shown in the right-most column.

Codon Bias

As used herein, a "rare" codon is one of at least two synonymous codons encoding a particular amino acid that is present in an mRNA at a significantly lower frequency than the most frequently used codon for that amino acid. Thus, the rare codon may be present at about a 2-fold lower frequency than the most frequently used codon. Preferably, the rare codon is present at least a 3-fold, more preferably at least a 5-fold, lower frequency than the most frequently used codon for the amino acid. Conversely, a "frequent" codon is one of at least two synonymous codons encoding a particular amino acid that is present in an mRNA at a significantly higher frequency than the least frequently used codon for that amino acid. The frequent codon may be present at about a 2-fold, preferably at least a 3-fold, more preferably at least a 5-fold, higher frequency than the least frequently used codon for the amino acid. For example, human genes use the leucine codon CTG 40% of the time, but use the synonymous CTA only 7% of the time (see Table 2). Thus, CTG is a frequent codon, whereas CTA is a rare codon. Roughly consistent with these frequencies of usage, there are 6 copies in the genome for the gene for the tRNA recognizing CTG, whereas there are only 2 copies of the gene for the tRNA recognizing CTA. Similarly, human genes use the frequent codons TCT and TCC for serine 18% and 22% of the time, respectively, but the rare codon TCG only 5% of the time. TCT and TCC are read, via wobble, by the same tRNA, which has 10 copies of its gene in the genome, while TCG is read by a tRNA with only 4 copies. It is well known that those mRNAs that are very actively translated are strongly biased to use only the most frequent codons. This includes genes for ribosomal proteins and glycolytic enzymes. On the other hand, mRNAs for relatively non-abundant proteins may use the rare codons.

TABLE 2

Codon usage in Homo sapiens (source: http://www.kazusa.or.jp/codon/)

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |
| Arg | AGG | 461676.00 | 11.93 | 0.21 |
| Arg | AGA | 466435.00 | 12.06 | 0.21 |
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

The propensity for highly expressed genes to use frequent codons is called "codon bias." A gene for a ribosomal protein might use only the 20 to 25 most frequent of the 61 codons, and have a high codon bias (a codon bias close to 1), while a poorly expressed gene might use all 61 codons, and have little or no codon bias (a codon bias close to 0). It is thought that the frequently used codons are codons where larger amounts of the cognate tRNA are expressed, and that use of these codons allows translation to proceed more rapidly, or more accurately, or both. The PV capsid protein, for example, is very actively translated, and has a high codon bias.

Codon Pair Bias

In addition, a given organism has a preference for the nearest codon neighbor of a given codon A, referred to a bias in codon pair utilization. A change of codon pair bias, without changing the existing codons, can influence the rate of protein synthesis and production of a protein.

Codon pair bias may be illustrated by considering the amino acid pair Ala-Glu, which can be encoded by 8 different codon pairs. If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation the codon pair GCA-GAA would be expected to occur at a frequency of 0.097 out of all Ala-Glu coding pairs (0.23×0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. This set of genes is the most comprehensive representation of human coding sequences. Using this set of genes the frequencies of codon usage were re-calculated by dividing the number of occurrences of a codon by the number of all synonymous codons coding for the same amino acid. As expected the frequencies correlated closely with previously published ones such as the ones given in Table 2. Slight frequency variations are possibly due to an oversampling effect in the data provided by the codon usage database at Kazusa DNA Research Institute (http://www.kazusa.or.jp/codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 3 expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.097 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 3; observed frequency). Frequency and observed/expected values for the complete set of 3721 ($61^2$) codon pairs, based on the set of 14,795 human genes, are provided herewith as Supplemental Table 1.

TABLE 3

Codon Pair Scores Exemplified by the Amino Acid Pair Ala-Glu

| amino acid pair | codon pair | expected frequency | observed frequency | obs/exp ratio |
|---|---|---|---|---|
| AE | GCAGAA | 0.098 | 0.163 | 1.65 |
| AE | GCAGAG | 0.132 | 0.198 | 1.51 |
| AE | GCCGAA | 0.171 | 0.031 | 0.18 |
| AE | GCCGAG | 0.229 | 0.142 | 0.62 |
| AE | GCGGAA | 0.046 | 0.027 | 0.57 |
| AE | GCGGAG | 0.062 | 0.089 | 1.44 |

TABLE 3-continued

Codon Pair Scores Exemplified by the Amino Acid Pair Ala-Glu

| amino acid pair | codon pair | expected frequency | observed frequency | obs/exp ratio |
|---|---|---|---|---|
| AE | GCTGAA | 0.112 | 0.145 | 1.29 |
| AE | GCTGAG | 0.150 | 0.206 | 1.37 |
| Total | | 1.000 | 1.000 | |

If the ratio of observed frequency/expected frequency of the codon pair is greater than one the codon pair is said to be overrepresented. If the ratio is smaller than one, it is said to be underrepresented. In the example the codon pair GCA-GAA is overrepresented 1.65 fold while the coding pair GCC-GAA is more than 5-fold underrepresented.

Many other codon pairs show very strong bias; some pairs are under-represented, while other pairs are over-represented. For instance, the codon pairs GCCGAA (AlaGlu) and GATCTG (AspLeu) are three- to six-fold under-represented (the preferred pairs being GCAGAG and GACCTG, respectively), while the codon pairs GCCAAG (AlaLys) and AATGAA (AsnGlu) are about two-fold over-represented. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

As discussed more fully below, codon pair bias takes into account the score for each codon pair in a coding sequence averaged over the entire length of the coding sequence. According to the invention, codon pair bias is determined by $$CPB = \sum_{i=1}^{k} \frac{CPSi}{k-1}.$$

Accordingly, similar codon pair bias for a coding sequence can be obtained, for example, by minimized codon pair scores over a subsequence or moderately diminished codon pair scores over the full length of the coding sequence.

Calculation of Codon Pair Bias.

Every individual codon pair of the possible 3721 non-"STOP" containing codon pairs (e.g., GTT-GCT) carries an assigned "codon pair score," or "CPS" that is specific for a given "training set" of genes. The CPS of a given codon pair is defined as the log ratio of the observed number of occurances over the number that would have been expected in this set of genes (in this example the human genome). Determining the actual number of occurrences of a particular codon pair (or in other words the likelyhood of a particular amino acid pair being encoded by a particular codon pair) is simply a matter of counting the actual number of occurances of a codon pair in a particular set of coding sequences. Determining the expected number, however, requires additional calculations. The expected number is calculated so as to be independent of both amino acid frequency and codon bias similarly to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically underrepresented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale.

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair.

$$S(P_{ij}) = \ln\left(\frac{N_O(P_{ij})}{N_E(P_{ij})}\right) = \ln\left(\frac{N_O(P_{ij})}{F(C_i)F(C_j)N_O(X_{ij})}\right)$$

In the calculation, $P_{ij}$ is a codon pair occurring with a frequency of $N_O(P_{ij})$ in its synonymous group. $C_i$ and $C_j$ are the two codons comprising $P_{ij}$, occuring with frequencies $F(C_i)$ and $F(C_j)$ in their synonymous groups respectively. More explicitly, $F(C_i)$ is the frequency that corresponding amino acid $X_i$ is coded by codon $C_i$ throughout all coding regions and $F(C_i)=N_O(C_i)/N_O(X_i)$, where $N_O(C_i)$ and $N_O(X_i)$ are the observed number of occurrences of codon $C_i$ and amino acid $X_i$ respectively. $F(C_j)$ is calculated accordingly. Further, $N_O(X_{ij})$ is the number of occurrences of amino acid pair $X_{ij}$ throughout all coding regions. The codon pair bias score $S(P_{ij})$ of $P_{ij}$ was calculated as the log-odds ratio of the observed frequency $N_O(P_{ij})$ over the expected number of occurrences of $N_e(P_{ij})$.

Using the formula above, it was then determined whether individual codon pairs in individual coding sequences are over- or under-represented when compared to the corresponding genomic $N_e(P_{ij})$ values that were calculated by using the entire human CCDS data set. This calculation resulted in positive $S(P_{ij})$ score values for over-represented and negative values for under-represented codon pairs in the human coding regions (FIG. 7).

The "combined" codon pair bias of an individual coding sequence was calculated by averaging all codon pair scores according to the following formula:

$$S(P_{ij}) = \sum_{l=1}^{k} \frac{S(Pij)l}{k-1}.$$

The codon pair bias of an entire coding region is thus calculated by adding all of the individual codon pair scores comprising the region and dividing this sum by the length of the coding sequence.

Calculation of Codon Pair Bias, Implementation of Algorithm to Alter Codon-Pair Bias.

An algorithm was developed to quantify codon pair bias. Every possible individual codon pair was given a "codon pair score", or "CPS". CPS is defined as the natural log of the ratio of the observed over the expected number of occurrences of each codon pair over all human coding regions, where humans represent the host species of the instant vaccine virus to be recoded.

$$CPS = \ln\left(\frac{F(AB)o}{\frac{F(A) \times F(B)}{F(X) \times F(Y)} \times F(XY)}\right)$$

Although the calculation of the observed occurences of a particular codon pair is straightforward (the actual count within the gene set), the expected number of occurrences of a codon pair requires additional calculation. We calculate this expected number to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome Using these calculated CPSs, any coding region can then be rated as using over- or under-represented codon pairs by taking the average of the codon pair scores, thus giving a Codon Pair Bias (CPB) for the entire gene.

$$CPB = \sum_{i=1}^{k} \frac{CPSi}{k-1}$$

Figure 4A:
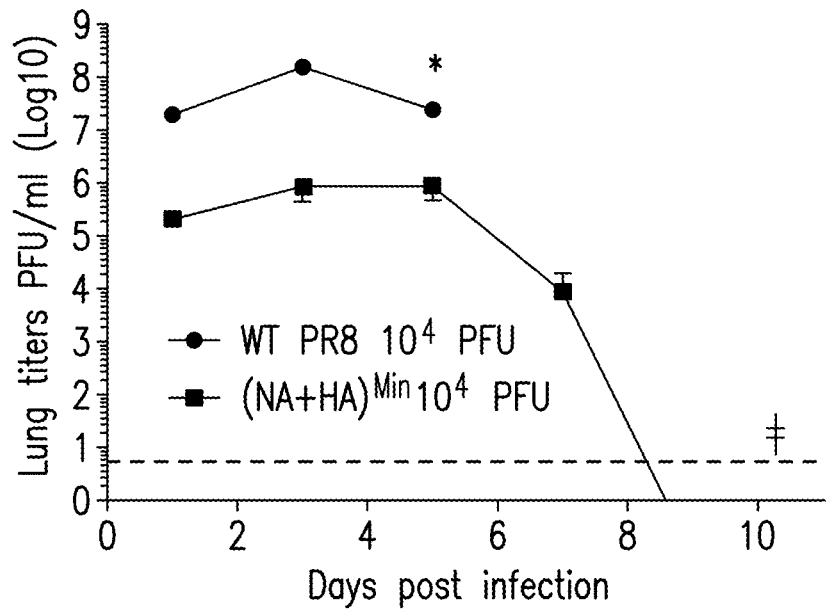
FIGS. 4A-4B. Virus titers in lungs of infected mice.
Figure 4B:
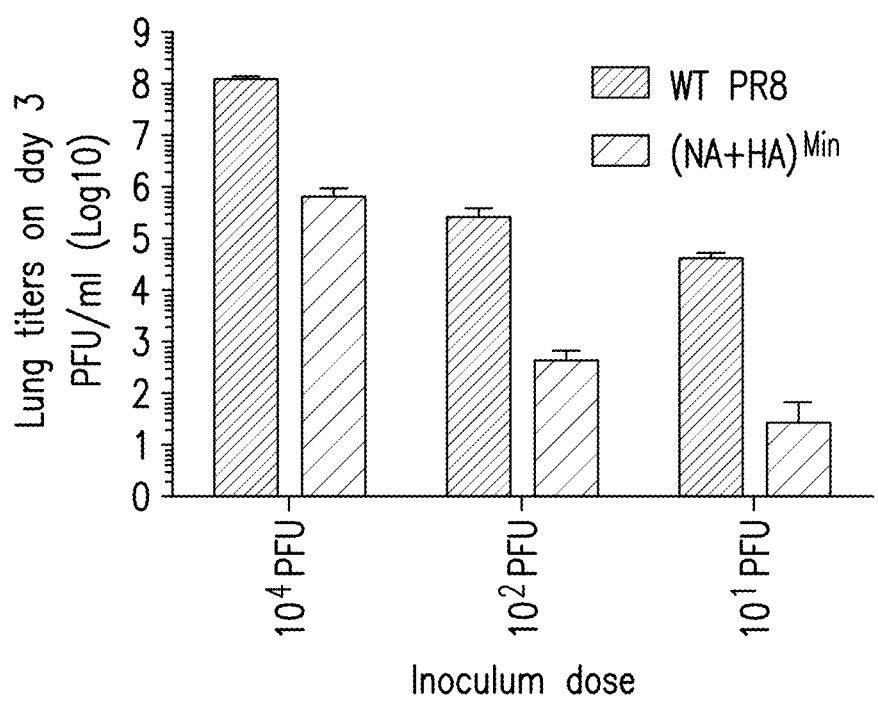
Figure 5A:
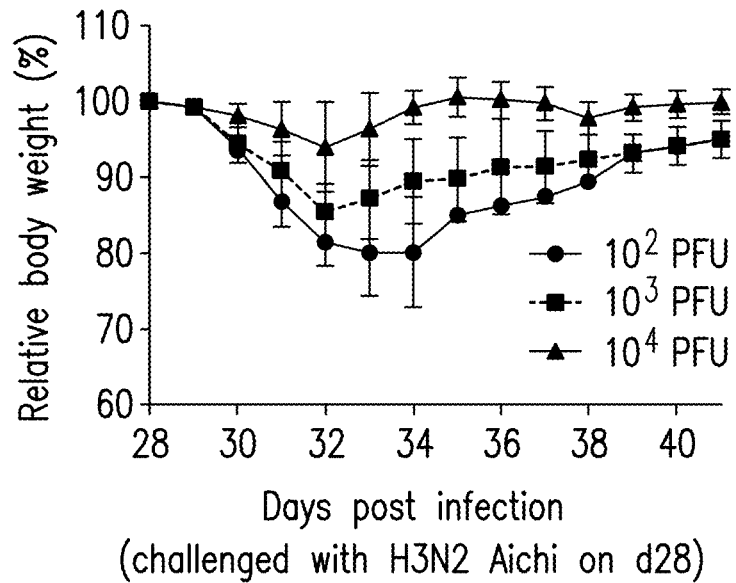
FIGS. 5A-5D. Cross protection against H3N2 virus infections in $(NA+HA)^{Min}$(H1N1)-vaccinated mice. Groups of five Balb/c mice were vaccinated with $(NA+HA)^{Min}$ at different doses. On day 28 post vaccination, mice were challenged with (FIGS. 5A and 5B) 100 $LD_{50}$ heterologous viruses A/Aichi/2/1968 (H3N2) virus (=$1.5 \times 10^4$ PFU). Survival rate and relative body weights were monitored for 14 days. All mice vaccinated with at least $10^3$ PFU of $(NA+HA)^{Min}$(H1N1) survived the lethal challenge. The cross protection $PD_{50}$ against H3N2 Aichi virus calculated is 237 PFU.
Figure 5B:
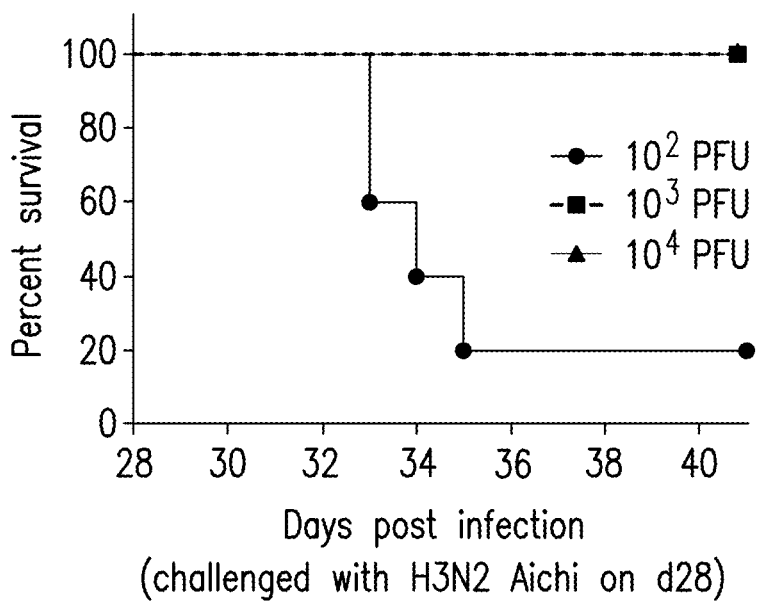
Figure 5C:
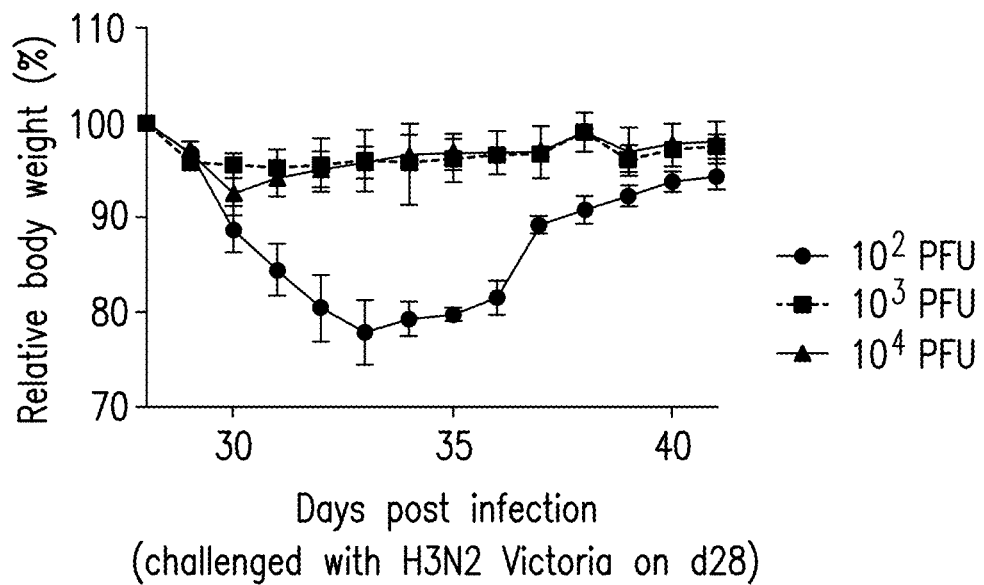
Figure 5D:
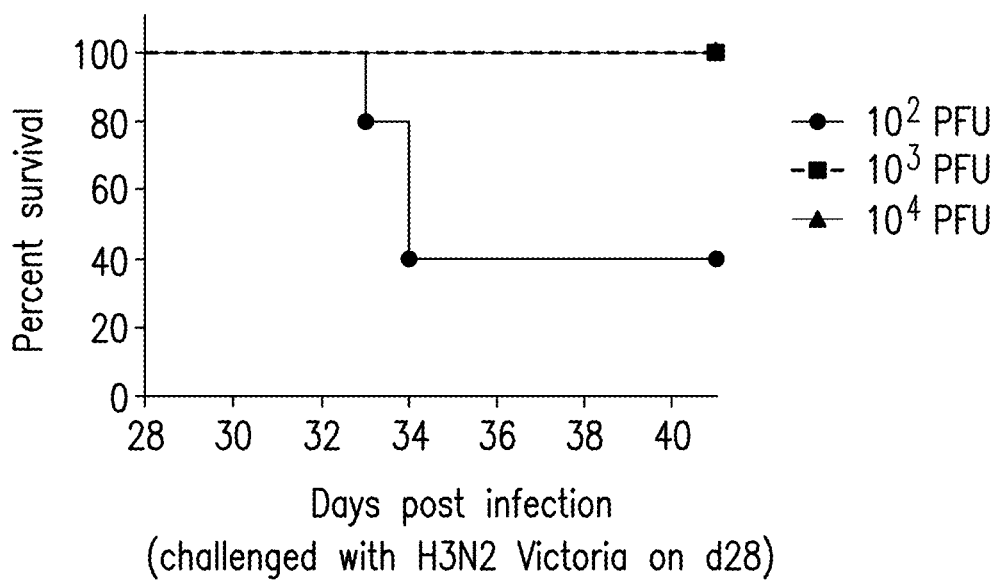
Figure 6:
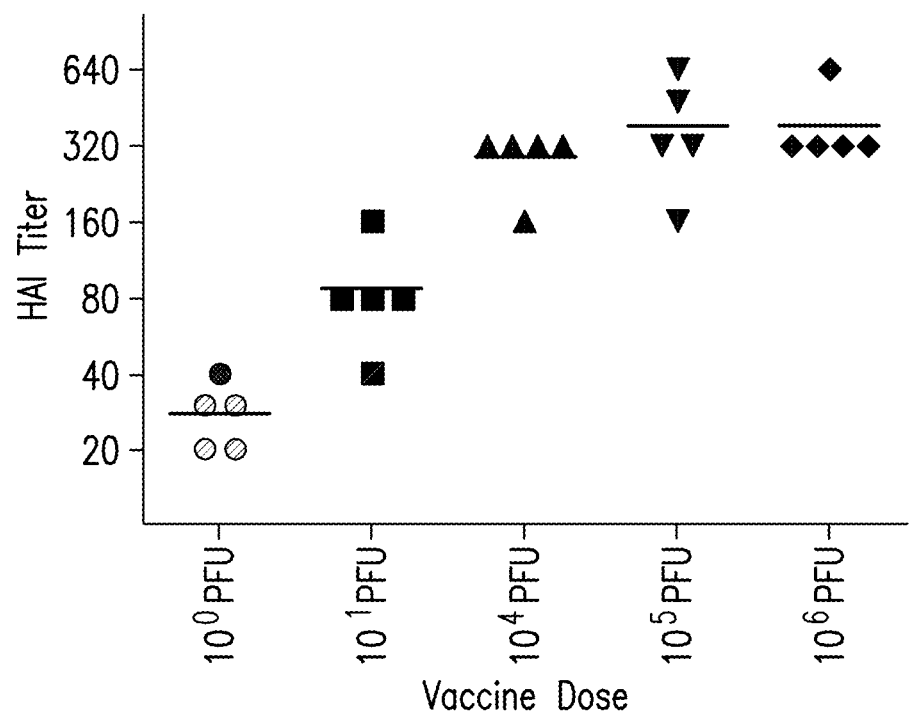
FIG. 6. Hemagglutination inhibition (HAI) assay with serum of vaccinated mice. Mice were infected at different doses with PR8 or $(NA+HA)^{Min}$. Serum was collected on day 28 p.i. and antibody titers were determined by hemagglutination inhibition assays, as described in Material and Methods. Mice were then challenged with $10^5$ PFU wt PR8 and survival rates were monitored. Gray labeled dots indicated mice that did not survive.
Figure 7A:
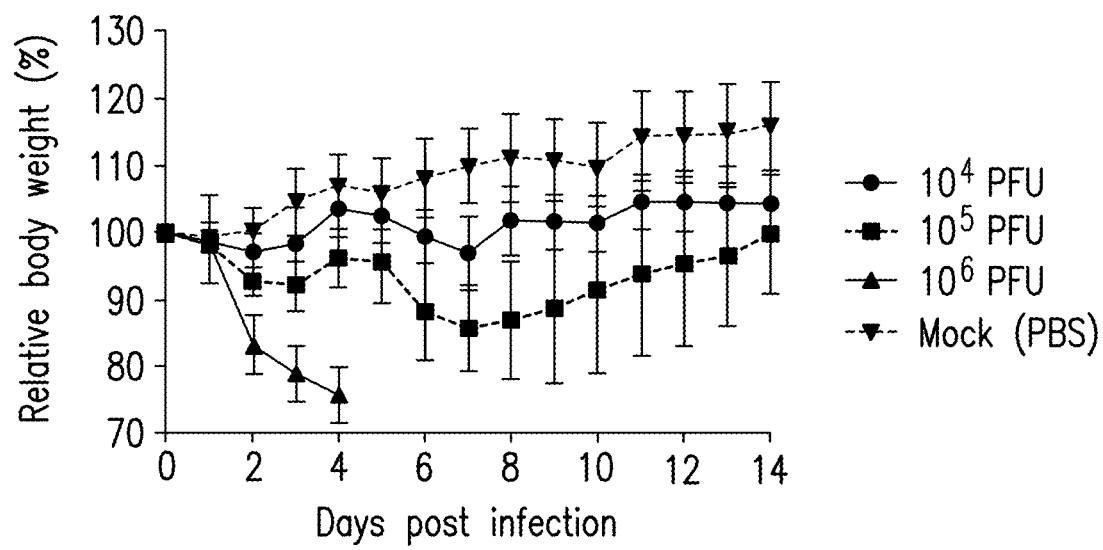
FIGS. 7A-7D. $LD_{50}$ and $PD_{50}$ values of $NA^{Min}$ in mice.
Figure 7B:
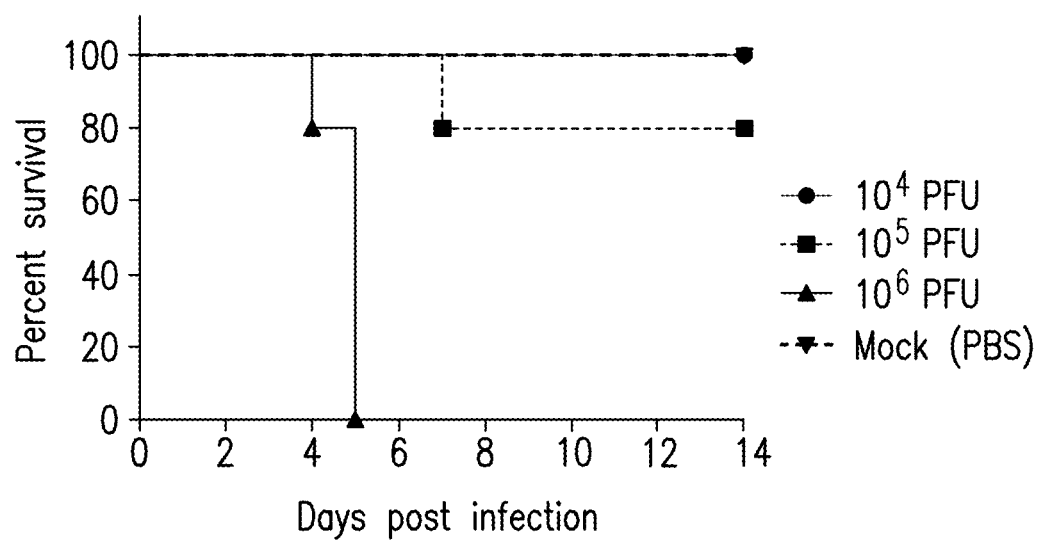
Figure 7C:
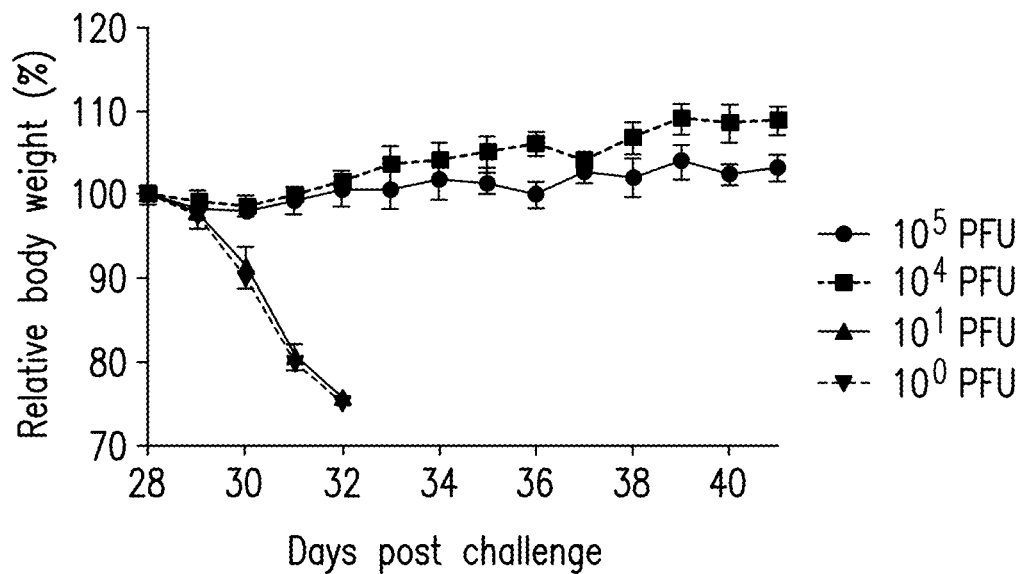
Figure 7D:
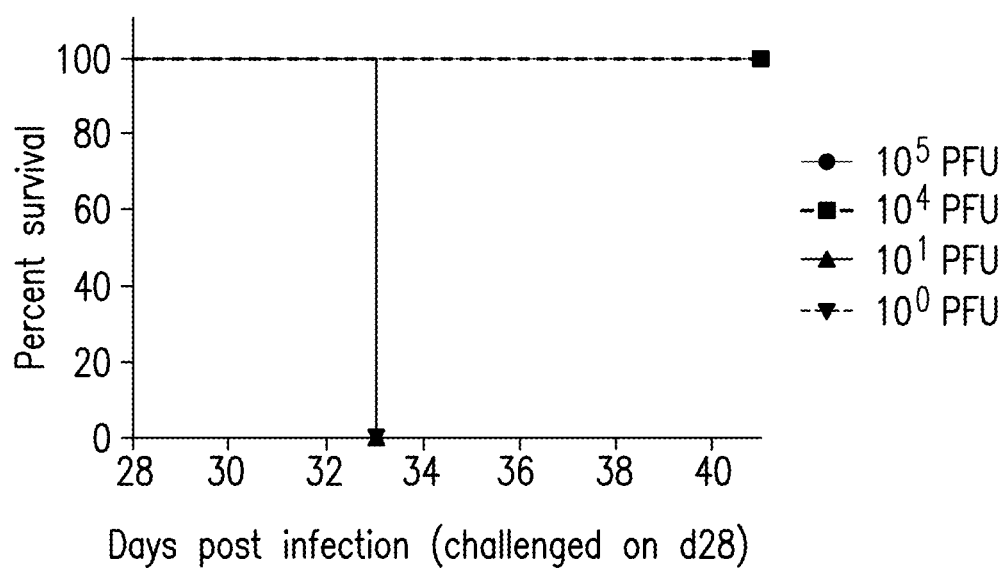
Figure 8A:
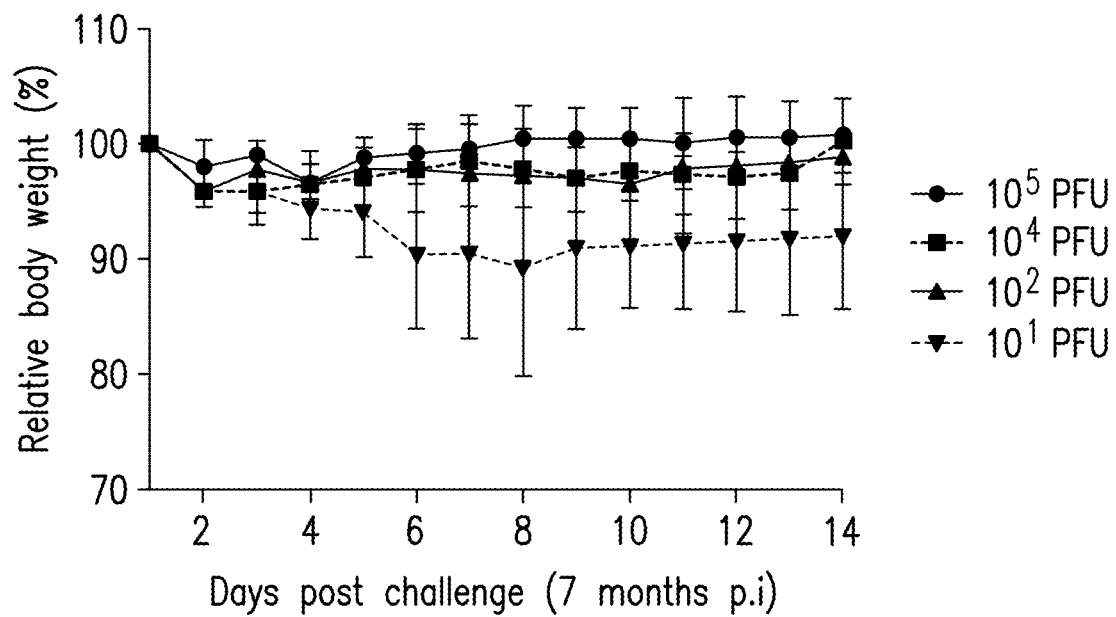
FIGS. 8A-8B. Long term protection of $(NA+HA)^{Min}$-vaccinated mice. Groups of five Balb/c mice (5-6 weeks) were infected intranasally with $(NA+HA)^{Min}$ at different doses. After seven months, mice were challenged with $10^5$ PFU wt PR8. Their body weight and survival rate were monitored for 14 days. Error bars represent SD.
Figure 8B:
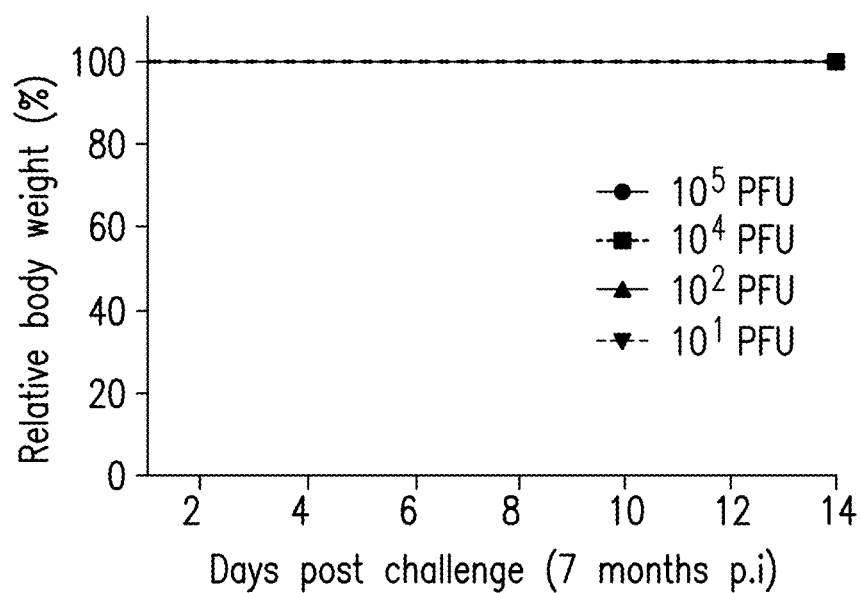
Figure 9A:
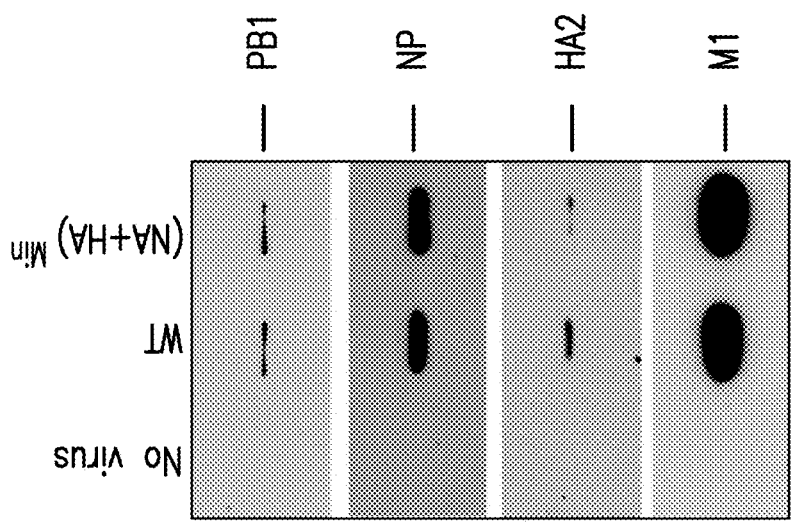
FIGS. 9A-9D. Composition of $(NA+HA)^{Min}$ virus. WT and $(NA+HA)^{Min}$ virus were purified by sucrose gradient. Equivalent amounts of PFUs were compared to determine the relative amounts of the indicated virus proteins.
Figure 9B:
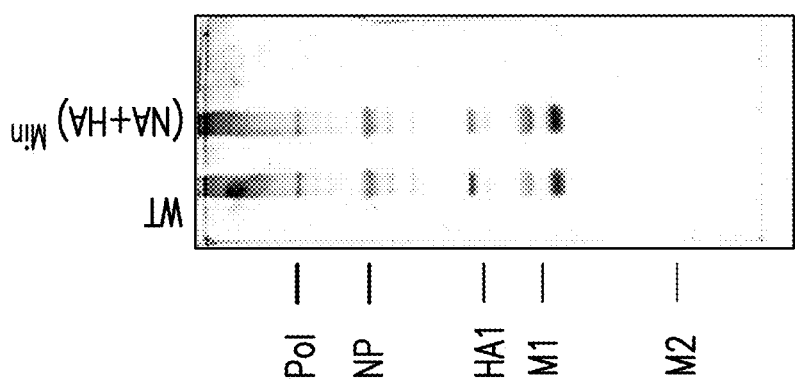
Figure 9C:
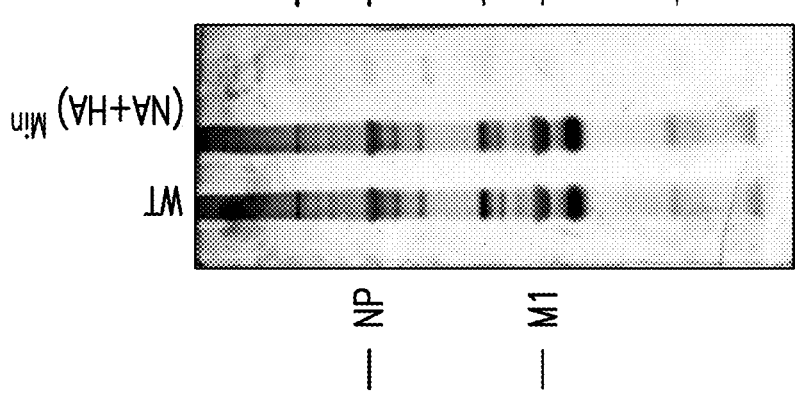
Figure 9D:
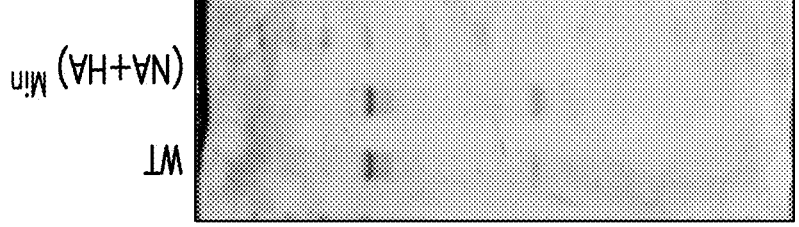

The CPB has been calculated for all annotated human genes using the equations shown and plotted (FIG. 4). Each point in the graph corresponds to the CPB of a single human gene. The peak of the distribution has a positive codon pair bias of 0.07, which is the mean score for all annotated human genes. Also there are very few genes with a negative codon pair bias. Equations established to define and calculate CPB were then used to manipulate this bias.

Algorithm for Reducing Codon-Pair Bias.

Recoding of protein-encoding sequences may be performed with or without the aid of a computer, using, for example, a gradient descent, or simulated annealing, or other minimization routine. An example of the procedure that rearranges codons present in a starting sequence can be represented by the following steps:

1) Obtain wildtype viral genome sequence.
2) Select protein coding sequences to target for attenuated design.
3) Lock down known or conjectured DNA segments with non-coding functions.
4) Select desired codon distribution for remaining amino acids in redesigned proteins.
5) Perform random shuffle of at least two synonymous unlocked codon positions and calculate codon-pair score.
6) Further reduce (or increase) codon-pair score optionally employing a simulated annealing procedure.
7) Inspect resulting design for excessive secondary structure and unwanted restriction site:
   if yes—>go to step (5) or correct the design by replacing problematic regions with wildtype sequences and go to step (8).
8. Synthesize DNA sequence corresponding to virus design.
9. Create viral construct and assess viral phenotype:
   if too attenuated, prepare subclone construct and go to 9;
if insufficiently attenuated, go to 2.

Attenuation of viruses by reducing codon pair bias is disclosed in WO 2008/121992 and WO 2011/044561, which are incorporated by reference.

Attenuated Influenza Viruses

According to the invention, viral attenuation is accomplished by reducing expression of HA and NA coding sequences. One way to reduce expression of the coding sequences is by a reduction in codon pair bias, but other methods can also be used, alone or in combination. While codon bias may be changed, adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties.

Codon pair bias of a protein-encoding sequence (i.e., an open reading frame) is calculated as set forth above and described in Coleman et al., 2000 (ref. 12).

Viral attenuation and induction or protective immune responses can be confirmed in ways that are well known to one of ordinary skill in the art, including but not limited to, the methods and assays disclosed herein. Non-limiting examples include plaque assays, growth measurements, reduced lethality in test animals, and protection against subsequent infection with a wild type virus.

In preferred embodiments, the invention provides viruses that are highly attenuated, and induce immunity against a plurality of influenza types and/or subtypes. Such flu varieties include viruses bearing all possible HA-NA combinations. Currently, there are 16 recognized hemagglutinins and nine neuraminidases, each of which has mutational variants. Examples of type A subtypes include, but are not limited to, H10N7, H10N1, H10N2, H10N3, H10N4, H10N5, H10N6, H10N7, H10N8, H10N9, H11N1, H11N2, H11N3, H11N4, H11N6, H11N8, H11N9, H12N1, H12N2, H12N4, H12N5, H12N6, H12N8, H12N9, H13N2, H13N3, H13N6, H13N9, H14N5, H14N6, H15N2, H15N8, H15N9, H16N3, H1N1, H1N2, H1N3, H1N5, H1N6, H1N8, H1N9, H2N1, H2N2, H2N3, H2N4, H2N5, H2N6, H2N7, H2N8, H2N9, H3N1, H3N2, H3N3, H3N4, H3N5, H3N6, H3N8, H3N9, H4N1, H4N2, H4N3, H4N4, H4N5, H4N6, H4N7, H4N8, H4N9, H5N1, H5N2, H5N3, H5N4, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H8N2, H8N4, H8N5, H9N1, H9N2, H9N3, H9N4, H9N5, H9N6, H9N7, H9N8, H9N9. Some subtypes of interest include, but are not limited to, H1N1 (one variant of which caused Spanish flu in 1918, another of which is pandemic in 2009), H2N2 (a variant of which caused Asian Flu in 1957), H3N2 (a variant of which caused Hong Kong Flu in 1968, H5N1 (a current pandemic threat), H7N7 (which has unusual zoonotic potential), and H1N2 (endemic in humans and pigs). Examples of attenuated influenza protein coding sequences are provided below.

TABLE 4

Reduced-Expression Influenza A Virus Genes

| | | WT Coding Sequence | | | Recoded Coding Sequence | |
|---|---|---|---|---|---|---|
| Gene | SEQ ID NO: | CDS | CPB | SEQ ID NO | Recoded Codons | CPB |
| H10N7 (A/northern shoveler/California/HKWF392sm/2007)(Avian) | | | | | | |
| HA | 1 | 1-1683 | 0.018 | 2 | 1-561 | -0.441 |
| NA | 3 | 1-1494 | 0.009 | 4 | 1-498 | -0.449 |

TABLE 4-continued

Reduced-Expression Influenza A Virus Genes

| | | WT Coding Sequence | | | Recoded Coding Sequence | |
|---|---|---|---|---|---|---|
| Gene | SEQ ID NO: | CDS | CPB | SEQ ID NO | Recoded Codons | CPB |
| H1N1 (A/New York/3568/2009)(Human) | | | | | | |
| HA | 5 | 1-1698 | 0.043 | 6 | 1-566 | -0.410 |
| NA | 7 | 1-1407 | 0.005 | 8 | 1-469 | -0.456 |
| H1N2 (A/New York/211/2003)(Human) | | | | | | |
| HA | 9 | 1-1695 | 0.036 | 10 | 1-565 | -0.421 |
| NA | 11 | 1-1407 | 0.034 | 12 | 1-469 | -0.476 |
| H2N2 (A/Albany/22/1957)(Human) | | | | | | |
| HA | 13 | 1-1686 | 0.040 | 14 | 1-562 | -0.422 |
| NA | 15 | 1-1407 | 0.008 | 16 | 1-469 | -0.453 |
| H3N2 (A/New York/933/2006)(Human) | | | | | | |
| HA | 17 | 1-1698 | 0.027 | 18 | 1-566 | -0.447 |
| NA | 19 | 1-1407 | 0.041 | 20 | 1-469 | -0.463 |
| H5N1 (A/Jiangsu/1/2007)(Human) | | | | | | |
| HA | 21 | 1-1701 | 0.017 | 22 | 1-567 | -0.435 |
| NA | 23 | 1-1347 | 0.009 | 24 | 1-449 | -0.407 |
| H7N2 (A/chicken/NJ/294508-12/2004)(Avian) | | | | | | |
| HA | 25 | 1-1656 | 0.036 | 26 | 1-552 | -0.377 |
| NA | 27 | 1-1359 | 0.013 | 28 | 1-453 | -0.491 |
| H7N3 (A/Canada/rv504/2004)(Human) | | | | | | |
| HA | 29 | 1-1701 | 0.029 | 30 | 1-567 | -0.405 |
| NA | 31 | 1-1407 | 0.042 | 32 | 1-469 | -0.413 |
| H7N7 (A/Netherlands/219/03)(Human) | | | | | | |
| HA | 33 | 1-1707 | 0.008 | 34 | 1-569 | -0.447 |
| NA | 35 | 1-1413 | -0.009 | 36 | 1-471 | -0.423 |
| H9N2 (A/Hong Kong/1073/99)(Human) | | | | | | |
| HA | 37 | 1-1680 | 0.021 | 38 | 1-560 | -0.440 |
| NA | 39 | 1-1401 | 0.020 | 40 | 1-467 | -0.453 |

Vaccine Compositions

The present invention provides a vaccine composition for inducing a protective immune response in a subject comprising any of the attenuated viruses described herein and a pharmaceutically acceptable carrier.

It should be understood that an attenuated virus of the invention, where used to elicit a protective immune response in a subject or to prevent a subject from becoming afflicted with a virus-associated disease, is administered to the subject in the form of a composition additionally comprising a pharmaceutically acceptable carrier. Pharmaceutically acceptable carriers are well known to those skilled in the art and include, but are not limited to, one or more of 0.01-0.1M and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Pharmaceutically acceptable carriers can further comprise minor amounts of auxiliary substances such as wetting or emulsifying agents, preservatives and other additives, such as, for example, antimicrobials, antioxidants and chelating agents, which enhance the shelf life and/or effectiveness of the active ingredients. The instant compositions can, as is well known in the art, be formulated so as to provide quick, sustained or delayed release of the active ingredient after administration to a subject.

In various embodiments of the instant vaccine composition, the attenuated virus (i) does not substantially alter the synthesis and processing of viral proteins in an infected cell; (ii) produces similar amounts of virions per infected cell as wt virus; and/or (iii) exhibits substantially lower virion-specific infectivity than wt virus. In further embodiments, the attenuated virus induces a substantially similar immune response in a host animal as the corresponding wt virus.

This invention also provides a modified host cell line specially isolated or engineered to be permissive for an attenuated virus that is inviable in a wild type host cell. Since the attenuated virus cannot grow in normal (wild type) host cells, it is absolutely dependent on the specific helper cell line for growth. This provides a very high level of safety for the generation of virus for vaccine production. Various embodiments of the instant modified cell line permit the growth of an attenuated virus, wherein the genome of said cell line has been altered to increase the number of genes encoding rare tRNAs.

In addition, the present invention provides a method for eliciting a protective immune response in a subject comprising administering to the subject a prophylactically or therapeutically effective dose of any of the vaccine compositions described herein. This invention also provides a method for preventing a subject from becoming afflicted with a virus-associated disease comprising administering to the subject a prophylactically effective dose of any of the instant vaccine compositions. In embodiments of the above methods, the subject has been exposed to a pathogenic virus. “Exposed” to a pathogenic virus means contact with the virus such that infection could result.

The invention further provides a method for delaying the onset, or slowing the rate of progression, of a virus-associated disease in a virus-infected subject comprising administering to the subject a therapeutically effective dose of any of the instant vaccine compositions.

As used herein, “administering” means delivering using any of the various methods and delivery systems known to those skilled in the art. Administering can be performed, for example, intranasally, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

Eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art, and is usually on the order of several weeks to months. The present invention is not limited, however, to any particular method, route or frequency of administration.

A “subject” means any animal or artificially modified animal. Animals include, but are not limited to, humans, non-human primates, cows, horses, sheep, pigs, dogs, cats, rabbits, ferrets, rodents such as mice, rats and guinea pigs, and birds. Artificially modified animals include, but are not limited to, SCID mice with human immune systems, and CD155tg transgenic mice expressing the human poliovirus receptor CD155. In a preferred embodiment, the subject is a human. Preferred embodiments of birds are domesticated poultry species, including, but not limited to, chickens, turkeys, ducks, and geese.

A “prophylactically effective dose” is any amount of a vaccine that, when administered to a subject prone to viral infection or prone to affliction with a virus-associated disorder, induces in the subject an immune response that protects the subject from becoming infected by the virus or afflicted with the disorder. “Protecting” the subject means either reducing the likelihood of the subject’s becoming infected with the virus, or lessening the likelihood of the disorder’s onset in the subject, by at least two-fold, preferably at least ten-fold. For example, if a subject has a 1% chance of becoming infected with a virus, a two-fold reduction in the likelihood of the subject becoming infected with the virus would result in the subject having a 0.5% chance of becoming infected with the virus. Most preferably, a “prophylactically effective dose” induces in the subject an immune response that completely prevents the subject from becoming infected by the virus or prevents the onset of the disorder in the subject entirely.

As used herein, a “therapeutically effective dose” is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

Certain embodiments of any of the instant immunization and therapeutic methods further comprise administering to the subject at least one adjuvant. An “adjuvant” shall mean any agent suitable for enhancing the immunogenicity of an antigen and boosting an immune response in a subject. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund’s incomplete adjuvant (FIA), saponin, Quil A, and QS-21.

The invention also provides a kit for immunization of a subject with an attenuated virus of the invention. The kit comprises the attenuated virus, a pharmaceutically acceptable carrier, an applicator, and an instructional material for the use thereof. In further embodiments, the attenuated virus may be one or more poliovirus, one or more rhinovirus, one or more influenza virus, etc. More than one virus may be preferred where it is desirable to immunize a host against a number of different isolates of a particular virus. The invention includes other embodiments of kits that are known to those skilled in the art. The instructions can provide any information that is useful for directing the administration of the attenuated viruses.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains. However, the citation of a reference herein should not be construed as an acknowledgement that such reference is prior art to the present invention.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994). All references mentioned herein are incorporated in their entirety by reference into this application. The contents of WO 2008/121992 and WO 2011/044561 are incorporated by reference.

EXAMPLES

Example 1

Construction and Characterization of an HA and NA Codon Pair-Bias Reduced Influenza Virus in Tissue Culture To achieve attenuation of influenza virus PR8, codon pair bias was reduced (introducing underrepresented codon pairs) in viral genes HA and NA according to computer algorithms (12, 13) and chemical synthesis (14), in order to reduce the expression level of the targeted viral genes.

Cells and viruses. MDCK, A549 and HEK293 T cell lines were maintained in DMEM supplemented with 10% FBS at 37° C. Influenza A/PR/8/34 (PR8) was cultured in MDCK cells.

Figure 1B:
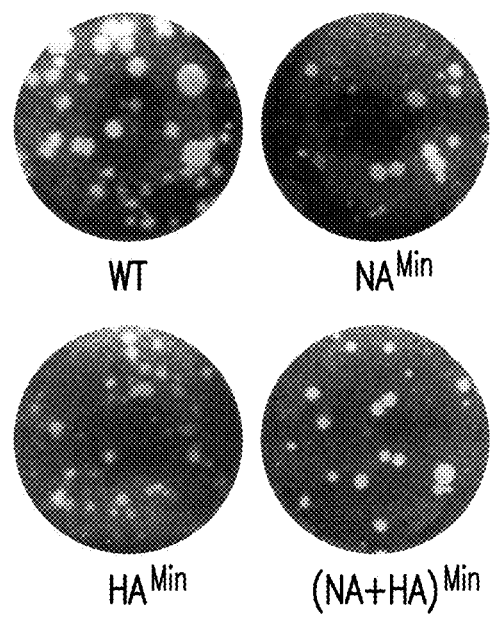
Figure 1C:
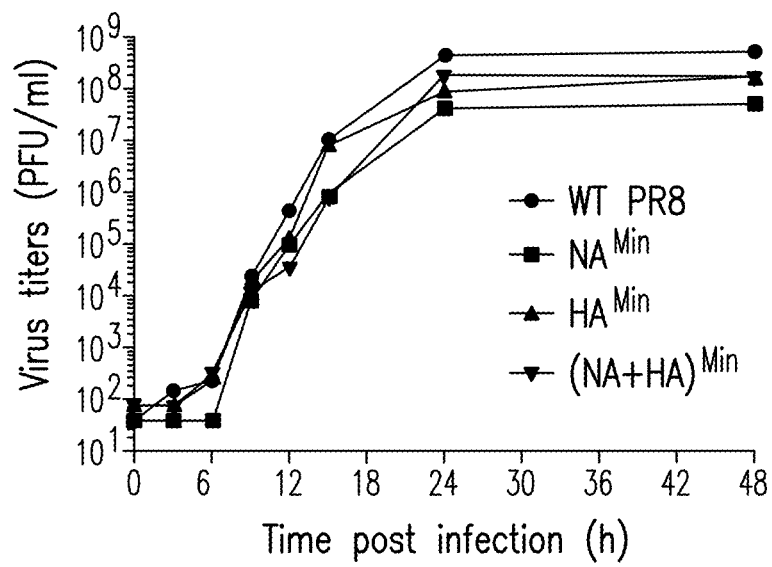
Figure 1D:
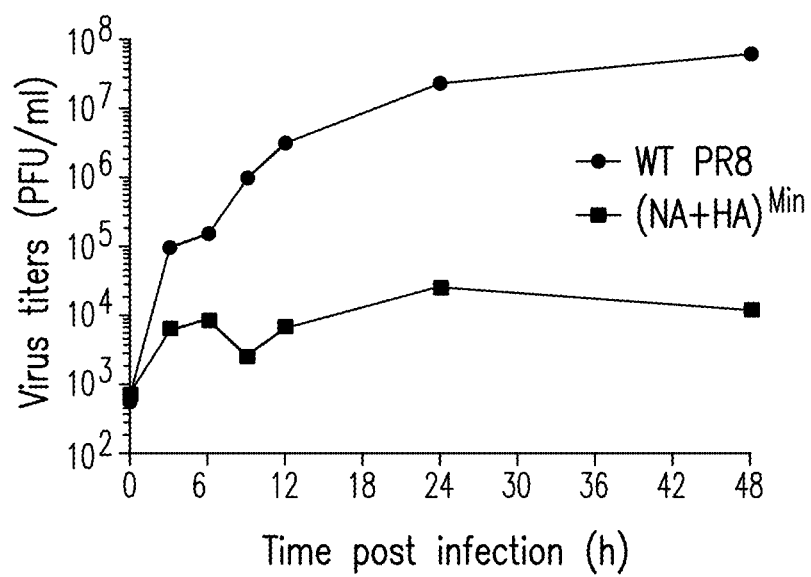

Variant $(NA+HA)^{Min}$ (618/3188 nt changes), combining the $HA^{Min}$ (SEQ ID NO:53) and $NA^{Min}$ (SEQ ID NO:60) genes, expressed growth and plaque phenotypes in MDCK cells comparable to those of the individual $HA^{Min}$ and $NA^{Min}$ variants (FIG. 1B, C). Similarly, a variant with a codon-pair bias reduced NA gene ($NA^{Min}$, 265/1413 synonymous mutations; FIG. 1A) also replicated well in MDCK cells (FIG. 1C) and expressed an only slightly smaller plaque size phenotype (FIG. 1B) than wt PR8. In A549 cells the $(NA+HA)^{Min}$ variant was highly attenuated (FIG. 1D), growing to a final titer three to four orders of magnitudes lower than wt PR8. A549 cells retain a complex signaling network that is related to the innate host response (15, 16).

Example 2

Levels of NA mRNA and HA Protein are Reduced in $(NA+HA)^{Min}$-Infected Cells

The apparent yield of HA polypeptide was examined by western blotting in MDCK cells at 3 h and 6 h post infection (p.i.) with 5 MOI of wt virus or $(NA+HA)^{Min}$. Remarkably, at 6 h p.i., expression of HA protein was significantly reduced in $(NA+HA)^{Min}$-infected cells when compared to PR8-infected cells whereas PB1 and NS1 were synthesized to equal levels by viruses (FIG. 2A). Using the levels of PB1 and GAPDH mRNAs as control, the Northern blot analysis of mRNA levels in $(NA+HA)^{Min}$-infected cells indicated only a slight reduction of $HA^{Min}$ mRNA at 3 h and 6 h (FIG. 2B).

In contrast, Northern blot analyses indicated an extensive reduction of the recoded $NA^{Min}$ mRNA after 6 h and particularly after 9 h p.i. (FIG. 2B). Early in infection (3 h), the level of $NA^{Min}$ mRNA was slightly reduced.

Example 3

Figure 3A:
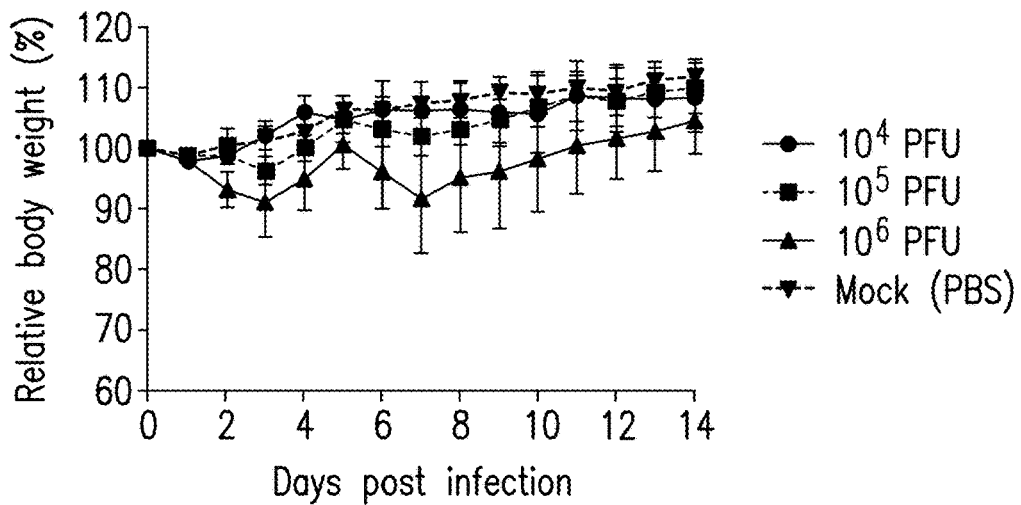
FIGS. 3A-3F. Virus phenotypes in infected mice.
Figure 3B:
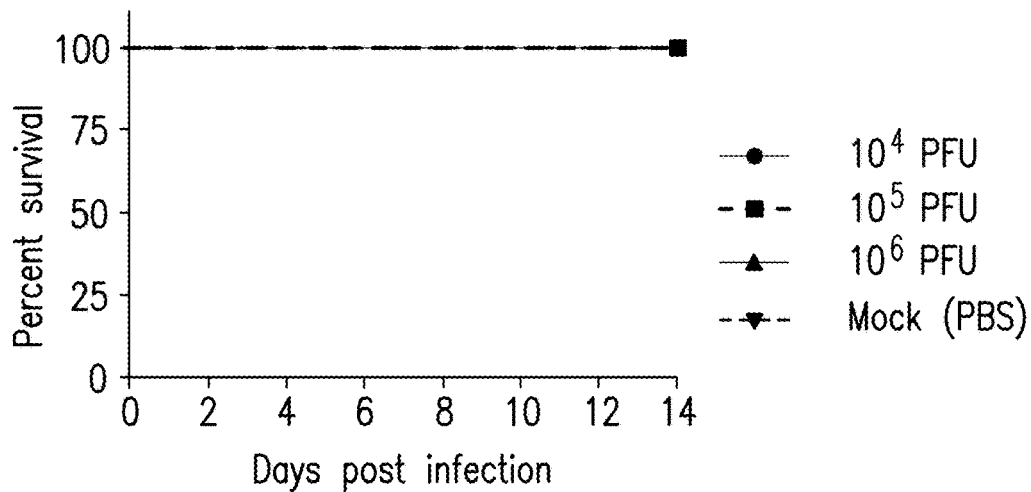

Characterization of the Reduced Codon-Pair Bias Variants as Vaccine Candidates in Mice The growth phenotype and pathogenesis of the $(NA+HA)^{Min}$ variant was examined in an animal model. Groups of five BALB/c mice received $(NA+HA)^{Min}$ at doses of $10^4$, $10^5$ or $10^6$ PFU intra-nasally, and body weight and survival of the animals was monitored continuously for 14 days p.i. (FIG. 3A, B). Morbidity and mortality (weight loss, reduced activity, death) was monitored. The Lethal Dose 50 ($LD_{50}$) of the wildtype virus and the vaccine candidates was calculated by the method of Reed and Muench (Reed, L. J.; Muench, H., 1938, The American Journal of Hygiene 27: 493-497). Remarkably, the $(NA+HA)^{Min}$ variant did not induce apparent disease after a dose up to $10^5$ PFU. Even at $10^6$ PFU, mice only suffered transient weight loss, but all animals survived. Therefore, the theoretical $LD_{50}$ of the $(NA+HA)^{Min}$ variant was calculated to be equal or greater than $3.16 \times 10^6$ PFU, which exceeds that of wt PR8 by a factor of at least 100,000 (Table 1).

Whereas the $(NA+HA)^{Min}$, $HA^{Min}$, and $NA^{Min}$ variants replicated with nearly equal efficiency and similar kinetics as wt PR8 in MDCK cells (FIG. 1C), the $LD_{50}$ of the variants were by orders of magnitude different: PR8=32 PFU, $HA^{Min}=1.7 \times 10^3$ PFU (13), $NA^{Min}=2.4 \times 10^5$ PFU (FIG. 7, Table 5), and $(NA+HA)^{Min} > 3.3 \times 10^6$. By itself, the $NA^{Min}$ gene is about 100-fold more attenuated than the $HA^{Min}$ gene, but reducing expression of NA and NP in the same virus significantly increases attenuation of the virus.

TABLE 5

$LD_{50}$ and $PD_{50}$ of Attenuated Virus

|  | $LD_{50}$ | $PD_{50}$ |
|---|---|---|
| WT PR8 | $3.2 \times 10^1$ | ~1 |
| $NA^{Min}$ | $2.4 \times 10^5$ | <32 |
| $HA^{Min}$ | $1.7 \times 10^3$ | n.d. |
| $(NA + HA)^{Min}$ | $>3.3 \times 10^6$ | 2.4 |

Figure 3C:
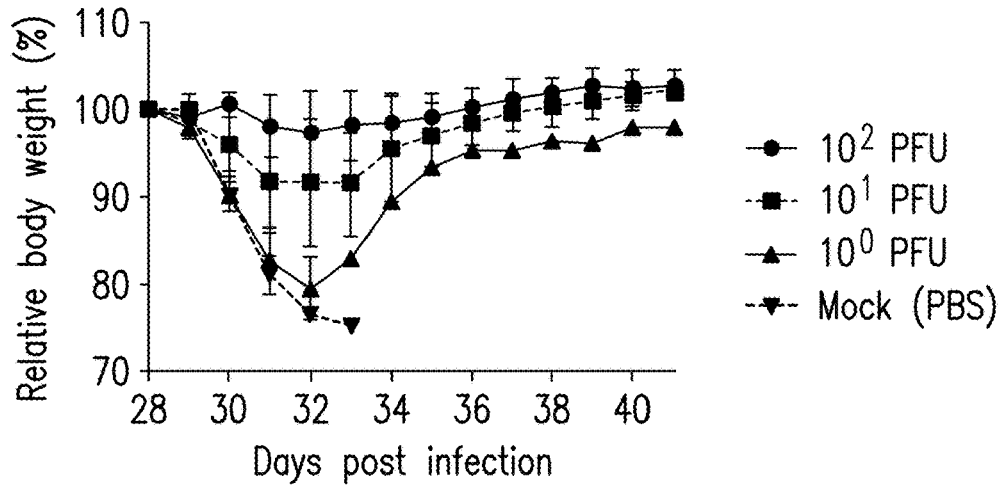
Figure 3D:
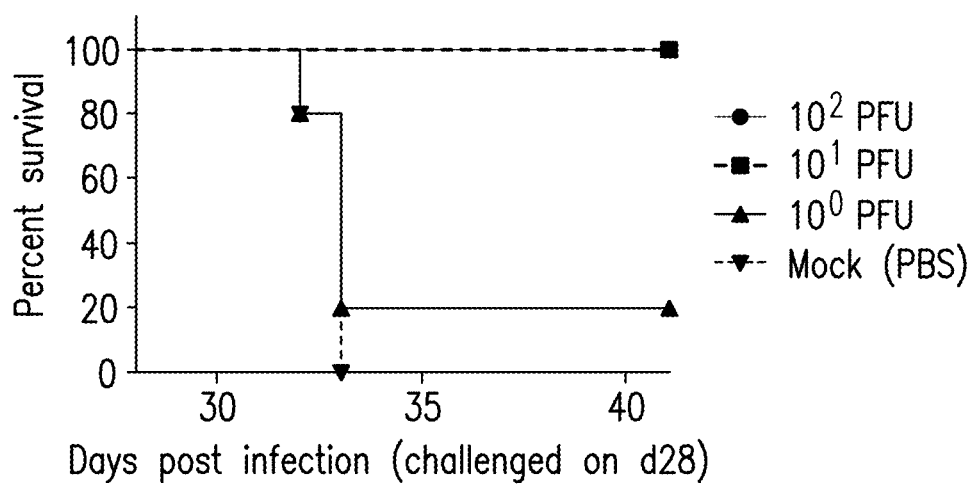
Figure 3E:
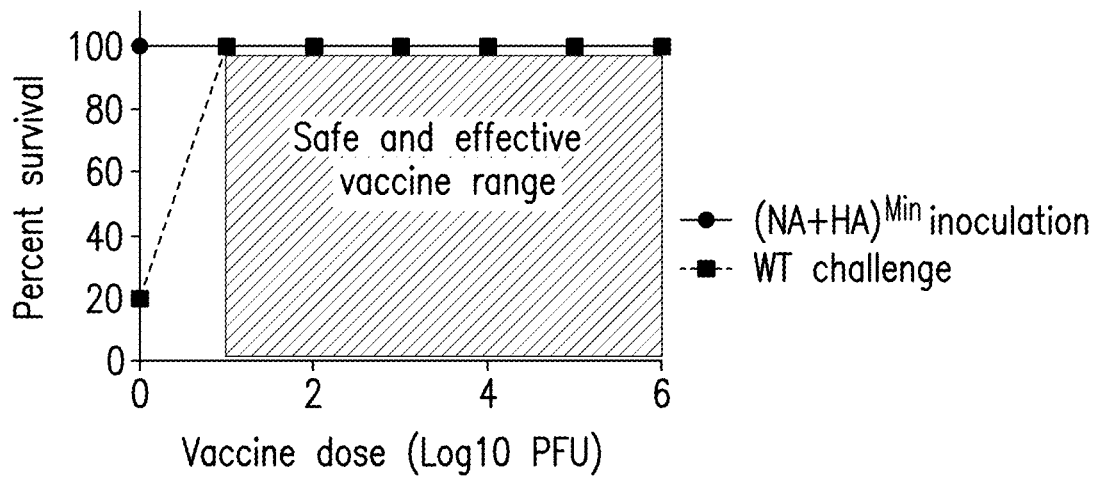
Figure 3F:
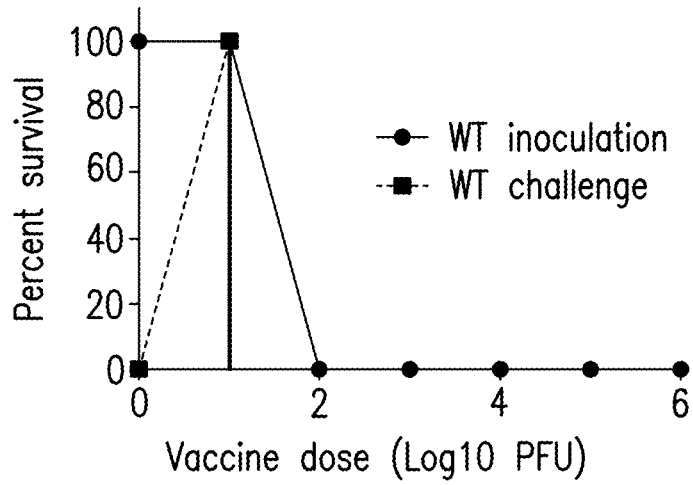

Vaccine candidates should be capable of providing, at low dose, long-term protection from challenge with a lethal dose of wt virus. The dose of $(NA+HA)^{Min}$ required to protect 50% of vaccinated animals from subsequent lethal wild type challenge (defined as "protective dose 50", $PD_{50}$) was determined. Groups of five Balb/c mice were vaccinated with a single dose of $10^0$, $10^1$, or $10^2$ PFU of $(NA+HA)^{Min}$. 28 days after vaccination, the animals were challenged with $10^5$ PFU ($3000 \times LD_{50}$) of wt PR8 virus. As with the original infections, we monitored body weight and survival of the animals 14 days after challenge. Remarkably, although $(NA+HA)^{Min}$ was highly attenuated in mice, it was also highly proficient at protecting against lethal challenge with wt virus. As little as 10 PFU of $(NA+HA)^{Min}$ protected all five mice from lethal challenge (FIGS. 3C, 3D). The $PD_{50}$ value calculated by the method of Reed-Muench was only 2.4 PFU. (Table 5) To our knowledge this is the lowest reported protective dose of an experimental vaccine in a mouse model.

Figures 10A, 10B:
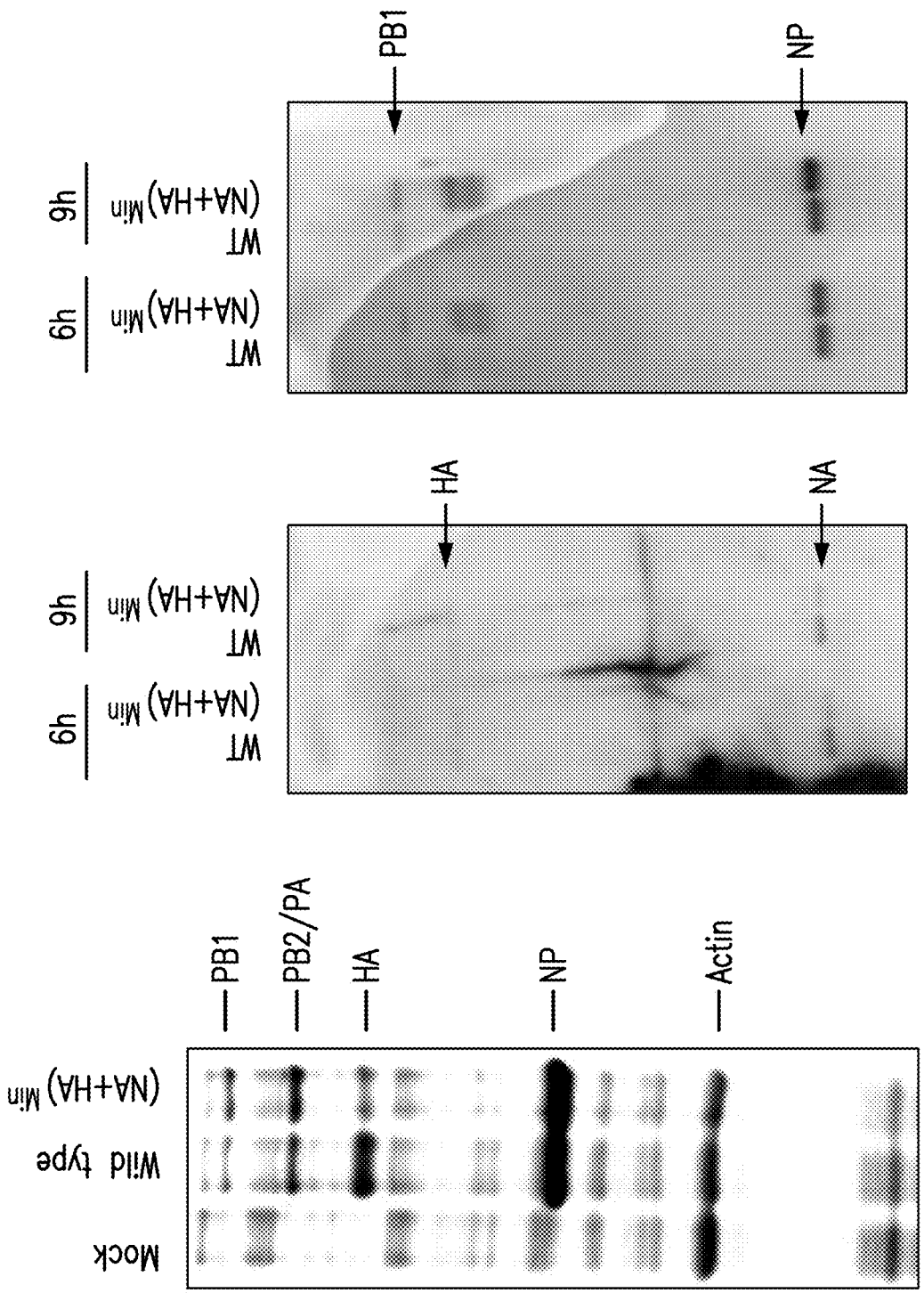
FIGS. 10A-10B. Expression of virus proteins and mRNAs in MDCK cells infected with WT influenza or (NA+HA)$^{Min}$.

Vaccine safety and protective range was evaluated with various doses of either $(NA+HA)^{Min}$ variant or wt PR8. As shown in FIG. 3E, a zone of five orders of magnitude (from 10 PFU to $10^6$ PFU) can be considered the "region of safety" of $(NA+HA)^{Min}$ vaccination since all mice receiving increasing doses of "vaccine" within this region were protected from lethal challenge with wt virus. In contrast, the safe and effective region for wt PR8 was extremely limited (FIG. 3F).

Example 4

The Growth of (NA+HA)Min is Greatly Reduced in the Lungs of Vaccinated Mice

To determine parameters of the $(NA+HA)^{Min}$ pathogenicity in vivo, groups of BALB/c mice were infected with $10^4$ PFU of wt PR8 or $(NA+HA)^{Min}$. On day 1, 3, 5, 7, 9 and 11, three mice each from the wt and $(NA+HA)^{Min}$ groups were euthanized, their lungs were homogenized, and virus titers in the homogenates were determined by plaque assays. As expected, wt PR8 replicated well, but even $(NA+HA)^{Min}$ replicated noticeably in lungs of the vaccinated animals. Both PR8 and variant achieved maximum titers around day 3 (FIG. 4A) although there was a ~100 fold difference in the titers between the two viruses. All wt PR8-infected mice died on day 5, whereas all $(NA+HA)^{Min}$-infected mice remained healthy. $(NA+HA)^{Min}$ was eventually cleared at 8 to 9 days p.i. (FIG. 4A). When mice were inoculated at different doses, the $(NA+HA)^{Min}$ titers were always 100-1000 fold lower in lungs when compare to those of wt PR8 on day 3 p.i. (FIG. 4B). Strikingly, at a vaccination dose of 10 PFU when $(NA+HA)^{Min}$ barely replicated in the lungs of the animals, it nevertheless provided complete protection against wt PR8 challenge (FIGS. 4B and 3D). Interestingly, the attenuation of $(NA+HA)^{Min}$ in mice correlates with the attenuation of $(NA+HA)^{Min}$ in A549 cells (FIG. 1D).

Example 5

Cross Protection and Long Term Protection Induced by the $(NA+HA)^{Min}$ Variant The $(NA+HA)^{Min}$ variant of PR8, which belongs to the influenza H1N1 subtype, was further tested for its capacity to cross protect animals against infections with a heterologous influenza virus strain, such as a mouse adapted H3N2 strain (A/Aichi/2/1968) (21). Groups of five BALB/c mice were vaccinated with $(NA+HA)^{Min}$ virus at doses ranging from $10^2$ to $10^4$ PFU and challenged 28 days post vaccination with $100\times LD_{50}$ doses of A/Aichi/2/1968 (H3N2) virus ($1.5\times10^4$ PFU). Remarkably, 1000 PFU of $(NA+HA)^{Min}$ were sufficient to protect mice from the heterologous lethal challenge, corresponding to a $PD_{50}$ value of only 237 PFU (FIGS. 5A, 5B). A similar result was obtained when the vaccinated $(NA+HA)^{Min}$ mice were challenged with a different strain of mouse adapted H3N2, A/Victoria/3/75. Again, as little as 1000 PFU of the H1N1 PR8-$(NA+HA)^{Min}$ variant protected all mice from lethal challenge with $100\times LD_{50}$ dose ($3.2\times10^4$ PFU) of A/Victoria/3/75. The $PD_{50}$ of $(NA+HA)^{Min}$ protecting against A/Victoria/3/75 (H3N2) was only 147 PFU (FIGS. 5C, 5D). Both results indicate that $(NA+HA)^{Min}$ of H1N1 PR8 can induce a robust cross protective immune response in mice against H3N2 subtypes.

$(NA+HA)^{Min}$-vaccinated animals were tested to determine whether they were protected against challenge after an extended period of time. Groups of five mice were vaccinated with different doses ($10^1$ to $10^5$ PFU) of $(NA+HA)^{Min}$ and the animals were challenged seven months later with $10^5$ PFU of wt PR8. All vaccinated animals were completely protected without signs of disease (FIG. 8).

Example 6

The $(NA+HA)^{Min}$ Variant Induces a Robust Antibody Response

The host response to $(NA+HA)^{Min}$ inoculation suggested a strong host response, including adaptive immunity. Groups of five Balb/c mice were vaccinated with varying doses of $(NA+HA)^{Min}$ or wt PR8 (see FIG. 6). Sera were collected on day 28 p.i., and antibody responses were determined by hemagglutination inhibition (HAI) assays performed according to the protocol in the WHO Manual on Animal Influenza Diagosis and Surveillance (23). The mice were challenged with a lethal dose of PR8 ($10^5$ PFU). An HAI titer of 40 or more in the serum is generally considered to be protective (22). This level was reached with just $10^1$ PFU of $(NA+HA)^{Min}$ (FIG. 6) and protected vaccinated mice from challenge with $10^5$ PFU wt PR8 virus (FIG. 6).

Example 7

Virus Composition

Both WT and $(NA+HA)^{Min}$ virus were purified by sucrose gradient. $5\times10^7$ PFU of both viruses were loaded onto SDS gels followed by Commassie blue stain (0.1% Coomassie blue R250 for 45 min.) (FIG. 9A) or silver stain (Bio-Rad silver stain kit) (FIG. 9B and C) to detect virion protein composition. At the same PFU, WT virions contain more HA1 molecues than the $(NA+HA)^{Min}$ virus, while the latter contains more M1 proteins.

WT and $(NA+HA)^{Min}$ virus were also analyzed by Western blot. $2\times10^7$ PFU of WT and $(NA+HA)^{Min}$ viruses were loaded onto SDS-PAGE gels and analyzed for content of PB1, NP, HA2, and M1. At the same PFU of purified virions, the virus preparations have similar amounts of NP and PB1 protein. Purified WT virions, however, have more HA2 protein, while purified $(NA+HA)^{Min}$ virions have more M1 protein. (FIG. 9D).

Example 8

Expression of Virus Proteins and mRNAs in Infected MDCK Cells

HA protein expression was measured by $^{35}S$ methionine incorporation. MDCK cells were infected with 10 MOI wild type PR8, or $(NA+HA)^{Min}$ virus. At 3 h post infection, cells were starved for 45 min, and then labeled for 30 min. Following cell lysis, equal amounts of cell lysates were resolved by SDS PAGE and labeled proteins were visualized by autoradiography. Expression of the HA protein is notably reduced relative to other viral proteins in $(NA+HA)^{Min}$ virus-infected cells. (FIG. 10A).

Viral mRNA in virus infected MDCK cells nucleus was analyzed by Northern blot. MDCK cells were infected with both WT and (NA+HA)$^{Min}$ viruses at an MOI of 1. At 6 h, and 9 h post infection, cells were lysed using Life Technologies PARIS Kit. Nucleus and cytoplasmic portions were separated and mRNA were extracted from both portions. Northern blotting was performed using isolated mRNAs. The nuclear NP mRNA signals were relatively similar between WT and (NA+HA)$^{Min}$ virus infected cells at all time points. Yet, WT virus infected cells, compared to (NA+HA)$^{Min}$ viruses infected cells, contained more nuclear HA and NA mRNA, and less nuclear PB1 mRNA. (FIG. 10B)

Example 9

Figure 11:
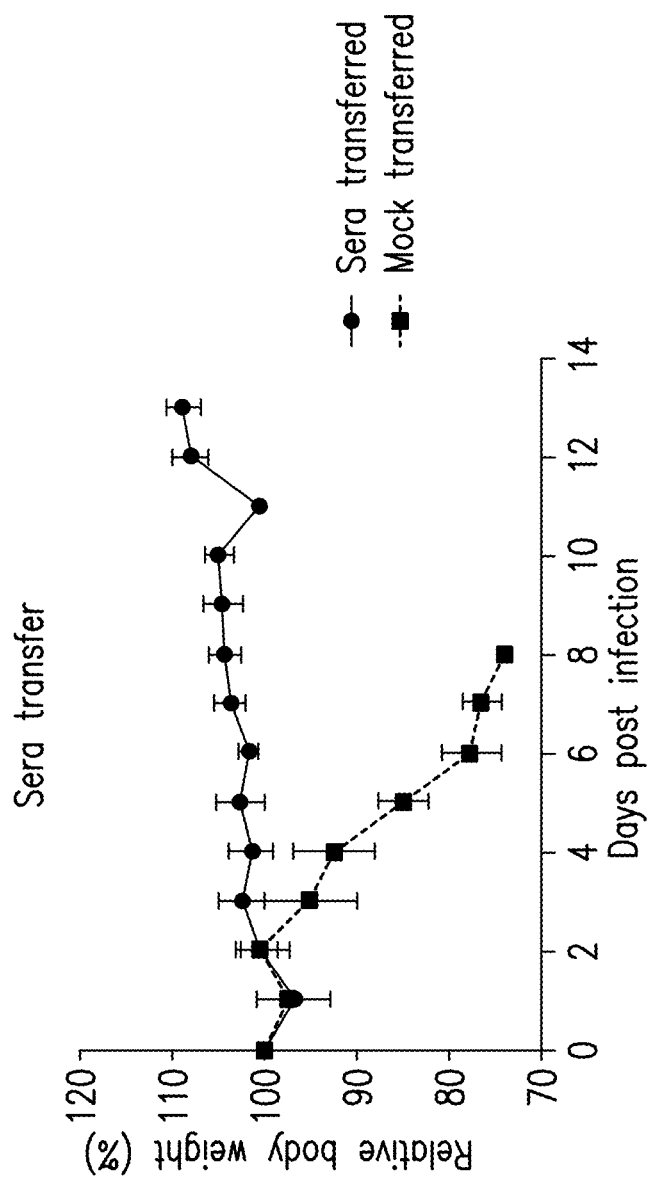
FIG. 11. Passive immunization with Serum from PR8-(NA+HA)$^{Min}$ vaccinated mice protects naïve mice from homologous WT PR8 challenge.

Passive Immunization by Serum Transfer from PR8-(NA+HA)$^{Min}$ Vaccinated Mice Protects Naïve Mice from Homologous WT PR8 Challenge Groups of five Balb/C mice were vaccinated with $10^4$ PFU (NA+HA)$^{Min}$ virus or PBS. 28 days after vaccination mouse sera were collected, and transferred to five naïve Balb/C mice in a volume of 250 ul. 24 h post transfer, mice were challenged with $10^5$ PFU of WT PR8, corresponding to $3000 \times LD_{50}$. All passively immunized mice survived and remained healthy upon challenge, while mock transferred mice died in 8 days. These results suggest that antibodies are the major mediator of immune protection induced by (NA+HA)$^{Min}$ virus vaccination. (FIG. 11).

Example 10

Figure 12A:
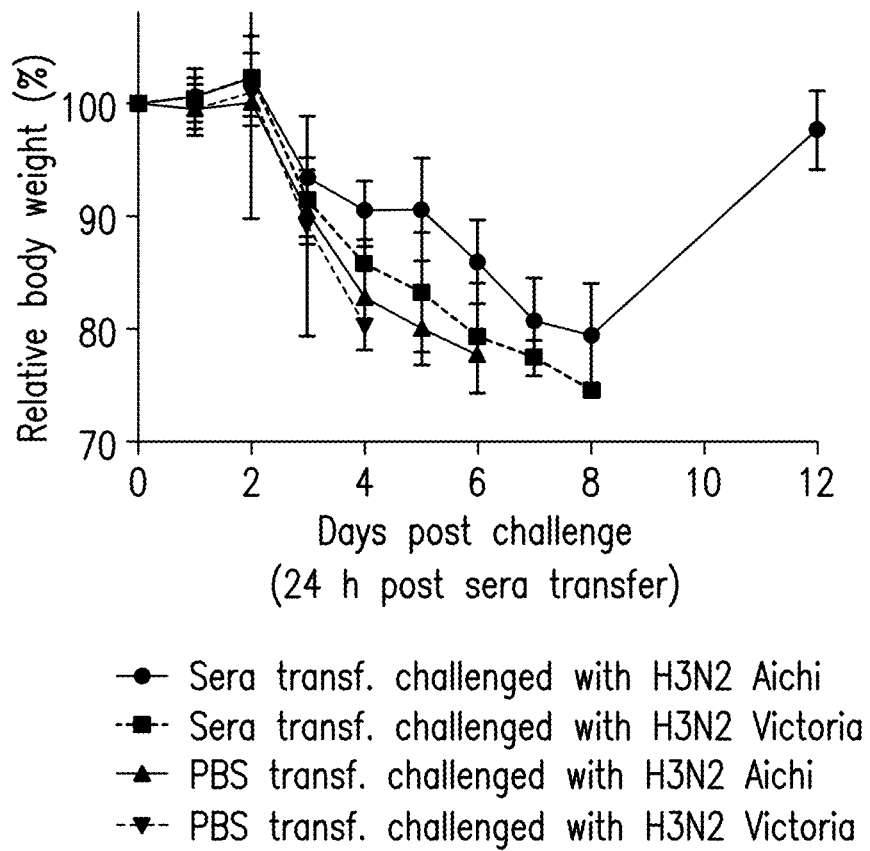
FIGS. 12A-12B. Passive immunization with serum from PR8-(NA+HA)$^{Min}$ (H1N1) vaccinated mice protects naïve mice from heterologous challenge with an H3N2 virus.
Figure 12B:
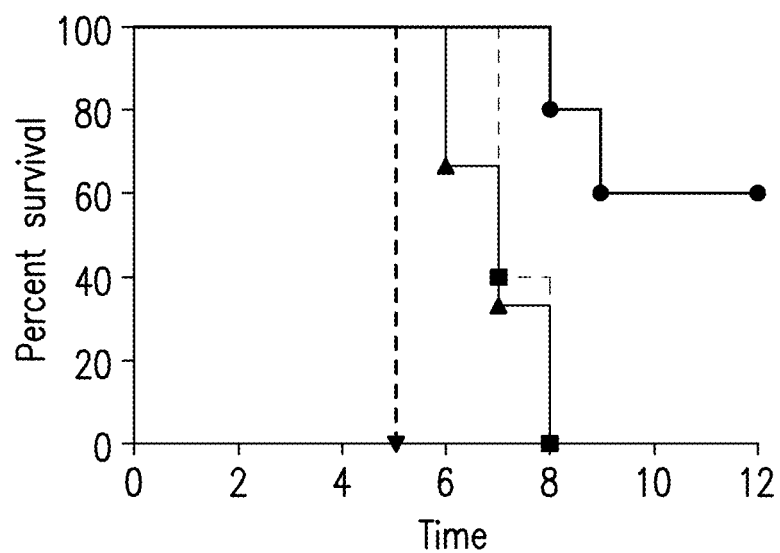

Passive Immunization by Serum Transfer From PR8-(NA+HA)$^{Min}$ Vaccinated Mice Protects Naïve Mice From Heterologous H3N2 Challenge Groups of five Balb/C mice were infected with $3 \times 10^5$ PFU H1N1-(NA+HA)$^{Min}$ virus or PBS. On day 28, all mice were euthanized and their blood was collected. Sera were prepared on the same day and immediately transferred to groups of five naïve Balb/c mice (i.p injection with 250 μl of sera). 24 h post transfer, mice were challenged with $10 \times LD_{50}$ of H1N1-WT PR8, H3N2 Aichi or H3N2 Victoria viruses. Their body weights (FIG. 12A) and survival rates (FIG. 12B) were monitored for 14 days post infection. 60% of sera transferred mice were protected from lethal H3N2 Aichi challenge, and survival times upon challenge of lethal H3N2 Victoria virus were extended.

Example 11

Cross Protection

Figure 13A:
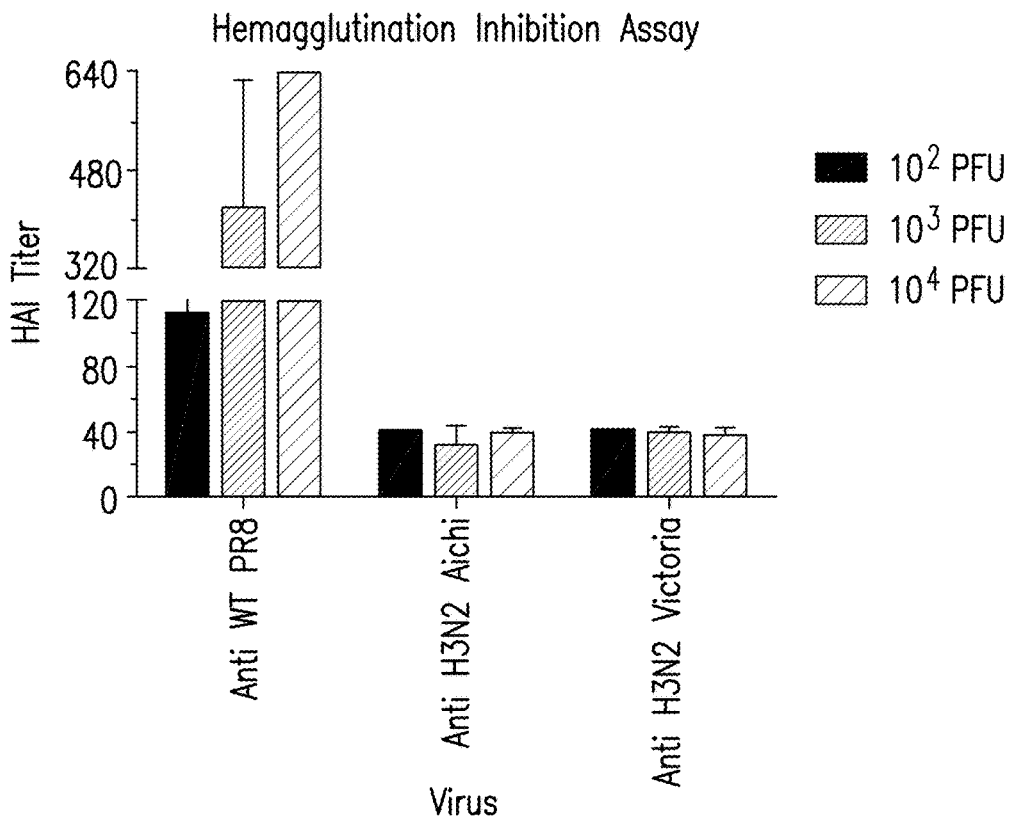
FIGS. 13A-13B. Assessment of cross protection against H3N2 viruses conferred by immunization with PR8-(NA+HA)$^{Min}$.

Cross protection was investigated by assay of hemagglutination inhibition and neutralization. To determine inhibition of hemagglutination, groups of five Balb/C mice were vaccinated with $10^2$-$10^4$ PFU of H1N1-(NA+HA)$^{Min}$ virus. Sera were collected on day 28 p.i. Hemagglutination inhibition assays were performed by incubating the serum with H1N1 PR8, H3N2 Aichi or H3N2 Victoria viruses. (FIG. 13A). H1N1-(NA+HA)$^{Min}$ virus infected mice contain abundant anti-H1N1 HA antibodies with a HAI titer from 100-640. The sera, however, do not contain much of the anti-H3N2 HA antibodies, since the HAI titer are 40 regardless of the vaccine dose. This data suggests that survival of (NA+HA)$^{Min}$ virus-vaccinated mice from heterologous challenge (as illustrated in Example 5) is mainly due to immunity not correlated with antibodies, such as cellular immunity.

To test neutralization, MDCK cells were seeded onto 96 well plate on day 0. 2 fold dilutions of sera from vaccinated mice were incubated with 100 TCID$_{50}$ viruses for 1 h and then added to pre-seeded MDCK cells on day 1. Cells were stained with crystal violet on day 4 to determine neutralization titers.

Figure 13B:
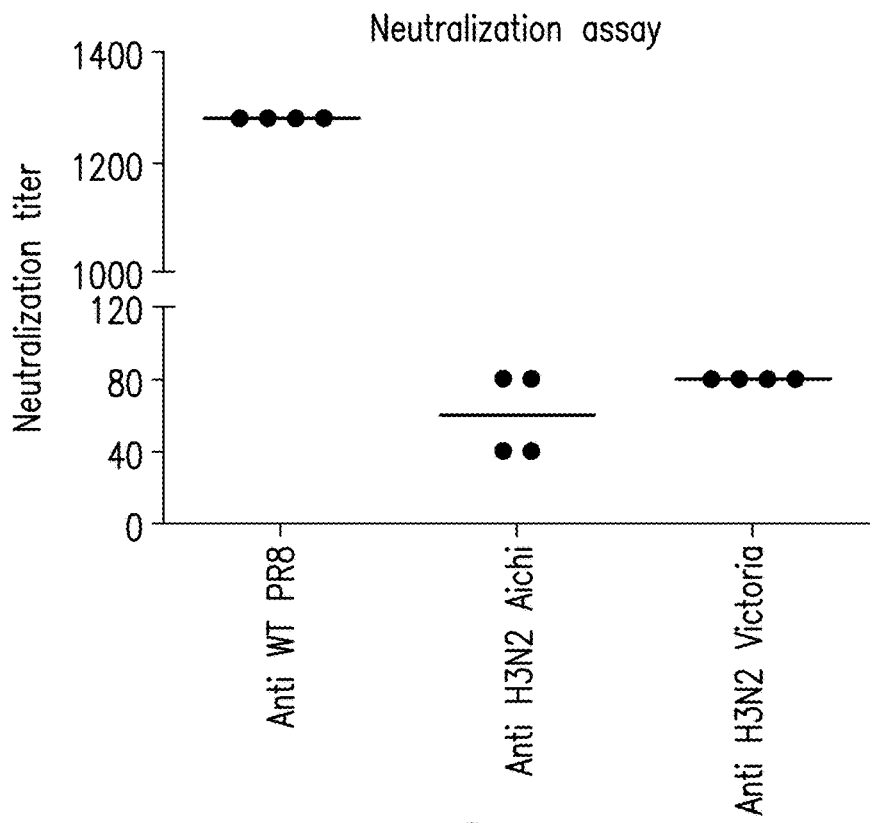

Groups of five Balb/C mice were vaccinated with $10^5$ PFU of H1N1-(NA+HA)$^{Min}$ virus. Sera were collected on day 28 p.i. Neutralization assays were performed by incubating the sera with H1N1 PR8, H3N2 Aichi or H3N2 Victoria viruses. H1N1-(NA+HA)$^{Min}$ virus infected mice were capable of neutralizing H1N1 PR8 with a neutralization titers above 1200. The sera, interestingly, were also able to neutralize H3N2 viruses. (FIG. 13B).

Example 12

Neuraminidase Encoded by (NA+HA)$^{Min}$

Figure 14:
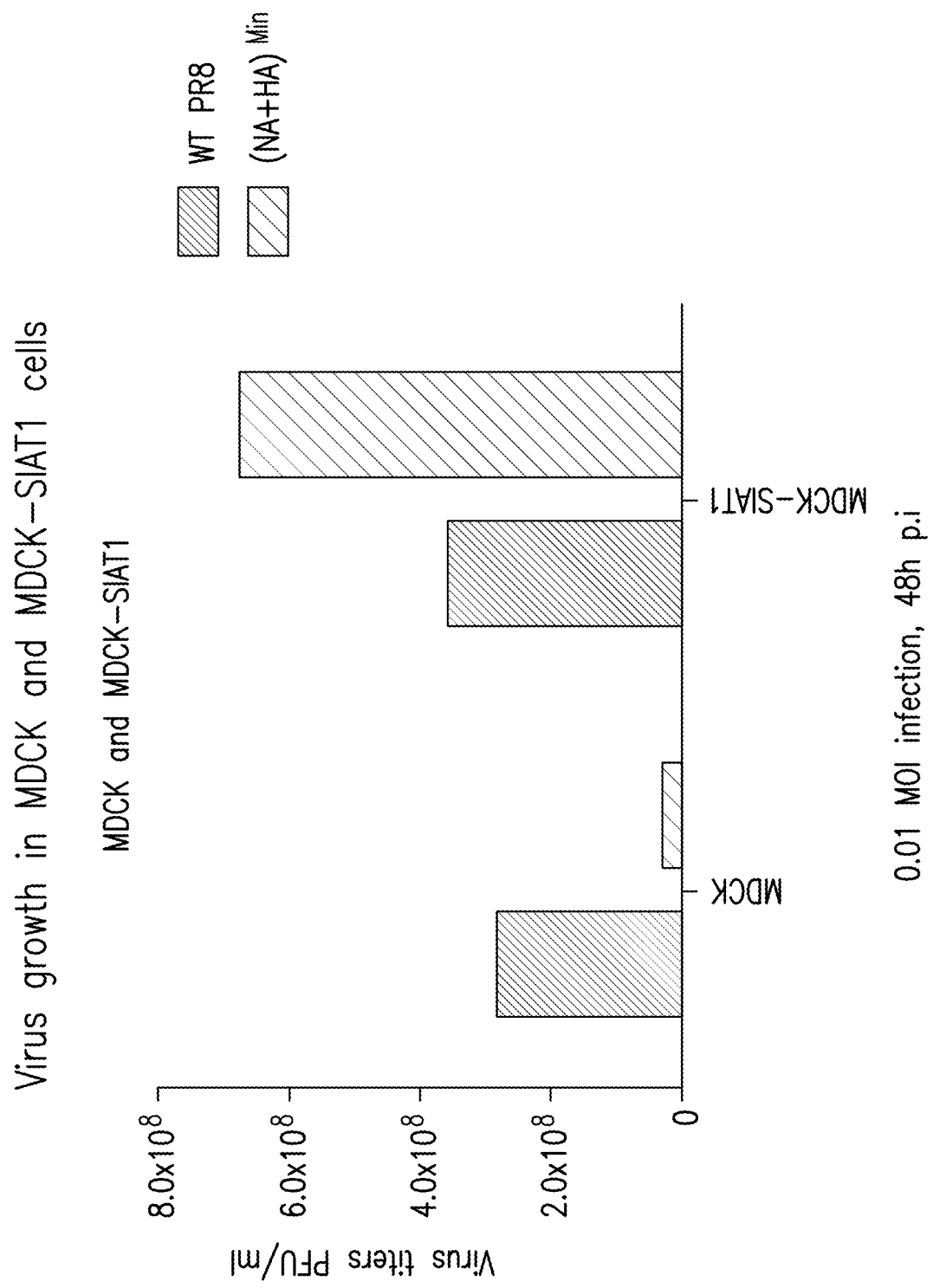
FIG. 14. Growth of WT and PR8-(NA+HA)$^{Min}$ virus in MDCK cells and MDCK cells transfected to express α-2, 6-sialyltransferase.

Viral neuraminidase cleaves terminal sialic acid residues from glycan structures on the surface of an infected cell, which promotes the release of progeny viruses. MDCK cells and MDCK-SIAT1 cells which overexpress overexpressing the α-2,6-Sialyltransferase, were infected with WT or (NA+HA)$^{Min}$ viruses at MOI of 0.01. Virus titers were examined at 48 h p.i. In MDCK-SIAT1 cells, which overexpressed influenza receptor sialic acid, both WT and (NA+HA)$^{Min}$ viruses grew better than MDCK cell lines. (FIG. 14). This indicates that (NA+HA)$^{Min}$ virus comprises neuraminidase molecules encoded by NA$^{Min}$ that cleave sialic acid residues normally.

Example 13

T and B Cell Responses in Lungs and Spleen

Figure 15:
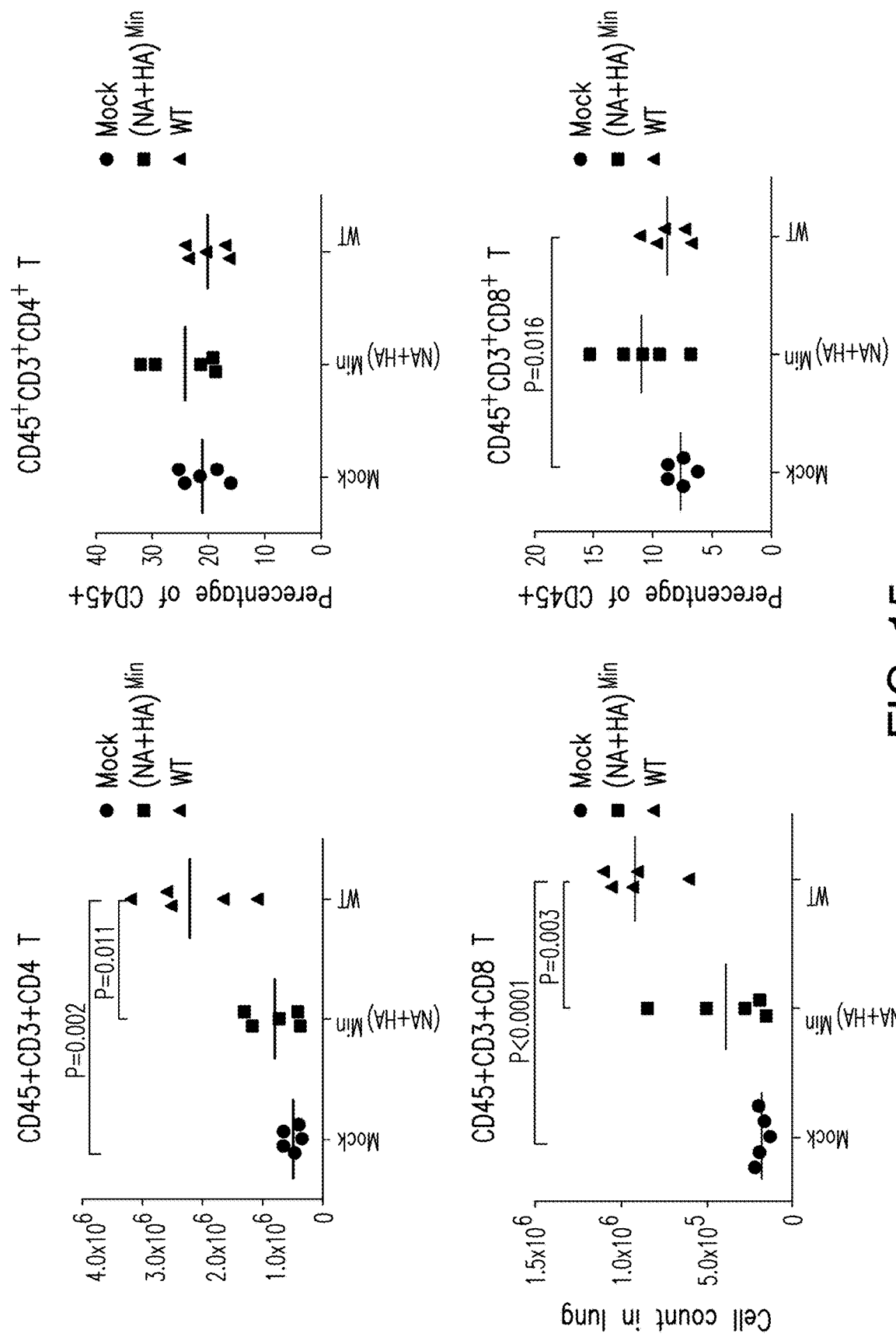
FIG. 15. T cell responses in lungs of Balb/C mice 7 days post-infection. Cell numbers are expressed as total cell count in lung (left panels) or percentage of CD45$^+$ cells (right panels).
Figure 15:
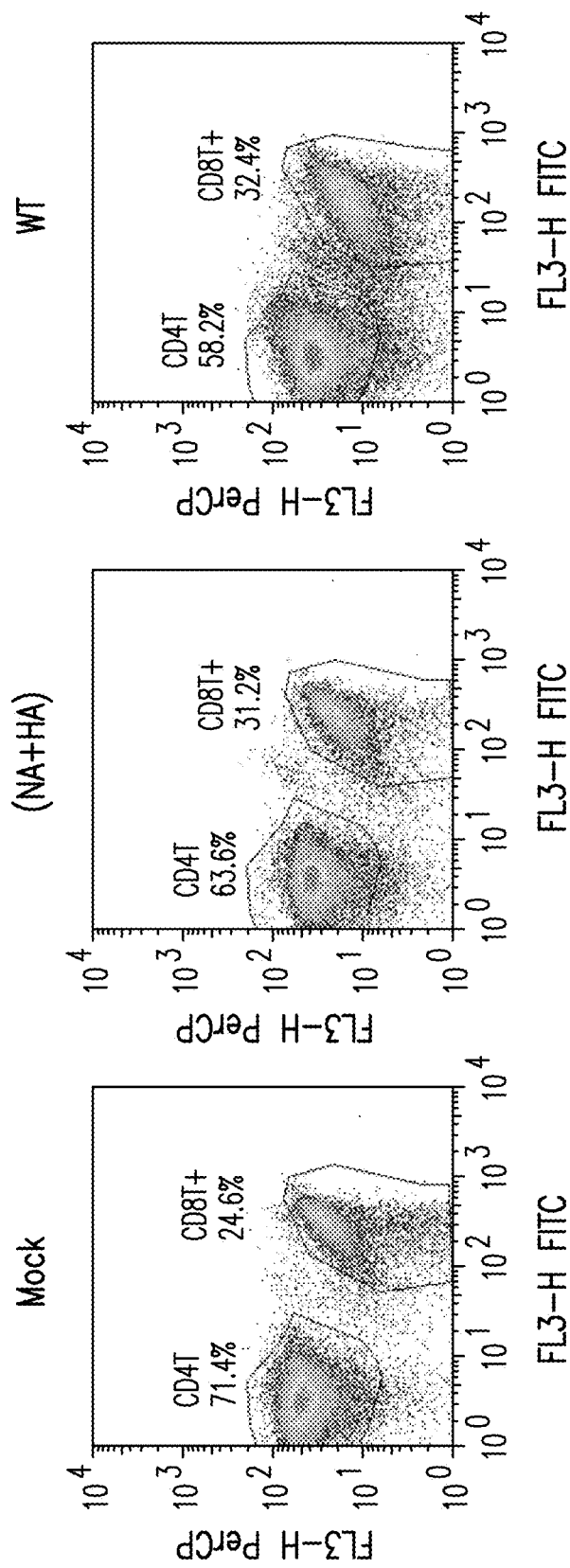

T cell responses in lungs. Groups of five Balb/C mice were with 10 PFU of WT (a dose close the LD$_{50}$ of this virus) or 10 PFU (NA+HA)$^{Min}$ (a dose over 300,000-fold below the LD$_{50}$ for this virus). On day 7 post infection, mice were euthanized and their lungs were collected for flow cytometry. (NA+HA)$^{Min}$ infected mice showed lower numbers of CD4+T and CD8+T cells than WT-infected mice, since (NA+HA)$^{Min}$ infection is cleared by 7 days, while WT infection is still ongoing. (FIG. 15).

Figure 16:
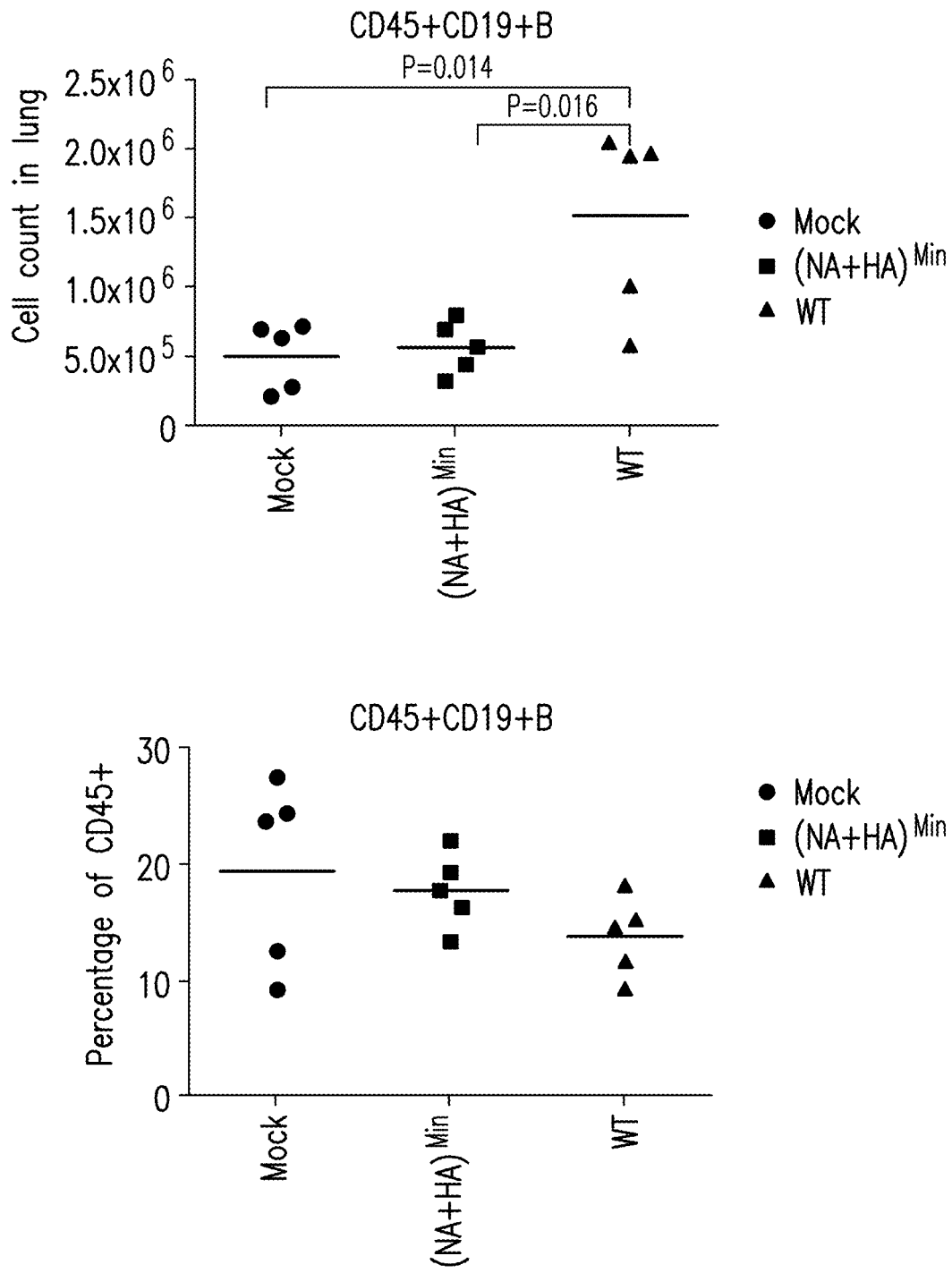
FIG. 16. B cell responses in lungs of Balb/C mice 7 days post-infection. Cell numbers are expressed as total cell count in lung (upper panel) or percentage of CD45$^+$ cells (lower panels).

B cell responses in lungs. Groups of five Balb/C mice were infected with 10 PFU of WT or (NA+HA)$^{Min}$ viruses. On day 7 post infection, mice were euthanized and their lungs were collected for flow cytometry. WT infected mice showed higher numbers of B cells than both the (NA+HA)$^{Min}$ viruses and the mock group, indicating the WT viruses were much harder to clear than the other two. Yet, the percentage of CD45$^+$ B cells in (NA+HA)$^{Min}$ virus infected mice were similar, or slightly higher, than the WT PR8 infected mice, which indicates they share similar ability in inducing long term protective antibodies. (FIG. 16)

Figure 17:
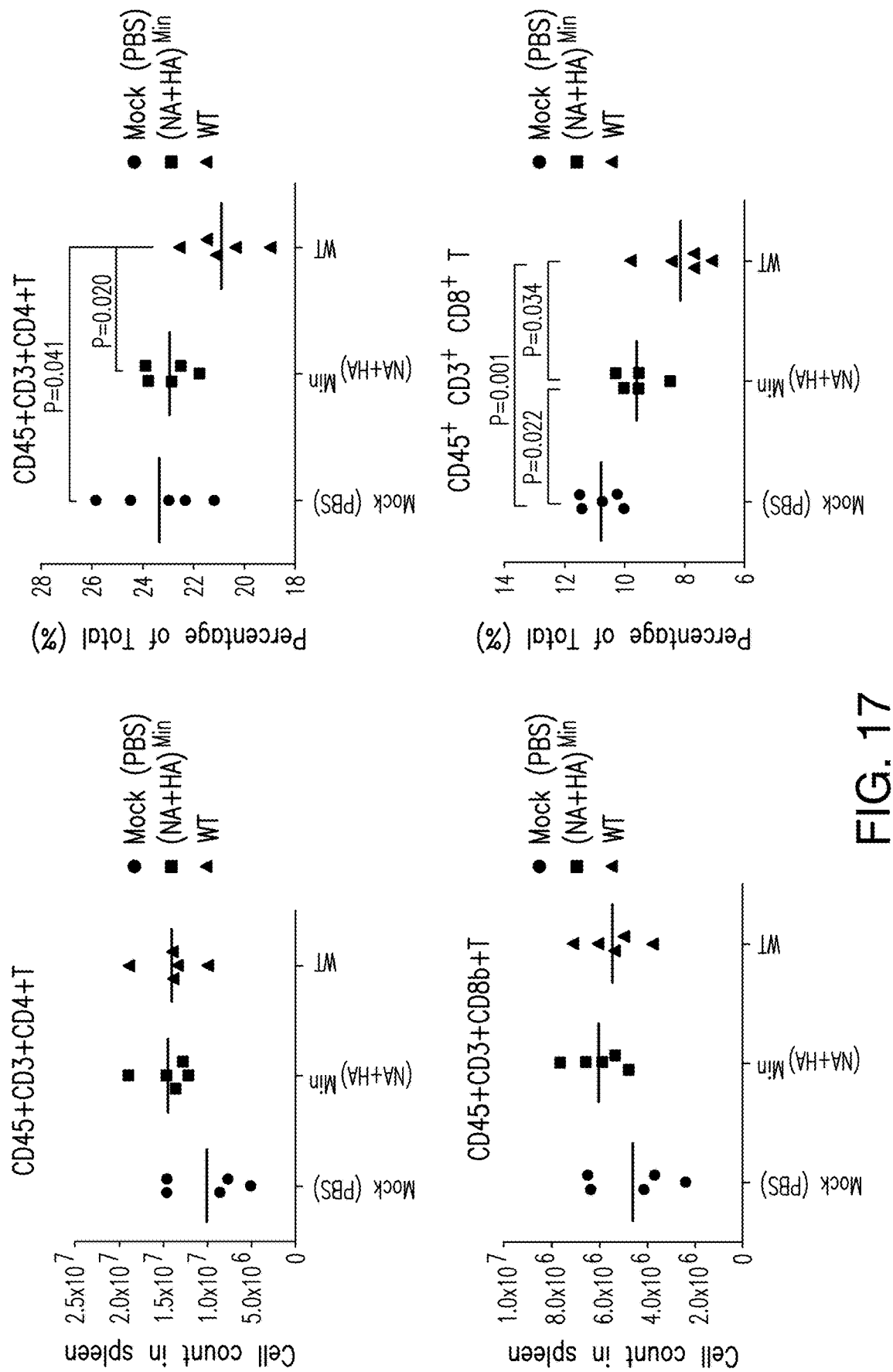
FIG. 17. T cell responses in spleens of Balb/C mice 7 days post-infection.
Figure 17:
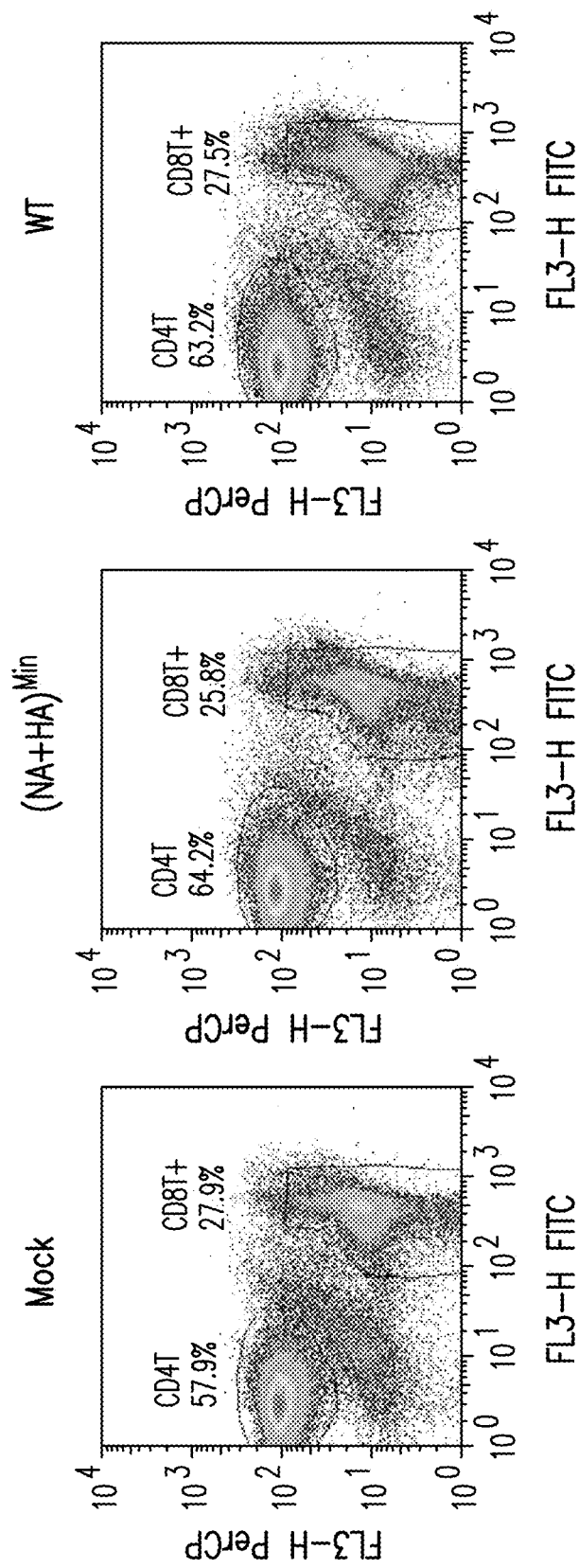

T cell responses in spleen. Groups of five Balb/C mice were infected with 10 PFU of WT or (NA+HA)$^{Min}$ viruses. On day 7 post infection, mice were euthanized and their spleens were collected for flow cytometry. Both WT and (NA+HA)$^{Min}$ virus infected mice showed higher number of CD4+T and CD8+T cells than the mock group, indicating a strong adaptive immune responses triggered by both viruses. (FIG. 17).

Figure 18:
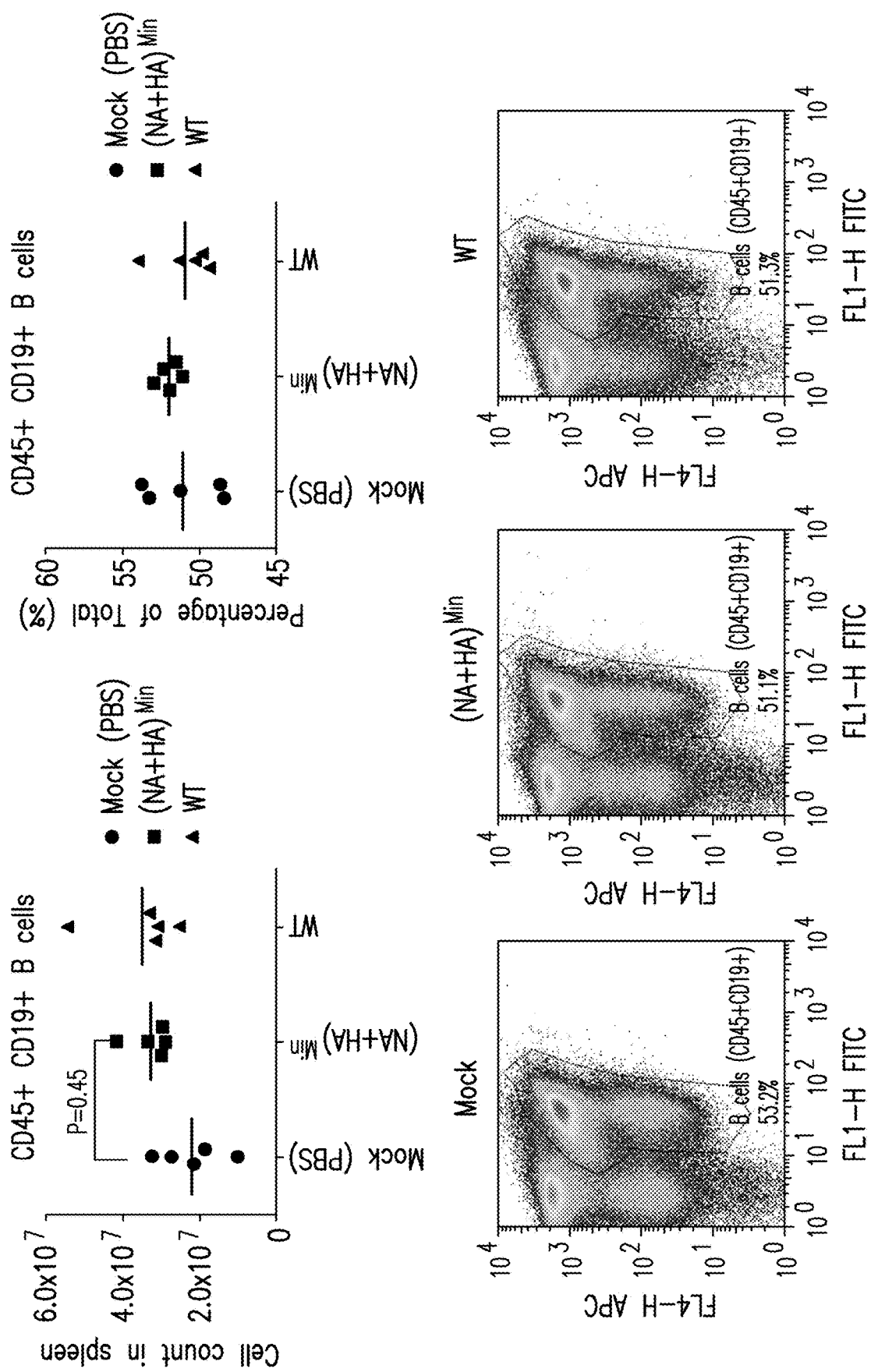
FIG. 18. T cell responses in spleens of Balb/C mice 7 days post-infection.
Figure 19E:
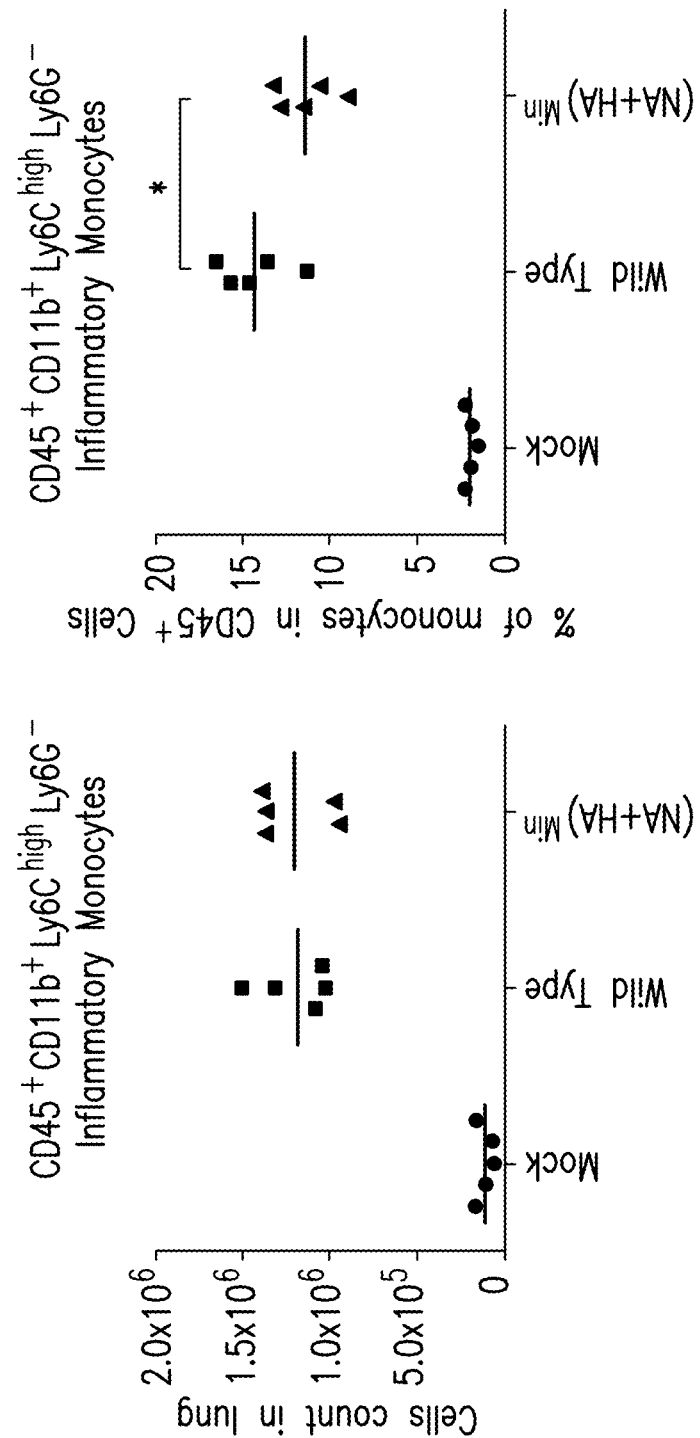
Figures 19F, 19G:
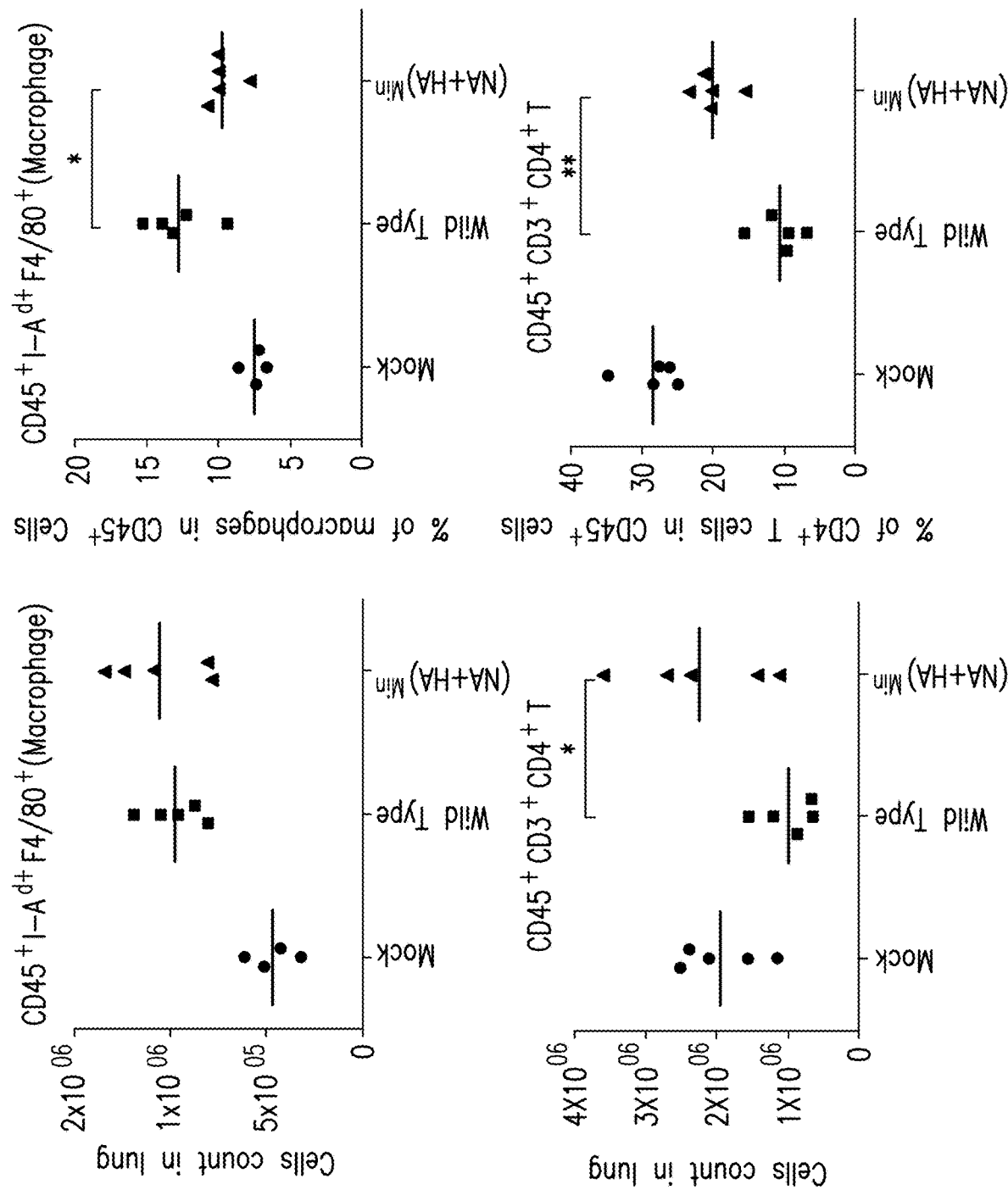
Figure 19H:
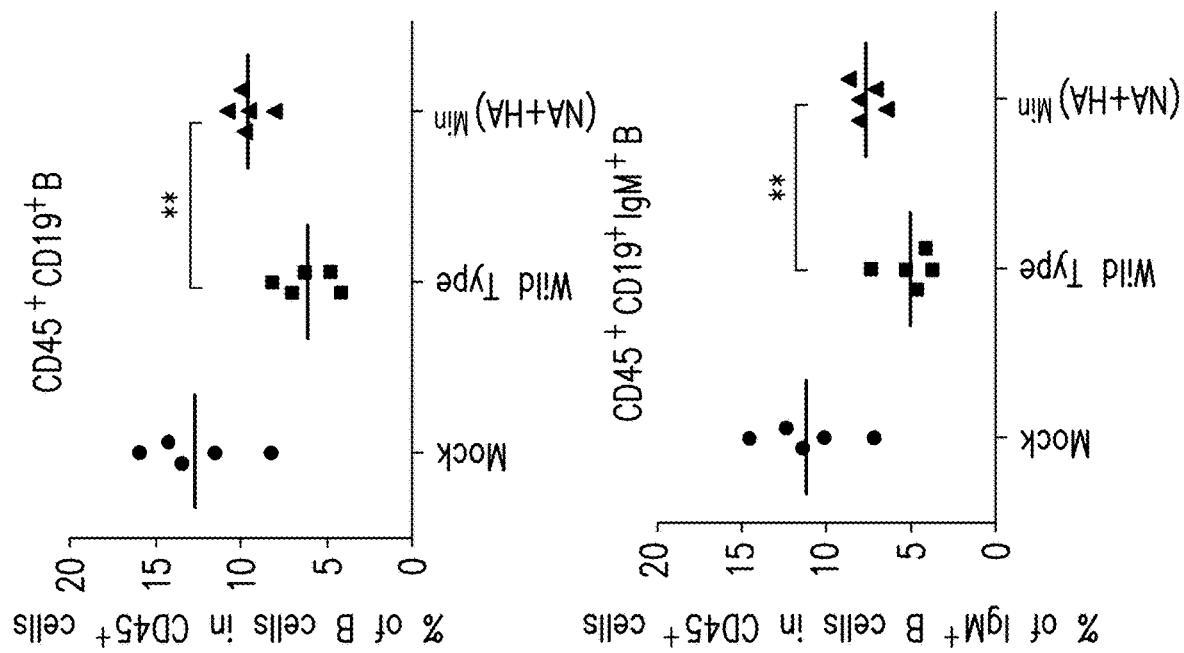
Figure 19I:
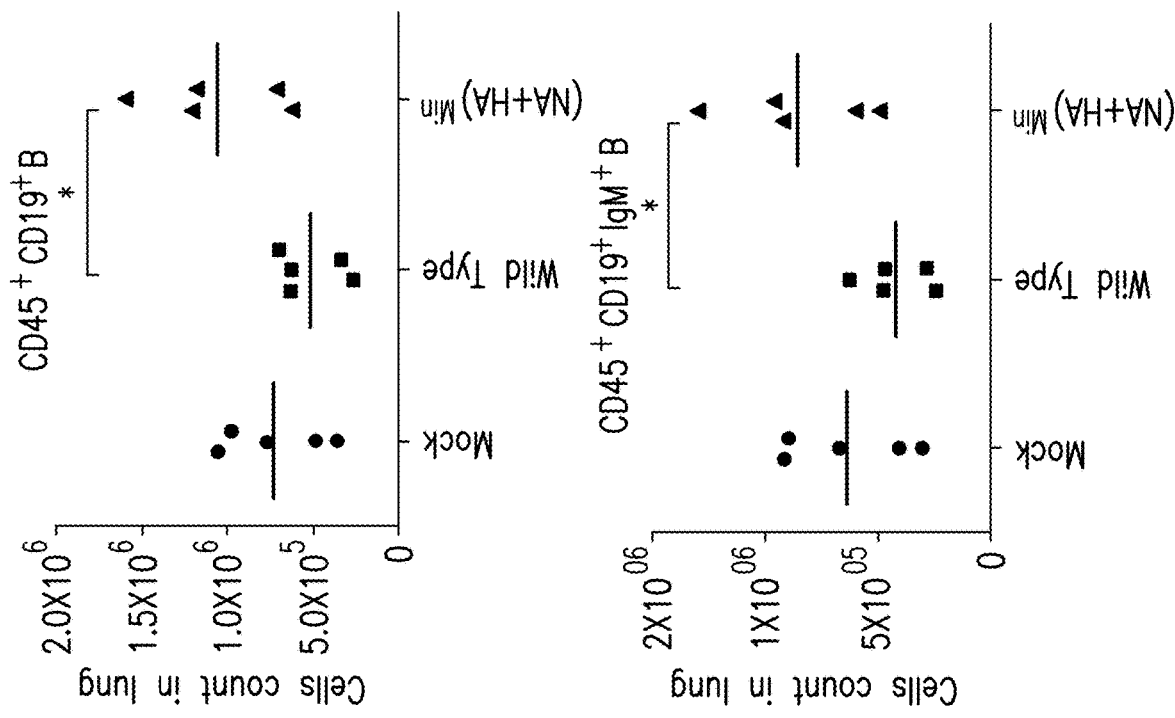

B cell responses in spleen. Groups of five Balb/C mice were infected with 10 PFU of WT or (NA+HA)$^{Min}$ viruses. On day 7 post infection, mice were euthanized and their spleens were collected for flow cytometry. (NA+HA)$^{Min}$ infected mice showed significantly higher numbers of B cells than mock group, indicating (NA+HA)$^{Min}$ virus is highly efficient in inducing protective antibodies. (FIG. 18).

In summary, at 7 days post infection, the response to WT virus in lung tissue involved greater numbers of CD4+T, CD8+T and B cells to clear the viruses than the response to (NA+HA)$^{Min}$. In spleen, (NA+HA)$^{Min}$ and WT infected mice both showed elevated T and B cells, indicating strong adaptive immune responses. Also, the T cell proportion of cells in spleen responding to infection by (NA+HA)$^{Min}$ was higher than the proportion responding to infection by WT virus. (FIG. 17).

Example 14

Flow Cytometry Analyses of Immune Cells Infiltrating Lung Tissue

Groups of five male Balb/C mice received 10$^4$ PFU wild type PR8 (a lethal dose equal to 300-fold the LD$_{50}$ for this virus), 10$^4$ PFU (NA+HA)$^{Min}$ (a safe dose at least 300-fold below the LD$_{50}$ for this virus), or PBS. Note: A the chosen dose of 10$^4$ PFU wild type PR8-infected mice invariably sucumb to the infection between 4 and 9 days. On day 3 post infection, lungs were collected and flow cytometry analyses were performed. FIG. 19 shows the results for various immune cells as follows: (A) CD45$^+$ leukocytes, (B) CD45$^+$ Ly6G$^{high}$ polymorphonuclear leukocytes (PMN), (C) CD45$^+$ CD11c$^+$ I-A$^{d+}$ F4/80$^-$ dendritic cells, (D) CD45$^+$ NKp46$^+$ natural killer cells, (E) CD45$^+$CD11b$^+$Ly6C$^{high}$Ly6G$^-$ inflammatory monocytes, (F) CD45$^+$ I-A$^{d+}$ F4/80$^+$ macrophages, (G) CD45$^+$CD3$^+$CD4$^+$ T helper cells, (H) CD45$^+$ CD19$^+$ B cells, and (I) CD45$^+$CD19$^+$IgM$^+$ B cells were monitored. Most notably (NA+HA)$^{Min}$ infection induced a significantly higher amount of natural killer cells, implicated in viral clearance, as well as a reduced infiltration of PMN, which are known to be associated with immune induced lung damage following natural influenza virus infection. Thus the marked lack of PMN infiltration during (NA+HA)$^{Min}$ infection may explain the high degree of attenuation (i.e the absence of virus induced disease and pathology) of (NA+HA)$^{Min}$.

REFERENCES

1. Thompson, W. W., Comanor, L., & Shay, D. K. (2006) Epidemiology of seasonal influenza: use of surveillance data and statistical models to estimate the burden of disease. *J. Infect. Dis.* 194 Suppl 2:S82-91.
2. Smith, D. J., et al. (2004) Mapping the antigenic and genetic evolution of influenza virus. *Science* 305(5682): 371-376.
3. Bouvier, N. M. & Palese, P. (2008) The biology of influenza viruses. *Vaccine* 26 Suppl. 4:D49-53.
4. Simonsen, L., et al. (2005) Impact of influenza vaccination on seasonal mortality in the U.S. elderly population. *Arch. Intern. Med.* 165(3):265-272.
5. Osterholm, M. T., Kelley, N. S., Sommer, A., & Belongia, E. A. (2012) Efficacy and effectiveness of influenza vaccines: a systematic review and meta-analysis. *Lancet Infect. Dis.* 12(1):36-44.
6. Belshe, R. B., et al. (2007) Live attenuated versus inactivated influenza vaccine in infants and young children. *N. Engl. J Med.* 356(7):685-696.
7. Hussain, A. I., Cordeiro, M., Sevilla, E., & Liu, J. (2010) Comparison of egg and high yielding MDCK cell-derived live attenuated influenza virus for commercial production of trivalent influenza vaccine: in vitro cell susceptibility and influenza virus replication kinetics in permissive and semi-permissive cells. *Vaccine* 28(22):3848-3855
8. Wang, Z., Tobler, S., Roayaei, J., & Eick, A. (2009) Live attenuated or inactivated influenza vaccines and medical encounters for respiratory illnesses among US military personnel. *JAMA* 301(9):945-953.
9. Gutman, G. A. & Hatfield, G. W. (1989) Nonrandom utilization of codon pairs in *Escherichia coli*. *Proc. Natl. Acad. Sci U.S.A.* 86(10):3699-3703.
10. Moura, G., et al. (2007) Large scale comparative codon-pair context analysis unveils general rules that fine-tune evolution of mRNA primary structure. *PLoS One* 2(9): e847.
11. Wang, F. P. & Li, H. (2009) Codon-pair usage and genome evolution. *Gene* 433(1-2):8-15.
12. Coleman, J. R., et al. (2008) Virus attenuation by genome-scale changes in codon pair bias. *Science* 320 (5884): 1784-1787.
13. Mueller, S., et al. (2010) Live attenuated influenza virus vaccines by computer-aided rational design. *Nat Biotechnol* 28(7):723-726.
14. Cello, J., Paul, A. V., & Wimmer, E. (2002) Chemical synthesis of poliovirus cDNA: generation of infectious virus in the absence of natural template. *Science* 297 (5583):1016-1018.
15. Sutejo, R., et al. (2012) Activation of type I and III interferon signalling pathways occurs in lung epithelial cells infected with low pathogenic avian influenza viruses. *PLoS One* 7(3):e33732.
16. Dove, B. K., et al. (2012) A quantitative proteomic analysis of lung epithelial (A549) cells infected with 2009 pandemic influenza A virus using stable isotope labelling with amino acids in cell culture. *Proteomics* 12(9):1431-1436.
17. Doma, M. K. & Parker, R. (2006) Endonucleolytic cleavage of eukaryotic mRNAs with stalls in translation elongation. *Nature* 440(7083):561-564.
18. Liu, C., Eichelberger, M. C., Compans, R. W., & Air, G. M. (1995) Influenza type A virus neuraminidase does not play a role in viral entry, replication, assembly, or budding. *J. Virol.* 69(2):1099-1106.
19. Palese, P., Tobita, K., Ueda, M., & Compans, R. W. (1974) Characterization of temperature sensitive influenza virus mutants defective in neuraminidase. *Virology* 61(2):397-410.
20. Muster, T., et al. (1995) Mucosal model of immunization against human immunodeficiency virus type 1 with a chimeric influenza virus. *J. Virol.* 69(11):6678-6686.
21. Koutsonanos, D. G., et al. (2009) Transdermal influenza immunization with vaccine-coated microneedle arrays. *PLoS One* 4(3):e4773.
22. de Jong, J. C., et al. (2003) Haemagglutination-inhibiting antibody to influenza virus. *Dev Biol* (*Basel*) 115:63-73.
23. WHO (2002) WHO Manual on Animal Influenza Diagnosis and Surveillance. www.who.int/vaccine_research/diseases/influenza/WHO_manual_on_animaldiagnosis_and_surveillance_2002_5.pdf.
24. Reed, L., Muench, M. (1938) A simple method for estimating fifty percent endpoints. *Am J. Hyg* 27(3):493-497.

SUPPLEMENTAL TABLE 1

Expected and Observed Codon Pair Frequencies and Codon Pair Scores for 14,795 Human Genes

| amino acid pair | codon pair | expected | observed | observed / expected | CPS |
|---|---|---|---|---|---|
| AA | GCGGCG | 630.04 | 2870 | 4.555 | 1.516 |
| AA | GCGGCC | 2330.20 | 4032 | 1.730 | 0.548 |
| AA | GCTGCT | 3727.41 | 5562 | 1.492 | 0.400 |
| AA | GCAGCA | 2856.40 | 4196 | 1.469 | 0.385 |
| AA | GCAGCT | 3262.97 | 4711 | 1.444 | 0.367 |
| AA | GCTGCA | 3262.97 | 4357 | 1.335 | 0.289 |
| AA | GCTGCC | 5667.77 | 7014 | 1.238 | 0.213 |
| AA | GCAGCC | 4961.56 | 6033 | 1.216 | 0.196 |
| AA | GCAGCG | 1341.51 | 1420 | 1.059 | 0.057 |
| AA | GCTGCG | 1532.46 | 1533 | 1.000 | 0.000 |
| AA | GCGGCT | 1532.46 | 1472 | 0.961 | -0.040 |
| AA | GCCGCG | 2330.20 | 2042 | 0.876 | -0.132 |
| AA | GCGGCA | 1341.51 | 1142 | 0.851 | -0.161 |
| AA | GCCGCC | 8618.21 | 5141 | 0.597 | -0.517 |
| AA | GCCGCT | 5667.77 | 1378 | 0.243 | -1.414 |
| AA | GCCGCA | 4961.56 | 1122 | 0.226 | -1.487 |
| AC | GCCTGC | 2333.61 | 3975 | 1.703 | 0.533 |
| AC | GCCTGT | 1965.56 | 2436 | 1.239 | 0.215 |
| AC | GCGTGC | 630.96 | 560 | 0.888 | -0.119 |
| AC | GCTTGT | 1292.65 | 1142 | 0.883 | -0.124 |
| AC | GCATGT | 1131.59 | 881 | 0.779 | -0.250 |
| AC | GCGTGT | 531.45 | 322 | 0.606 | -0.501 |
| AC | GCTTGC | 1534.70 | 894 | 0.583 | -0.540 |
| AC | GCATGC | 1343.47 | 554 | 0.412 | -0.886 |
| AD | GCAGAT | 2373.33 | 4215 | 1.776 | 0.574 |
| AD | GCTGAT | 2711.15 | 3887 | 1.434 | 0.360 |
| AD | GCTGAC | 3062.55 | 4374 | 1.428 | 0.356 |
| AD | GCGGAC | 1259.11 | 1625 | 1.291 | 0.255 |
| AD | GCAGAC | 2680.95 | 3395 | 1.266 | 0.236 |
| AD | GCGGAT | 1114.64 | 839 | 0.753 | -0.284 |
| AD | GCCGAC | 4656.80 | 2726 | 0.585 | -0.535 |
| AD | GCCGAT | 4122.47 | 920 | 0.223 | -1.500 |
| AE | GCAGAA | 3517.48 | 5814 | 1.653 | 0.503 |
| AE | GCAGAG | 4703.98 | 7094 | 1.508 | 0.411 |
| AE | GCGGAG | 2209.23 | 3171 | 1.435 | 0.361 |
| AE | GCTGAG | 5373.53 | 7362 | 1.370 | 0.315 |
| AE | GCTGAA | 4018.14 | 5186 | 1.291 | 0.255 |
| AE | GCCGAG | 8170.80 | 5082 | 0.622 | -0.475 |
| AE | GCGGAA | 1651.99 | 949 | 0.574 | -0.554 |
| AE | GCCGAA | 6109.85 | 1097 | 0.180 | -1.717 |
| AF | GCCTTC | 4447.90 | 7382 | 1.660 | 0.507 |
| AF | GCATTT | 2237.22 | 2332 | 1.042 | 0.041 |
| AF | GCTTTT | 2555.66 | 2580 | 1.010 | 0.009 |
| AF | GCCTTT | 3886.04 | 3842 | 0.989 | -0.011 |
| AF | GCTTTC | 2925.16 | 2315 | 0.791 | -0.234 |
| AF | GCGTTC | 1202.63 | 636 | 0.529 | -0.637 |
| AF | GCGTTT | 1050.71 | 518 | 0.493 | -0.707 |
| AF | GCATTC | 2560.68 | 1261 | 0.492 | -0.708 |
| AG | GCGGGC | 1369.64 | 2638 | 1.926 | 0.655 |
| AG | GCGGGG | 986.17 | 1738 | 1.762 | 0.567 |
| AG | GCTGGG | 2398.67 | 3855 | 1.607 | 0.474 |
| AG | GCTGGT | 1590.73 | 2524 | 1.587 | 0.462 |
| AG | GCTGGA | 2457.02 | 3783 | 1.540 | 0.432 |
| AG | GCAGGA | 2150.87 | 3074 | 1.429 | 0.357 |
| AG | GCAGGG | 2099.79 | 2782 | 1.325 | 0.281 |
| AG | GCAGGT | 1392.52 | 1748 | 1.255 | 0.227 |
| AG | GCTGGC | 3331.38 | 3961 | 1.189 | 0.173 |
| AG | GCAGGC | 2916.28 | 3119 | 1.070 | 0.067 |
| AG | GCGGGT | 654.00 | 617 | 0.943 | -0.058 |
| AG | GCGGGA | 1010.16 | 793 | 0.785 | -0.242 |
| AG | GCCGGG | 3647.33 | 2240 | 0.614 | -0.488 |
| AG | GCCGGC | 5065.58 | 2977 | 0.588 | -0.532 |
| AG | GCCGGT | 2418.80 | 581 | 0.240 | -1.426 |
| AG | GCCGGA | 3736.06 | 795 | 0.213 | -1.547 |
| AH | GCGCAC | 748.29 | 983 | 1.314 | 0.273 |
| AH | GCCCAC | 2767.53 | 3465 | 1.252 | 0.225 |
| AH | GCTCAT | 1319.86 | 1471 | 1.115 | 0.108 |
| AH | GCACAT | 1155.40 | 1122 | 0.971 | -0.029 |
| AH | GCCCAT | 2006.93 | 1827 | 0.910 | -0.094 |
| AH | GCTCAC | 1820.07 | 1526 | 0.838 | -0.176 |
| AH | GCACAC | 1593.29 | 1312 | 0.823 | -0.194 |
| AH | GCGCAT | 542.64 | 248 | 0.457 | -0.783 |
| AI | GCCATC | 3894.51 | 7798 | 2.002 | 0.694 |
| AI | GCCATT | 3079.73 | 3761 | 1.221 | 0.200 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| AI | GCAATA | 815.43 | 924 | 1.133 | 0.125 |
| AI | GCAATT | 1773.02 | 1684 | 0.950 | -0.052 |
| AI | GCCATA | 1416.41 | 1257 | 0.887 | -0.119 |
| AI | GCTATT | 2025.39 | 1709 | 0.844 | -0.170 |
| AI | GCTATA | 931.50 | 771 | 0.828 | -0.189 |
| AI | GCTATC | 2561.23 | 1194 | 0.466 | -0.763 |
| AI | GCGATT | 832.70 | 373 | 0.448 | -0.803 |
| AI | GCAATC | 2242.09 | 984 | 0.439 | -0.824 |
| AI | GCGATA | 382.97 | 149 | 0.389 | -0.944 |
| AI | GCGATC | 1053.00 | 404 | 0.384 | -0.958 |
| AK | GCCAAG | 5767.01 | 9818 | 1.702 | 0.532 |
| AK | GCAAAA | 2563.57 | 3011 | 1.175 | 0.161 |
| AK | GCCAAA | 4452.91 | 4794 | 1.077 | 0.074 |
| AK | GCAAAG | 3320.10 | 3044 | 0.917 | -0.087 |
| AK | GCTAAA | 2928.46 | 2022 | 0.690 | -0.370 |
| AK | GCGAAG | 1559.29 | 765 | 0.491 | -0.712 |
| AK | GCTAAG | 3792.68 | 1725 | 0.455 | -0.788 |
| AK | GCGAAA | 1203.98 | 409 | 0.340 | -1.080 |
| AL | GCGCTG | 2369.16 | 4619 | 1.950 | 0.668 |
| AL | GCGCTC | 1140.05 | 1765 | 1.548 | 0.437 |
| AL | GCTTTG | 1873.51 | 2601 | 1.388 | 0.328 |
| AL | GCCCTG | 8762.30 | 11409 | 1.302 | 0.264 |
| AL | GCCTTG | 2848.79 | 3695 | 1.297 | 0.260 |
| AL | GCTTTA | 1115.24 | 1385 | 1.242 | 0.217 |
| AL | GCCCTC | 4216.45 | 4499 | 1.067 | 0.065 |
| AL | GCTCTT | 1912.07 | 2038 | 1.066 | 0.064 |
| AL | GCATTA | 976.28 | 986 | 1.010 | 0.010 |
| AL | GCTCTA | 1031.16 | 940 | 0.912 | -0.093 |
| AL | GCACTT | 1673.82 | 1444 | 0.863 | -0.148 |
| AL | GCATTG | 1640.07 | 1364 | 0.832 | -0.184 |
| AL | GCACTA | 902.68 | 747 | 0.828 | -0.189 |
| AL | GCGCTA | 423.94 | 342 | 0.807 | -0.215 |
| AL | GCCCTA | 1567.95 | 1228 | 0.783 | -0.244 |
| AL | GCTCTG | 5762.53 | 4505 | 0.782 | -0.246 |
| AL | GCCCTT | 2907.42 | 2230 | 0.767 | -0.265 |
| AL | GCTCTC | 2772.95 | 2036 | 0.734 | -0.309 |
| AL | GCCTTA | 1695.80 | 1205 | 0.711 | -0.342 |
| AL | GCACTG | 5044.51 | 3522 | 0.698 | -0.359 |
| AL | GCGTTG | 770.26 | 476 | 0.618 | -0.481 |
| AL | GCGCTT | 786.11 | 459 | 0.584 | -0.538 |
| AL | GCACTC | 2427.43 | 1415 | 0.583 | -0.540 |
| AL | GCGTTA | 458.51 | 169 | 0.369 | -0.998 |
| AM | GCCATG | 4236.47 | 6521 | 1.539 | 0.431 |
| AM | GCAATG | 2438.96 | 1900 | 0.779 | -0.250 |
| AM | GCTATG | 2786.11 | 1561 | 0.560 | -0.579 |
| AM | GCGATG | 1145.46 | 625 | 0.546 | -0.606 |
| AN | GCCAAC | 3190.28 | 5452 | 1.709 | 0.536 |
| AN | GCAAAT | 1667.60 | 2282 | 1.368 | 0.314 |
| AN | GCCAAT | 2896.62 | 3122 | 1.078 | 0.075 |
| AN | GCAAAC | 1836.66 | 1512 | 0.823 | -0.195 |
| AN | GCTAAT | 1904.97 | 1356 | 0.712 | -0.340 |
| AN | GCTAAC | 2098.09 | 925 | 0.441 | -0.819 |
| AN | GCGAAC | 862.59 | 331 | 0.384 | -0.958 |
| AN | GCGAAT | 783.19 | 260 | 0.332 | -1.103 |
| AP | GCGCCG | 406.74 | 1172 | 2.881 | 1.058 |
| AP | GCGCCC | 1122.56 | 2271 | 2.023 | 0.705 |
| AP | GCCCCG | 1504.34 | 2335 | 1.552 | 0.440 |
| AP | GCTCCA | 2360.19 | 2463 | 1.044 | 0.043 |
| AP | GCTCCT | 2445.47 | 2548 | 1.042 | 0.041 |
| AP | GCCCCC | 4151.78 | 3957 | 0.953 | -0.048 |
| AP | GCACCT | 2140.76 | 2028 | 0.947 | -0.054 |
| AP | GCCCCA | 3588.82 | 3371 | 0.939 | -0.063 |
| AP | GCACCA | 2066.10 | 1831 | 0.886 | -0.121 |
| AP | GCACCC | 2390.20 | 2111 | 0.883 | -0.124 |
| AP | GCCCCT | 3718.49 | 3269 | 0.879 | -0.129 |
| AP | GCTCCC | 2730.42 | 2384 | 0.873 | -0.136 |
| AP | GCTCCG | 989.33 | 773 | 0.781 | -0.247 |
| AP | GCGCCT | 1005.41 | 778 | 0.774 | -0.256 |
| AP | GCACCG | 866.06 | 571 | 0.659 | -0.417 |
| AP | GCGCCA | 970.35 | 595 | 0.613 | -0.489 |
| AQ | GCCCAG | 7143.67 | 9550 | 1.337 | 0.290 |
| AQ | GCGCAG | 1931.51 | 2101 | 1.088 | 0.084 |
| AQ | GCACAA | 1472.79 | 1416 | 0.961 | -0.039 |
| AQ | GCTCAA | 1682.42 | 1522 | 0.905 | -0.100 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| AQ | GCTCAG | 4698.04 | 4141 | 0.881 | −0.126 |
| AQ | GCACAG | 4112.65 | 3374 | 0.820 | −0.198 |
| AQ | GCCCAA | 2558.23 | 1943 | 0.760 | −0.275 |
| AQ | GCGCAA | 691.70 | 244 | 0.353 | −1.042 |
| AR | GCGCGC | 580.17 | 1255 | 2.163 | 0.772 |
| AR | GCGCGG | 634.54 | 1175 | 1.852 | 0.616 |
| AR | GCCCGG | 2346.82 | 3946 | 1.681 | 0.520 |
| AR | GCCCGC | 2145.76 | 3135 | 1.461 | 0.379 |
| AR | GCCAGG | 2323.57 | 3242 | 1.395 | 0.333 |
| AR | GCAAGA | 1362.59 | 1559 | 1.144 | 0.135 |
| AR | GCTCGA | 836.64 | 943 | 1.127 | 0.120 |
| AR | GCCCGA | 1272.16 | 1418 | 1.115 | 0.109 |
| AR | GCCCGT | 918.67 | 935 | 1.018 | 0.018 |
| AR | GCTCGT | 604.17 | 595 | 0.985 | −0.015 |
| AR | GCCAGA | 2366.81 | 2219 | 0.938 | −0.064 |
| AR | GCTCGG | 1543.39 | 1295 | 0.839 | −0.175 |
| AR | GCGCGT | 248.39 | 205 | 0.825 | −0.192 |
| AR | GCAAGG | 1337.69 | 1089 | 0.814 | −0.206 |
| AR | GCGAGG | 628.25 | 486 | 0.774 | −0.257 |
| AR | GCACGA | 732.39 | 533 | 0.728 | −0.318 |
| AR | GCTCGC | 1411.16 | 941 | 0.667 | −0.405 |
| AR | GCGCGA | 343.97 | 226 | 0.657 | −0.420 |
| AR | GCACGT | 528.89 | 338 | 0.639 | −0.448 |
| AR | GCACGG | 1351.08 | 859 | 0.636 | −0.453 |
| AR | GCACGC | 1235.33 | 619 | 0.501 | −0.691 |
| AR | GCTAGA | 1556.53 | 714 | 0.459 | −0.779 |
| AR | GCGAGA | 639.94 | 263 | 0.411 | −0.889 |
| AR | GCTAGG | 1528.10 | 487 | 0.319 | −1.144 |
| AS | GCCTCG | 963.41 | 1977 | 2.052 | 0.719 |
| AS | GCGTCG | 260.49 | 465 | 1.785 | 0.579 |
| AS | GCCAGC | 4127.58 | 6466 | 1.567 | 0.449 |
| AS | GCCTCC | 3643.21 | 5443 | 1.494 | 0.401 |
| AS | GCTTCT | 2084.25 | 2488 | 1.194 | 0.177 |
| AS | GCCAGT | 2604.12 | 3085 | 1.185 | 0.169 |
| AS | GCATCT | 1824.55 | 2154 | 1.181 | 0.166 |
| AS | GCTTCA | 1684.99 | 1932 | 1.147 | 0.137 |
| AS | GCGTCC | 985.05 | 1079 | 1.095 | 0.091 |
| AS | GCATCA | 1475.04 | 1531 | 1.038 | 0.037 |
| AS | GCCTCT | 3169.23 | 3235 | 1.021 | 0.021 |
| AS | GCCTCA | 2562.14 | 2514 | 0.981 | −0.019 |
| AS | GCTTCC | 2395.96 | 2295 | 0.958 | −0.043 |
| AS | GCAAGT | 1499.21 | 1307 | 0.872 | −0.137 |
| AS | GCTTCG | 633.59 | 516 | 0.814 | −0.205 |
| AS | GCATCC | 2097.42 | 1658 | 0.790 | −0.235 |
| AS | GCATCG | 554.64 | 403 | 0.727 | −0.319 |
| AS | GCGTCT | 856.90 | 521 | 0.608 | −0.498 |
| AS | GCGAGC | 1116.02 | 595 | 0.533 | −0.629 |
| AS | GCGTCA | 692.75 | 319 | 0.460 | −0.775 |
| AS | GCAAGC | 2376.27 | 1080 | 0.454 | −0.789 |
| AS | GCTAGT | 1712.60 | 737 | 0.430 | −0.843 |
| AS | GCGAGT | 704.10 | 265 | 0.376 | −0.977 |
| AS | GCTAGC | 2714.51 | 673 | 0.248 | −1.395 |
| AT | GCCACG | 1262.40 | 2478 | 1.963 | 0.674 |
| AT | GCCACC | 3842.98 | 6598 | 1.717 | 0.541 |
| AT | GCCACA | 3111.04 | 4031 | 1.296 | 0.259 |
| AT | GCCACT | 2751.18 | 3205 | 1.165 | 0.153 |
| AT | GCAACA | 1791.05 | 1761 | 0.983 | −0.017 |
| AT | GCGACG | 341.33 | 329 | 0.964 | −0.037 |
| AT | GCAACT | 1583.87 | 1509 | 0.953 | −0.048 |
| AT | GCTACT | 1809.31 | 1395 | 0.771 | −0.260 |
| AT | GCTACA | 2045.98 | 1528 | 0.747 | −0.292 |
| AT | GCGACC | 1039.07 | 601 | 0.578 | −0.547 |
| AT | GCAACC | 2212.43 | 1259 | 0.569 | −0.564 |
| AT | GCTACC | 2527.34 | 1364 | 0.540 | −0.617 |
| AT | GCAACG | 726.77 | 384 | 0.528 | −0.638 |
| AT | GCTACG | 830.22 | 363 | 0.437 | −0.827 |
| AT | GCGACT | 743.87 | 308 | 0.414 | −0.882 |
| AT | GCGACA | 841.17 | 347 | 0.413 | −0.885 |
| AV | GCTGTT | 1736.99 | 3025 | 1.742 | 0.555 |
| AV | GCTGTG | 4399.56 | 7279 | 1.654 | 0.503 |
| AV | GCTGTA | 1127.89 | 1750 | 1.552 | 0.439 |
| AV | GCTGTC | 2223.90 | 3351 | 1.507 | 0.410 |
| AV | GCAGTA | 987.35 | 1401 | 1.419 | 0.350 |
| AV | GCGGTG | 1808.80 | 2487 | 1.375 | 0.318 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| AV | GCAGTT | 1520.56 | 2087 | 1.373 | 0.317 |
| AV | GCAGTG | 3851.36 | 4349 | 1.129 | 0.122 |
| AV | GCGGTC | 914.32 | 883 | 0.966 | -0.035 |
| AV | GCAGTC | 1946.80 | 1806 | 0.928 | -0.075 |
| AV | GCCGTG | 6689.81 | 4322 | 0.646 | -0.437 |
| AV | GCGGTT | 714.13 | 423 | 0.592 | -0.524 |
| AV | GCGGTA | 463.71 | 270 | 0.582 | -0.541 |
| AV | GCCGTC | 3381.59 | 1798 | 0.532 | -0.632 |
| AV | GCCGTT | 2641.21 | 563 | 0.213 | -1.546 |
| AV | GCCGTA | 1715.03 | 329 | 0.192 | -1.651 |
| AW | GCCTGG | 2528.22 | 3848 | 1.522 | 0.420 |
| AW | GCGTGG | 683.58 | 558 | 0.816 | -0.203 |
| AW | GCTTGG | 1662.69 | 1066 | 0.641 | -0.445 |
| AW | GCATGG | 1455.51 | 858 | 0.589 | -0.529 |
| AY | GCCTAC | 2643.77 | 4073 | 1.541 | 0.432 |
| AY | GCCTAT | 2148.26 | 2457 | 1.144 | 0.134 |
| AY | GCTTAT | 1412.81 | 1478 | 1.046 | 0.045 |
| AY | GCATAT | 1236.77 | 1244 | 1.006 | 0.006 |
| AY | GCTTAC | 1738.68 | 1139 | 0.655 | -0.423 |
| AY | GCGTAC | 714.83 | 429 | 0.600 | -0.511 |
| AY | GCATAC | 1522.04 | 868 | 0.570 | -0.562 |
| AY | GCGTAT | 580.85 | 310 | 0.534 | -0.628 |
| CA | TGTGCT | 1164.04 | 2021 | 1.736 | 0.552 |
| CA | TGTGCC | 1769.99 | 2992 | 1.690 | 0.525 |
| CA | TGTGCA | 1019.00 | 1708 | 1.676 | 0.517 |
| CA | TGTGCG | 478.57 | 477 | 0.997 | -0.003 |
| CA | TGCGCG | 568.18 | 502 | 0.884 | -0.124 |
| CA | TGCGCC | 2101.42 | 1313 | 0.625 | -0.470 |
| CA | TGCGCT | 1382.00 | 368 | 0.266 | -1.323 |
| CA | TGCGCA | 1209.80 | 312 | 0.258 | -1.355 |
| CC | TGCTGC | 1534.17 | 2610 | 1.701 | 0.531 |
| CC | TGCTGT | 1292.21 | 1571 | 1.216 | 0.195 |
| CC | TGTTGT | 1088.41 | 529 | 0.486 | -0.721 |
| CC | TGTTGC | 1292.21 | 497 | 0.385 | -0.956 |
| CD | TGTGAC | 1920.20 | 3470 | 1.807 | 0.592 |
| CD | TGTGAT | 1699.87 | 2853 | 1.678 | 0.518 |
| CD | TGCGAC | 2279.75 | 1134 | 0.497 | -0.698 |
| CD | TGCGAT | 2018.17 | 461 | 0.228 | -1.477 |
| CE | TGTGAA | 1901.69 | 3636 | 1.912 | 0.648 |
| CE | TGTGAG | 2543.16 | 3935 | 1.547 | 0.437 |
| CE | TGCGAG | 3019.37 | 1709 | 0.566 | -0.569 |
| CE | TGCGAA | 2257.78 | 442 | 0.196 | -1.631 |
| CF | TGCTTC | 1891.74 | 2684 | 1.419 | 0.350 |
| CF | TGCTTT | 1652.78 | 1685 | 1.019 | 0.019 |
| CF | TGTTTT | 1392.11 | 1096 | 0.787 | -0.239 |
| CF | TGTTTC | 1593.38 | 1065 | 0.668 | -0.403 |
| CG | TGTGGG | 1594.78 | 3240 | 2.032 | 0.709 |
| CG | TGTGGA | 1633.57 | 2846 | 1.742 | 0.555 |
| CG | TGTGGT | 1057.61 | 1627 | 1.538 | 0.431 |
| CG | TGTGGC | 2214.90 | 3133 | 1.415 | 0.347 |
| CG | TGCGGG | 1893.40 | 1137 | 0.601 | -0.510 |
| CG | TGCGGC | 2629.63 | 1461 | 0.556 | -0.588 |
| CG | TGCGGT | 1255.64 | 344 | 0.274 | -1.295 |
| CG | TGCGGA | 1939.46 | 431 | 0.222 | -1.504 |
| CH | TGCCAC | 1618.50 | 2144 | 1.325 | 0.281 |
| CH | TGCCAT | 1173.68 | 1253 | 1.068 | 0.065 |
| CH | TGTCAT | 988.58 | 831 | 0.841 | -0.174 |
| CH | TGTCAC | 1363.24 | 916 | 0.672 | -0.398 |
| CI | TGCATC | 1821.04 | 2813 | 1.545 | 0.435 |
| CI | TGCATT | 1440.05 | 1579 | 1.096 | 0.092 |
| CI | TGCATA | 662.30 | 576 | 0.870 | -0.140 |
| CI | TGTATA | 557.84 | 474 | 0.850 | -0.163 |
| CI | TGTATT | 1212.94 | 927 | 0.764 | -0.269 |
| CI | TGTATC | 1533.83 | 859 | 0.560 | -0.580 |
| CK | TGCAAG | 2777.53 | 3348 | 1.205 | 0.187 |
| CK | TGCAAA | 2144.62 | 2441 | 1.138 | 0.129 |
| CK | TGTAAA | 1806.38 | 1770 | 0.980 | -0.020 |
| CK | TGTAAG | 2339.47 | 1509 | 0.645 | -0.438 |
| CL | TGCCTC | 1722.14 | 2468 | 1.433 | 0.360 |
| CL | TGCCTG | 3578.83 | 4525 | 1.264 | 0.235 |
| CL | TGTTTA | 583.38 | 704 | 1.207 | 0.188 |
| CL | TGCCTT | 1187.49 | 1384 | 1.165 | 0.153 |
| CL | TGTTTG | 980.04 | 1079 | 1.101 | 0.096 |
| CL | TGCTTG | 1163.55 | 1179 | 1.013 | 0.013 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| CL | TGTCTT | 1000.21 | 940 | 0.940 | -0.062 |
| CL | TGCCTA | 640.41 | 585 | 0.913 | -0.090 |
| CL | TGTCTA | 539.40 | 481 | 0.892 | -0.115 |
| CL | TGCTTA | 692.62 | 565 | 0.816 | -0.204 |
| CL | TGTCTC | 1450.53 | 1010 | 0.696 | -0.362 |
| CL | TGTCTG | 3014.39 | 1633 | 0.542 | -0.613 |
| CM | TGCATG | 1518.22 | 1979 | 1.304 | 0.265 |
| CM | TGTATG | 1278.78 | 818 | 0.640 | -0.447 |
| CN | TGCAAC | 1825.04 | 2351 | 1.288 | 0.253 |
| CN | TGCAAT | 1657.05 | 1636 | 0.987 | -0.013 |
| CN | TGTAAT | 1395.71 | 1349 | 0.967 | -0.034 |
| CN | TGTAAC | 1537.20 | 1079 | 0.702 | -0.354 |
| CP | TGCCCG | 687.28 | 978 | 1.423 | 0.353 |
| CP | TGCCCC | 1896.80 | 2279 | 1.201 | 0.184 |
| CP | TGCCCA | 1639.61 | 1728 | 1.054 | 0.053 |
| CP | TGCCCT | 1698.85 | 1690 | 0.995 | -0.005 |
| CP | TGTCCT | 1430.91 | 1333 | 0.932 | -0.071 |
| CP | TGTCCA | 1381.01 | 1263 | 0.915 | -0.089 |
| CP | TGTCCC | 1597.65 | 1369 | 0.857 | -0.154 |
| CP | TGTCCG | 578.88 | 271 | 0.468 | -0.759 |
| CQ | TGCCAG | 3338.89 | 4321 | 1.294 | 0.258 |
| CQ | TGCCAA | 1195.69 | 1319 | 1.103 | 0.098 |
| CQ | TGTCAA | 1007.11 | 905 | 0.899 | -0.107 |
| CQ | TGTCAG | 2812.30 | 1809 | 0.643 | -0.441 |
| CR | TGCCGC | 1031.52 | 1860 | 1.803 | 0.590 |
| CR | TGCCGG | 1128.18 | 1543 | 1.368 | 0.313 |
| CR | TGCAGG | 1117.00 | 1450 | 1.298 | 0.261 |
| CR | TGCCGT | 441.63 | 541 | 1.225 | 0.203 |
| CR | TGCCGA | 611.56 | 742 | 1.213 | 0.193 |
| CR | TGCAGA | 1137.78 | 1252 | 1.100 | 0.096 |
| CR | TGTCGA | 515.11 | 458 | 0.889 | -0.118 |
| CR | TGTCGT | 371.98 | 308 | 0.828 | -0.189 |
| CR | TGTAGA | 958.34 | 570 | 0.595 | -0.520 |
| CR | TGTCGC | 868.83 | 497 | 0.572 | -0.559 |
| CR | TGTCGG | 950.24 | 463 | 0.487 | -0.719 |
| CR | TGTAGG | 940.83 | 389 | 0.413 | -0.883 |
| CS | TGCAGC | 1990.73 | 3150 | 1.582 | 0.459 |
| CS | TGCTCC | 1757.12 | 2397 | 1.364 | 0.311 |
| CS | TGCAGT | 1255.97 | 1701 | 1.354 | 0.303 |
| CS | TGCTCG | 464.65 | 571 | 1.229 | 0.206 |
| CS | TGTTCT | 1287.45 | 1184 | 0.920 | -0.084 |
| CS | TGCTCT | 1528.52 | 1393 | 0.911 | -0.093 |
| CS | TGTTCA | 1040.83 | 932 | 0.895 | -0.110 |
| CS | TGCTCA | 1235.72 | 1079 | 0.873 | -0.136 |
| CS | TGTTCC | 1479.99 | 1102 | 0.745 | -0.295 |
| CS | TGTAGT | 1057.88 | 699 | 0.661 | -0.414 |
| CS | TGTTCG | 391.37 | 192 | 0.491 | -0.712 |
| CS | TGTAGC | 1676.76 | 767 | 0.457 | -0.782 |
| CT | TGCACG | 535.88 | 829 | 1.547 | 0.436 |
| CT | TGCACC | 1631.31 | 2321 | 1.423 | 0.353 |
| CT | TGCACA | 1320.60 | 1508 | 1.142 | 0.133 |
| CT | TGCACT | 1167.85 | 1185 | 1.015 | 0.015 |
| CT | TGTACT | 983.66 | 802 | 0.815 | -0.204 |
| CT | TGTACA | 1112.32 | 830 | 0.746 | -0.293 |
| CT | TGTACC | 1374.02 | 942 | 0.686 | -0.377 |
| CT | TGTACG | 451.36 | 160 | 0.354 | -1.037 |
| CV | TGTGTC | 1064.94 | 1821 | 1.710 | 0.536 |
| CV | TGTGTT | 831.78 | 1383 | 1.663 | 0.508 |
| CV | TGTGTA | 540.10 | 866 | 1.603 | 0.472 |
| CV | TGTGTG | 2106.78 | 3241 | 1.538 | 0.431 |
| CV | TGCGTG | 2501.27 | 1537 | 0.614 | -0.487 |
| CV | TGCGTC | 1264.35 | 734 | 0.581 | -0.544 |
| CV | TGCGTT | 987.53 | 219 | 0.222 | -1.506 |
| CV | TGCGTA | 641.24 | 137 | 0.214 | -1.543 |
| CW | TGCTGG | 1275.05 | 1842 | 1.445 | 0.368 |
| CW | TGTTGG | 1073.95 | 507 | 0.472 | -0.751 |
| CY | TGCTAC | 1379.34 | 1995 | 1.446 | 0.369 |
| CY | TGCTAT | 1120.82 | 1170 | 1.044 | 0.043 |
| CY | TGTTAT | 944.05 | 653 | 0.692 | -0.369 |
| CY | TGTTAC | 1161.80 | 788 | 0.678 | -0.388 |
| DA | GATGCT | 2675.13 | 5292 | 1.978 | 0.682 |
| DA | GATGCA | 2341.80 | 3898 | 1.665 | 0.510 |
| DA | GATGCC | 4067.71 | 5983 | 1.471 | 0.386 |
| DA | GACGCG | 1242.39 | 1116 | 0.898 | -0.107 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| DA | GATGCG | 1099.83 | 972 | 0.884 | -0.124 |
| DA | GACGCC | 4594.94 | 2668 | 0.581 | -0.544 |
| DA | GACGCA | 2645.34 | 852 | 0.322 | -1.133 |
| DA | GACGCT | 3021.87 | 908 | 0.300 | -1.202 |
| DC | GACTGC | 2386.86 | 3465 | 1.452 | 0.373 |
| DC | GACTGT | 2010.41 | 2804 | 1.395 | 0.333 |
| DC | GATTGT | 1779.74 | 1163 | 0.653 | -0.425 |
| DC | GATTGC | 2112.99 | 858 | 0.406 | -0.901 |
| DD | GATGAT | 4271.42 | 7846 | 1.837 | 0.608 |
| DD | GATGAC | 4825.06 | 7181 | 1.488 | 0.398 |
| DD | GACGAC | 5450.46 | 2965 | 0.544 | -0.609 |
| DD | GACGAT | 4825.06 | 1380 | 0.286 | -1.252 |
| DE | GATGAA | 5114.33 | 10045 | 1.964 | 0.675 |
| DE | GATGAG | 6839.48 | 9573 | 1.400 | 0.336 |
| DE | GACGAG | 7725.97 | 4498 | 0.582 | -0.541 |
| DE | GACGAA | 5777.22 | 1341 | 0.232 | -1.461 |
| DF | GACTTC | 4696.28 | 6094 | 1.298 | 0.261 |
| DF | GACTTT | 4103.05 | 4250 | 1.036 | 0.035 |
| DF | GATTTT | 3632.26 | 3485 | 0.959 | -0.041 |
| DF | GATTTC | 4157.42 | 2760 | 0.664 | -0.410 |
| DG | GATGGT | 1910.36 | 3443 | 1.802 | 0.589 |
| DG | GATGGA | 2950.72 | 5133 | 1.740 | 0.554 |
| DG | GATGGG | 2880.65 | 4437 | 1.540 | 0.432 |
| DG | GATGGC | 4000.77 | 5419 | 1.354 | 0.303 |
| DG | GACGGC | 4519.33 | 2987 | 0.661 | -0.414 |
| DG | GACGGG | 3254.02 | 1979 | 0.608 | -0.497 |
| DG | GACGGT | 2157.97 | 723 | 0.335 | -1.094 |
| DG | GACGGA | 3333.18 | 886 | 0.266 | -1.325 |
| DH | GACCAC | 2653.74 | 3480 | 1.311 | 0.271 |
| DH | GACCAT | 1924.41 | 2014 | 1.047 | 0.046 |
| DH | GATCAT | 1703.60 | 1623 | 0.953 | -0.048 |
| DH | GATCAC | 2349.25 | 1514 | 0.644 | -0.439 |
| DI | GACATC | 4715.94 | 6532 | 1.385 | 0.326 |
| DI | GACATT | 3729.31 | 4087 | 1.096 | 0.092 |
| DI | GATATT | 3301.40 | 3271 | 0.991 | -0.009 |
| DI | GATATA | 1518.36 | 1495 | 0.985 | -0.016 |
| DI | GACATA | 1715.16 | 1565 | 0.912 | -0.092 |
| DI | GATATC | 4174.83 | 2205 | 0.528 | -0.638 |
| DK | GACAAG | 5562.52 | 7324 | 1.317 | 0.275 |
| DK | GACAAA | 4295.02 | 4794 | 1.116 | 0.110 |
| DK | GATAAA | 3802.20 | 3855 | 1.014 | 0.014 |
| DK | GATAAG | 4924.27 | 2611 | 0.530 | -0.634 |
| DL | GACCTC | 3785.97 | 5029 | 1.328 | 0.284 |
| DL | GACTTG | 2557.95 | 3396 | 1.328 | 0.283 |
| DL | GATTTA | 1347.95 | 1740 | 1.291 | 0.255 |
| DL | GACCTG | 7867.71 | 9796 | 1.245 | 0.219 |
| DL | GATTTG | 2264.44 | 2687 | 1.187 | 0.171 |
| DL | GACCTT | 2610.58 | 2774 | 1.063 | 0.061 |
| DL | GATCTT | 2311.04 | 2416 | 1.045 | 0.044 |
| DL | GACCTA | 1407.87 | 1416 | 1.006 | 0.006 |
| DL | GACTTA | 1522.66 | 1403 | 0.921 | -0.082 |
| DL | GATCTA | 1246.33 | 1020 | 0.818 | -0.200 |
| DL | GATCTC | 3351.56 | 2214 | 0.661 | -0.415 |
| DL | GATCTG | 6964.95 | 3348 | 0.481 | -0.733 |
| DM | GACATG | 4089.63 | 5411 | 1.323 | 0.280 |
| DM | GATATG | 3620.37 | 2299 | 0.635 | -0.454 |
| DN | GACAAC | 3511.00 | 4849 | 1.381 | 0.323 |
| DN | GACAAT | 3187.82 | 3349 | 1.051 | 0.049 |
| DN | GATAAT | 2822.05 | 2549 | 0.903 | -0.102 |
| DN | GATAAC | 3108.14 | 1882 | 0.606 | -0.502 |
| DP | GACCCC | 3732.11 | 5119 | 1.372 | 0.316 |
| DP | GACCCG | 1352.28 | 1692 | 1.251 | 0.224 |
| DP | GACCCT | 3342.62 | 3700 | 1.107 | 0.102 |
| DP | GATCCT | 2959.08 | 3111 | 1.051 | 0.050 |
| DP | GACCCA | 3226.05 | 3205 | 0.993 | -0.007 |
| DP | GATCCA | 2855.89 | 2349 | 0.823 | -0.195 |
| DP | GATCCC | 3303.88 | 2338 | 0.708 | -0.346 |
| DP | GATCCG | 1197.11 | 455 | 0.380 | -0.967 |
| DQ | GACCAG | 5250.37 | 6524 | 1.243 | 0.217 |
| DQ | GACCAA | 1880.22 | 2169 | 1.154 | 0.143 |
| DQ | GATCAA | 1664.48 | 1808 | 1.086 | 0.083 |
| DQ | GATCAG | 4647.93 | 2942 | 0.633 | -0.457 |
| DR | GACCGC | 1807.77 | 2634 | 1.457 | 0.376 |
| DR | GACAGA | 1994.00 | 2869 | 1.439 | 0.364 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| DR | GACAGG | 1957.57 | 2730 | 1.395 | 0.333 |
| DR | GACCGT | 773.97 | 1029 | 1.330 | 0.285 |
| DR | GACCGG | 1977.16 | 2568 | 1.299 | 0.261 |
| DR | GACCGA | 1071.78 | 1292 | 1.205 | 0.187 |
| DR | GATCGA | 948.80 | 923 | 0.973 | -0.028 |
| DR | GATCGT | 685.16 | 626 | 0.914 | -0.090 |
| DR | GATAGA | 1765.20 | 1123 | 0.636 | -0.452 |
| DR | GATCGG | 1750.30 | 859 | 0.491 | -0.712 |
| DR | GATCGC | 1600.34 | 754 | 0.471 | -0.753 |
| DR | GATAGG | 1732.96 | 658 | 0.380 | -0.968 |
| DS | GACTCG | 918.57 | 1527 | 1.662 | 0.508 |
| DS | GACAGC | 3935.48 | 6143 | 1.561 | 0.445 |
| DS | GACAGT | 2482.92 | 3657 | 1.473 | 0.387 |
| DS | GATTCT | 2675.01 | 2968 | 1.110 | 0.104 |
| DS | GACTCC | 3473.65 | 3800 | 1.094 | 0.090 |
| DS | GATTCA | 2162.59 | 2129 | 0.984 | -0.016 |
| DS | GACTCA | 2442.89 | 2382 | 0.975 | -0.025 |
| DS | GACTCT | 3021.73 | 2910 | 0.963 | -0.038 |
| DS | GATTCC | 3075.07 | 2186 | 0.711 | -0.341 |
| DS | GATAGT | 2198.02 | 1355 | 0.616 | -0.484 |
| DS | GATTCG | 813.17 | 414 | 0.509 | -0.675 |
| DS | GATAGC | 3483.91 | 1212 | 0.348 | -1.056 |
| DT | GACACG | 1110.58 | 1842 | 1.659 | 0.506 |
| DT | GACACC | 3380.79 | 4666 | 1.380 | 0.322 |
| DT | GACACA | 2736.88 | 3538 | 1.293 | 0.257 |
| DT | GACACT | 2420.30 | 2688 | 1.111 | 0.105 |
| DT | GATACT | 2142.59 | 1731 | 0.808 | -0.213 |
| DT | GATACA | 2422.85 | 1788 | 0.738 | -0.304 |
| DT | GATACC | 2992.87 | 1586 | 0.530 | -0.635 |
| DT | GATACG | 983.15 | 351 | 0.357 | -1.030 |
| DV | GATGTT | 1957.96 | 3699 | 1.889 | 0.636 |
| DV | GATGTA | 1271.37 | 2214 | 1.741 | 0.555 |
| DV | GATGTC | 2506.81 | 3869 | 1.543 | 0.434 |
| DV | GATGTG | 4959.23 | 6668 | 1.345 | 0.296 |
| DV | GACGTG | 5602.02 | 3616 | 0.645 | -0.438 |
| DV | GACGTC | 2831.73 | 1654 | 0.584 | -0.538 |
| DV | GACGTT | 2211.73 | 672 | 0.304 | -1.191 |
| DV | GACGTA | 1436.16 | 385 | 0.268 | -1.316 |
| DW | GACTGG | 2619.27 | 3853 | 1.471 | 0.386 |
| DW | GATTGG | 2318.73 | 1085 | 0.468 | -0.759 |
| DY | GACTAC | 3307.71 | 3930 | 1.188 | 0.172 |
| DY | GATTAT | 2379.36 | 2608 | 1.096 | 0.092 |
| DY | GACTAT | 2687.76 | 2853 | 1.061 | 0.060 |
| DY | GATTAC | 2928.18 | 1912 | 0.653 | -0.426 |
| EA | GAGGCG | 2437.29 | 3179 | 1.304 | 0.266 |
| EA | GAAGCA | 3880.59 | 4844 | 1.248 | 0.222 |
| EA | GAAGCT | 4432.94 | 5143 | 1.160 | 0.149 |
| EA | GAGGCC | 9014.27 | 9805 | 1.088 | 0.084 |
| EA | GAGGCT | 5928.25 | 5314 | 0.896 | -0.109 |
| EA | GAGGCA | 5189.57 | 4530 | 0.873 | -0.136 |
| EA | GAAGCC | 6740.57 | 5649 | 0.838 | -0.177 |
| EA | GAAGCG | 1822.52 | 982 | 0.539 | -0.618 |
| EC | GAATGT | 2182.58 | 3541 | 1.622 | 0.484 |
| EC | GAGTGT | 2918.80 | 2792 | 0.957 | -0.044 |
| EC | GAGTGC | 3465.35 | 2987 | 0.862 | -0.149 |
| EC | GAATGC | 2591.27 | 1838 | 0.709 | -0.343 |
| ED | GAAGAT | 6605.82 | 9691 | 1.467 | 0.383 |
| ED | GAGGAC | 9979.09 | 9684 | 0.970 | -0.030 |
| ED | GAAGAC | 7462.02 | 6820 | 0.914 | -0.090 |
| ED | GAGGAT | 8834.07 | 6686 | 0.757 | -0.279 |
| EE | GAAGAA | 10747.11 | 14461 | 1.346 | 0.297 |
| EE | GAGGAG | 19220.31 | 21731 | 1.131 | 0.123 |
| EE | GAAGAG | 14372.29 | 11875 | 0.826 | -0.191 |
| EE | GAGGAA | 14372.29 | 10645 | 0.741 | -0.300 |
| EF | GAATTT | 3136.91 | 4237 | 1.351 | 0.301 |
| EF | GAGTTC | 4801.58 | 4739 | 0.987 | -0.013 |
| EF | GAGTTT | 4195.05 | 4095 | 0.976 | -0.024 |
| EF | GAATTC | 3590.46 | 2653 | 0.739 | -0.303 |
| EG | GAAGGA | 3358.73 | 5032 | 1.498 | 0.404 |
| EG | GAAGGT | 2174.51 | 2839 | 1.306 | 0.267 |
| EG | GAAGGG | 3278.97 | 3559 | 1.085 | 0.082 |
| EG | GAGGGC | 6090.10 | 6505 | 1.068 | 0.066 |
| EG | GAAGGC | 4553.97 | 4340 | 0.953 | -0.048 |
| EG | GAGGGG | 4385.02 | 3795 | 0.865 | -0.145 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| EG | GAGGGT | 2908.01 | 2378 | 0.818 | −0.201 |
| EG | GAGGGA | 4491.69 | 2793 | 0.622 | −0.475 |
| EH | GAACAT | 2017.28 | 2539 | 1.259 | 0.230 |
| EH | GAGCAC | 3720.16 | 4190 | 1.126 | 0.119 |
| EH | GAGCAT | 2697.74 | 2448 | 0.907 | −0.097 |
| EH | GAACAC | 2781.81 | 2040 | 0.733 | −0.310 |
| EI | GAAATA | 1687.78 | 3007 | 1.782 | 0.578 |
| EI | GAAATT | 3669.78 | 4788 | 1.305 | 0.266 |
| EI | GAGATC | 6206.03 | 6191 | 0.998 | −0.002 |
| EI | GAGATT | 4907.66 | 3978 | 0.811 | −0.210 |
| EI | GAGATA | 2257.09 | 1785 | 0.791 | −0.235 |
| EI | GAAATC | 4640.66 | 3620 | 0.780 | −0.248 |
| EK | GAGAAG | 12729.57 | 15133 | 1.189 | 0.173 |
| EK | GAAAAA | 7349.75 | 7522 | 1.023 | 0.023 |
| EK | GAGAAA | 9828.94 | 9127 | 0.929 | −0.074 |
| EK | GAAAAG | 9518.74 | 7645 | 0.803 | −0.219 |
| EL | GAGCTG | 10945.64 | 15625 | 1.428 | 0.356 |
| EL | GAATTA | 1584.03 | 2256 | 1.424 | 0.354 |
| EL | GAACTA | 1464.61 | 1830 | 1.249 | 0.223 |
| EL | GAACTT | 2715.79 | 3371 | 1.241 | 0.216 |
| EL | GAGCTC | 5267.08 | 5877 | 1.116 | 0.110 |
| EL | GAGCTA | 1958.64 | 2049 | 1.046 | 0.045 |
| EL | GAATTG | 2661.03 | 2335 | 0.877 | −0.131 |
| EL | GAGCTT | 3631.87 | 3084 | 0.849 | −0.164 |
| EL | GAGTTG | 3558.64 | 2719 | 0.764 | −0.269 |
| EL | GAACTC | 3938.54 | 2632 | 0.668 | −0.403 |
| EL | GAGTTA | 2118.35 | 1357 | 0.641 | −0.445 |
| EL | GAACTG | 8184.78 | 4894 | 0.598 | −0.514 |
| EM | GAAATG | 4983.92 | 5010 | 1.005 | 0.005 |
| EM | GAGATG | 6665.08 | 6639 | 0.996 | −0.004 |
| EN | GAAAAT | 4791.73 | 6977 | 1.456 | 0.376 |
| EN | GAGAAC | 7057.70 | 6756 | 0.957 | −0.044 |
| EN | GAAAAC | 5277.51 | 4930 | 0.934 | −0.068 |
| EN | GAGAAT | 6408.07 | 4872 | 0.760 | −0.274 |
| EP | GAGCCG | 1650.94 | 2438 | 1.477 | 0.390 |
| EP | GAGCCC | 4556.38 | 6270 | 1.376 | 0.319 |
| EP | GAGCCT | 4080.86 | 4236 | 1.038 | 0.037 |
| EP | GAGCCA | 3938.55 | 4067 | 1.033 | 0.032 |
| EP | GAACCA | 2945.12 | 2684 | 0.911 | −0.093 |
| EP | GAACCT | 3051.53 | 2547 | 0.835 | −0.181 |
| EP | GAACCC | 3407.10 | 2106 | 0.618 | −0.481 |
| EP | GAACCG | 1234.52 | 517 | 0.419 | −0.870 |
| EQ | GAACAA | 2579.50 | 3396 | 1.317 | 0.275 |
| EQ | GAGCAG | 9632.80 | 11185 | 1.161 | 0.149 |
| EQ | GAGCAA | 3449.61 | 3185 | 0.923 | −0.080 |
| EQ | GAACAG | 7203.08 | 5099 | 0.708 | −0.345 |
| ER | GAAAGA | 2650.27 | 3769 | 1.422 | 0.352 |
| ER | GAGAGG | 3479.50 | 4315 | 1.240 | 0.215 |
| ER | GAGCGG | 3514.32 | 4356 | 1.240 | 0.215 |
| ER | GAGCGC | 3213.23 | 3682 | 1.146 | 0.136 |
| ER | GAAAGG | 2601.85 | 2679 | 1.030 | 0.029 |
| ER | GAGAGA | 3544.25 | 3633 | 1.025 | 0.025 |
| ER | GAGCGT | 1375.70 | 1286 | 0.935 | −0.067 |
| ER | GAACGT | 1028.70 | 894 | 0.869 | −0.140 |
| ER | GAACGA | 1424.52 | 1188 | 0.834 | −0.182 |
| ER | GAGCGA | 1905.04 | 1562 | 0.820 | −0.199 |
| ER | GAACGG | 2627.88 | 1333 | 0.507 | −0.679 |
| ER | GAACGC | 2402.74 | 1071 | 0.446 | −0.808 |
| ES | GAAAGT | 2081.93 | 3138 | 1.507 | 0.410 |
| ES | GAGAGC | 4413.03 | 5786 | 1.311 | 0.271 |
| ES | GAGAGT | 2784.21 | 3237 | 1.163 | 0.151 |
| ES | GAGTCG | 1030.03 | 1174 | 1.140 | 0.131 |
| ES | GAATCT | 2533.73 | 2812 | 1.110 | 0.104 |
| ES | GAATCA | 2048.37 | 2131 | 1.040 | 0.040 |
| ES | GAAAGC | 3299.91 | 2880 | 0.873 | −0.136 |
| ES | GAGTCC | 3895.16 | 3392 | 0.871 | −0.138 |
| ES | GAGTCT | 3388.40 | 2799 | 0.826 | −0.191 |
| ES | GAGTCA | 2739.33 | 2198 | 0.802 | −0.220 |
| ES | GAATCC | 2912.67 | 1943 | 0.667 | −0.405 |
| ES | GAATCG | 770.22 | 407 | 0.528 | −0.638 |
| ET | GAGACG | 1658.42 | 2190 | 1.321 | 0.278 |
| ET | GAAACA | 3056.09 | 3851 | 1.260 | 0.231 |
| ET | GAAACT | 2702.59 | 3224 | 1.193 | 0.176 |
| ET | GAGACC | 5048.51 | 5514 | 1.092 | 0.088 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| ET | GAGACA | 4086.97 | 3619 | 0.885 | −0.122 |
| ET | GAGACT | 3614.21 | 3028 | 0.838 | −0.177 |
| ET | GAAACC | 3775.11 | 2950 | 0.781 | −0.247 |
| ET | GAAACG | 1240.11 | 806 | 0.650 | −0.431 |
| EV | GAAGTA | 1580.16 | 2675 | 1.693 | 0.526 |
| EV | GAAGTT | 2433.50 | 3724 | 1.530 | 0.425 |
| EV | GAGGTG | 8242.83 | 9074 | 1.101 | 0.096 |
| EV | GAAGTC | 3115.66 | 2860 | 0.918 | −0.086 |
| EV | GAGGTC | 4166.62 | 3741 | 0.898 | −0.108 |
| EV | GAAGTG | 6163.71 | 5122 | 0.831 | −0.185 |
| EV | GAGGTT | 3254.36 | 2359 | 0.725 | −0.322 |
| EV | GAGGTA | 2113.17 | 1515 | 0.717 | −0.333 |
| EW | GAGTGG | 3085.08 | 3238 | 1.050 | 0.048 |
| EW | GAATGG | 2306.92 | 2154 | 0.934 | −0.069 |
| EY | GAATAT | 2307.55 | 3428 | 1.486 | 0.396 |
| EY | GAGTAC | 3797.72 | 3796 | 1.000 | 0.000 |
| EY | GAGTAT | 3085.93 | 2596 | 0.841 | −0.173 |
| EY | GAATAC | 2839.80 | 2211 | 0.779 | −0.250 |
| FA | TTTGCA | 1643.98 | 3299 | 2.007 | 0.696 |
| FA | TTTGCT | 1877.98 | 3746 | 1.995 | 0.690 |
| FA | TTTGCC | 2855.59 | 4348 | 1.523 | 0.420 |
| FA | TTTGCG | 772.10 | 622 | 0.806 | −0.216 |
| FA | TTCGCG | 883.73 | 598 | 0.677 | −0.391 |
| FA | TTCGCC | 3268.46 | 1802 | 0.551 | −0.595 |
| FA | TTCGCT | 2149.50 | 516 | 0.240 | −1.427 |
| FA | TTCGCA | 1881.67 | 402 | 0.214 | −1.543 |
| FC | TTCTGC | 2058.60 | 3045 | 1.479 | 0.391 |
| FC | TTCTGT | 1733.93 | 2055 | 1.185 | 0.170 |
| FC | TTTTGT | 1514.90 | 1159 | 0.765 | −0.268 |
| FC | TTTTGC | 1798.56 | 847 | 0.471 | −0.753 |
| FD | TTTGAT | 2786.65 | 5380 | 1.931 | 0.658 |
| FD | TTTGAC | 3147.84 | 4737 | 1.505 | 0.409 |
| FD | TTCGAC | 3602.96 | 1746 | 0.485 | −0.724 |
| FD | TTCGAT | 3189.55 | 864 | 0.271 | −1.306 |
| FE | TTTGAA | 3016.02 | 6247 | 2.071 | 0.728 |
| FE | TTTGAG | 4033.37 | 6066 | 1.504 | 0.408 |
| FE | TTCGAG | 4616.53 | 2165 | 0.469 | −0.757 |
| FE | TTCGAA | 3452.08 | 640 | 0.185 | −1.685 |
| FF | TTCTTC | 3429.53 | 5168 | 1.507 | 0.410 |
| FF | TTCTTT | 2996.32 | 2989 | 0.998 | −0.002 |
| FF | TTTTTT | 2617.83 | 1937 | 0.740 | −0.301 |
| FF | TTTTTC | 2996.32 | 1946 | 0.649 | −0.432 |
| FG | TTTGGA | 2068.21 | 4271 | 2.065 | 0.725 |
| FG | TTTGGT | 1339.00 | 2552 | 1.906 | 0.645 |
| FG | TTTGGG | 2019.09 | 3449 | 1.708 | 0.535 |
| FG | TTTGGC | 2804.20 | 3462 | 1.235 | 0.211 |
| FG | TTCGGG | 2311.02 | 1292 | 0.559 | −0.581 |
| FG | TTCGGC | 3209.64 | 1648 | 0.513 | −0.667 |
| FG | TTCGGT | 1532.60 | 419 | 0.273 | −1.297 |
| FG | TTCGGA | 2367.24 | 558 | 0.236 | −1.445 |
| FH | TTCCAC | 2463.48 | 3200 | 1.299 | 0.262 |
| FH | TTTCAT | 1560.78 | 1697 | 1.087 | 0.084 |
| FH | TTCCAT | 1786.44 | 1866 | 1.045 | 0.044 |
| FH | TTCAC | 2152.30 | 1200 | 0.558 | −0.584 |
| FI | TTCATC | 3454.46 | 5156 | 1.493 | 0.400 |
| FI | TTCATT | 2731.75 | 2953 | 1.081 | 0.078 |
| FI | TTTATT | 2386.67 | 2296 | 0.962 | −0.039 |
| FI | TTTATA | 1097.66 | 950 | 0.865 | −0.144 |
| FI | TTCATA | 1256.36 | 1035 | 0.824 | −0.194 |
| FI | TTTATC | 3018.10 | 1555 | 0.515 | −0.663 |
| FK | TTCAAG | 4090.45 | 5137 | 1.256 | 0.228 |
| FK | TTCAAA | 3158.38 | 3245 | 1.027 | 0.027 |
| FK | TTTAAA | 2759.42 | 2762 | 1.001 | 0.001 |
| FK | TTTAAG | 3573.75 | 2438 | 0.682 | −0.382 |
| FL | TTCCTC | 3228.53 | 4426 | 1.371 | 0.315 |
| FL | TTCCTG | 6709.28 | 8734 | 1.302 | 0.264 |
| FL | TTTTTA | 1134.45 | 1334 | 1.176 | 0.162 |
| FL | TTTCTT | 1945.00 | 2267 | 1.166 | 0.153 |
| FL | TTCCTA | 1200.58 | 1280 | 1.066 | 0.064 |
| FL | TTTCTA | 1048.92 | 1087 | 1.036 | 0.036 |
| FL | TTCCTG | 2181.32 | 2239 | 1.026 | 0.026 |
| FL | TTCCTT | 2226.21 | 2150 | 0.966 | −0.035 |
| FL | TTTTTG | 1905.78 | 1799 | 0.944 | −0.058 |
| FL | TTCTTA | 1298.47 | 1144 | 0.881 | −0.127 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| FL | TTTCTC | 2820.70 | 1904 | 0.675 | −0.393 |
| FL | TTTCTG | 5861.77 | 3197 | 0.545 | −0.606 |
| FM | TTCATG | 2804.11 | 3662 | 1.306 | 0.267 |
| FM | TTTATG | 2449.89 | 1592 | 0.650 | −0.431 |
| FN | TTCAAC | 2855.47 | 3919 | 1.372 | 0.317 |
| FN | TTTAAT | 2265.13 | 2185 | 0.965 | −0.036 |
| FN | TTCAAT | 2592.63 | 2456 | 0.947 | −0.054 |
| FN | TTTAAC | 2494.77 | 1648 | 0.661 | −0.415 |
| FP | TTCCCG | 961.40 | 1205 | 1.253 | 0.226 |
| FP | TTTCCT | 2076.25 | 2539 | 1.223 | 0.201 |
| FP | TTCCCC | 2653.35 | 3099 | 1.168 | 0.155 |
| FP | TTTCCA | 2003.85 | 2141 | 1.068 | 0.066 |
| FP | TTCCCA | 2293.57 | 2310 | 1.007 | 0.007 |
| FP | TTCCCT | 2376.44 | 2379 | 1.001 | 0.001 |
| FP | TTTCCC | 2318.18 | 1529 | 0.660 | −0.416 |
| FP | TTTCCG | 839.96 | 321 | 0.382 | −0.962 |
| FQ | TTCCAG | 5468.69 | 7069 | 1.293 | 0.257 |
| FQ | TTTCAA | 1711.02 | 1803 | 1.054 | 0.052 |
| FQ | TTCCAA | 1958.40 | 1980 | 1.011 | 0.011 |
| FQ | TTTCAG | 4777.89 | 3064 | 0.641 | −0.444 |
| FR | TTCCGC | 1531.47 | 2588 | 1.690 | 0.525 |
| FR | TTCCGA | 907.97 | 1410 | 1.553 | 0.440 |
| FR | TTCCGG | 1674.97 | 2451 | 1.463 | 0.381 |
| FR | TTCCGT | 655.68 | 893 | 1.362 | 0.309 |
| FR | TTCAGA | 1689.24 | 1852 | 1.096 | 0.092 |
| FR | TTCAGG | 1658.38 | 1810 | 1.091 | 0.087 |
| FR | TTTCGA | 793.28 | 850 | 1.072 | 0.069 |
| FR | TTTCGT | 572.85 | 490 | 0.855 | −0.156 |
| FR | TTTAGA | 1475.86 | 947 | 0.642 | −0.444 |
| FR | TTTAGG | 1448.90 | 691 | 0.477 | −0.740 |
| FR | TTTCGG | 1463.39 | 688 | 0.470 | −0.755 |
| FR | TTTCGC | 1338.02 | 540 | 0.404 | −0.907 |
| FS | TTCTCC | 2990.83 | 4507 | 1.507 | 0.410 |
| FS | TTCAGC | 3388.47 | 4577 | 1.351 | 0.301 |
| FS | TTCAGT | 2137.80 | 2692 | 1.259 | 0.231 |
| FS | TTCTCG | 790.89 | 910 | 1.151 | 0.140 |
| FS | TTTTCT | 2273.08 | 2536 | 1.116 | 0.109 |
| FS | TTCTCT | 2601.73 | 2741 | 1.054 | 0.052 |
| FS | TTTTCA | 1837.65 | 1903 | 1.036 | 0.035 |
| FS | TTCTCA | 2103.34 | 1997 | 0.949 | −0.052 |
| FS | TTTTCC | 2613.03 | 1872 | 0.716 | −0.334 |
| FS | TTTAGT | 1867.76 | 1201 | 0.643 | −0.442 |
| FS | TTTTCG | 690.99 | 258 | 0.373 | −0.985 |
| FS | TTTAGC | 2960.44 | 1062 | 0.359 | −1.025 |
| FT | TTCACC | 2909.29 | 4513 | 1.551 | 0.439 |
| FT | TTCACG | 955.69 | 1315 | 1.376 | 0.319 |
| FT | TTCACT | 2082.75 | 2494 | 1.197 | 0.180 |
| FT | TTCACA | 2355.18 | 2372 | 1.007 | 0.007 |
| FT | TTTACT | 1819.66 | 1622 | 0.891 | −0.115 |
| FT | TTTACA | 2057.68 | 1485 | 0.722 | −0.326 |
| FT | TTTACC | 2541.79 | 1495 | 0.588 | −0.531 |
| FT | TTTACG | 834.97 | 261 | 0.313 | −1.163 |
| FV | TTTGTA | 912.19 | 1711 | 1.876 | 0.629 |
| FV | TTTGTT | 1404.80 | 2620 | 1.865 | 0.623 |
| FV | TTTGTC | 1798.60 | 2635 | 1.465 | 0.382 |
| FV | TTTGTG | 3558.17 | 5206 | 1.463 | 0.381 |
| FV | TTCGTG | 4072.62 | 2589 | 0.636 | −0.453 |
| FV | TTCGTC | 2058.64 | 1086 | 0.528 | −0.640 |
| FV | TTCGTT | 1607.91 | 386 | 0.240 | −1.427 |
| FV | TTCGTA | 1044.07 | 224 | 0.215 | −1.539 |
| FW | TTCTGG | 2126.30 | 2834 | 1.333 | 0.287 |
| FW | TTTTGG | 1857.70 | 1150 | 0.619 | −0.480 |
| FY | TTCTAC | 2720.70 | 3710 | 1.364 | 0.310 |
| FY | TTTTAT | 1931.51 | 2003 | 1.037 | 0.036 |
| FY | TTCTAT | 2210.77 | 2145 | 0.970 | −0.030 |
| FY | TTTTAC | 2377.02 | 1382 | 0.581 | −0.542 |
| GA | GGTGCT | 1531.20 | 2505 | 1.636 | 0.492 |
| GA | GGGGCG | 949.27 | 1433 | 1.510 | 0.412 |
| GA | GGGGCC | 3510.85 | 5061 | 1.442 | 0.366 |
| GA | GGTGCC | 2328.29 | 3109 | 1.335 | 0.289 |
| GA | GGAGCA | 2070.38 | 2678 | 1.293 | 0.257 |
| GA | GGTGCA | 1340.41 | 1715 | 1.279 | 0.246 |
| GA | GGCGCG | 1318.38 | 1659 | 1.258 | 0.230 |
| GA | GGAGCT | 2365.08 | 2975 | 1.258 | 0.229 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| GA | GGGGCT | 2308.91 | 2850 | 1.234 | 0.211 |
| GA | GGAGCC | 3596.25 | 3845 | 1.069 | 0.067 |
| GA | GGGGCA | 2021.22 | 2074 | 1.026 | 0.026 |
| GA | GGTGCG | 629.52 | 501 | 0.796 | −0.228 |
| GA | GGAGCG | 972.36 | 712 | 0.732 | −0.312 |
| GA | GGCGCC | 4876.02 | 3121 | 0.640 | −0.446 |
| GA | GGCGCT | 3206.72 | 906 | 0.283 | −1.264 |
| GA | GGCGCA | 2807.15 | 688 | 0.245 | −1.406 |
| GC | GGCTGC | 1888.96 | 4102 | 2.172 | 0.775 |
| GC | GGCTGT | 1591.04 | 2360 | 1.483 | 0.394 |
| GC | GGTTGT | 759.72 | 658 | 0.866 | −0.144 |
| GC | GGATGT | 1173.45 | 793 | 0.676 | −0.392 |
| GC | GGTTGC | 901.97 | 523 | 0.580 | −0.545 |
| GC | GGATGC | 1393.18 | 655 | 0.470 | −0.755 |
| GC | GGGTGC | 1360.09 | 628 | 0.462 | −0.773 |
| GC | GGGTGT | 1145.59 | 495 | 0.432 | −0.839 |
| GD | GGGGAC | 3126.50 | 4967 | 1.589 | 0.463 |
| GD | GGTGAT | 1835.49 | 2621 | 1.428 | 0.356 |
| GD | GGTGAC | 2073.40 | 2960 | 1.428 | 0.356 |
| GD | GGAGAT | 2835.09 | 3829 | 1.351 | 0.301 |
| GD | GGAGAC | 3202.56 | 4240 | 1.324 | 0.281 |
| GD | GGGGAT | 2767.76 | 2575 | 0.930 | −0.072 |
| GD | GGCGAC | 4342.22 | 1955 | 0.450 | −0.798 |
| GD | GGCGAT | 3843.98 | 880 | 0.229 | −1.474 |
| GE | GGAGAA | 3433.99 | 5903 | 1.719 | 0.542 |
| GE | GGGGAG | 4483.27 | 6552 | 1.461 | 0.379 |
| GE | GGTGAA | 2223.23 | 3248 | 1.461 | 0.379 |
| GE | GGAGAG | 4592.33 | 5961 | 1.298 | 0.261 |
| GE | GGTGAG | 2973.17 | 2988 | 1.005 | 0.005 |
| GE | GGGGAA | 3352.44 | 3041 | 0.907 | −0.098 |
| GE | GGCGAG | 6226.56 | 3530 | 0.567 | −0.568 |
| GE | GGCGAA | 4656.01 | 718 | 0.154 | −1.869 |
| GF | GGCTTC | 3466.22 | 6121 | 1.766 | 0.569 |
| GF | GGATTT | 2233.54 | 2666 | 1.194 | 0.177 |
| GF | GGTTTT | 1446.04 | 1665 | 1.151 | 0.141 |
| GF | GGCTTT | 3028.37 | 3201 | 1.057 | 0.055 |
| GF | GGTTTC | 1655.11 | 1548 | 0.935 | −0.067 |
| GF | GGATTC | 2556.47 | 1534 | 0.600 | −0.511 |
| GF | GGGTTT | 2180.50 | 1244 | 0.571 | −0.561 |
| GF | GGGTTC | 2495.76 | 1083 | 0.434 | −0.835 |
| GG | GGTGGT | 1061.28 | 2286 | 2.154 | 0.767 |
| GG | GGTGGC | 2222.59 | 3657 | 1.645 | 0.498 |
| GG | GGTGGA | 1639.25 | 2618 | 1.597 | 0.468 |
| GG | GGAGGA | 2531.97 | 3609 | 1.425 | 0.354 |
| GG | GGTGGG | 1600.32 | 2267 | 1.417 | 0.348 |
| GG | GGGGGC | 3351.47 | 4673 | 1.394 | 0.332 |
| GG | GGAGGT | 1639.25 | 2152 | 1.313 | 0.272 |
| GG | GGAGGC | 3433.00 | 3776 | 1.100 | 0.095 |
| GG | GGCGGC | 4654.67 | 4787 | 1.028 | 0.028 |
| GG | GGGGGT | 1600.32 | 1543 | 0.964 | −0.036 |
| GG | GGAGGG | 2471.84 | 2351 | 0.951 | −0.050 |
| GG | GGGGGA | 2471.84 | 1517 | 0.614 | −0.488 |
| GG | GGCGGG | 3351.47 | 2001 | 0.597 | −0.516 |
| GG | GGGGGG | 2413.14 | 1080 | 0.448 | −0.804 |
| GG | GGCGGT | 2222.59 | 936 | 0.421 | −0.865 |
| GG | GGCGGA | 3433.00 | 845 | 0.246 | −1.402 |
| GH | GGCCAC | 2540.15 | 3679 | 1.448 | 0.370 |
| GH | GGTCAT | 879.57 | 1022 | 1.162 | 0.150 |
| GH | GGACAT | 1358.57 | 1438 | 1.058 | 0.057 |
| GH | GGCCAT | 1842.04 | 1679 | 0.911 | −0.093 |
| GH | GGGCAC | 1828.97 | 1629 | 0.891 | −0.116 |
| GH | GGTCAC | 1212.92 | 1008 | 0.831 | −0.185 |
| GH | GGACAC | 1873.46 | 1479 | 0.789 | −0.236 |
| GH | GGGCAT | 1326.31 | 928 | 0.700 | −0.357 |
| GI | GGCATC | 3372.48 | 5474 | 1.623 | 0.484 |
| GI | GGAATA | 904.63 | 1338 | 1.479 | 0.391 |
| GI | GGAATT | 1966.96 | 2560 | 1.302 | 0.264 |
| GI | GGCATT | 2666.92 | 2670 | 1.001 | 0.001 |
| GI | GGTATT | 1273.45 | 1052 | 0.826 | −0.191 |
| GI | GGGATC | 2428.27 | 1958 | 0.806 | −0.215 |
| GI | GGTATA | 585.67 | 461 | 0.787 | −0.239 |
| GI | GGAATC | 2487.34 | 1910 | 0.768 | −0.264 |
| GI | GGGATA | 883.14 | 666 | 0.754 | −0.282 |
| GI | GGGATT | 1920.24 | 1421 | 0.740 | −0.301 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| GI | GGCATA | 1226.55 | 885 | 0.722 | -0.326 |
| GI | GGTATC | 1610.35 | 931 | 0.578 | -0.548 |
| GK | GGAAAA | 3199.11 | 4553 | 1.423 | 0.353 |
| GK | GGGAAG | 4044.81 | 5674 | 1.403 | 0.338 |
| GK | GGGAAA | 3123.14 | 4119 | 1.319 | 0.277 |
| GK | GGCAAG | 5617.61 | 5712 | 1.017 | 0.017 |
| GK | GGAAAG | 4143.21 | 3706 | 0.894 | -0.112 |
| GK | GGCAAA | 4337.55 | 3581 | 0.826 | -0.192 |
| GK | GGTAAA | 2071.17 | 1334 | 0.644 | -0.440 |
| GK | GGTAAG | 2682.40 | 540 | 0.201 | -1.603 |
| GL | GGCCTC | 3017.19 | 4559 | 1.511 | 0.413 |
| GL | GGTTTA | 579.43 | 820 | 1.415 | 0.347 |
| GL | GGTTTG | 973.39 | 1294 | 1.329 | 0.285 |
| GL | GGGCTG | 4514.62 | 5878 | 1.302 | 0.264 |
| GL | GGTCTT | 993.42 | 1258 | 1.266 | 0.236 |
| GL | GGCCTG | 6270.10 | 7822 | 1.248 | 0.221 |
| GL | GGGCTC | 2172.45 | 2563 | 1.180 | 0.165 |
| GL | GGATTA | 894.98 | 991 | 1.107 | 0.102 |
| GL | GGACTT | 1534.44 | 1613 | 1.051 | 0.050 |
| GL | GGCTTG | 2038.53 | 2109 | 1.035 | 0.034 |
| GL | GGCCTT | 2080.48 | 2098 | 1.008 | 0.008 |
| GL | GGACTA | 827.51 | 799 | 0.966 | -0.035 |
| GL | GGGCTT | 1497.99 | 1445 | 0.965 | -0.036 |
| GL | GGTCTC | 1440.70 | 1365 | 0.947 | -0.054 |
| GL | GGTCTA | 535.75 | 487 | 0.909 | -0.095 |
| GL | GGGCTA | 807.86 | 726 | 0.899 | -0.107 |
| GL | GGCCTA | 1121.99 | 968 | 0.863 | -0.148 |
| GL | GGCTTA | 1213.47 | 935 | 0.771 | -0.261 |
| GL | GGACTC | 2225.29 | 1656 | 0.744 | -0.295 |
| GL | GGATTG | 1503.50 | 1062 | 0.706 | -0.348 |
| GL | GGTCTG | 2993.96 | 2034 | 0.679 | -0.387 |
| GL | GGGTTG | 1467.79 | 870 | 0.593 | -0.523 |
| GL | GGGTTA | 873.73 | 467 | 0.534 | -0.626 |
| GL | GGACTG | 4624.44 | 2384 | 0.516 | -0.663 |
| GM | GGCATG | 3177.11 | 3953 | 1.244 | 0.219 |
| GM | GGAATG | 2343.24 | 2482 | 1.059 | 0.058 |
| GM | GGGATG | 2287.59 | 2247 | 0.982 | -0.018 |
| GM | GGTATG | 1517.06 | 643 | 0.424 | -0.858 |
| GN | GGAAAT | 2150.19 | 3332 | 1.550 | 0.438 |
| GN | GGGAAC | 2311.93 | 2816 | 1.218 | 0.197 |
| GN | GGCAAC | 3210.92 | 3701 | 1.153 | 0.142 |
| GN | GGAAAC | 2368.18 | 2679 | 1.131 | 0.123 |
| GN | GGGAAT | 2099.13 | 1823 | 0.868 | -0.141 |
| GN | GGCAAT | 2915.36 | 2061 | 0.707 | -0.347 |
| GN | GGTAAT | 1392.08 | 784 | 0.563 | -0.574 |
| GN | GGTAAC | 1533.21 | 785 | 0.512 | -0.669 |
| GP | GGGCCC | 2634.22 | 3947 | 1.498 | 0.404 |
| GP | GGGCCG | 954.47 | 1417 | 1.485 | 0.395 |
| GP | GGCCCC | 3658.52 | 4576 | 1.251 | 0.224 |
| GP | GGCCCG | 1325.61 | 1623 | 1.224 | 0.202 |
| GP | GGTCCT | 1564.62 | 1910 | 1.221 | 0.199 |
| GP | GGGCCT | 2359.31 | 2542 | 1.077 | 0.075 |
| GP | GGTCCC | 1746.93 | 1827 | 1.046 | 0.045 |
| GP | GGCCCT | 3276.71 | 2994 | 0.914 | -0.090 |
| GP | GGGCCA | 2277.03 | 2003 | 0.880 | -0.128 |
| GP | GGTCCA | 1510.06 | 1264 | 0.837 | -0.178 |
| GP | GGACCC | 2698.30 | 2240 | 0.830 | -0.186 |
| GP | GGACCA | 2332.42 | 1908 | 0.818 | -0.201 |
| GP | GGACCT | 2416.70 | 1957 | 0.810 | -0.211 |
| GP | GGCCCA | 3162.44 | 2548 | 0.806 | -0.216 |
| GP | GGTCCG | 632.98 | 351 | 0.555 | -0.590 |
| GP | GGACCG | 977.69 | 421 | 0.431 | -0.843 |
| GQ | GGACAA | 1382.58 | 1677 | 1.213 | 0.193 |
| GQ | GGGCAG | 3769.06 | 4425 | 1.174 | 0.160 |
| GQ | GGCCAG | 5234.64 | 6081 | 1.162 | 0.150 |
| GQ | GGTCAA | 895.11 | 953 | 1.065 | 0.063 |
| GQ | GGCCAA | 1874.58 | 1593 | 0.850 | -0.163 |
| GQ | GGGCAA | 1349.74 | 1124 | 0.833 | -0.183 |
| GQ | GGACAG | 3860.75 | 3134 | 0.812 | -0.209 |
| GQ | GGTCAG | 2499.53 | 1879 | 0.752 | -0.285 |
| GR | GGCCGC | 1832.29 | 3615 | 1.973 | 0.680 |
| GR | GGAAGA | 1490.60 | 2294 | 1.539 | 0.431 |
| GR | GGCCGG | 2003.98 | 2892 | 1.443 | 0.367 |
| GR | GGCCGT | 784.47 | 1022 | 1.303 | 0.265 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| GR | GGTCGT | 374.58 | 450 | 1.201 | 0.183 |
| GR | GGCCGA | 1086.32 | 1252 | 1.153 | 0.142 |
| GR | GGGCGC | 1319.29 | 1471 | 1.115 | 0.109 |
| GR | GGTCGA | 518.71 | 546 | 1.053 | 0.051 |
| GR | GGCAGG | 1984.13 | 2022 | 1.019 | 0.019 |
| GR | GGGAGG | 1428.62 | 1435 | 1.004 | 0.004 |
| GR | GGGCGG | 1442.91 | 1437 | 0.996 | -0.004 |
| GR | GGAAGG | 1463.37 | 1370 | 0.936 | -0.066 |
| GR | GGGAGA | 1455.20 | 1344 | 0.924 | -0.079 |
| GR | GGACGT | 578.58 | 514 | 0.888 | -0.118 |
| GR | GGACGA | 801.20 | 671 | 0.837 | -0.177 |
| GR | GGGCGT | 564.84 | 471 | 0.834 | -0.182 |
| GR | GGCAGA | 2021.05 | 1684 | 0.833 | -0.182 |
| GR | GGGCGA | 782.17 | 626 | 0.800 | -0.223 |
| GR | GGTCGC | 874.92 | 596 | 0.681 | -0.384 |
| GR | GGTCGG | 956.90 | 555 | 0.580 | -0.545 |
| GR | GGTAGA | 965.05 | 529 | 0.548 | -0.601 |
| GR | GGACGC | 1351.39 | 729 | 0.539 | -0.617 |
| GR | GGACGG | 1478.01 | 737 | 0.499 | -0.696 |
| GR | GGTAGG | 947.42 | 244 | 0.258 | -1.357 |
| GS | GGCAGC | 3581.32 | 6542 | 1.827 | 0.603 |
| GS | GGCTCC | 3161.05 | 5376 | 1.701 | 0.531 |
| GS | GGCTCG | 835.91 | 1323 | 1.583 | 0.459 |
| GS | GGCAGT | 2259.47 | 2875 | 1.272 | 0.241 |
| GS | GGAAGT | 1666.45 | 2085 | 1.251 | 0.224 |
| GS | GGTTCT | 1313.02 | 1563 | 1.190 | 0.174 |
| GS | GGCTCT | 2749.80 | 3087 | 1.123 | 0.116 |
| GS | GGGAGC | 2578.63 | 2566 | 0.995 | -0.005 |
| GS | GGTTCC | 1509.39 | 1428 | 0.946 | -0.055 |
| GS | GGCTCA | 2223.05 | 2101 | 0.945 | -0.056 |
| GS | GGTTCA | 1061.50 | 981 | 0.924 | -0.079 |
| GS | GGAAGC | 2641.36 | 2137 | 0.809 | -0.212 |
| GS | GGATCA | 1639.59 | 1281 | 0.781 | -0.247 |
| GS | GGGAGT | 1626.88 | 1267 | 0.779 | -0.250 |
| GS | GGATCT | 2028.08 | 1470 | 0.725 | -0.322 |
| GS | GGGTCC | 2276.03 | 1646 | 0.723 | -0.324 |
| GS | GGGTCT | 1979.92 | 1280 | 0.646 | -0.436 |
| GS | GGGTCG | 601.87 | 379 | 0.630 | -0.463 |
| GS | GGTAGT | 1078.89 | 646 | 0.599 | -0.513 |
| GS | GGATCC | 2331.40 | 1342 | 0.576 | -0.552 |
| GS | GGGTCA | 1600.65 | 887 | 0.554 | -0.590 |
| GS | GGTTCG | 399.14 | 209 | 0.524 | -0.647 |
| GS | GGATCG | 616.51 | 276 | 0.448 | -0.804 |
| GS | GGTAGC | 1710.07 | 723 | 0.423 | -0.861 |
| GT | GGCACC | 3271.07 | 4870 | 1.489 | 0.398 |
| GT | GGCACG | 1074.53 | 1368 | 1.273 | 0.241 |
| GT | GGGACC | 2355.25 | 2817 | 1.196 | 0.179 |
| GT | GGAACA | 1953.05 | 2290 | 1.173 | 0.159 |
| GT | GGAACT | 1727.13 | 1900 | 1.100 | 0.095 |
| GT | GGGACG | 773.69 | 838 | 1.083 | 0.080 |
| GT | GGGACA | 1906.66 | 1903 | 0.998 | -0.002 |
| GT | GGCACT | 2341.75 | 2331 | 0.995 | -0.005 |
| GT | GGCACA | 2648.06 | 2499 | 0.944 | -0.058 |
| GT | GGGACT | 1686.11 | 1534 | 0.910 | -0.095 |
| GT | GGAACC | 2412.54 | 1841 | 0.763 | -0.270 |
| GT | GGTACT | 1118.18 | 840 | 0.751 | -0.286 |
| GT | GGTACC | 1561.93 | 994 | 0.636 | -0.452 |
| GT | GGTACA | 1264.44 | 780 | 0.617 | -0.483 |
| GT | GGAACG | 792.51 | 445 | 0.562 | -0.577 |
| GT | GGTACG | 513.09 | 150 | 0.292 | -1.230 |
| GV | GGTGTT | 816.93 | 1802 | 2.206 | 0.791 |
| GV | GGTGTC | 1045.94 | 2070 | 1.979 | 0.683 |
| GV | GGTGTA | 530.46 | 957 | 1.804 | 0.590 |
| GV | GGTGTG | 2069.18 | 3207 | 1.550 | 0.438 |
| GV | GGAGTA | 819.35 | 1225 | 1.495 | 0.402 |
| GV | GGAGTT | 1261.83 | 1841 | 1.459 | 0.378 |
| GV | GGGGTC | 1577.18 | 2150 | 1.363 | 0.310 |
| GV | GGAGTC | 1615.55 | 1839 | 1.138 | 0.130 |
| GV | GGGGTT | 1231.86 | 1123 | 0.912 | -0.093 |
| GV | GGGGTG | 3120.14 | 2770 | 0.888 | -0.119 |
| GV | GGAGTG | 3196.04 | 2641 | 0.826 | -0.191 |
| GV | GGGGTA | 799.89 | 631 | 0.789 | -0.237 |
| GV | GGCGTC | 2190.46 | 1653 | 0.755 | -0.282 |
| GV | GGCGTG | 4333.39 | 2790 | 0.644 | -0.440 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| GV | GGCGTT | 1710.87 | 499 | 0.292 | −1.232 |
| GV | GGCGTA | 1110.93 | 232 | 0.209 | −1.566 |
| GW | GGCTGG | 2102.85 | 3748 | 1.782 | 0.578 |
| GW | GGTTGG | 1004.11 | 690 | 0.687 | −0.375 |
| GW | GGATGG | 1550.94 | 1012 | 0.653 | −0.427 |
| GW | GGGTGG | 1514.10 | 722 | 0.477 | −0.741 |
| GY | GGCTAC | 2577.81 | 4581 | 1.777 | 0.575 |
| GY | GGTTAT | 1000.20 | 1309 | 1.309 | 0.269 |
| GY | GGCTAT | 2094.66 | 2528 | 1.207 | 0.188 |
| GY | GGATAT | 1544.90 | 1478 | 0.957 | −0.044 |
| GY | GGTTAC | 1230.90 | 1074 | 0.873 | −0.136 |
| GY | GGATAC | 1901.24 | 1052 | 0.553 | −0.592 |
| GY | GGGTAC | 1856.09 | 982 | 0.529 | −0.637 |
| GY | GGGTAT | 1508.21 | 710 | 0.471 | −0.753 |
| HA | CATGCT | 1101.90 | 1959 | 1.778 | 0.575 |
| HA | CATGCA | 964.61 | 1670 | 1.731 | 0.549 |
| HA | CATGCC | 1675.52 | 2408 | 1.437 | 0.363 |
| HA | CACGCG | 624.72 | 681 | 1.090 | 0.086 |
| HA | CATGCG | 453.03 | 447 | 0.987 | −0.013 |
| HA | CACGCC | 2310.52 | 1649 | 0.714 | −0.337 |
| HA | CACGCA | 1330.18 | 617 | 0.464 | −0.768 |
| HA | CACGCT | 1519.52 | 549 | 0.361 | −1.018 |
| HC | CACTGC | 1778.65 | 2629 | 1.478 | 0.391 |
| HC | CACTGT | 1498.13 | 1717 | 1.146 | 0.136 |
| HC | CATTGT | 1086.40 | 673 | 0.619 | −0.479 |
| HC | CATTGC | 1289.82 | 634 | 0.492 | −0.710 |
| HD | CATGAT | 1329.76 | 2349 | 1.766 | 0.569 |
| HD | CATGAC | 1502.11 | 2329 | 1.550 | 0.439 |
| HD | CACGAC | 2071.40 | 1343 | 0.648 | −0.433 |
| HD | CACGAT | 1833.73 | 716 | 0.390 | −0.940 |
| HE | CATGAA | 1769.46 | 3512 | 1.985 | 0.686 |
| HE | CATGAG | 2366.33 | 3307 | 1.398 | 0.335 |
| HE | CACGAG | 3263.15 | 2230 | 0.683 | −0.381 |
| HE | CACGAA | 2440.07 | 790 | 0.324 | −1.128 |
| HF | CACTTC | 2538.66 | 3116 | 1.227 | 0.205 |
| HF | CATTTT | 1608.41 | 1806 | 1.123 | 0.116 |
| HF | CACTTT | 2217.98 | 1884 | 0.849 | −0.163 |
| HF | CATTTC | 1840.95 | 1400 | 0.760 | −0.274 |
| HG | CATGGA | 1246.72 | 2238 | 1.795 | 0.585 |
| HG | CATGGT | 807.15 | 1426 | 1.767 | 0.569 |
| HG | CATGGG | 1217.11 | 1849 | 1.519 | 0.418 |
| HG | CATGGC | 1690.37 | 2320 | 1.372 | 0.317 |
| HG | CACGGC | 2331.01 | 1680 | 0.721 | −0.328 |
| HG | CACGGG | 1678.38 | 1184 | 0.705 | −0.349 |
| HG | CACGGT | 1113.05 | 468 | 0.420 | −0.866 |
| HG | CACGGA | 1719.21 | 638 | 0.371 | −0.991 |
| HH | CACCAC | 2269.33 | 2795 | 1.232 | 0.208 |
| HH | CATCAT | 1193.37 | 1250 | 1.047 | 0.046 |
| HH | CACCAT | 1645.65 | 1453 | 0.883 | −0.125 |
| HH | CATCAC | 1645.65 | 1256 | 0.763 | −0.270 |
| HI | CACATC | 2433.52 | 3538 | 1.454 | 0.374 |
| HI | CACATT | 1924.40 | 1924 | 1.000 | 0.000 |
| HI | CACATA | 885.05 | 867 | 0.980 | −0.021 |
| HI | CATATT | 1395.51 | 1260 | 0.903 | −0.102 |
| HI | CATATA | 641.81 | 552 | 0.860 | −0.151 |
| HI | CATATC | 1764.71 | 904 | 0.512 | −0.669 |
| HK | CACAAG | 3102.81 | 3928 | 1.266 | 0.236 |
| HK | CACAAA | 2395.79 | 2432 | 1.015 | 0.015 |
| HK | CATAAA | 1737.35 | 1690 | 0.973 | −0.028 |
| HK | CATAAG | 2250.06 | 1436 | 0.638 | −0.449 |
| HL | CATTTA | 707.71 | 1053 | 1.488 | 0.397 |
| HL | CATTTG | 1188.90 | 1485 | 1.249 | 0.222 |
| HL | CACCTG | 5042.69 | 6030 | 1.196 | 0.179 |
| HL | CACCTC | 2426.56 | 2850 | 1.175 | 0.161 |
| HL | CATCTT | 1213.36 | 1409 | 1.161 | 0.149 |
| HL | CACTTG | 1639.48 | 1700 | 1.037 | 0.036 |
| HL | CATCTA | 654.36 | 649 | 0.992 | −0.008 |
| HL | CACCTT | 1673.21 | 1499 | 0.896 | −0.110 |
| HL | CACCTA | 902.35 | 761 | 0.843 | −0.170 |
| HL | CATCTC | 1759.66 | 1422 | 0.808 | −0.213 |
| HL | CACTTA | 975.93 | 781 | 0.800 | −0.223 |
| HL | CATCTG | 3656.80 | 2202 | 0.602 | −0.507 |
| HM | CACATG | 2348.18 | 3023 | 1.287 | 0.253 |
| HM | CATATG | 1702.82 | 1028 | 0.604 | −0.505 |

SUPPLEMENTAL TABLE 1-continued

Expected and Observed Codon Pair Frequencies and
Codon Pair Scores for 14,795 Human Genes

| amino acid pair | codon pair | expected | observed | observed / expected | CPS |
|---|---|---|---|---|---|
| HN | CACAAC | 2031.88 | 2762 | 1.359 | 0.307 |
| HN | CACAAT | 1844.85 | 1832 | 0.993 | -0.007 |
| HN | CATAAT | 1337.83 | 1225 | 0.916 | -0.088 |
| HN | CATAAC | 1473.45 | 869 | 0.590 | -0.528 |
| HP | CACCCG | 846.94 | 1341 | 1.583 | 0.460 |
| HP | CATCCT | 1518.15 | 1770 | 1.166 | 0.153 |
| HP | CACCCC | 2337.46 | 2530 | 1.082 | 0.079 |
| HP | CATCCA | 1465.21 | 1577 | 1.076 | 0.074 |
| HP | CACCCA | 2020.51 | 1919 | 0.950 | -0.052 |
| HP | CACCCT | 2093.51 | 1859 | 0.888 | -0.119 |
| HP | CATCCC | 1695.05 | 1265 | 0.746 | -0.293 |
| HP | CATCCG | 614.18 | 330 | 0.537 | -0.621 |
| HQ | CATCAA | 1143.96 | 1358 | 1.187 | 0.172 |
| HQ | CACCAG | 4405.09 | 4761 | 1.081 | 0.078 |
| HQ | CATCAG | 3194.43 | 2957 | 0.926 | -0.077 |
| HQ | CACCAA | 1577.51 | 1245 | 0.789 | -0.237 |
| HR | CACAGG | 1447.19 | 1936 | 1.338 | 0.291 |
| HR | CACCGC | 1336.44 | 1772 | 1.326 | 0.282 |
| HR | CACAGA | 1474.12 | 1788 | 1.213 | 0.193 |
| HR | CACCGG | 1461.67 | 1772 | 1.212 | 0.193 |
| HR | CACCGT | 572.18 | 667 | 1.166 | 0.153 |
| HR | CATCGA | 574.58 | 627 | 1.091 | 0.087 |
| HR | CATCGT | 414.93 | 452 | 1.089 | 0.086 |
| HR | CACCGA | 792.34 | 855 | 1.079 | 0.076 |
| HR | CATCGG | 1059.96 | 729 | 0.688 | -0.374 |
| HR | CATAGA | 1068.98 | 635 | 0.594 | -0.521 |
| HR | CATCGC | 969.15 | 565 | 0.583 | -0.540 |
| HR | CATAGG | 1049.46 | 423 | 0.403 | -0.909 |
| HS | CACTCG | 551.81 | 880 | 1.595 | 0.467 |
| HS | CACAGC | 2364.16 | 3726 | 1.576 | 0.455 |
| HS | CACAGT | 1491.56 | 1957 | 1.312 | 0.272 |
| HS | CATTCA | 1064.20 | 1307 | 1.228 | 0.206 |
| HS | CATTCT | 1316.36 | 1517 | 1.152 | 0.142 |
| HS | CACTCC | 2086.72 | 1964 | 0.941 | -0.061 |
| HS | CACTCA | 1467.52 | 1318 | 0.898 | -0.107 |
| HS | CATTCC | 1513.23 | 1219 | 0.806 | -0.216 |
| HS | CACTCT | 1815.24 | 1231 | 0.678 | -0.388 |
| HS | CATAGT | 1081.63 | 710 | 0.656 | -0.421 |
| HS | CATTCG | 400.16 | 256 | 0.640 | -0.447 |
| HS | CATAGC | 1714.41 | 782 | 0.456 | -0.785 |
| HT | CACACG | 778.62 | 1526 | 1.960 | 0.673 |
| HT | CACACT | 1696.86 | 2036 | 1.200 | 0.182 |
| HT | CACACA | 1918.82 | 2255 | 1.175 | 0.161 |
| HT | CACACC | 2370.26 | 2537 | 1.070 | 0.068 |
| HT | CATACT | 1230.51 | 1306 | 1.061 | 0.060 |
| HT | CATACA | 1391.46 | 979 | 0.704 | -0.352 |
| HT | CATACC | 1718.84 | 806 | 0.469 | -0.757 |
| HT | CATACG | 564.63 | 225 | 0.398 | -0.920 |
| HV | CATGTT | 869.32 | 1563 | 1.798 | 0.587 |
| HV | CATGTA | 564.48 | 880 | 1.559 | 0.444 |
| HV | CATGTC | 1113.00 | 1607 | 1.444 | 0.367 |
| HV | CATGTG | 2201.86 | 2797 | 1.270 | 0.239 |
| HV | CACGTG | 3036.34 | 2579 | 0.849 | -0.163 |
| HV | CACGTC | 1534.82 | 1158 | 0.754 | -0.282 |
| HV | CACGTT | 1198.78 | 434 | 0.362 | -1.016 |
| HV | CACGTA | 778.41 | 279 | 0.358 | -1.026 |
| HW | CACTGG | 1602.74 | 2197 | 1.371 | 0.315 |
| HW | CATTGG | 1162.26 | 568 | 0.489 | -0.716 |
| HY | CACTAC | 1943.40 | 2385 | 1.227 | 0.205 |
| HY | CATTAT | 1145.15 | 1240 | 1.083 | 0.080 |
| HY | CACTAT | 1579.16 | 1378 | 0.873 | -0.136 |
| HY | CATTAC | 1409.29 | 1074 | 0.762 | -0.272 |
| IA | ATTGCT | 1886.56 | 3678 | 1.950 | 0.668 |
| IA | ATAGCA | 759.54 | 1446 | 1.904 | 0.644 |
| IA | ATTGCA | 1651.49 | 2818 | 1.706 | 0.534 |
| IA | ATAGCT | 867.65 | 1289 | 1.486 | 0.396 |
| IA | ATTGCC | 2868.63 | 3435 | 1.197 | 0.180 |
| IA | ATAGCC | 1319.32 | 1191 | 0.903 | -0.102 |
| IA | ATCGCG | 980.82 | 708 | 0.722 | -0.326 |
| IA | ATCGCC | 3627.56 | 2570 | 0.708 | -0.345 |
| IA | ATTGCG | 775.62 | 494 | 0.637 | -0.451 |
| IA | ATAGCG | 356.72 | 198 | 0.555 | -0.589 |
| IA | ATCGCA | 2088.41 | 831 | 0.398 | -0.922 |
| IA | ATCGCT | 2385.67 | 910 | 0.381 | -0.964 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| IC | ATCTGC | 2115.05 | 3055 | 1.444 | 0.368 |
| IC | ATCTGT | 1781.48 | 2074 | 1.164 | 0.152 |
| IC | ATATGT | 647.91 | 731 | 1.128 | 0.121 |
| IC | ATTTGT | 1408.77 | 1197 | 0.850 | -0.163 |
| IC | ATATGC | 769.23 | 470 | 0.611 | -0.493 |
| IC | ATTTGC | 1672.56 | 868 | 0.519 | -0.656 |
| ID | ATTGAT | 2604.76 | 4341 | 1.667 | 0.511 |
| ID | ATAGAT | 1197.96 | 1947 | 1.625 | 0.486 |
| ID | ATTGAC | 2942.37 | 3938 | 1.338 | 0.291 |
| ID | ATAGAC | 1353.23 | 1476 | 1.091 | 0.087 |
| ID | ATCGAC | 3720.81 | 2270 | 0.610 | -0.494 |
| ID | ATCGAT | 3293.87 | 1141 | 0.346 | -1.060 |
| IE | ATAGAA | 1371.51 | 2939 | 2.143 | 0.762 |
| IE | ATTGAA | 2982.12 | 5518 | 1.850 | 0.615 |
| IE | ATTGAG | 3988.04 | 4634 | 1.162 | 0.150 |
| IE | ATAGAG | 1834.15 | 1898 | 1.035 | 0.034 |
| IE | ATCGAG | 5043.12 | 3007 | 0.596 | -0.517 |
| IE | ATCGAA | 3771.07 | 994 | 0.264 | -1.333 |
| IF | ATATTT | 1144.73 | 1929 | 1.685 | 0.522 |
| IF | ATCTTC | 3602.60 | 4836 | 1.342 | 0.294 |
| IF | ATTTTT | 2489.02 | 2226 | 0.894 | -0.112 |
| IF | ATCTTT | 3147.52 | 2779 | 0.883 | -0.125 |
| IF | ATATTC | 1310.24 | 886 | 0.676 | -0.391 |
| IF | ATTTTC | 2848.89 | 1887 | 0.662 | -0.412 |
| IG | ATTGGT | 1013.16 | 2102 | 2.075 | 0.730 |
| IG | ATTGGA | 1564.91 | 3151 | 2.014 | 0.700 |
| IG | ATAGGA | 719.72 | 1054 | 1.464 | 0.381 |
| IG | ATTGGG | 1527.75 | 2144 | 1.403 | 0.339 |
| IG | ATAGGT | 465.96 | 596 | 1.279 | 0.246 |
| IG | ATTGGC | 2121.81 | 2706 | 1.275 | 0.243 |
| IG | ATAGGG | 702.63 | 549 | 0.781 | -0.247 |
| IG | ATAGGC | 975.84 | 700 | 0.717 | -0.332 |
| IG | ATCGGG | 1931.93 | 1244 | 0.644 | -0.440 |
| IG | ATCGGC | 2683.15 | 1619 | 0.603 | -0.505 |
| IG | ATCGGT | 1281.20 | 498 | 0.389 | -0.945 |
| IG | ATCGGA | 1978.93 | 604 | 0.305 | -1.187 |
| IH | ATTCAT | 1622.93 | 2242 | 1.381 | 0.323 |
| IH | ATCCAC | 2830.09 | 3367 | 1.190 | 0.174 |
| IH | ATACAT | 746.40 | 760 | 1.018 | 0.018 |
| IH | ATCCAT | 2052.29 | 1814 | 0.884 | -0.123 |
| IH | ATTCAC | 2238.00 | 1778 | 0.794 | -0.230 |
| IH | ATACAC | 1029.28 | 558 | 0.542 | -0.612 |
| II | ATCATC | 3797.03 | 5979 | 1.575 | 0.454 |
| II | ATAATA | 502.24 | 700 | 1.394 | 0.332 |
| II | ATAATT | 1092.04 | 1309 | 1.199 | 0.181 |
| II | ATCATT | 3002.64 | 3321 | 1.106 | 0.101 |
| II | ATTATT | 2374.46 | 2157 | 0.908 | -0.096 |
| II | ATCATA | 1380.95 | 1183 | 0.857 | -0.155 |
| II | ATTATA | 1092.04 | 921 | 0.843 | -0.170 |
| II | ATAATC | 1380.95 | 715 | 0.518 | -0.658 |
| II | ATTATC | 3002.64 | 1340 | 0.446 | -0.807 |
| IK | ATAAAA | 1419.09 | 2244 | 1.581 | 0.458 |
| IK | ATCAAG | 5053.39 | 5884 | 1.164 | 0.152 |
| IK | ATAAAG | 1837.88 | 1943 | 1.057 | 0.056 |
| IK | ATTAAA | 3085.58 | 3107 | 1.007 | 0.007 |
| IK | ATCAAA | 3901.90 | 3830 | 0.982 | -0.019 |
| IK | ATTAAG | 3996.16 | 2286 | 0.572 | -0.559 |
| IL | ATTTTA | 977.08 | 1679 | 1.718 | 0.541 |
| IL | ATATTA | 449.37 | 723 | 1.609 | 0.476 |
| IL | ATTTTG | 1641.41 | 2339 | 1.425 | 0.354 |
| IL | ATTCTT | 1675.18 | 2271 | 1.356 | 0.304 |
| IL | ATCCTC | 3072.14 | 4017 | 1.308 | 0.268 |
| IL | ATCCTG | 6384.29 | 7754 | 1.215 | 0.194 |
| IL | ATTCTA | 903.41 | 1021 | 1.130 | 0.122 |
| IL | ATCTTG | 2075.66 | 2250 | 1.084 | 0.081 |
| IL | ATCCTA | 1142.42 | 1170 | 1.024 | 0.024 |
| IL | ATACTA | 415.49 | 416 | 1.001 | 0.001 |
| IL | ATCCTT | 2118.37 | 2058 | 0.972 | -0.029 |
| IL | ATATTG | 754.90 | 717 | 0.950 | -0.052 |
| IL | ATACTT | 770.44 | 726 | 0.942 | -0.059 |
| IL | ATCTTA | 1235.57 | 1077 | 0.872 | -0.137 |
| IL | ATTCTC | 2429.41 | 1918 | 0.789 | -0.236 |
| IL | ATTCTG | 5048.62 | 3005 | 0.595 | -0.519 |
| IL | ATACTC | 1117.32 | 458 | 0.410 | -0.892 |

SUPPLEMENTAL TABLE 1-continued

Expected and Observed Codon Pair Frequencies and
Codon Pair Scores for 14,795 Human Genes

| amino acid pair | codon pair | expected | observed | observed / expected | CPS |
|---|---|---|---|---|---|
| IL | ATACTG | 2321.92 | 934 | 0.402 | -0.911 |
| IM | ATCATG | 3206.80 | 4314 | 1.345 | 0.297 |
| IM | ATAATG | 1166.29 | 1196 | 1.025 | 0.025 |
| IM | ATTATG | 2535.90 | 1399 | 0.552 | -0.595 |
| IN | ATAAAT | 1088.42 | 1649 | 1.515 | 0.415 |
| IN | ATCAAC | 3296.07 | 4599 | 1.395 | 0.333 |
| IN | ATCAAT | 2992.68 | 2890 | 0.966 | -0.035 |
| IN | ATAAAC | 1198.76 | 1113 | 0.928 | -0.074 |
| IN | ATTAAT | 2366.58 | 1967 | 0.831 | -0.185 |
| IN | ATTAAC | 2606.49 | 1331 | 0.511 | -0.672 |
| IP | ATTCCT | 2051.78 | 2787 | 1.358 | 0.306 |
| IP | ATTCCA | 1980.23 | 2644 | 1.335 | 0.289 |
| IP | ATACCA | 910.73 | 1047 | 1.150 | 0.139 |
| IP | ATCCCC | 2896.94 | 3229 | 1.115 | 0.109 |
| IP | ATACCT | 943.64 | 995 | 1.054 | 0.053 |
| IP | ATCCCG | 1049.66 | 1073 | 1.022 | 0.022 |
| IP | ATCCCA | 2504.13 | 2366 | 0.945 | -0.057 |
| IP | ATCCCT | 2594.61 | 2451 | 0.945 | -0.057 |
| IP | ATTCCC | 2290.86 | 1775 | 0.775 | -0.255 |
| IP | ATACCC | 1053.60 | 610 | 0.579 | -0.547 |
| IP | ATTCCG | 830.06 | 386 | 0.465 | -0.766 |
| IP | ATACCG | 381.76 | 125 | 0.327 | -1.116 |
| IQ | ATACAA | 765.47 | 950 | 1.241 | 0.216 |
| IQ | ATTCAA | 1664.38 | 2045 | 1.229 | 0.206 |
| IQ | ATCCAG | 5877.26 | 6881 | 1.171 | 0.158 |
| IQ | ATTCAG | 4647.67 | 3987 | 0.858 | -0.153 |
| IQ | ATCCAA | 2104.71 | 1765 | 0.839 | -0.176 |
| IQ | ATACAG | 2137.52 | 1569 | 0.734 | -0.309 |
| IR | ATCCGC | 1552.18 | 2623 | 1.690 | 0.525 |
| IR | ATTCGA | 727.72 | 1142 | 1.569 | 0.451 |
| IR | ATCCGA | 920.25 | 1434 | 1.558 | 0.444 |
| IR | ATCCGT | 664.55 | 943 | 1.419 | 0.350 |
| IR | ATAAGA | 622.67 | 877 | 1.408 | 0.342 |
| IR | ATCCGG | 1697.63 | 2265 | 1.334 | 0.288 |
| IR | ATTCGT | 525.51 | 677 | 1.288 | 0.253 |
| IR | ATCAGA | 1712.09 | 1680 | 0.981 | -0.019 |
| IR | ATCAGG | 1680.81 | 1513 | 0.900 | -0.105 |
| IR | ATAAGG | 611.30 | 547 | 0.895 | -0.111 |
| IR | ATACGT | 241.69 | 213 | 0.881 | -0.126 |
| IR | ATACGA | 334.69 | 292 | 0.872 | -0.136 |
| IR | ATTCGG | 1342.46 | 907 | 0.676 | -0.392 |
| IR | ATTAGA | 1353.90 | 900 | 0.665 | -0.408 |
| IR | ATTCGC | 1227.45 | 780 | 0.635 | -0.453 |
| IR | ATACGG | 617.42 | 260 | 0.421 | -0.865 |
| IR | ATTAGG | 1329.16 | 503 | 0.378 | -0.972 |
| IR | ATACGC | 564.52 | 170 | 0.301 | -1.200 |
| IS | ATCTCC | 2689.59 | 3743 | 1.392 | 0.330 |
| IS | ATATCA | 687.92 | 954 | 1.387 | 0.327 |
| IS | ATCAGC | 3047.17 | 3998 | 1.312 | 0.272 |
| IS | ATTTCT | 1850.19 | 2423 | 1.310 | 0.270 |
| IS | ATTTCA | 1495.77 | 1957 | 1.308 | 0.269 |
| IS | ATCAGT | 1922.48 | 2287 | 1.190 | 0.174 |
| IS | ATATCT | 850.92 | 1012 | 1.189 | 0.173 |
| IS | ATCTCG | 711.23 | 773 | 1.087 | 0.083 |
| IS | ATAAGT | 699.19 | 695 | 0.994 | -0.006 |
| IS | ATCTCT | 2339.68 | 2317 | 0.990 | -0.010 |
| IS | ATCTCA | 1891.49 | 1767 | 0.934 | -0.068 |
| IS | ATTTCC | 2126.89 | 1795 | 0.844 | -0.170 |
| IS | ATATCC | 978.18 | 703 | 0.719 | -0.330 |
| IS | ATTAGT | 1520.28 | 906 | 0.596 | -0.518 |
| IS | ATAAGC | 1108.24 | 636 | 0.574 | -0.555 |
| IS | ATATCG | 258.67 | 132 | 0.510 | -0.673 |
| IS | ATTTCG | 562.43 | 255 | 0.453 | -0.791 |
| IS | ATTAGC | 2409.67 | 797 | 0.331 | -1.106 |
| IT | ATCACC | 3094.94 | 4722 | 1.526 | 0.422 |
| IT | ATCACG | 1016.68 | 1306 | 1.285 | 0.250 |
| IT | ATAACT | 805.82 | 1009 | 1.252 | 0.225 |
| IT | ATCACT | 2215.66 | 2751 | 1.242 | 0.216 |
| IT | ATCACA | 2505.48 | 2989 | 1.193 | 0.176 |
| IT | ATAACA | 911.22 | 1079 | 1.184 | 0.169 |
| IT | ATTACT | 1752.12 | 1369 | 0.781 | -0.247 |
| IT | ATTACA | 1981.30 | 1531 | 0.773 | -0.258 |
| IT | ATAACC | 1125.61 | 741 | 0.658 | -0.418 |
| IT | ATAACG | 369.76 | 204 | 0.552 | -0.595 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
| --- | --- | --- | --- | --- | --- |
| IT | ATTACC | 2447.44 | 1083 | 0.443 | -0.815 |
| IT | ATTACG | 803.98 | 246 | 0.306 | -1.184 |
| IV | ATTGTT | 1261.28 | 2414 | 1.914 | 0.649 |
| IV | ATTGTA | 819.00 | 1478 | 1.805 | 0.590 |
| IV | ATAGTA | 376.67 | 645 | 1.712 | 0.538 |
| IV | ATAGTT | 580.08 | 877 | 1.512 | 0.413 |
| IV | ATTGTC | 1614.84 | 2315 | 1.434 | 0.360 |
| IV | ATTGTG | 3194.65 | 3762 | 1.178 | 0.163 |
| IV | ATCGTC | 2042.07 | 1679 | 0.822 | -0.196 |
| IV | ATAGTG | 1469.26 | 1196 | 0.814 | -0.206 |
| IV | ATAGTC | 742.69 | 575 | 0.774 | -0.256 |
| IV | ATCGTG | 4039.83 | 2922 | 0.723 | -0.324 |
| IV | ATCGTA | 1035.67 | 361 | 0.349 | -1.054 |
| IV | ATCGTT | 1594.97 | 547 | 0.343 | -1.070 |
| IW | ATCTGG | 1887.23 | 2427 | 1.286 | 0.252 |
| IW | ATATGG | 686.37 | 622 | 0.906 | -0.098 |
| IW | ATTTGG | 1492.40 | 1017 | 0.681 | -0.384 |
| IY | ATCTAC | 2708.47 | 3486 | 1.287 | 0.252 |
| IY | ATATAT | 800.43 | 953 | 1.191 | 0.174 |
| IY | ATTTAT | 1740.39 | 1984 | 1.140 | 0.131 |
| IY | ATCTAT | 2200.83 | 2196 | 0.998 | -0.002 |
| IY | ATTTAC | 2141.83 | 1403 | 0.655 | -0.423 |
| IY | ATATAC | 985.05 | 555 | 0.563 | -0.574 |
| KA | AAAGCA | 3029.93 | 4322 | 1.426 | 0.355 |
| KA | AAAGCT | 3461.21 | 4262 | 1.231 | 0.208 |
| KA | AAGGCC | 6816.15 | 6676 | 0.979 | -0.021 |
| KA | AAGGCG | 1842.96 | 1790 | 0.971 | -0.029 |
| KA | AAGGCA | 3924.10 | 3654 | 0.931 | -0.071 |
| KA | AAAGCC | 5262.99 | 4742 | 0.901 | -0.104 |
| KA | AAGGCT | 4482.65 | 4032 | 0.899 | -0.106 |
| KA | AAAGCG | 1423.01 | 765 | 0.538 | -0.621 |
| KC | AAATGT | 1815.55 | 2671 | 1.471 | 0.386 |
| KC | AAGTGT | 2351.33 | 2267 | 0.964 | -0.037 |
| KC | AAGTGC | 2791.62 | 2498 | 0.895 | -0.111 |
| KC | AAATGC | 2155.50 | 1678 | 0.778 | -0.250 |
| KD | AAAGAT | 4684.00 | 6115 | 1.306 | 0.267 |
| KD | AAGGAC | 6852.58 | 6836 | 0.998 | -0.002 |
| KD | AAGGAT | 6066.30 | 5379 | 0.887 | -0.120 |
| KD | AAAGAC | 5291.12 | 4564 | 0.863 | -0.148 |
| KE | AAAGAA | 6989.41 | 9895 | 1.416 | 0.348 |
| KE | AAGGAG | 12105.47 | 12287 | 1.015 | 0.015 |
| KE | AAGGAA | 9052.06 | 8366 | 0.924 | -0.079 |
| KE | AAAGAG | 9347.06 | 6946 | 0.743 | -0.297 |
| KF | AAATTT | 2631.62 | 3140 | 1.193 | 0.177 |
| KF | AAGTTT | 3408.25 | 3638 | 1.067 | 0.065 |
| KF | AAGTTC | 3901.02 | 3950 | 1.013 | 0.012 |
| KF | AAATTC | 3012.11 | 2225 | 0.739 | -0.303 |
| KG | AAAGGA | 2672.15 | 4509 | 1.687 | 0.523 |
| KG | AAAGGT | 1730.00 | 2402 | 1.388 | 0.328 |
| KG | AAAGGC | 3623.06 | 3435 | 0.948 | -0.053 |
| KG | AAAGGG | 2608.69 | 2465 | 0.945 | -0.057 |
| KG | AAGGGC | 4692.27 | 4309 | 0.918 | -0.085 |
| KG | AAGGGT | 2240.55 | 1978 | 0.883 | -0.125 |
| KG | AAGGGG | 3378.54 | 2740 | 0.811 | -0.209 |
| KG | AAGGGA | 3460.73 | 2568 | 0.742 | -0.298 |
| KH | AAACAT | 1929.29 | 2356 | 1.221 | 0.200 |
| KH | AAGCAC | 3445.60 | 3583 | 1.040 | 0.039 |
| KH | AAGCAT | 2498.64 | 2430 | 0.973 | -0.028 |
| KH | AAACAC | 2660.47 | 2165 | 0.814 | -0.206 |
| KI | AAAATA | 1547.96 | 2667 | 1.723 | 0.544 |
| KI | AAAATT | 3365.76 | 3894 | 1.157 | 0.146 |
| KI | AAGATC | 5512.26 | 5523 | 1.002 | 0.002 |
| KI | AAGATA | 2004.77 | 1943 | 0.969 | -0.031 |
| KI | AAGATT | 4359.03 | 3732 | 0.856 | -0.155 |
| KI | AAAATC | 4256.21 | 3287 | 0.772 | -0.258 |
| KK | AAGAAG | 11070.03 | 13815 | 1.248 | 0.222 |
| KK | AAGAAA | 8547.55 | 10129 | 1.185 | 0.170 |
| KK | AAAAAG | 8547.55 | 6145 | 0.719 | -0.330 |
| KK | AAAAAA | 6599.86 | 4676 | 0.708 | -0.345 |
| KL | AAATTA | 1273.72 | 2084 | 1.636 | 0.492 |
| KL | AAACTA | 1177.70 | 1750 | 1.486 | 0.396 |
| KL | AAACTT | 2183.78 | 3014 | 1.380 | 0.322 |
| KL | AAGCTG | 8523.68 | 9600 | 1.126 | 0.119 |
| KL | AAGCTA | 1525.25 | 1660 | 1.088 | 0.085 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| KL | AAGCTC | 4101.62 | 4076 | 0.994 | -0.006 |
| KL | AAATTG | 2139.75 | 2113 | 0.987 | -0.013 |
| KL | AAGCTT | 2828.24 | 2772 | 0.980 | -0.020 |
| KL | AAGTTA | 1649.61 | 1459 | 0.884 | -0.123 |
| KL | AAACTC | 3167.00 | 2653 | 0.838 | -0.177 |
| KL | AAGTTG | 2771.21 | 2280 | 0.823 | -0.195 |
| KL | AAACTG | 6581.43 | 4462 | 0.678 | -0.389 |
| KM | AAGATG | 5479.27 | 5650 | 1.031 | 0.031 |
| KM | AAAATG | 4230.73 | 4060 | 0.960 | -0.041 |
| KN | AAAAAT | 3683.47 | 4378 | 1.189 | 0.173 |
| KN | AAGAAC | 5254.13 | 5515 | 1.050 | 0.048 |
| KN | AAGAAT | 4770.51 | 4618 | 0.968 | -0.032 |
| KN | AAAAAC | 4056.89 | 3254 | 0.802 | -0.221 |
| KP | AAACCA | 2803.51 | 3370 | 1.202 | 0.184 |
| KP | AAGCCC | 4200.41 | 4673 | 1.113 | 0.107 |
| KP | AAGCCA | 3630.85 | 4035 | 1.111 | 0.106 |
| KP | AAACCT | 2904.80 | 3118 | 1.073 | 0.071 |
| KP | AAGCCG | 1521.96 | 1544 | 1.014 | 0.014 |
| KP | AAGCCT | 3762.04 | 3396 | 0.903 | -0.102 |
| KP | AAACCC | 3243.28 | 2624 | 0.809 | -0.212 |
| KP | AAACCG | 1175.16 | 482 | 0.410 | -0.891 |
| KQ | AAACAA | 2178.87 | 3274 | 1.503 | 0.407 |
| KQ | AAGCAA | 2821.88 | 3177 | 1.126 | 0.119 |
| KQ | AAGCAG | 7879.90 | 8081 | 1.026 | 0.025 |
| KQ | AAACAG | 6084.35 | 4433 | 0.729 | -0.317 |
| KR | AAAAGA | 2247.57 | 3147 | 1.400 | 0.337 |
| KR | AAGAGG | 2857.67 | 3975 | 1.391 | 0.330 |
| KR | AAGAGA | 2910.85 | 3511 | 1.206 | 0.187 |
| KR | AAAAGG | 2206.51 | 2325 | 1.054 | 0.052 |
| KR | AAACGT | 872.39 | 862 | 0.988 | -0.012 |
| KR | AAGCGG | 2886.27 | 2828 | 0.980 | -0.020 |
| KR | AAGCGC | 2638.99 | 2532 | 0.959 | -0.041 |
| KR | AAACGA | 1208.07 | 1087 | 0.900 | -0.106 |
| KR | AAGCGT | 1129.84 | 978 | 0.866 | -0.144 |
| KR | AAGCGA | 1564.59 | 1325 | 0.847 | -0.166 |
| KR | AAACGG | 2228.59 | 1178 | 0.529 | -0.638 |
| KR | AAACGC | 2037.65 | 1041 | 0.511 | -0.672 |
| KS | AAATCA | 1871.14 | 2533 | 1.354 | 0.303 |
| KS | AAAAGT | 1901.80 | 2389 | 1.256 | 0.228 |
| KS | AAATCT | 2314.50 | 2793 | 1.207 | 0.188 |
| KS | AAGTCA | 2423.33 | 2566 | 1.059 | 0.057 |
| KS | AAGAGC | 3903.97 | 4045 | 1.036 | 0.035 |
| KS | AAGAGT | 2463.04 | 2459 | 0.998 | -0.002 |
| KS | AAGTCG | 911.22 | 904 | 0.992 | -0.008 |
| KS | AAGTCC | 3445.84 | 3100 | 0.900 | -0.106 |
| KS | AAGTCT | 2997.54 | 2675 | 0.892 | -0.114 |
| KS | AAATCC | 2660.65 | 2304 | 0.866 | -0.144 |
| KS | AAAAGC | 3014.39 | 2381 | 0.790 | -0.236 |
| KS | AAATCG | 703.58 | 462 | 0.657 | -0.421 |
| KT | AAAACA | 2831.74 | 3611 | 1.275 | 0.243 |
| KT | AAGACG | 1488.17 | 1790 | 1.203 | 0.185 |
| KT | AAAACT | 2504.18 | 2969 | 1.186 | 0.170 |
| KT | AAGACC | 4530.26 | 4475 | 0.988 | -0.012 |
| KT | AAGACA | 3667.42 | 3574 | 0.975 | -0.026 |
| KT | AAGACT | 3243.20 | 2876 | 0.887 | -0.120 |
| KT | AAAACC | 3497.97 | 2854 | 0.816 | -0.203 |
| KT | AAAACG | 1149.07 | 763 | 0.664 | -0.409 |
| KV | AAAGTA | 1317.00 | 2214 | 1.681 | 0.519 |
| KV | AAAGTT | 2028.22 | 3042 | 1.500 | 0.405 |
| KV | AAAGTC | 2596.78 | 2642 | 1.017 | 0.017 |
| KV | AAGGTG | 6653.25 | 6512 | 0.979 | -0.021 |
| KV | AAGGTC | 3363.11 | 3016 | 0.897 | -0.109 |
| KV | AAGGTT | 2626.77 | 2294 | 0.873 | -0.135 |
| KV | AAAGTG | 5137.21 | 4417 | 0.860 | -0.151 |
| KV | AAGGTA | 1705.66 | 1291 | 0.757 | -0.279 |
| KW | AAGTGG | 2598.56 | 2701 | 1.039 | 0.039 |
| KW | AAATGG | 2006.44 | 1904 | 0.949 | -0.052 |
| KY | AAATAT | 2319.32 | 2982 | 1.286 | 0.251 |
| KY | AAGTAC | 3696.62 | 3603 | 0.975 | -0.026 |
| KY | AAATAC | 2854.29 | 2763 | 0.968 | -0.033 |
| KY | AAGTAT | 3003.78 | 2526 | 0.841 | -0.173 |
| LA | CTGGCG | 2275.39 | 3643 | 1.601 | 0.471 |
| LA | TTGGCA | 1575.16 | 2350 | 1.492 | 0.400 |
| LA | CTGGCC | 8415.49 | 12456 | 1.480 | 0.392 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| LA | TTGGCT | 1799.36 | 2643 | 1.469 | 0.384 |
| LA | TTAGCA | 937.64 | 1314 | 1.401 | 0.337 |
| LA | CTTGCT | 1836.39 | 2345 | 1.277 | 0.244 |
| LA | CTAGCA | 866.95 | 1107 | 1.277 | 0.244 |
| LA | CTTGCA | 1607.57 | 1861 | 1.158 | 0.146 |
| LA | TTAGCT | 1071.10 | 1239 | 1.157 | 0.146 |
| LA | CTGGCT | 5534.46 | 6333 | 1.144 | 0.135 |
| LA | CTAGCT | 990.35 | 1099 | 1.110 | 0.104 |
| LA | CTGGCA | 4844.85 | 5013 | 1.035 | 0.034 |
| LA | TTGGCC | 2736.04 | 2824 | 1.032 | 0.032 |
| LA | TTGGCG | 739.77 | 623 | 0.842 | -0.172 |
| LA | CTTGCC | 2792.34 | 2201 | 0.788 | -0.238 |
| LA | CTAGCC | 1505.89 | 1159 | 0.770 | -0.262 |
| LA | CTAGCG | 407.16 | 253 | 0.621 | -0.476 |
| LA | TTAGCC | 1628.68 | 941 | 0.578 | -0.549 |
| LA | CTTGCG | 755.00 | 346 | 0.458 | -0.780 |
| LA | TTAGCG | 440.36 | 198 | 0.450 | -0.799 |
| LA | CTCGCC | 4049.56 | 1527 | 0.377 | -0.975 |
| LA | CTCGCG | 1094.93 | 390 | 0.356 | -1.032 |
| LA | CTCGCT | 2663.20 | 605 | 0.227 | -1.482 |
| LA | CTCGCA | 2331.36 | 429 | 0.184 | -1.693 |
| LC | CTCTGC | 1769.27 | 3523 | 1.991 | 0.689 |
| LC | CTCTGT | 1490.23 | 2145 | 1.439 | 0.364 |
| LC | CTTTGT | 1027.58 | 1155 | 1.124 | 0.117 |
| LC | TTATGT | 599.35 | 627 | 1.046 | 0.045 |
| LC | CTGTGC | 3676.77 | 3517 | 0.957 | -0.044 |
| LC | TTGTGT | 1006.86 | 856 | 0.850 | -0.162 |
| LC | CTTTGC | 1219.99 | 974 | 0.798 | -0.225 |
| LC | CTGTGT | 3096.89 | 2370 | 0.765 | -0.268 |
| LC | CTATGT | 554.17 | 417 | 0.752 | -0.284 |
| LC | TTGTGC | 1195.39 | 722 | 0.604 | -0.504 |
| LC | TTATGC | 711.58 | 368 | 0.517 | -0.659 |
| LC | CTATGC | 657.93 | 332 | 0.505 | -0.684 |
| LD | TTGGAT | 2174.51 | 3688 | 1.696 | 0.528 |
| LD | TTAGAT | 1294.41 | 1977 | 1.527 | 0.424 |
| LD | CTGGAC | 7555.23 | 10531 | 1.394 | 0.332 |
| LD | CTAGAT | 1196.83 | 1584 | 1.323 | 0.280 |
| LD | TTGGAC | 2456.35 | 2775 | 1.130 | 0.122 |
| LD | CTTGAT | 2219.25 | 2463 | 1.110 | 0.104 |
| LD | CTGGAT | 6688.33 | 6912 | 1.033 | 0.033 |
| LD | CTAGAC | 1351.95 | 1390 | 1.028 | 0.028 |
| LD | CTTGAC | 2506.90 | 1832 | 0.731 | -0.314 |
| LD | TTAGAC | 1462.19 | 969 | 0.663 | -0.411 |
| LD | CTCGAC | 3635.60 | 981 | 0.270 | -1.310 |
| LD | CTCGAT | 3218.44 | 658 | 0.204 | -1.587 |
| LE | TTAGAA | 1739.66 | 3085 | 1.773 | 0.573 |
| LE | CTAGAA | 1608.51 | 2701 | 1.679 | 0.518 |
| LE | TTGGAA | 2922.49 | 4652 | 1.592 | 0.465 |
| LE | CTGGAG | 12021.09 | 18044 | 1.501 | 0.406 |
| LE | TTGGAG | 3908.29 | 4774 | 1.222 | 0.200 |
| LE | CTAGAG | 2151.09 | 2515 | 1.169 | 0.156 |
| LE | CTTGAA | 2982.63 | 3161 | 1.060 | 0.058 |
| LE | CTGGAA | 8988.96 | 7642 | 0.850 | -0.162 |
| LE | TTAGAG | 2326.48 | 1873 | 0.805 | -0.217 |
| LE | CTTGAG | 3988.72 | 2484 | 0.623 | -0.474 |
| LE | CTCGAG | 5784.58 | 1305 | 0.226 | -1.489 |
| LE | CTCGAA | 4325.51 | 512 | 0.118 | -2.134 |
| LF | CTCTTC | 2629.18 | 6495 | 2.470 | 0.904 |
| LF | TTATTT | 923.85 | 1405 | 1.521 | 0.419 |
| LF | CTCTTT | 2297.07 | 3446 | 1.500 | 0.406 |
| LF | CTTTTT | 1583.93 | 1937 | 1.223 | 0.201 |
| LF | CTTTTC | 1812.93 | 1936 | 1.068 | 0.066 |
| LF | CTATTT | 854.20 | 876 | 1.026 | 0.025 |
| LF | TTGTTT | 1551.99 | 1544 | 0.995 | -0.005 |
| LF | CTGTTT | 4773.59 | 2957 | 0.619 | -0.479 |
| LF | CTGTTC | 5463.77 | 3119 | 0.571 | -0.561 |
| LF | TTATTC | 1057.42 | 583 | 0.551 | -0.595 |
| LF | TTGTTC | 1776.38 | 940 | 0.529 | -0.636 |
| LF | CTATTC | 977.70 | 464 | 0.475 | -0.745 |
| LG | CTTGGA | 1534.14 | 2667 | 1.738 | 0.553 |
| LG | CTTGGT | 993.23 | 1579 | 1.590 | 0.464 |
| LG | CTGGGC | 6268.87 | 9794 | 1.562 | 0.446 |
| LG | CTAGGA | 827.35 | 1087 | 1.314 | 0.273 |
| LG | CTTGGG | 1497.70 | 1881 | 1.256 | 0.228 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| LG | TTAGGA | 894.81 | 1114 | 1.245 | 0.219 |
| LG | CTGGGG | 4513.74 | 5602 | 1.241 | 0.216 |
| LG | TTGGGT | 973.20 | 1194 | 1.227 | 0.204 |
| LG | TTGGGA | 1503.20 | 1820 | 1.211 | 0.191 |
| LG | CTAGGT | 535.64 | 611 | 1.141 | 0.132 |
| LG | TTAGGT | 579.32 | 611 | 1.055 | 0.053 |
| LG | TTGGGG | 1467.50 | 1452 | 0.989 | −0.011 |
| LG | CTGGGT | 2993.37 | 2947 | 0.985 | −0.016 |
| LG | CTTGGC | 2080.08 | 2009 | 0.966 | −0.035 |
| LG | CTAGGG | 807.70 | 766 | 0.948 | −0.053 |
| LG | TTGGGC | 2038.13 | 1786 | 0.876 | −0.132 |
| LG | CTGGGA | 4623.54 | 4034 | 0.872 | −0.136 |
| LG | CTAGGC | 1121.77 | 940 | 0.838 | −0.177 |
| LG | TTAGGG | 873.56 | 529 | 0.606 | −0.502 |
| LG | CTCGGG | 2172.02 | 1076 | 0.495 | −0.702 |
| LG | CTCGGC | 3016.60 | 1313 | 0.435 | −0.832 |
| LG | TTAGGC | 1213.24 | 507 | 0.418 | −0.873 |
| LG | CTCGGT | 1440.42 | 365 | 0.253 | −1.373 |
| LG | CTCGGA | 2224.86 | 510 | 0.229 | −1.473 |
| LH | CTTCAT | 1127.31 | 1980 | 1.756 | 0.563 |
| LH | TTACAT | 657.52 | 935 | 1.422 | 0.352 |
| LH | CTACAT | 607.95 | 741 | 1.219 | 0.198 |
| LH | CTGCAC | 4685.05 | 5459 | 1.165 | 0.153 |
| LH | CTCCAC | 2254.46 | 2204 | 0.978 | −0.023 |
| LH | CTTCAC | 1554.55 | 1490 | 0.958 | −0.042 |
| LH | CTCCAT | 1634.86 | 1521 | 0.930 | −0.072 |
| LH | CTACAC | 838.36 | 777 | 0.927 | −0.076 |
| LH | TTGCAT | 1104.58 | 1017 | 0.921 | −0.083 |
| LH | TTGCAC | 1523.20 | 1140 | 0.748 | −0.290 |
| LH | CTGCAT | 3397.45 | 2394 | 0.705 | −0.350 |
| LH | TTACAC | 906.71 | 634 | 0.699 | −0.358 |
| LI | CTCATC | 2602.42 | 6250 | 2.402 | 0.876 |
| LI | TTAATA | 380.66 | 798 | 2.096 | 0.740 |
| LI | TTAATT | 827.68 | 1290 | 1.559 | 0.444 |
| LI | CTCATT | 2057.96 | 3117 | 1.515 | 0.415 |
| LI | CTAATA | 351.96 | 516 | 1.466 | 0.383 |
| LI | CTAATT | 765.28 | 952 | 1.244 | 0.218 |
| LI | CTTATT | 1419.05 | 1761 | 1.241 | 0.216 |
| LI | TTGATA | 639.48 | 791 | 1.237 | 0.213 |
| LI | TTGATT | 1390.44 | 1468 | 1.056 | 0.054 |
| LI | CTTATA | 652.64 | 683 | 1.047 | 0.045 |
| LI | CTCATA | 946.48 | 919 | 0.971 | −0.029 |
| LI | CTTATC | 1794.48 | 1189 | 0.663 | −0.412 |
| LI | TTGATC | 1758.29 | 1135 | 0.646 | −0.438 |
| LI | CTGATC | 5408.15 | 3356 | 0.621 | −0.477 |
| LI | CTGATT | 4276.70 | 2639 | 0.617 | −0.483 |
| LI | CTGATA | 1966.91 | 1193 | 0.607 | −0.500 |
| LI | TTAATC | 1046.66 | 633 | 0.605 | −0.503 |
| LI | CTAATC | 967.75 | 563 | 0.582 | −0.542 |
| LK | TTAAAA | 1429.91 | 2557 | 1.788 | 0.581 |
| LK | CTAAAA | 1322.10 | 1842 | 1.393 | 0.332 |
| LK | TTGAAA | 2402.12 | 3193 | 1.329 | 0.285 |
| LK | CTCAAG | 4604.55 | 6048 | 1.313 | 0.273 |
| LK | CTAAAG | 1712.27 | 2078 | 1.214 | 0.194 |
| LK | TTAAAG | 1851.89 | 2128 | 1.149 | 0.139 |
| LK | CTGAAG | 9568.82 | 10212 | 1.067 | 0.065 |
| LK | TTGAAG | 3111.01 | 3222 | 1.036 | 0.035 |
| LK | CTCAAA | 3555.33 | 2768 | 0.779 | −0.250 |
| LK | CTTAAA | 2451.55 | 1850 | 0.755 | −0.282 |
| LK | CTGAAA | 7388.42 | 5227 | 0.707 | −0.346 |
| LK | CTTAAG | 3175.03 | 1448 | 0.456 | −0.785 |
| LL | TTATTA | 500.55 | 802 | 1.602 | 0.471 |
| LL | CTTCTA | 793.49 | 1132 | 1.427 | 0.355 |
| LL | CTTCTT | 1471.36 | 2099 | 1.427 | 0.355 |
| LL | CTTTTA | 858.19 | 1203 | 1.402 | 0.338 |
| LL | CTGCTG | 13364.10 | 18236 | 1.365 | 0.311 |
| LL | CTTTTG | 1441.69 | 1945 | 1.349 | 0.299 |
| LL | TTACTA | 462.82 | 608 | 1.314 | 0.273 |
| LL | CTCCTC | 3094.54 | 3800 | 1.228 | 0.205 |
| LL | CTCCTG | 6430.85 | 7786 | 1.211 | 0.191 |
| LL | TTACTT | 858.19 | 1039 | 1.211 | 0.191 |
| LL | TTGCTA | 777.49 | 929 | 1.195 | 0.178 |
| LL | CTGCTC | 6430.85 | 7550 | 1.174 | 0.160 |
| LL | CTACTA | 427.93 | 474 | 1.108 | 0.102 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| LL | CTTCTC | 2133.82 | 2292 | 1.074 | 0.072 |
| LL | CTACTT | 793.49 | 839 | 1.057 | 0.056 |
| LL | CTCTTG | 2090.79 | 2131 | 1.019 | 0.019 |
| LL | TTGCTT | 1441.69 | 1464 | 1.015 | 0.015 |
| LL | TTATTG | 840.89 | 818 | 0.973 | -0.028 |
| LL | CTCCTT | 2133.82 | 2034 | 0.953 | -0.048 |
| LL | TTGTTA | 840.89 | 771 | 0.917 | -0.087 |
| LL | TTGTTG | 1412.62 | 1289 | 0.912 | -0.092 |
| LL | CTCCTA | 1150.75 | 1034 | 0.899 | -0.107 |
| LL | TTGCTG | 4344.93 | 3820 | 0.879 | -0.129 |
| LL | CTTCTG | 4434.34 | 3837 | 0.865 | -0.145 |
| LL | CTGCTA | 2391.41 | 1913 | 0.800 | -0.223 |
| LL | CTCTTA | 1244.58 | 959 | 0.771 | -0.261 |
| LL | CTATTA | 462.82 | 354 | 0.765 | -0.268 |
| LL | CTGCTT | 4434.34 | 3148 | 0.710 | -0.343 |
| LL | TTGCTC | 2090.79 | 1440 | 0.689 | -0.373 |
| LL | CTACTC | 1150.75 | 792 | 0.688 | -0.374 |
| LL | CTATTG | 777.49 | 532 | 0.684 | -0.379 |
| LL | CTACTG | 2391.41 | 1583 | 0.662 | -0.413 |
| LL | CTGTTG | 4344.93 | 2615 | 0.602 | -0.508 |
| LL | TTACTC | 1244.58 | 657 | 0.528 | -0.639 |
| LL | TTACTG | 2586.40 | 1358 | 0.525 | -0.644 |
| LL | CTGTTA | 2586.40 | 953 | 0.368 | -0.998 |
| LM | CTCATG | 2631.41 | 4030 | 1.531 | 0.426 |
| LM | TTAATG | 1058.32 | 1228 | 1.160 | 0.149 |
| LM | CTAATG | 978.53 | 1101 | 1.125 | 0.118 |
| LM | TTGATG | 1777.88 | 1763 | 0.992 | -0.008 |
| LM | CTGATG | 5468.39 | 4470 | 0.817 | -0.202 |
| LM | CTTATG | 1814.47 | 1137 | 0.627 | -0.467 |
| LN | TTAAAT | 962.36 | 1926 | 2.001 | 0.694 |
| LN | CTCAAC | 2635.40 | 4681 | 1.776 | 0.574 |
| LN | CTAAAT | 889.81 | 1446 | 1.625 | 0.486 |
| LN | TTGAAT | 1616.68 | 2048 | 1.267 | 0.236 |
| LN | CTCAAT | 2392.82 | 2652 | 1.108 | 0.103 |
| LN | CTAAAC | 980.01 | 922 | 0.941 | -0.061 |
| LN | TTAAAC | 1059.92 | 965 | 0.910 | -0.094 |
| LN | CTTAAT | 1649.95 | 1441 | 0.873 | -0.135 |
| LN | TTGAAC | 1780.58 | 1541 | 0.865 | -0.145 |
| LN | CTGAAC | 5476.68 | 4308 | 0.787 | -0.240 |
| LN | CTGAAT | 4972.58 | 3413 | 0.686 | -0.376 |
| LN | CTTAAC | 1817.22 | 891 | 0.490 | -0.713 |
| LP | CTTCCT | 1728.14 | 2795 | 1.617 | 0.481 |
| LP | CTTCCA | 1667.88 | 2369 | 1.420 | 0.351 |
| LP | CTGCCC | 5815.10 | 7856 | 1.351 | 0.301 |
| LP | TTACCT | 1007.96 | 1244 | 1.234 | 0.210 |
| LP | CTGCCG | 2107.02 | 2489 | 1.181 | 0.167 |
| LP | TTACCA | 972.81 | 1140 | 1.172 | 0.159 |
| LP | CTCCCG | 1013.90 | 1184 | 1.168 | 0.155 |
| LP | TTGCCA | 1634.25 | 1897 | 1.161 | 0.149 |
| LP | CTACCT | 931.97 | 1045 | 1.121 | 0.114 |
| LP | TTGCCT | 1693.30 | 1800 | 1.063 | 0.061 |
| LP | CTTCCC | 1929.51 | 1889 | 0.979 | -0.021 |
| LP | CTACCA | 899.47 | 850 | 0.945 | -0.057 |
| LP | CTCCCA | 2418.82 | 2126 | 0.879 | -0.129 |
| LP | CTGCCT | 5208.23 | 4563 | 0.876 | -0.132 |
| LP | CTCCCT | 2506.21 | 2192 | 0.875 | -0.134 |
| LP | CTACCC | 1040.57 | 888 | 0.853 | -0.159 |
| LP | CTCCCC | 2798.25 | 2369 | 0.847 | -0.167 |
| LP | TTGCCC | 1890.60 | 1560 | 0.825 | -0.192 |
| LP | TTGCCG | 685.03 | 478 | 0.698 | -0.360 |
| LP | CTGCCA | 5026.60 | 3348 | 0.666 | -0.406 |
| LP | CTTCCG | 699.13 | 451 | 0.645 | -0.438 |
| LP | TTACCC | 1125.42 | 666 | 0.592 | -0.525 |
| LP | CTACCG | 377.04 | 211 | 0.560 | -0.580 |
| LP | TTACCG | 407.78 | 175 | 0.429 | -0.846 |
| LQ | TTACAA | 864.28 | 1290 | 1.493 | 0.401 |
| LQ | CTACAA | 799.12 | 1188 | 1.487 | 0.397 |
| LQ | CTTCAA | 1481.79 | 2098 | 1.416 | 0.348 |
| LQ | CTACAG | 2231.48 | 2674 | 1.198 | 0.181 |
| LQ | CTGCAG | 12470.36 | 14508 | 1.163 | 0.151 |
| LQ | CTTCAG | 4137.79 | 4363 | 1.054 | 0.053 |
| LQ | TTGCAA | 1451.91 | 1467 | 1.010 | 0.010 |
| LQ | CTCCAG | 6000.78 | 5430 | 0.905 | -0.100 |
| LQ | TTACAG | 2413.43 | 2107 | 0.873 | -0.136 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| LQ | TTGCAG | 4054.36 | 3177 | 0.784 | -0.244 |
| LQ | CTCCAA | 2148.94 | 1524 | 0.709 | -0.344 |
| LQ | CTGCAA | 4465.77 | 2694 | 0.603 | -0.505 |
| LR | CTTCGA | 661.43 | 1365 | 2.064 | 0.725 |
| LR | CTTCGT | 477.64 | 784 | 1.641 | 0.496 |
| LR | CTGCGG | 3677.31 | 5467 | 1.487 | 0.397 |
| LR | TTAAGA | 717.74 | 1026 | 1.429 | 0.357 |
| LR | CTGCGC | 3362.26 | 4574 | 1.360 | 0.308 |
| LR | CTCCGA | 959.23 | 1289 | 1.344 | 0.295 |
| LR | CTCCGG | 1769.53 | 2229 | 1.260 | 0.231 |
| LR | CTAAGA | 663.63 | 821 | 1.237 | 0.213 |
| LR | CTCAGG | 1752.00 | 2047 | 1.168 | 0.156 |
| LR | CTTCGG | 1220.17 | 1415 | 1.160 | 0.148 |
| LR | CTCCGT | 692.69 | 771 | 1.113 | 0.107 |
| LR | TTACGA | 385.79 | 427 | 1.107 | 0.101 |
| LR | CTAAGG | 651.51 | 721 | 1.107 | 0.101 |
| LR | CTCCGC | 1617.93 | 1790 | 1.106 | 0.101 |
| LR | TTGAGA | 1205.75 | 1290 | 1.070 | 0.068 |
| LR | CTACGT | 257.59 | 275 | 1.068 | 0.065 |
| LR | CTACGA | 356.70 | 378 | 1.060 | 0.058 |
| LR | CTGAGG | 3640.88 | 3637 | 0.999 | -0.001 |
| LR | TTAAGG | 704.63 | 678 | 0.962 | -0.039 |
| LR | TTACGT | 278.59 | 264 | 0.948 | -0.054 |
| LR | CTGCGT | 1439.50 | 1363 | 0.947 | -0.055 |
| LR | TTGAGG | 1183.72 | 1080 | 0.912 | -0.092 |
| LR | CTACGG | 658.03 | 577 | 0.877 | -0.131 |
| LR | CTCAGA | 1784.60 | 1469 | 0.823 | -0.195 |
| LR | CTTCGC | 1115.63 | 819 | 0.734 | -0.309 |
| LR | CTACGC | 601.65 | 438 | 0.728 | -0.317 |
| LR | CTGCGA | 1993.40 | 1399 | 0.702 | -0.354 |
| LR | TTGCGT | 468.01 | 321 | 0.686 | -0.377 |
| LR | CTGAGA | 3708.63 | 2486 | 0.670 | -0.400 |
| LR | TTGCGG | 1195.56 | 772 | 0.646 | -0.437 |
| LR | TTGCGA | 648.09 | 418 | 0.645 | -0.439 |
| LR | CTTAGA | 1230.56 | 694 | 0.564 | -0.573 |
| LR | TTACGG | 711.68 | 383 | 0.538 | -0.620 |
| LR | TTGCGC | 1093.14 | 542 | 0.496 | -0.702 |
| LR | CTTAGG | 1208.08 | 503 | 0.416 | -0.876 |
| LR | TTACGC | 650.71 | 232 | 0.357 | -1.031 |
| LS | CTCAGC | 2740.30 | 5167 | 1.886 | 0.634 |
| LS | CTTTCT | 1450.83 | 2502 | 1.725 | 0.545 |
| LS | CTCTCC | 2418.72 | 4070 | 1.683 | 0.520 |
| LS | CTCTCG | 639.61 | 1016 | 1.588 | 0.463 |
| LS | CTCAGT | 1728.87 | 2589 | 1.498 | 0.404 |
| LS | TTATCA | 684.12 | 963 | 1.408 | 0.342 |
| LS | TTATCT | 846.22 | 1175 | 1.389 | 0.328 |
| LS | CTTTCA | 1172.91 | 1626 | 1.386 | 0.327 |
| LS | TTAAGT | 695.33 | 886 | 1.274 | 0.242 |
| LS | CTCTCT | 2104.05 | 2553 | 1.213 | 0.193 |
| LS | CTAAGT | 642.91 | 770 | 1.198 | 0.180 |
| LS | CTCTCA | 1701.00 | 2003 | 1.178 | 0.163 |
| LS | CTTTCC | 1667.81 | 1819 | 1.091 | 0.087 |
| LS | TTGTCA | 1149.26 | 1210 | 1.053 | 0.052 |
| LS | CTGTCG | 1329.18 | 1392 | 1.047 | 0.046 |
| LS | TTGTCT | 1421.58 | 1461 | 1.028 | 0.027 |
| LS | CTGAGC | 5694.68 | 5805 | 1.019 | 0.019 |
| LS | CTGTCC | 5026.41 | 4628 | 0.921 | -0.083 |
| LS | TTGAGT | 1168.09 | 1035 | 0.886 | -0.121 |
| LS | TTGTCC | 1634.18 | 1334 | 0.816 | -0.203 |
| LS | CTATCA | 632.54 | 512 | 0.809 | -0.211 |
| LS | CTAAGC | 1019.02 | 791 | 0.776 | -0.253 |
| LS | TTATCC | 972.78 | 727 | 0.747 | -0.291 |
| LS | CTGAGT | 3592.81 | 2665 | 0.742 | -0.299 |
| LS | CTTAGT | 1192.13 | 856 | 0.718 | -0.331 |
| LS | CTATCT | 782.42 | 557 | 0.712 | -0.340 |
| LS | CTGTCT | 4372.48 | 2950 | 0.675 | -0.394 |
| LS | CTTTCG | 441.04 | 291 | 0.660 | -0.416 |
| LS | TTGTCG | 432.14 | 278 | 0.643 | -0.441 |
| LS | CTGTCA | 3534.89 | 2228 | 0.630 | -0.462 |
| LS | TTGAGC | 1851.45 | 1128 | 0.609 | -0.496 |
| LS | CTATCC | 899.44 | 541 | 0.601 | -0.508 |
| LS | TTATCG | 257.24 | 152 | 0.591 | -0.526 |
| LS | TTAAGC | 1102.11 | 551 | 0.500 | -0.693 |
| LS | CTATCG | 237.85 | 102 | 0.429 | -0.847 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| LS | CTTAGC | 1889.55 | 793 | 0.420 | -0.868 |
| LT | CTCACC | 2534.19 | 4959 | 1.957 | 0.671 |
| LT | CTCACG | 832.47 | 1510 | 1.814 | 0.595 |
| LT | TTAACA | 825.09 | 1163 | 1.410 | 0.343 |
| LT | CTCACT | 1814.22 | 2521 | 1.390 | 0.329 |
| LT | TTAACT | 729.65 | 969 | 1.328 | 0.284 |
| LT | CTAACT | 674.64 | 817 | 1.211 | 0.191 |
| LT | CTAACA | 762.89 | 898 | 1.177 | 0.163 |
| LT | CTCACA | 2051.52 | 2374 | 1.157 | 0.146 |
| LT | CTGACG | 1729.98 | 1795 | 1.038 | 0.037 |
| LT | TTGACT | 1225.76 | 1259 | 1.027 | 0.027 |
| LT | TTGACA | 1386.09 | 1401 | 1.011 | 0.011 |
| LT | CTTACT | 1250.98 | 1259 | 1.006 | 0.006 |
| LT | CTGACC | 5266.36 | 5160 | 0.980 | -0.020 |
| LT | CTTACA | 1414.61 | 1109 | 0.784 | -0.243 |
| LT | CTGACT | 3770.17 | 2808 | 0.745 | -0.295 |
| LT | TTGACC | 1712.20 | 1235 | 0.721 | -0.327 |
| LT | CTAACC | 942.38 | 678 | 0.719 | -0.329 |
| LT | TTGACG | 562.45 | 399 | 0.709 | -0.343 |
| LT | CTGACA | 4263.32 | 3003 | 0.704 | -0.350 |
| LT | CTAACG | 309.57 | 215 | 0.695 | -0.365 |
| LT | TTAACC | 1019.22 | 687 | 0.674 | -0.394 |
| LT | CTTACC | 1747.43 | 1104 | 0.632 | -0.459 |
| LT | TTAACG | 334.81 | 164 | 0.490 | -0.714 |
| LT | CTTACG | 574.02 | 247 | 0.430 | -0.843 |
| LV | CTTGTT | 1029.60 | 1741 | 1.691 | 0.525 |
| LV | TTAGTA | 389.95 | 602 | 1.544 | 0.434 |
| LV | TTGGTA | 655.07 | 980 | 1.496 | 0.403 |
| LV | CTTGTA | 668.56 | 993 | 1.485 | 0.396 |
| LV | CTGGTG | 7859.41 | 11424 | 1.454 | 0.374 |
| LV | CTAGTA | 360.55 | 519 | 1.439 | 0.364 |
| LV | TTGGTT | 1008.84 | 1427 | 1.414 | 0.347 |
| LV | CTTGTC | 1318.22 | 1541 | 1.169 | 0.156 |
| LV | TTAGTT | 600.53 | 690 | 1.149 | 0.139 |
| LV | CTGGTC | 3972.81 | 4541 | 1.143 | 0.134 |
| LV | TTGGTG | 2555.25 | 2882 | 1.128 | 0.120 |
| LV | CTAGTT | 555.26 | 580 | 1.045 | 0.044 |
| LV | TTGGTC | 1291.64 | 1345 | 1.041 | 0.040 |
| LV | CTTGTG | 2607.83 | 2540 | 0.974 | -0.026 |
| LV | CTAGTG | 1406.38 | 1272 | 0.904 | -0.100 |
| LV | CTGGTA | 2014.87 | 1720 | 0.854 | -0.158 |
| LV | CTGGTT | 3102.98 | 2576 | 0.830 | -0.186 |
| LV | CTAGTC | 710.90 | 551 | 0.775 | -0.255 |
| LV | TTAGTG | 1521.06 | 947 | 0.623 | -0.474 |
| LV | TTAGTC | 768.87 | 416 | 0.541 | -0.614 |
| LV | CTCGTC | 1911.73 | 1013 | 0.530 | -0.635 |
| LV | CTCGTG | 3781.97 | 1691 | 0.447 | -0.805 |
| LV | CTCGTT | 1493.16 | 373 | 0.250 | -1.387 |
| LV | CTCGTA | 969.56 | 191 | 0.197 | -1.625 |
| LW | CTCTGG | 1742.64 | 2796 | 1.604 | 0.473 |
| LW | CTGTGG | 3621.43 | 3365 | 0.929 | -0.073 |
| LW | CTTTGG | 1201.63 | 1018 | 0.847 | -0.166 |
| LW | CTATGG | 648.03 | 501 | 0.773 | -0.257 |
| LW | TTATGG | 700.87 | 535 | 0.763 | -0.270 |
| LW | TTGTGG | 1177.40 | 877 | 0.745 | -0.295 |
| LY | CTCTAC | 2082.09 | 4204 | 2.019 | 0.703 |
| LY | TTATAT | 680.44 | 1022 | 1.502 | 0.407 |
| LY | CTCTAT | 1691.85 | 2487 | 1.470 | 0.385 |
| LY | CTTTAT | 1166.60 | 1591 | 1.364 | 0.310 |
| LY | CTATAT | 629.14 | 596 | 0.947 | -0.054 |
| LY | TTGTAT | 1143.08 | 1063 | 0.930 | -0.073 |
| LY | CTGTAC | 4326.84 | 3390 | 0.783 | -0.244 |
| LY | CTTTAC | 1435.69 | 1069 | 0.745 | -0.295 |
| LY | TTGTAC | 1406.74 | 1006 | 0.715 | -0.335 |
| LY | TTATAC | 837.39 | 579 | 0.691 | -0.369 |
| LY | CTGTAT | 3515.88 | 2202 | 0.626 | -0.468 |
| LY | CTATAC | 774.26 | 481 | 0.621 | -0.476 |
| MA | ATGGCG | 1645.46 | 2370 | 1.440 | 0.365 |
| MA | ATGGCA | 3503.58 | 3580 | 1.022 | 0.022 |
| MA | ATGGCT | 4002.27 | 4003 | 1.000 | 0.000 |
| MA | ATGGCC | 6085.70 | 5284 | 0.868 | -0.141 |
| MC | ATGTGT | 1386.67 | 1448 | 1.044 | 0.043 |
| MC | ATGTGC | 1646.33 | 1585 | 0.963 | -0.038 |
| MD | ATGGAT | 4467.48 | 4634 | 1.037 | 0.037 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| MD | ATGGAC | 5046.52 | 4880 | 0.967 | -0.034 |
| ME | ATGGAG | 8054.28 | 8223 | 1.021 | 0.021 |
| ME | ATGGAA | 6022.72 | 5854 | 0.972 | -0.028 |
| MF | ATGTTT | 2565.53 | 2833 | 1.104 | 0.099 |
| MF | ATGTTC | 2936.47 | 2669 | 0.909 | -0.096 |
| MG | ATGGGC | 3467.73 | 3533 | 1.019 | 0.019 |
| MG | ATGGGT | 1655.83 | 1675 | 1.012 | 0.012 |
| MG | ATGGGA | 2557.59 | 2526 | 0.988 | -0.012 |
| MG | ATGGGG | 2496.85 | 2444 | 0.979 | -0.021 |
| MH | ATGCAT | 1465.33 | 1478 | 1.009 | 0.009 |
| MH | ATGCAC | 2020.67 | 2008 | 0.994 | -0.006 |
| MI | ATGATT | 2305.40 | 2382 | 1.033 | 0.033 |
| MI | ATGATA | 1060.28 | 1094 | 1.032 | 0.031 |
| MI | ATGATC | 2915.32 | 2805 | 0.962 | -0.039 |
| MK | ATGAAG | 6107.32 | 6423 | 1.052 | 0.050 |
| MK | ATGAAA | 4715.68 | 4400 | 0.933 | -0.069 |
| ML | ATGCTG | 5938.40 | 6536 | 1.101 | 0.096 |
| ML | ATGCTA | 1062.63 | 1122 | 1.056 | 0.054 |
| ML | ATGTTG | 1930.69 | 1922 | 0.995 | -0.005 |
| ML | ATGTTA | 1149.28 | 1134 | 0.987 | -0.013 |
| ML | ATGCTT | 1970.42 | 1887 | 0.958 | -0.043 |
| ML | ATGCTC | 2857.58 | 2308 | 0.808 | -0.214 |
| MM | ATGATG | 3925.00 | 3925 | 1.000 | 0.000 |
| MN | ATGAAT | 3249.30 | 3301 | 1.016 | 0.016 |
| MN | ATGAAC | 3578.70 | 3527 | 0.986 | -0.015 |
| MP | ATGCCC | 2676.16 | 2752 | 1.028 | 0.028 |
| MP | ATGCCA | 2313.29 | 2313 | 1.000 | 0.000 |
| MP | ATGCCT | 2396.87 | 2372 | 0.990 | -0.010 |
| MP | ATGCCG | 969.67 | 919 | 0.948 | -0.054 |
| MQ | ATGCAG | 5141.70 | 5165 | 1.005 | 0.005 |
| MQ | ATGCAA | 1841.30 | 1818 | 0.987 | -0.013 |
| MR | ATGAGG | 1626.37 | 2127 | 1.308 | 0.268 |
| MR | ATGAGA | 1656.63 | 1974 | 1.192 | 0.175 |
| MR | ATGCGG | 1642.64 | 1513 | 0.921 | -0.082 |
| MR | ATGCGT | 643.02 | 531 | 0.826 | -0.191 |
| MR | ATGCGA | 890.44 | 684 | 0.768 | -0.264 |
| MR | ATGCGC | 1501.91 | 1132 | 0.754 | -0.283 |
| MS | ATGTCG | 666.33 | 809 | 1.214 | 0.194 |
| MS | ATGTCT | 2191.95 | 2338 | 1.067 | 0.065 |
| MS | ATGTCA | 1772.07 | 1781 | 1.005 | 0.005 |
| MS | ATGTCC | 2519.77 | 2493 | 0.989 | -0.011 |
| MS | ATGAGT | 1801.10 | 1770 | 0.983 | -0.017 |
| MS | ATGAGC | 2854.78 | 2615 | 0.916 | -0.088 |
| MT | ATGACT | 2098.83 | 2195 | 1.046 | 0.045 |
| MT | ATGACC | 2931.75 | 2927 | 0.998 | -0.002 |
| MT | ATGACA | 2373.36 | 2337 | 0.985 | -0.015 |
| MT | ATGACG | 963.07 | 908 | 0.943 | -0.059 |
| MV | ATGGTG | 4813.46 | 5122 | 1.064 | 0.062 |
| MV | ATGGTT | 1900.41 | 1915 | 1.008 | 0.008 |
| MV | ATGGTA | 1234.00 | 1191 | 0.965 | -0.035 |
| MV | ATGGTC | 2433.13 | 2153 | 0.885 | -0.122 |
| MW | ATGTGG | 1876.00 | 1876 | 1.000 | 0.000 |
| MY | ATGTAC | 2354.66 | 2363 | 1.004 | 0.004 |
| MY | ATGTAT | 1913.34 | 1905 | 0.996 | -0.004 |
| NA | AATGCA | 1705.68 | 3344 | 1.961 | 0.673 |
| NA | AATGCT | 1948.47 | 3458 | 1.775 | 0.574 |
| NA | AATGCC | 2962.77 | 4259 | 1.438 | 0.363 |
| NA | AATGCG | 801.08 | 624 | 0.779 | -0.250 |
| NA | AACGCG | 882.29 | 661 | 0.749 | -0.289 |
| NA | AACGCC | 3263.12 | 1899 | 0.582 | -0.541 |
| NA | AACGCA | 1878.60 | 700 | 0.373 | -0.987 |
| NA | AACGCT | 2146.00 | 643 | 0.300 | -1.205 |
| NC | AACTGC | 1868.57 | 2826 | 1.512 | 0.414 |
| NC | AACTGT | 1573.86 | 2016 | 1.281 | 0.248 |
| NC | AATTGT | 1429.00 | 935 | 0.654 | -0.424 |
| NC | AATTGC | 1696.57 | 791 | 0.466 | -0.763 |
| ND | AATGAT | 2555.01 | 4420 | 1.730 | 0.548 |
| ND | AATGAC | 2886.18 | 4521 | 1.566 | 0.449 |
| ND | AACGAC | 3178.77 | 1654 | 0.520 | -0.653 |
| ND | AACGAT | 2814.03 | 839 | 0.298 | -1.210 |
| NE | AATGAA | 3381.19 | 7367 | 2.179 | 0.779 |
| NE | AATGAG | 4521.72 | 5796 | 1.282 | 0.248 |
| NE | AACGAG | 4980.12 | 2476 | 0.497 | -0.699 |
| NE | AACGAA | 3723.97 | 968 | 0.260 | -1.347 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| NF | AACTTC | 3150.86 | 4259 | 1.352 | 0.301 |
| NF | AACTTT | 2752.85 | 2846 | 1.034 | 0.033 |
| NF | AATTTT | 2499.46 | 2350 | 0.940 | -0.062 |
| NF | AATTTC | 2860.84 | 1809 | 0.632 | -0.458 |
| NG | AATGGA | 2235.93 | 4484 | 2.005 | 0.696 |
| NG | AATGGT | 1447.59 | 2430 | 1.679 | 0.518 |
| NG | AATGGG | 2182.83 | 3202 | 1.467 | 0.383 |
| NG | AATGGC | 3031.62 | 4001 | 1.320 | 0.277 |
| NG | AACGGG | 2404.12 | 1508 | 0.627 | -0.466 |
| NG | AACGGC | 3338.95 | 1752 | 0.525 | -0.645 |
| NG | AACGGA | 2462.61 | 804 | 0.326 | -1.119 |
| NG | AACGGT | 1594.34 | 517 | 0.324 | -1.126 |
| NH | AACCAC | 2167.68 | 2776 | 1.281 | 0.247 |
| NH | AACCAT | 1571.93 | 1639 | 1.043 | 0.042 |
| NH | AATCAT | 1427.24 | 1456 | 1.020 | 0.020 |
| NH | AATCAC | 1968.15 | 1264 | 0.642 | -0.443 |
| NI | AACATC | 3876.27 | 5487 | 1.416 | 0.348 |
| NI | AACATT | 3065.31 | 3184 | 1.039 | 0.038 |
| NI | AATATA | 1280.01 | 1309 | 1.023 | 0.022 |
| NI | AACATA | 1409.77 | 1384 | 0.982 | -0.018 |
| NI | AATATT | 2783.16 | 2725 | 0.979 | -0.021 |
| NI | AATATC | 3519.48 | 1845 | 0.524 | -0.646 |
| NK | AACAAG | 4824.98 | 5918 | 1.227 | 0.204 |
| NK | AACAAA | 3725.54 | 4221 | 1.133 | 0.125 |
| NK | AATAAA | 3382.62 | 3607 | 1.066 | 0.064 |
| NK | AATAAG | 4380.86 | 2568 | 0.586 | -0.534 |
| NL | AATTTA | 1025.31 | 1571 | 1.532 | 0.427 |
| NL | AACCTC | 2807.78 | 3954 | 1.408 | 0.342 |
| NL | AACTTG | 1897.05 | 2429 | 1.280 | 0.247 |
| NL | AACCTG | 5834.92 | 6690 | 1.147 | 0.137 |
| NL | AATTTG | 1722.43 | 1947 | 1.130 | 0.123 |
| NL | AATCTT | 1757.88 | 1943 | 1.105 | 0.100 |
| NL | AACCTA | 1044.12 | 1135 | 1.087 | 0.083 |
| NL | AACCTT | 1936.08 | 2021 | 1.044 | 0.043 |
| NL | AACTTA | 1129.25 | 1129 | 1.000 | 0.000 |
| NL | AATCTA | 948.01 | 893 | 0.942 | -0.060 |
| NL | AATCTC | 2549.34 | 1713 | 0.672 | -0.398 |
| NL | AATCTG | 5297.84 | 2525 | 0.477 | -0.741 |
| NM | AACATG | 3351.76 | 4374 | 1.305 | 0.266 |
| NM | AATATG | 3043.24 | 2021 | 0.664 | -0.409 |
| NN | AACAAC | 3150.02 | 4430 | 1.406 | 0.341 |
| NN | AACAAT | 2860.08 | 2830 | 0.989 | -0.011 |
| NN | AATAAT | 2596.82 | 2424 | 0.933 | -0.069 |
| NN | AATAAC | 2860.08 | 1783 | 0.623 | -0.473 |
| NP | AACCCC | 2770.02 | 3474 | 1.254 | 0.226 |
| NP | AATCCA | 2174.02 | 2380 | 1.095 | 0.091 |
| NP | AACCCA | 2394.42 | 2612 | 1.091 | 0.087 |
| NP | AATCCT | 2252.58 | 2414 | 1.072 | 0.069 |
| NP | AACCCG | 1003.68 | 1048 | 1.044 | 0.043 |
| NP | AACCCT | 2480.94 | 2578 | 1.039 | 0.038 |
| NP | AATCCC | 2515.05 | 1641 | 0.652 | -0.427 |
| NP | AATCCG | 911.29 | 355 | 0.390 | -0.943 |
| NQ | AATCAA | 1516.57 | 1905 | 1.256 | 0.228 |
| NQ | AACCAA | 1670.31 | 1955 | 1.170 | 0.157 |
| NQ | AACCAG | 4664.22 | 5409 | 1.160 | 0.148 |
| NQ | AATCAG | 4234.90 | 2817 | 0.665 | -0.408 |
| NR | AACAGA | 1511.98 | 2383 | 1.576 | 0.455 |
| NR | AACCGC | 1370.77 | 1966 | 1.434 | 0.361 |
| NR | AACAGG | 1484.36 | 1903 | 1.282 | 0.248 |
| NR | AACCGA | 812.69 | 998 | 1.228 | 0.205 |
| NR | AACCGT | 586.88 | 706 | 1.203 | 0.185 |
| NR | AACCGG | 1499.21 | 1779 | 1.187 | 0.171 |
| NR | AATCGA | 737.89 | 687 | 0.931 | -0.071 |
| NR | AATCGT | 532.86 | 486 | 0.912 | -0.092 |
| NR | AATAGA | 1372.81 | 1117 | 0.814 | -0.206 |
| NR | AATCGC | 1244.60 | 602 | 0.484 | -0.726 |
| NR | AATAGG | 1347.73 | 643 | 0.477 | -0.740 |
| NR | AATCGG | 1361.22 | 593 | 0.436 | -0.831 |
| NS | AACAGC | 2917.73 | 4490 | 1.539 | 0.431 |
| NS | AACAGT | 1840.81 | 2414 | 1.311 | 0.271 |
| NS | AACTCG | 681.02 | 821 | 1.206 | 0.187 |
| NS | AATTCA | 1644.43 | 1970 | 1.198 | 0.181 |
| NS | AATTCT | 2034.08 | 2383 | 1.172 | 0.158 |
| NS | AACTCC | 2575.33 | 2818 | 1.094 | 0.090 |

SUPPLEMENTAL TABLE 1-continued

Expected and Observed Codon Pair Frequencies and
Codon Pair Scores for 14,795 Human Genes

| amino acid pair | codon pair | expected | observed | observed / expected | CPS |
|---|---|---|---|---|---|
| NS | AACTCA | 1811.14 | 1783 | 0.984 | -0.016 |
| NS | AACTCT | 2240.29 | 1981 | 0.884 | -0.123 |
| NS | AATAGT | 1671.38 | 1193 | 0.714 | -0.337 |
| NS | AATTCC | 2338.29 | 1655 | 0.708 | -0.346 |
| NS | AATAGC | 2649.17 | 1273 | 0.481 | -0.733 |
| NS | AATTCG | 618.33 | 241 | 0.390 | -0.942 |
| NT | AACACG | 860.22 | 1238 | 1.439 | 0.364 |
| NT | AACACA | 2119.90 | 2783 | 1.313 | 0.272 |
| NT | AACACC | 2618.65 | 3278 | 1.252 | 0.225 |
| NT | AACACT | 1874.68 | 2099 | 1.120 | 0.113 |
| NT | AATACT | 1702.13 | 1540 | 0.905 | -0.100 |
| NT | AATACA | 1924.77 | 1692 | 0.879 | -0.129 |
| NT | AATACC | 2377.62 | 1312 | 0.552 | -0.595 |
| NT | AATACG | 781.04 | 317 | 0.406 | -0.902 |
| NV | AATGTA | 927.15 | 1710 | 1.844 | 0.612 |
| NV | AATGTT | 1427.85 | 2573 | 1.802 | 0.589 |
| NV | AATGTC | 1828.10 | 2877 | 1.574 | 0.453 |
| NV | AATGTG | 3616.54 | 4314 | 1.193 | 0.176 |
| NV | AACGTG | 3983.18 | 2772 | 0.696 | -0.363 |
| NV | AACGTC | 2013.43 | 1341 | 0.666 | -0.406 |
| NV | AACGTT | 1572.60 | 509 | 0.324 | -1.128 |
| NV | AACGTA | 1021.14 | 294 | 0.288 | -1.245 |
| NW | AACTGG | 1808.22 | 2595 | 1.435 | 0.361 |
| NW | AATTGG | 1641.78 | 855 | 0.521 | -0.652 |
| NY | AACTAC | 2506.72 | 3191 | 1.273 | 0.241 |
| NY | AACTAT | 2036.89 | 2145 | 1.053 | 0.052 |
| NY | AATTAT | 1849.41 | 1795 | 0.971 | -0.030 |
| NY | AATTAC | 2275.98 | 1538 | 0.676 | -0.392 |
| PA | CCGGCG | 470.57 | 1166 | 2.478 | 0.907 |
| PA | CCGGCC | 1740.39 | 2666 | 1.532 | 0.426 |
| PA | CCAGCA | 2390.31 | 3368 | 1.409 | 0.343 |
| PA | CCAGCT | 2730.54 | 3622 | 1.326 | 0.283 |
| PA | CCTGCT | 2829.20 | 3750 | 1.325 | 0.282 |
| PA | CCTGCA | 2476.67 | 3178 | 1.283 | 0.249 |
| PA | CCAGCC | 4151.96 | 4942 | 1.190 | 0.174 |
| PA | CCCGCG | 1298.71 | 1528 | 1.177 | 0.163 |
| PA | CCTGCC | 4301.98 | 5000 | 1.162 | 0.150 |
| PA | CCAGCG | 1122.61 | 1078 | 0.960 | -0.041 |
| PA | CCTGCG | 1163.17 | 1105 | 0.950 | -0.051 |
| PA | CCGGCT | 1144.57 | 1013 | 0.885 | -0.122 |
| PA | CCGGCA | 1001.95 | 777 | 0.775 | -0.254 |
| PA | CCCGCC | 4803.25 | 2690 | 0.560 | -0.580 |
| PA | CCCGCA | 2765.26 | 846 | 0.306 | -1.184 |
| PA | CCCGCT | 3158.86 | 821 | 0.260 | -1.347 |
| PC | CCCTGC | 1550.51 | 2870 | 1.851 | 0.616 |
| PC | CCCTGT | 1305.97 | 1577 | 1.208 | 0.189 |
| PC | CCGTGC | 561.80 | 630 | 1.121 | 0.115 |
| PC | CCTTGT | 1169.67 | 1001 | 0.856 | -0.156 |
| PC | CCATGT | 1128.89 | 831 | 0.736 | -0.306 |
| PC | CCGTGT | 473.20 | 340 | 0.719 | -0.331 |
| PC | CCTTGC | 1388.69 | 937 | 0.675 | -0.393 |
| PC | CCATGC | 1340.27 | 733 | 0.547 | -0.603 |
| PD | CCAGAT | 2721.60 | 4165 | 1.530 | 0.425 |
| PD | CCTGAT | 2819.94 | 3781 | 1.341 | 0.293 |
| PD | CCGGAC | 1288.69 | 1659 | 1.287 | 0.253 |
| PD | CCAGAC | 3074.36 | 3766 | 1.225 | 0.203 |
| PD | CCTGAC | 3185.44 | 3646 | 1.145 | 0.135 |
| PD | CCGGAT | 1140.82 | 895 | 0.785 | -0.243 |
| PD | CCCGAC | 3556.62 | 2215 | 0.623 | -0.474 |
| PD | CCCGAT | 3148.53 | 809 | 0.257 | -1.359 |
| PE | CCAGAA | 3999.86 | 5699 | 1.425 | 0.354 |
| PE | CCTGAG | 5542.36 | 7122 | 1.285 | 0.251 |
| PE | CCGGAG | 2242.20 | 2870 | 1.280 | 0.247 |
| PE | CCAGAG | 5349.08 | 6777 | 1.267 | 0.237 |
| PE | CCTGAA | 4144.39 | 5108 | 1.233 | 0.209 |
| PE | CCCGAG | 6188.17 | 4149 | 0.670 | -0.400 |
| PE | CCGGAA | 1676.64 | 1032 | 0.616 | -0.485 |
| PE | CCCGAA | 4627.30 | 1013 | 0.219 | -1.519 |
| PF | CCCTTC | 2555.92 | 4301 | 1.683 | 0.520 |
| PF | CCATTT | 1930.27 | 2057 | 1.066 | 0.064 |
| PF | CCTTTT | 2000.01 | 1967 | 0.983 | -0.017 |
| PF | CCCTTT | 2233.06 | 2159 | 0.967 | -0.034 |
| PF | CCTTTC | 2289.18 | 2078 | 0.908 | -0.097 |
| PF | CCGTTC | 926.10 | 662 | 0.715 | -0.336 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| PF | CCATTC | 2209.35 | 1290 | 0.584 | -0.538 |
| PF | CCGTTT | 809.12 | 439 | 0.543 | -0.611 |
| PG | CCTGGG | 2918.52 | 4310 | 1.477 | 0.390 |
| PG | CCTGGA | 2989.52 | 4317 | 1.444 | 0.367 |
| PG | CCGGGC | 1639.82 | 2353 | 1.435 | 0.361 |
| PG | CCGGGG | 1180.71 | 1657 | 1.403 | 0.339 |
| PG | CCTGGT | 1935.48 | 2673 | 1.381 | 0.323 |
| PG | CCAGGA | 2885.27 | 3897 | 1.351 | 0.301 |
| PG | CCAGGG | 2816.75 | 3472 | 1.233 | 0.209 |
| PG | CCAGGT | 1867.98 | 2259 | 1.209 | 0.190 |
| PG | CCTGGC | 4053.37 | 4622 | 1.140 | 0.131 |
| PG | CCAGGC | 3912.02 | 4106 | 1.050 | 0.048 |
| PG | CCGGGT | 783.01 | 661 | 0.844 | -0.169 |
| PG | CCGGGA | 1209.43 | 963 | 0.796 | -0.228 |
| PG | CCCGGG | 3258.60 | 2136 | 0.655 | -0.422 |
| PG | CCCGGC | 4525.68 | 2555 | 0.565 | -0.572 |
| PG | CCCGGA | 3337.86 | 968 | 0.290 | -1.238 |
| PG | CCCGGT | 2161.00 | 526 | 0.243 | -1.413 |
| PH | CCGCAC | 725.13 | 972 | 1.340 | 0.293 |
| PH | CCCCAC | 2001.25 | 2505 | 1.252 | 0.225 |
| PH | CCTCAT | 1299.79 | 1592 | 1.225 | 0.203 |
| PH | CCACAT | 1254.46 | 1222 | 0.974 | -0.026 |
| PH | CCCCAT | 1451.24 | 1303 | 0.898 | -0.108 |
| PH | CCTCAC | 1792.40 | 1531 | 0.854 | -0.158 |
| PH | CCACAC | 1729.89 | 1366 | 0.790 | -0.236 |
| PH | CCGCAT | 525.84 | 289 | 0.550 | -0.599 |
| PI | CCCATC | 2119.04 | 4651 | 2.195 | 0.786 |
| PI | CCCATT | 1675.71 | 2102 | 1.254 | 0.227 |
| PI | CCAATA | 666.18 | 819 | 1.229 | 0.207 |
| PI | CCCATA | 770.68 | 776 | 1.007 | 0.007 |
| PI | CCAATT | 1448.49 | 1386 | 0.957 | -0.044 |
| PI | CCTATA | 690.25 | 603 | 0.874 | -0.135 |
| PI | CCTATT | 1500.83 | 1266 | 0.844 | -0.170 |
| PI | CCAATC | 1831.71 | 939 | 0.513 | -0.668 |
| PI | CCTATC | 1897.89 | 957 | 0.504 | -0.685 |
| PI | CCGATT | 607.17 | 299 | 0.492 | -0.708 |
| PI | CCGATC | 767.80 | 342 | 0.445 | -0.809 |
| PI | CCGATA | 279.24 | 115 | 0.412 | -0.887 |
| PK | CCCAAG | 3738.47 | 6383 | 1.707 | 0.535 |
| PK | CCCAAA | 2886.60 | 3787 | 1.312 | 0.271 |
| PK | CCAAAA | 2495.20 | 2489 | 0.998 | -0.002 |
| PK | CCAAAG | 3231.55 | 3127 | 0.968 | -0.033 |
| PK | CCTAAA | 2585.35 | 1840 | 0.712 | -0.340 |
| PK | CCGAAG | 1354.58 | 940 | 0.694 | -0.365 |
| PK | CCTAAG | 3348.32 | 1660 | 0.496 | -0.702 |
| PK | CCGAAA | 1045.92 | 460 | 0.440 | -0.821 |
| PL | CCGCTG | 1824.84 | 3343 | 1.832 | 0.605 |
| PL | CCGCTC | 878.12 | 1254 | 1.428 | 0.356 |
| PL | CCTTTG | 1466.52 | 2054 | 1.401 | 0.337 |
| PL | CCTTTA | 872.97 | 1195 | 1.369 | 0.314 |
| PL | CCCTTG | 1637.40 | 2122 | 1.296 | 0.259 |
| PL | CCTCTT | 1496.70 | 1827 | 1.221 | 0.199 |
| PL | CCCCTG | 5036.31 | 5760 | 1.144 | 0.134 |
| PL | CCCCTC | 2423.49 | 2646 | 1.092 | 0.088 |
| PL | CCTCTA | 807.16 | 871 | 1.079 | 0.076 |
| PL | CCATTA | 842.53 | 826 | 0.980 | -0.020 |
| PL | CCACTT | 1444.51 | 1371 | 0.949 | -0.052 |
| PL | CCACTA | 779.01 | 729 | 0.936 | -0.066 |
| PL | CCTCTC | 2170.57 | 1934 | 0.891 | -0.115 |
| PL | CCTCTG | 4510.71 | 3745 | 0.830 | -0.186 |
| PL | CCATTG | 1415.38 | 1172 | 0.828 | -0.189 |
| PL | CCCCTT | 1671.10 | 1324 | 0.792 | -0.233 |
| PL | CCGCTA | 326.54 | 255 | 0.781 | -0.247 |
| PL | CCCCTA | 901.21 | 689 | 0.765 | -0.268 |
| PL | CCACTG | 4353.41 | 3218 | 0.739 | -0.302 |
| PL | CCCTTA | 974.69 | 709 | 0.727 | -0.318 |
| PL | CCACTC | 2094.88 | 1475 | 0.704 | -0.351 |
| PL | CCGTTG | 593.29 | 402 | 0.678 | -0.389 |
| PL | CCGCTT | 605.50 | 402 | 0.664 | -0.410 |
| PL | CCGTTA | 353.17 | 157 | 0.445 | -0.811 |
| PM | CCCATG | 2307.54 | 3923 | 1.700 | 0.531 |
| PM | CCAATG | 1994.65 | 1552 | 0.778 | -0.251 |
| PM | CCGATG | 836.10 | 520 | 0.622 | -0.475 |
| PM | CCTATG | 2066.72 | 1210 | 0.585 | -0.535 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| PN | CCCAAC | 2313.61 | 4255 | 1.839 | 0.609 |
| PN | CCAAAT | 1815.81 | 2453 | 1.351 | 0.301 |
| PN | CCCAAT | 2100.65 | 2296 | 1.093 | 0.089 |
| PN | CCAAAC | 1999.90 | 1735 | 0.868 | -0.142 |
| PN | CCTAAT | 1881.42 | 1342 | 0.713 | -0.338 |
| PN | CCTAAC | 2072.16 | 997 | 0.481 | -0.732 |
| PN | CCGAAT | 761.14 | 340 | 0.447 | -0.806 |
| PN | CCGAAC | 838.30 | 365 | 0.435 | -0.831 |
| PP | CCGCCG | 608.57 | 2335 | 3.837 | 1.345 |
| PP | CCGCCC | 1679.58 | 2697 | 1.606 | 0.474 |
| PP | CCCCCG | 1679.58 | 2420 | 1.441 | 0.365 |
| PP | CCTCCA | 3588.72 | 4314 | 1.202 | 0.184 |
| PP | CCTCCT | 3718.39 | 4305 | 1.158 | 0.146 |
| PP | CCACCA | 3463.58 | 3850 | 1.112 | 0.106 |
| PP | CCACCT | 3588.72 | 3798 | 1.058 | 0.057 |
| PP | CCCCCA | 4006.89 | 4095 | 1.022 | 0.022 |
| PP | CCACCC | 4006.89 | 3595 | 0.897 | -0.108 |
| PP | CCGCCA | 1451.84 | 1280 | 0.882 | -0.126 |
| PP | CCACCG | 1451.84 | 1252 | 0.862 | -0.148 |
| PP | CCGCCT | 1504.30 | 1286 | 0.855 | -0.157 |
| PP | CCTCCC | 4151.67 | 3338 | 0.804 | -0.218 |
| PP | CCTCCG | 1504.30 | 1152 | 0.766 | -0.267 |
| PP | CCCCCT | 4151.67 | 3160 | 0.761 | -0.273 |
| PP | CCCCCC | 4635.43 | 2315 | 0.499 | -0.694 |
| PQ | CCCCAG | 5063.98 | 6421 | 1.268 | 0.237 |
| PQ | CCGCAG | 1834.86 | 2187 | 1.192 | 0.176 |
| PQ | CCTCAA | 1624.21 | 1752 | 1.079 | 0.076 |
| PQ | CCTCAG | 4535.49 | 4221 | 0.931 | -0.072 |
| PQ | CCACAA | 1567.57 | 1405 | 0.896 | -0.109 |
| PQ | CCACAG | 4377.33 | 3670 | 0.838 | -0.176 |
| PQ | CCCCAA | 1813.47 | 1497 | 0.825 | -0.192 |
| PQ | CCGCAA | 657.08 | 321 | 0.489 | -0.716 |
| PR | CCGCGC | 563.43 | 1094 | 1.942 | 0.664 |
| PR | CCGCGG | 616.23 | 1113 | 1.806 | 0.591 |
| PR | CCCAGG | 1683.86 | 2927 | 1.738 | 0.553 |
| PR | CCCCGG | 1700.71 | 2608 | 1.533 | 0.428 |
| PR | CCCCGC | 1555.00 | 1979 | 1.273 | 0.241 |
| PR | CCCCGA | 921.92 | 1166 | 1.265 | 0.235 |
| PR | CCTCGA | 825.71 | 1015 | 1.229 | 0.206 |
| PR | CCAAGA | 1482.62 | 1608 | 1.085 | 0.081 |
| PR | CCTCGT | 596.27 | 644 | 1.080 | 0.077 |
| PR | CCCAGA | 1715.19 | 1801 | 1.050 | 0.049 |
| PR | CCGAGG | 610.12 | 636 | 1.042 | 0.042 |
| PR | CCTCGG | 1523.22 | 1511 | 0.992 | -0.008 |
| PR | CCCCGT | 665.75 | 655 | 0.984 | -0.016 |
| PR | CCAAGG | 1455.54 | 1347 | 0.925 | -0.077 |
| PR | CCACGA | 796.91 | 632 | 0.793 | -0.232 |
| PR | CCGCGT | 241.23 | 191 | 0.792 | -0.233 |
| PR | CCACGT | 575.48 | 418 | 0.726 | -0.320 |
| PR | CCACGG | 1470.10 | 1040 | 0.707 | -0.346 |
| PR | CCGCGA | 334.04 | 226 | 0.677 | -0.391 |
| PR | CCTCGC | 1392.72 | 838 | 0.602 | -0.508 |
| PR | CCACGC | 1344.15 | 701 | 0.522 | -0.651 |
| PR | CCGAGA | 621.48 | 308 | 0.496 | -0.702 |
| PR | CCTAGA | 1536.19 | 692 | 0.450 | -0.797 |
| PR | CCTAGG | 1508.13 | 586 | 0.389 | -0.945 |
| PS | CCCAGC | 3196.25 | 6398 | 2.002 | 0.694 |
| PS | CCCTCG | 746.03 | 1385 | 1.856 | 0.619 |
| PS | CCGTCG | 270.31 | 483 | 1.787 | 0.580 |
| PS | CCCAGT | 2016.53 | 2743 | 1.360 | 0.308 |
| PS | CCTTCA | 1776.97 | 2263 | 1.274 | 0.242 |
| PS | CCTTCT | 2198.02 | 2711 | 1.233 | 0.210 |
| PS | CCCTCC | 2821.16 | 3353 | 1.189 | 0.173 |
| PS | CCATCA | 1715.00 | 1819 | 1.061 | 0.059 |
| PS | CCATCT | 2121.37 | 2183 | 1.029 | 0.029 |
| PS | CCTTCC | 2526.74 | 2594 | 1.027 | 0.026 |
| PS | CCGTCC | 1022.21 | 1048 | 1.025 | 0.025 |
| PS | CCCTCA | 1984.02 | 1945 | 0.980 | -0.020 |
| PS | CCAAGT | 1743.10 | 1582 | 0.908 | -0.097 |
| PS | CCCTCT | 2454.14 | 2113 | 0.861 | -0.150 |
| PS | CCTTCG | 668.17 | 552 | 0.826 | -0.191 |
| PS | CCATCC | 2438.63 | 1995 | 0.818 | -0.201 |
| PS | CCGAGC | 1158.11 | 885 | 0.764 | -0.269 |
| PS | CCATCG | 644.87 | 475 | 0.737 | -0.306 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| PS | CCAAGC | 2762.85 | 1659 | 0.600 | -0.510 |
| PS | CCGTCT | 889.22 | 523 | 0.588 | -0.531 |
| PS | CCGAGT | 730.66 | 371 | 0.508 | -0.678 |
| PS | CCGTCA | 718.88 | 364 | 0.506 | -0.681 |
| PS | CCTAGT | 1806.08 | 860 | 0.476 | -0.742 |
| PS | CCTAGC | 2862.68 | 968 | 0.338 | -1.084 |
| PT | CCCACG | 829.55 | 1764 | 2.126 | 0.754 |
| PT | CCCACC | 2525.29 | 4586 | 1.816 | 0.597 |
| PT | CCCACA | 2044.32 | 2719 | 1.330 | 0.285 |
| PT | CCCACT | 1807.85 | 2282 | 1.262 | 0.233 |
| PT | CCAACA | 1767.12 | 1895 | 1.072 | 0.070 |
| PT | CCAACT | 1562.71 | 1593 | 1.019 | 0.019 |
| PT | CCGACG | 300.57 | 305 | 1.015 | 0.015 |
| PT | CCTACT | 1619.18 | 1252 | 0.773 | -0.257 |
| PT | CCAACC | 2182.87 | 1514 | 0.694 | -0.366 |
| PT | CCTACA | 1830.97 | 1241 | 0.678 | -0.389 |
| PT | CCGACC | 915.00 | 592 | 0.647 | -0.435 |
| PT | CCAACG | 717.06 | 463 | 0.646 | -0.437 |
| PT | CCTACC | 2261.75 | 1251 | 0.553 | -0.592 |
| PT | CCGACT | 655.05 | 342 | 0.522 | -0.650 |
| PT | CCGACA | 740.73 | 352 | 0.475 | -0.744 |
| PT | CCTACG | 742.97 | 352 | 0.474 | -0.747 |
| PV | CCTGTT | 1493.79 | 2375 | 1.590 | 0.464 |
| PV | CCTGTA | 969.97 | 1482 | 1.528 | 0.424 |
| PV | CCAGTA | 936.15 | 1352 | 1.444 | 0.368 |
| PV | CCTGTG | 3783.57 | 5362 | 1.417 | 0.349 |
| PV | CCAGTT | 1441.70 | 2038 | 1.414 | 0.346 |
| PV | CCTGTC | 1912.53 | 2666 | 1.394 | 0.332 |
| PV | CCGGTG | 1530.67 | 1911 | 1.248 | 0.222 |
| PV | CCAGTG | 3651.63 | 3787 | 1.037 | 0.036 |
| PV | CCAGTC | 1845.84 | 1863 | 1.009 | 0.009 |
| PV | CCGGTC | 773.73 | 778 | 1.006 | 0.006 |
| PV | CCCGTG | 4224.44 | 2576 | 0.610 | -0.495 |
| PV | CCGGTT | 604.32 | 351 | 0.581 | -0.543 |
| PV | CCGGTA | 392.41 | 215 | 0.548 | -0.602 |
| PV | CCCGTC | 2135.39 | 1084 | 0.508 | -0.678 |
| PV | CCCGTT | 1667.85 | 391 | 0.234 | -1.451 |
| PV | CCCGTA | 1083.00 | 216 | 0.199 | -1.612 |
| PW | CCCTGG | 1769.80 | 2753 | 1.556 | 0.442 |
| PW | CCGTGG | 641.26 | 661 | 1.031 | 0.030 |
| PW | CCATGG | 1529.83 | 1060 | 0.693 | -0.367 |
| PW | CCTTGG | 1585.10 | 1052 | 0.664 | -0.410 |
| PY | CCCTAC | 2166.25 | 3378 | 1.559 | 0.444 |
| PY | CCCTAT | 1760.24 | 2097 | 1.191 | 0.175 |
| PY | CCTTAT | 1576.54 | 1702 | 1.080 | 0.077 |
| PY | CCATAT | 1521.56 | 1513 | 0.994 | -0.006 |
| PY | CCTTAC | 1940.18 | 1485 | 0.765 | -0.267 |
| PY | CCGTAC | 784.91 | 592 | 0.754 | -0.282 |
| PY | CCGTAT | 637.80 | 429 | 0.673 | -0.397 |
| PY | CCATAC | 1872.52 | 1064 | 0.568 | -0.565 |
| QA | CAAGCA | 1597.87 | 2339 | 1.464 | 0.381 |
| QA | CAAGCT | 1825.31 | 2409 | 1.320 | 0.277 |
| QA | CAGGCG | 2095.55 | 2271 | 1.084 | 0.080 |
| QA | CAGGCC | 7750.37 | 7695 | 0.993 | -0.007 |
| QA | CAAGCC | 2775.49 | 2655 | 0.957 | -0.044 |
| QA | CAGGCT | 5097.04 | 4584 | 0.899 | -0.106 |
| QA | CAGGCA | 4461.94 | 3943 | 0.884 | -0.124 |
| QA | CAAGCG | 750.44 | 458 | 0.610 | -0.494 |
| QC | CAGTGT | 2490.13 | 2791 | 1.121 | 0.114 |
| QC | CAGTGC | 2956.40 | 3260 | 1.103 | 0.098 |
| QC | CAATGT | 891.74 | 822 | 0.922 | -0.081 |
| QC | CAATGC | 1058.72 | 524 | 0.495 | -0.703 |
| QD | CAAGAT | 2128.42 | 3326 | 1.563 | 0.446 |
| QD | CAAGAC | 2404.29 | 2506 | 1.042 | 0.041 |
| QD | CAGGAC | 6713.82 | 6642 | 0.989 | -0.011 |
| QD | CAGGAT | 5943.46 | 4716 | 0.793 | -0.231 |
| QE | CAAGAA | 3247.03 | 5286 | 1.628 | 0.487 |
| QE | CAGGAG | 12125.58 | 12556 | 1.035 | 0.035 |
| QE | CAAGAG | 4342.30 | 4206 | 0.969 | -0.032 |
| QE | CAGGAA | 9067.09 | 6734 | 0.743 | -0.297 |
| QF | CAGTTT | 3509.26 | 4032 | 1.149 | 0.139 |
| QF | CAGTTC | 4016.64 | 4205 | 1.047 | 0.046 |
| QF | CAATTT | 1256.70 | 1156 | 0.920 | -0.084 |
| QF | CAATTC | 1438.40 | 828 | 0.576 | -0.552 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| QG | CAAGGA | 1440.03 | 2837 | 1.970 | 0.678 |
| QG | CAAGGT | 932.30 | 1506 | 1.615 | 0.480 |
| QG | CAAGGG | 1405.83 | 1700 | 1.209 | 0.190 |
| QG | CAAGGC | 1952.47 | 2192 | 1.123 | 0.116 |
| QG | CAGGGC | 5452.14 | 5605 | 1.028 | 0.028 |
| QG | CAGGGT | 2603.39 | 2292 | 0.880 | -0.127 |
| QG | CAGGGA | 4021.17 | 2871 | 0.714 | -0.337 |
| QG | CAGGGG | 3925.67 | 2730 | 0.695 | -0.363 |
| QH | CAACAT | 1067.82 | 1364 | 1.277 | 0.245 |
| QH | CAGCAC | 4111.88 | 4483 | 1.090 | 0.086 |
| QH | CAGCAT | 2981.80 | 2794 | 0.937 | -0.065 |
| QH | CAACAC | 1472.51 | 993 | 0.674 | -0.394 |
| QI | CAAATA | 656.37 | 1125 | 1.714 | 0.539 |
| QI | CAAATT | 1427.17 | 1667 | 1.168 | 0.155 |
| QI | CAGATC | 5039.60 | 5197 | 1.031 | 0.031 |
| QI | CAGATA | 1832.87 | 1802 | 0.983 | -0.017 |
| QI | CAGATT | 3985.26 | 3693 | 0.927 | -0.076 |
| QI | CAAATC | 1804.74 | 1262 | 0.699 | -0.358 |
| QK | CAGAAG | 8990.94 | 9726 | 1.082 | 0.079 |
| QK | CAAAAA | 2486.09 | 2610 | 1.050 | 0.049 |
| QK | CAGAAA | 6942.22 | 6532 | 0.941 | -0.061 |
| QK | CAAAAG | 3219.76 | 2771 | 0.861 | -0.150 |
| QL | CAGCTG | 10304.18 | 12629 | 1.226 | 0.203 |
| QL | CAACTA | 660.31 | 798 | 1.209 | 0.189 |
| QL | CAACTT | 1224.39 | 1479 | 1.208 | 0.189 |
| QL | CAGCTC | 4958.40 | 5986 | 1.207 | 0.188 |
| QL | CAGCTA | 1843.86 | 2002 | 1.086 | 0.082 |
| QL | CAGCTT | 3419.03 | 3476 | 1.017 | 0.017 |
| QL | CAATTA | 714.15 | 642 | 0.899 | -0.107 |
| QL | CAGTTG | 3350.09 | 2597 | 0.775 | -0.255 |
| QL | CAGTTA | 1994.20 | 1518 | 0.761 | -0.273 |
| QL | CAACTC | 1775.66 | 1279 | 0.720 | -0.328 |
| QL | CAACTG | 3690.04 | 2093 | 0.567 | -0.567 |
| QL | CAATTG | 1199.70 | 635 | 0.529 | -0.636 |
| QM | CAGATG | 5587.91 | 5592 | 1.001 | 0.001 |
| QM | CAAATG | 2001.09 | 1997 | 0.998 | -0.002 |
| QN | CAAAAT | 1720.47 | 2394 | 1.391 | 0.330 |
| QN | CAGAAC | 5291.34 | 5195 | 0.982 | -0.018 |
| QN | CAGAAT | 4804.30 | 4430 | 0.922 | -0.081 |
| QN | CAAAAC | 1894.89 | 1692 | 0.893 | -0.113 |
| QP | CAGCCG | 1816.66 | 2237 | 1.231 | 0.208 |
| QP | CAGCCC | 5013.75 | 6143 | 1.225 | 0.203 |
| QP | CAGCCT | 4490.51 | 4526 | 1.008 | 0.008 |
| QP | CAGCCA | 4333.91 | 4235 | 0.977 | -0.023 |
| QP | CAACCA | 1552.02 | 1441 | 0.928 | -0.074 |
| QP | CAACCT | 1608.10 | 1304 | 0.811 | -0.210 |
| QP | CAACCC | 1795.48 | 1132 | 0.630 | -0.461 |
| QP | CAACCG | 650.57 | 243 | 0.374 | -0.985 |
| QQ | CAACAA | 1545.49 | 1866 | 1.207 | 0.188 |
| QQ | CAGCAG | 12051.19 | 13131 | 1.090 | 0.086 |
| QQ | CAGCAA | 4315.66 | 4034 | 0.935 | -0.067 |
| QQ | CAACAG | 4315.66 | 3197 | 0.741 | -0.300 |
| QR | CAAAGA | 1214.45 | 1863 | 1.534 | 0.428 |
| QR | CAGAGG | 3329.32 | 4331 | 1.301 | 0.263 |
| QR | CAAAGG | 1192.27 | 1360 | 1.141 | 0.132 |
| QR | CAGAGA | 3391.27 | 3777 | 1.114 | 0.108 |
| QR | CAGCGC | 3074.54 | 3169 | 1.031 | 0.030 |
| QR | CAGCGG | 3362.63 | 3352 | 0.997 | -0.003 |
| QR | CAGCGT | 1316.32 | 1215 | 0.923 | -0.080 |
| QR | CAGCGA | 1822.82 | 1469 | 0.806 | -0.216 |
| QR | CAACGT | 471.39 | 327 | 0.694 | -0.366 |
| QR | CAACGA | 652.77 | 413 | 0.633 | -0.458 |
| QR | CAACGG | 1204.20 | 453 | 0.376 | -0.978 |
| QR | CAACGC | 1101.03 | 404 | 0.367 | -1.003 |
| QS | CAAAGT | 904.91 | 1408 | 1.556 | 0.442 |
| QS | CAGAGC | 4005.17 | 5248 | 1.310 | 0.270 |
| QS | CAGAGT | 2526.89 | 2963 | 1.173 | 0.159 |
| QS | CAAAGC | 1434.30 | 1465 | 1.021 | 0.021 |
| QS | CAGTCG | 934.84 | 923 | 0.987 | -0.013 |
| QS | CAGTCA | 2486.15 | 2379 | 0.957 | -0.044 |
| QS | CAGTCT | 3075.24 | 2806 | 0.912 | -0.092 |
| QS | CAATCA | 890.32 | 781 | 0.877 | -0.131 |
| QS | CAGTCC | 3535.16 | 3051 | 0.863 | -0.147 |
| QS | CAATCT | 1101.28 | 765 | 0.695 | -0.364 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| QS | CAATCC | 1265.98 | 587 | 0.464 | -0.769 |
| QS | CAATCG | 334.78 | 119 | 0.355 | -1.034 |
| QT | CAAACT | 1116.05 | 1463 | 1.311 | 0.271 |
| QT | CAAACA | 1262.03 | 1602 | 1.269 | 0.239 |
| QT | CAGACG | 1430.02 | 1665 | 1.164 | 0.152 |
| QT | CAGACC | 4353.25 | 4301 | 0.988 | -0.012 |
| QT | CAGACA | 3524.12 | 3445 | 0.978 | -0.023 |
| QT | CAGACT | 3116.48 | 2792 | 0.896 | -0.110 |
| QT | CAAACC | 1558.95 | 1232 | 0.790 | -0.235 |
| QT | CAAACG | 512.11 | 373 | 0.728 | -0.317 |
| QV | CAAGTA | 657.01 | 1210 | 1.842 | 0.611 |
| QV | CAAGTT | 1011.82 | 1737 | 1.717 | 0.540 |
| QV | CAAGTC | 1295.45 | 1468 | 1.133 | 0.125 |
| QV | CAAGTG | 2562.79 | 2712 | 1.058 | 0.057 |
| QV | CAGGTG | 7156.41 | 7062 | 0.987 | -0.013 |
| QV | CAGGTC | 3617.45 | 3213 | 0.888 | -0.119 |
| QV | CAGGTT | 2825.43 | 2269 | 0.803 | -0.219 |
| QV | CAGGTA | 1834.65 | 1290 | 0.703 | -0.352 |
| QW | CAGTGG | 3057.92 | 3447 | 1.127 | 0.120 |
| QW | CAATGG | 1095.08 | 706 | 0.645 | -0.439 |
| QY | CAATAT | 1029.01 | 1120 | 1.088 | 0.085 |
| QY | CAGTAC | 3536.21 | 3820 | 1.080 | 0.077 |
| QY | CAGTAT | 2873.43 | 2979 | 1.037 | 0.036 |
| QY | CAATAC | 1266.36 | 786 | 0.621 | -0.477 |
| RA | CGGGCG | 659.18 | 1185 | 1.798 | 0.587 |
| RA | CGGGCC | 2437.97 | 3513 | 1.441 | 0.365 |
| RA | AGAGCA | 1415.51 | 1970 | 1.392 | 0.331 |
| RA | CGCGCG | 602.71 | 827 | 1.372 | 0.316 |
| RA | CGTGCC | 954.35 | 1266 | 1.327 | 0.283 |
| RA | CGAGCA | 760.84 | 970 | 1.275 | 0.243 |
| RA | CGAGCT | 869.13 | 1108 | 1.275 | 0.243 |
| RA | CGAGCC | 1321.57 | 1595 | 1.207 | 0.188 |
| RA | AGAGCT | 1616.99 | 1949 | 1.205 | 0.187 |
| RA | CGTGCT | 627.63 | 744 | 1.185 | 0.170 |
| RA | CGGGCA | 1403.55 | 1612 | 1.149 | 0.138 |
| RA | CGTGCA | 549.43 | 570 | 1.037 | 0.037 |
| RA | CGTGCG | 258.04 | 250 | 0.969 | -0.032 |
| RA | CGAGCG | 357.33 | 341 | 0.954 | -0.047 |
| RA | AGGGCC | 2413.81 | 2173 | 0.900 | -0.105 |
| RA | AGAGCC | 2458.73 | 2202 | 0.896 | -0.110 |
| RA | CGGGCT | 1603.33 | 1435 | 0.895 | -0.111 |
| RA | AGGGCA | 1389.65 | 1242 | 0.894 | -0.112 |
| RA | AGGGCT | 1587.45 | 1311 | 0.826 | -0.191 |
| RA | AGGGCG | 652.65 | 524 | 0.803 | -0.220 |
| RA | CGCGCC | 2229.09 | 1712 | 0.768 | -0.264 |
| RA | AGAGCG | 664.79 | 384 | 0.578 | -0.549 |
| RA | CGCGCA | 1283.30 | 331 | 0.258 | -1.355 |
| RA | CGCGCT | 1465.97 | 369 | 0.252 | -1.379 |
| RC | CGCTGC | 986.26 | 2873 | 2.913 | 1.069 |
| RC | CGCTGT | 830.71 | 1313 | 1.581 | 0.458 |
| RC | CGTTGT | 355.66 | 320 | 0.900 | -0.106 |
| RC | CGTTGC | 422.25 | 372 | 0.881 | -0.127 |
| RC | AGATGT | 916.29 | 806 | 0.880 | -0.128 |
| RC | CGATGT | 492.51 | 421 | 0.855 | -0.157 |
| RC | AGGTGT | 899.55 | 671 | 0.746 | -0.293 |
| RC | AGGTGC | 1067.99 | 758 | 0.710 | -0.343 |
| RC | CGATGC | 584.73 | 381 | 0.652 | -0.428 |
| RC | CGGTGC | 1078.67 | 660 | 0.612 | -0.491 |
| RC | AGATGC | 1087.86 | 642 | 0.590 | -0.527 |
| RC | CGGTGT | 908.55 | 414 | 0.456 | -0.786 |
| RD | AGAGAT | 2027.66 | 2952 | 1.456 | 0.376 |
| RD | CGGGAC | 2271.13 | 3231 | 1.423 | 0.353 |
| RD | CGAGAT | 1089.87 | 1500 | 1.376 | 0.319 |
| RD | CGAGAC | 1231.14 | 1693 | 1.375 | 0.319 |
| RD | CGTGAC | 889.05 | 1044 | 1.174 | 0.161 |
| RD | AGAGAC | 2290.48 | 2433 | 1.062 | 0.060 |
| RD | CGTGAT | 787.04 | 833 | 1.058 | 0.057 |
| RD | AGGGAC | 2248.63 | 2322 | 1.033 | 0.032 |
| RD | AGGGAT | 1990.62 | 1732 | 0.870 | -0.139 |
| RD | CGGGAT | 2010.54 | 1606 | 0.799 | -0.225 |
| RD | CGCGAC | 2076.56 | 1092 | 0.526 | -0.643 |
| RD | CGCGAT | 1838.29 | 313 | 0.170 | -1.770 |
| RE | AGAGAA | 2644.21 | 4195 | 1.586 | 0.462 |
| RE | CGGGAG | 3506.29 | 5344 | 1.524 | 0.421 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| RE | CGAGAG | 1900.69 | 2475 | 1.302 | 0.264 |
| RE | CGAGAA | 1421.27 | 1844 | 1.297 | 0.260 |
| RE | CGTGAG | 1372.55 | 1453 | 1.059 | 0.057 |
| RE | AGGGAG | 3471.55 | 3469 | 0.999 | -0.001 |
| RE | AGAGAG | 3536.15 | 3392 | 0.959 | -0.042 |
| RE | CGTGAA | 1026.35 | 947 | 0.923 | -0.080 |
| RE | AGGGAA | 2595.91 | 2343 | 0.903 | -0.103 |
| RE | CGGGAA | 2621.88 | 2131 | 0.813 | -0.207 |
| RE | CGCGAG | 3205.89 | 1839 | 0.574 | -0.556 |
| RE | CGCGAA | 2397.25 | 268 | 0.112 | -2.191 |
| RF | CGCTTC | 1446.49 | 3411 | 2.358 | 0.858 |
| RF | CGTTTC | 619.29 | 823 | 1.329 | 0.284 |
| RF | CGTTTT | 541.07 | 705 | 1.303 | 0.265 |
| RF | AGATTT | 1393.96 | 1531 | 1.098 | 0.094 |
| RF | CGCTTT | 1263.77 | 1366 | 1.081 | 0.078 |
| RF | CGATTT | 749.26 | 772 | 1.030 | 0.030 |
| RF | AGGTTT | 1368.50 | 1295 | 0.946 | -0.055 |
| RF | AGGTTC | 1566.36 | 1192 | 0.761 | -0.273 |
| RF | CGATTC | 857.59 | 632 | 0.737 | -0.305 |
| RF | CGGTTC | 1582.03 | 951 | 0.601 | -0.509 |
| RF | AGATTC | 1595.50 | 944 | 0.592 | -0.525 |
| RF | CGGTTT | 1382.19 | 744 | 0.538 | -0.619 |
| RG | CGTGGT | 370.38 | 685 | 1.849 | 0.615 |
| RG | CGTGGG | 558.50 | 980 | 1.755 | 0.562 |
| RG | CGTGGC | 775.66 | 1315 | 1.695 | 0.528 |
| RG | CGAGGA | 792.21 | 1266 | 1.598 | 0.469 |
| RG | CGAGGG | 773.39 | 1219 | 1.576 | 0.455 |
| RG | AGAGGA | 1473.87 | 2281 | 1.548 | 0.437 |
| RG | CGAGGT | 512.89 | 789 | 1.538 | 0.431 |
| RG | CGGGGC | 1981.48 | 2952 | 1.490 | 0.399 |
| RG | CGTGGA | 572.08 | 844 | 1.475 | 0.389 |
| RG | CGAGGC | 1074.12 | 1569 | 1.461 | 0.379 |
| RG | AGAGGT | 954.21 | 1128 | 1.182 | 0.167 |
| RG | CGGGGT | 946.15 | 918 | 0.970 | -0.030 |
| RG | CGCGGC | 1811.72 | 1574 | 0.869 | -0.141 |
| RG | AGGGGC | 1961.86 | 1660 | 0.846 | -0.167 |
| RG | AGAGGC | 1998.36 | 1680 | 0.841 | -0.174 |
| RG | AGAGGG | 1438.87 | 1203 | 0.836 | -0.179 |
| RG | AGGGGT | 936.78 | 777 | 0.829 | -0.187 |
| RG | CGGGGG | 1426.72 | 1146 | 0.803 | -0.219 |
| RG | CGGGGA | 1461.42 | 1140 | 0.780 | -0.248 |
| RG | CGCGGG | 1304.48 | 904 | 0.693 | -0.367 |
| RG | AGGGGA | 1446.94 | 923 | 0.638 | -0.450 |
| RG | AGGGGG | 1412.58 | 683 | 0.484 | -0.727 |
| RG | CGCGGT | 865.09 | 248 | 0.287 | -1.249 |
| RG | CGCGGA | 1336.22 | 302 | 0.226 | -1.487 |
| RH | CGCCAC | 1288.00 | 1861 | 1.445 | 0.368 |
| RH | CGGCAC | 1408.69 | 1707 | 1.212 | 0.192 |
| RH | AGACAT | 1030.24 | 1201 | 1.166 | 0.153 |
| RH | CGTCAT | 399.89 | 447 | 1.118 | 0.111 |
| RH | AGGCAT | 1011.41 | 988 | 0.977 | -0.023 |
| RH | CGACAT | 553.75 | 530 | 0.957 | -0.044 |
| RH | AGGCAC | 1394.73 | 1292 | 0.926 | -0.077 |
| RH | AGACAC | 1420.69 | 1212 | 0.853 | -0.159 |
| RH | CGTCAC | 551.44 | 468 | 0.849 | -0.164 |
| RH | CGACAC | 763.62 | 614 | 0.804 | -0.218 |
| RH | CGCCAT | 934.02 | 728 | 0.779 | -0.249 |
| RH | CGGCAT | 1021.53 | 730 | 0.715 | -0.336 |
| RI | CGCATC | 1625.56 | 2948 | 1.814 | 0.595 |
| RI | AGAATA | 652.11 | 1175 | 1.802 | 0.589 |
| RI | AGAATT | 1417.90 | 2185 | 1.541 | 0.432 |
| RI | AGGATA | 640.20 | 804 | 1.256 | 0.228 |
| RI | CGAATA | 350.51 | 439 | 1.252 | 0.225 |
| RI | CGAATT | 762.13 | 850 | 1.115 | 0.109 |
| RI | AGGATT | 1392.00 | 1366 | 0.981 | -0.019 |
| RI | AGGATC | 1760.27 | 1662 | 0.944 | -0.057 |
| RI | CGAATC | 963.75 | 802 | 0.832 | -0.184 |
| RI | CGGATC | 1777.88 | 1479 | 0.832 | -0.184 |
| RI | AGAATC | 1793.03 | 1389 | 0.775 | -0.255 |
| RI | CGTATT | 550.36 | 408 | 0.741 | -0.299 |
| RI | CGCATT | 1285.48 | 913 | 0.710 | -0.342 |
| RI | CGGATA | 646.60 | 451 | 0.697 | -0.360 |
| RI | CGTATC | 695.96 | 440 | 0.632 | -0.459 |
| RI | CGTATA | 253.12 | 152 | 0.601 | -0.510 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| RI | CGGATT | 1405.93 | 825 | 0.587 | -0.533 |
| RI | CGCATA | 591.21 | 276 | 0.467 | -0.762 |
| RK | AGGAAG | 3199.71 | 4856 | 1.518 | 0.417 |
| RK | AGGAAA | 2470.61 | 3737 | 1.513 | 0.414 |
| RK | AGAAAA | 2516.58 | 3482 | 1.384 | 0.325 |
| RK | CGCAAG | 2954.85 | 2981 | 1.009 | 0.009 |
| RK | CGGAAG | 3231.73 | 3225 | 0.998 | -0.002 |
| RK | AGAAAG | 3259.25 | 2909 | 0.893 | -0.114 |
| RK | CGAAAA | 1352.67 | 1189 | 0.879 | -0.129 |
| RK | CGGAAA | 2495.33 | 1834 | 0.735 | -0.308 |
| RK | CGAAAG | 1751.85 | 1265 | 0.722 | -0.326 |
| RK | CGTAAA | 976.81 | 566 | 0.579 | -0.546 |
| RK | CGCAAA | 2281.54 | 1209 | 0.530 | -0.635 |
| RK | CGTAAG | 1265.08 | 503 | 0.398 | -0.922 |
| RL | CGCCTC | 1491.12 | 2511 | 1.684 | 0.521 |
| RL | CGCCTG | 3098.73 | 4809 | 1.552 | 0.439 |
| RL | CGGCTG | 3389.08 | 5029 | 1.484 | 0.395 |
| RL | CGGCTC | 1630.84 | 2301 | 1.411 | 0.344 |
| RL | CGTTTA | 256.76 | 337 | 1.313 | 0.272 |
| RL | AGATTA | 661.49 | 862 | 1.303 | 0.265 |
| RL | CGTCTT | 440.20 | 562 | 1.277 | 0.244 |
| RL | CGTCTA | 237.40 | 296 | 1.247 | 0.221 |
| RL | CGTTTG | 431.33 | 526 | 1.219 | 0.198 |
| RL | CGTCTC | 638.40 | 723 | 1.133 | 0.124 |
| RL | AGGCTA | 600.44 | 669 | 1.114 | 0.108 |
| RL | AGACTT | 1134.11 | 1227 | 1.082 | 0.079 |
| RL | AGGCTG | 3355.51 | 3531 | 1.052 | 0.051 |
| RL | AGACTA | 611.62 | 617 | 1.009 | 0.009 |
| RL | AGGCTT | 1113.39 | 1104 | 0.992 | -0.008 |
| RL | CGACTA | 328.75 | 324 | 0.986 | -0.015 |
| RL | CGGCTA | 606.45 | 593 | 0.978 | -0.022 |
| RL | CGTCTG | 1326.68 | 1281 | 0.966 | -0.035 |
| RL | AGGCTC | 1614.68 | 1540 | 0.954 | -0.047 |
| RL | CGATTA | 355.55 | 337 | 0.948 | -0.054 |
| RL | CGACTT | 609.59 | 576 | 0.945 | -0.057 |
| RL | CGCCTA | 554.49 | 501 | 0.904 | -0.101 |
| RL | AGGTTA | 649.40 | 586 | 0.902 | -0.103 |
| RL | CGCCTT | 1028.19 | 862 | 0.838 | -0.176 |
| RL | CGCTTG | 1007.46 | 804 | 0.798 | -0.226 |
| RL | CGGCTT | 1124.53 | 866 | 0.770 | -0.261 |
| RL | AGATTG | 1111.24 | 839 | 0.755 | -0.281 |
| RL | CGACTC | 884.04 | 663 | 0.750 | -0.288 |
| RL | AGGTTG | 1090.94 | 774 | 0.709 | -0.343 |
| RL | AGACTC | 1644.73 | 1142 | 0.694 | -0.365 |
| RL | CGATTG | 597.29 | 408 | 0.683 | -0.381 |
| RL | CGACTG | 1837.15 | 1128 | 0.614 | -0.488 |
| RL | CGCTTA | 599.71 | 345 | 0.575 | -0.553 |
| RL | CGGTTG | 1101.86 | 566 | 0.514 | -0.666 |
| RL | AGACTG | 3417.95 | 1701 | 0.498 | -0.698 |
| RL | CGGTTA | 655.90 | 297 | 0.453 | -0.792 |
| RM | CGCATG | 1558.32 | 1961 | 1.258 | 0.230 |
| RM | AGGATG | 1687.45 | 1974 | 1.170 | 0.157 |
| RM | CGAATG | 923.88 | 932 | 1.009 | 0.009 |
| RM | AGAATG | 1718.85 | 1690 | 0.983 | -0.017 |
| RM | CGGATG | 1704.33 | 1374 | 0.806 | -0.215 |
| RM | CGTATG | 667.17 | 329 | 0.493 | -0.707 |
| RN | AGAAAT | 1568.88 | 2627 | 1.674 | 0.515 |
| RN | AGGAAC | 1696.37 | 2200 | 1.297 | 0.260 |
| RN | AGGAAT | 1540.22 | 1796 | 1.166 | 0.154 |
| RN | AGAAAC | 1727.93 | 1949 | 1.128 | 0.120 |
| RN | CGAAAT | 843.28 | 930 | 1.103 | 0.098 |
| RN | CGCAAC | 1566.55 | 1575 | 1.005 | 0.005 |
| RN | CGGAAC | 1713.34 | 1621 | 0.946 | -0.055 |
| RN | CGAAAC | 928.77 | 784 | 0.844 | -0.169 |
| RN | CGGAAT | 1555.63 | 1002 | 0.644 | -0.440 |
| RN | CGTAAT | 608.96 | 340 | 0.558 | -0.583 |
| RN | CGCAAT | 1422.36 | 711 | 0.500 | -0.693 |
| RN | CGTAAC | 670.70 | 308 | 0.459 | -0.778 |
| RP | CGGCCG | 587.88 | 1226 | 2.085 | 0.735 |
| RP | CGGCCC | 1622.47 | 2939 | 1.811 | 0.594 |
| RP | CGCCCG | 537.51 | 717 | 1.334 | 0.288 |
| RP | AGGCCC | 1606.39 | 1982 | 1.234 | 0.210 |
| RP | AGGCCG | 582.05 | 666 | 1.144 | 0.135 |
| RP | AGGCCT | 1438.75 | 1642 | 1.141 | 0.132 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| RP | AGGCCA | 1388.57 | 1511 | 1.088 | 0.084 |
| RP | CGTCCT | 568.84 | 589 | 1.035 | 0.035 |
| RP | AGACCA | 1414.41 | 1387 | 0.981 | -0.020 |
| RP | CGGCCT | 1453.14 | 1390 | 0.957 | -0.044 |
| RP | AGACCT | 1465.52 | 1398 | 0.954 | -0.047 |
| RP | CGTCCC | 635.12 | 582 | 0.916 | -0.087 |
| RP | CGGCCA | 1402.47 | 1285 | 0.916 | -0.087 |
| RP | CGCCCC | 1483.46 | 1320 | 0.890 | -0.117 |
| RP | CGTCCA | 549.00 | 487 | 0.887 | -0.120 |
| RP | AGACCC | 1636.29 | 1283 | 0.784 | -0.243 |
| RP | CGACCA | 760.25 | 591 | 0.777 | -0.252 |
| RP | CGACCC | 879.51 | 671 | 0.763 | -0.271 |
| RP | CGACCT | 787.72 | 580 | 0.736 | -0.306 |
| RP | CGCCCA | 1282.31 | 887 | 0.692 | -0.369 |
| RP | CGTCCG | 230.13 | 159 | 0.691 | -0.370 |
| RP | CGCCCT | 1328.65 | 830 | 0.625 | -0.470 |
| RP | CGACCG | 318.68 | 184 | 0.577 | -0.549 |
| RP | AGACCG | 592.88 | 246 | 0.415 | -0.880 |
| RQ | AGACAA | 1054.78 | 1456 | 1.380 | 0.322 |
| RQ | CGGCAG | 2920.52 | 3950 | 1.352 | 0.302 |
| RQ | CGCCAG | 2670.31 | 3160 | 1.183 | 0.168 |
| RQ | AGGCAA | 1035.51 | 1177 | 1.137 | 0.128 |
| RQ | AGGCAG | 2891.59 | 3013 | 1.042 | 0.041 |
| RQ | CGACAA | 566.95 | 522 | 0.921 | -0.083 |
| RQ | CGTCAG | 1143.25 | 953 | 0.834 | -0.182 |
| RQ | CGTCAA | 409.41 | 327 | 0.799 | -0.225 |
| RQ | CGACAG | 1583.16 | 1249 | 0.789 | -0.237 |
| RQ | CGGCAA | 1045.87 | 763 | 0.730 | -0.315 |
| RQ | AGACAG | 2945.39 | 2062 | 0.700 | -0.357 |
| RQ | CGCCAA | 956.27 | 591 | 0.618 | -0.481 |
| RR | CGCCGC | 1172.08 | 2232 | 1.904 | 0.644 |
| RR | CGGCGG | 1402.02 | 2316 | 1.652 | 0.502 |
| RR | AGAAGA | 1426.00 | 2307 | 1.618 | 0.481 |
| RR | CGGCGC | 1281.90 | 2064 | 1.610 | 0.476 |
| RR | AGGAGG | 1374.38 | 1973 | 1.436 | 0.362 |
| RR | CGCCGG | 1281.90 | 1679 | 1.310 | 0.270 |
| RR | CGAAGA | 766.48 | 987 | 1.288 | 0.253 |
| RR | AGGAGA | 1399.95 | 1758 | 1.256 | 0.228 |
| RR | CGCAGG | 1269.20 | 1565 | 1.233 | 0.209 |
| RR | CGGAGG | 1388.13 | 1670 | 1.203 | 0.185 |
| RR | CGTCGT | 214.84 | 228 | 1.061 | 0.059 |
| RR | CGAAGG | 752.48 | 770 | 1.023 | 0.023 |
| RR | CGCCGT | 501.81 | 502 | 1.000 | 0.000 |
| RR | AGAAGG | 1399.95 | 1325 | 0.946 | -0.055 |
| RR | CGGCGT | 548.83 | 498 | 0.907 | -0.097 |
| RR | CGTCGA | 297.51 | 265 | 0.891 | -0.116 |
| RR | CGGCGA | 760.01 | 675 | 0.888 | -0.119 |
| RR | CGTCGC | 501.81 | 438 | 0.873 | -0.136 |
| RR | AGGCGG | 1388.13 | 1177 | 0.848 | -0.165 |
| RR | CGTCGG | 548.83 | 450 | 0.820 | -0.199 |
| RR | CGACGT | 297.51 | 241 | 0.810 | -0.211 |
| RR | CGCCGA | 694.89 | 547 | 0.787 | -0.239 |
| RR | AGGCGA | 752.48 | 570 | 0.757 | -0.278 |
| RR | CGGAGA | 1413.96 | 1068 | 0.755 | -0.281 |
| RR | AGACGA | 766.48 | 557 | 0.727 | -0.319 |
| RR | AGGCGT | 543.39 | 383 | 0.705 | -0.350 |
| RR | AGGCGC | 1269.20 | 889 | 0.700 | -0.356 |
| RR | AGACGT | 553.50 | 376 | 0.679 | -0.387 |
| RR | CGACGA | 411.98 | 272 | 0.660 | -0.415 |
| RR | CGCAGA | 1292.82 | 771 | 0.596 | -0.517 |
| RR | CGACGG | 760.01 | 411 | 0.541 | -0.615 |
| RR | CGACGC | 694.89 | 368 | 0.530 | -0.636 |
| RR | CGTAGA | 553.50 | 271 | 0.490 | -0.714 |
| RR | CGTAGG | 543.39 | 235 | 0.432 | -0.838 |
| RR | AGACGC | 1292.82 | 524 | 0.405 | -0.903 |
| RR | AGACGG | 1413.96 | 569 | 0.402 | -0.910 |
| RS | CGCTCG | 332.61 | 817 | 2.456 | 0.899 |
| RS | CGCAGC | 1425.00 | 2853 | 2.002 | 0.694 |
| RS | CGCTCC | 1257.78 | 2184 | 1.736 | 0.552 |
| RS | AGAAGT | 991.66 | 1532 | 1.545 | 0.435 |
| RS | CGTTCT | 468.44 | 687 | 1.467 | 0.383 |
| RS | CGAAGT | 533.02 | 728 | 1.366 | 0.312 |
| RS | CGTTCC | 538.50 | 707 | 1.313 | 0.272 |
| RS | AGGAGC | 1543.09 | 1992 | 1.291 | 0.255 |

SUPPLEMENTAL TABLE 1-continued

Expected and Observed Codon Pair Frequencies and
Codon Pair Scores for 14,795 Human Genes

| amino acid pair | codon pair | expected | observed | observed / expected | CPS |
|---|---|---|---|---|---|
| RS | CGTTCA | 378.71 | 471 | 1.244 | 0.218 |
| RS | CGGAGC | 1558.53 | 1856 | 1.191 | 0.175 |
| RS | AGGAGT | 973.54 | 1071 | 1.100 | 0.095 |
| RS | AGAAGC | 1571.80 | 1628 | 1.036 | 0.035 |
| RS | AGATCA | 975.67 | 1000 | 1.025 | 0.025 |
| RS | CGAAGC | 844.85 | 859 | 1.017 | 0.017 |
| RS | CGCTCA | 884.55 | 860 | 0.972 | -0.028 |
| RS | CGCAGT | 899.04 | 853 | 0.949 | -0.053 |
| RS | AGATCT | 1206.86 | 1106 | 0.916 | -0.087 |
| RS | CGCTCT | 1094.14 | 942 | 0.861 | -0.150 |
| RS | CGTTCG | 142.40 | 121 | 0.850 | -0.163 |
| RS | AGGTCA | 957.85 | 808 | 0.844 | -0.170 |
| RS | CGATCA | 524.43 | 416 | 0.793 | -0.232 |
| RS | AGGTCT | 1184.81 | 939 | 0.793 | -0.233 |
| RS | AGGTCG | 360.17 | 284 | 0.789 | -0.238 |
| RS | CGATCT | 648.69 | 497 | 0.766 | -0.266 |
| RS | AGGTCC | 1362.00 | 1036 | 0.761 | -0.274 |
| RS | CGGAGT | 983.28 | 745 | 0.758 | -0.278 |
| RS | CGTAGT | 384.91 | 278 | 0.722 | -0.325 |
| RS | CGGTCG | 363.77 | 235 | 0.646 | -0.437 |
| RS | CGATCC | 745.70 | 455 | 0.610 | -0.494 |
| RS | AGATCC | 1387.35 | 830 | 0.598 | -0.514 |
| RS | CGGTCC | 1375.63 | 821 | 0.597 | -0.516 |
| RS | CGATCG | 197.19 | 107 | 0.543 | -0.611 |
| RS | CGGTCA | 967.43 | 507 | 0.524 | -0.646 |
| RS | CGTAGC | 610.09 | 317 | 0.520 | -0.655 |
| RS | AGATCG | 366.87 | 177 | 0.482 | -0.729 |
| RS | CGGTCT | 1196.66 | 518 | 0.433 | -0.837 |
| RT | CGCACG | 450.78 | 858 | 1.903 | 0.644 |
| RT | AGAACT | 1083.61 | 1467 | 1.354 | 0.303 |
| RT | CGCACC | 1372.27 | 1821 | 1.327 | 0.283 |
| RT | AGGACG | 488.14 | 646 | 1.323 | 0.280 |
| RT | AGGACT | 1063.81 | 1389 | 1.306 | 0.267 |
| RT | AGAACA | 1225.34 | 1575 | 1.285 | 0.251 |
| RT | AGGACA | 1202.96 | 1523 | 1.266 | 0.236 |
| RT | AGGACC | 1485.98 | 1773 | 1.193 | 0.177 |
| RT | CGGACG | 493.02 | 537 | 1.089 | 0.085 |
| RT | CGAACA | 658.62 | 661 | 1.004 | 0.004 |
| RT | CGAACT | 582.44 | 556 | 0.955 | -0.046 |
| RT | CGGACC | 1500.85 | 1408 | 0.938 | -0.064 |
| RT | CGCACA | 1110.90 | 984 | 0.886 | -0.121 |
| RT | CGGACA | 1215.00 | 949 | 0.781 | -0.247 |
| RT | AGAACC | 1513.63 | 1166 | 0.770 | -0.261 |
| RT | CGTACT | 420.60 | 313 | 0.744 | -0.295 |
| RT | CGAACC | 813.58 | 599 | 0.736 | -0.306 |
| RT | CGGACT | 1074.45 | 712 | 0.663 | -0.411 |
| RT | CGCACT | 982.40 | 638 | 0.649 | -0.432 |
| RT | CGTACC | 587.52 | 361 | 0.614 | -0.487 |
| RT | AGAACG | 497.22 | 302 | 0.607 | -0.499 |
| RT | CGTACA | 475.62 | 288 | 0.606 | -0.502 |
| RT | CGAACG | 267.26 | 154 | 0.576 | -0.551 |
| RT | CGTACG | 193.00 | 79 | 0.409 | -0.893 |
| RV | CGTGTG | 889.90 | 1699 | 1.909 | 0.647 |
| RV | CGTGTC | 449.83 | 826 | 1.836 | 0.608 |
| RV | CGAGTA | 315.92 | 562 | 1.779 | 0.576 |
| RV | CGTGTA | 228.14 | 391 | 1.714 | 0.539 |
| RV | CGTGTT | 351.34 | 565 | 1.608 | 0.475 |
| RV | AGAGTT | 905.17 | 1350 | 1.491 | 0.400 |
| RV | AGAGTA | 587.76 | 876 | 1.490 | 0.399 |
| RV | CGAGTC | 622.91 | 914 | 1.467 | 0.383 |
| RV | CGAGTT | 486.53 | 681 | 1.400 | 0.336 |
| RV | CGAGTG | 1232.31 | 1576 | 1.279 | 0.246 |
| RV | CGGGTC | 1149.12 | 1310 | 1.140 | 0.131 |
| RV | AGGGTC | 1137.73 | 1221 | 1.073 | 0.071 |
| RV | CGGGTG | 2273.30 | 2328 | 1.024 | 0.024 |
| RV | AGAGTC | 1158.91 | 1154 | 0.996 | -0.004 |
| RV | CGCGTG | 2078.54 | 1725 | 0.830 | -0.186 |
| RV | AGGGTA | 577.02 | 471 | 0.816 | -0.203 |
| RV | AGAGTG | 2292.67 | 1750 | 0.763 | -0.270 |
| RV | CGGGTA | 582.79 | 438 | 0.752 | -0.286 |
| RV | AGGGTG | 2250.78 | 1658 | 0.737 | -0.306 |
| RV | CGCGTC | 1050.67 | 763 | 0.726 | -0.320 |
| RV | AGGGTT | 888.63 | 645 | 0.726 | -0.320 |
| RV | CGGGTT | 897.52 | 548 | 0.611 | -0.493 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| RV | CGCGTA | 532.86 | 132 | 0.248 | −1.395 |
| RV | CGCGTT | 820.63 | 178 | 0.217 | −1.528 |
| RW | CGCTGG | 1038.00 | 2199 | 2.118 | 0.751 |
| RW | CGTTGG | 444.40 | 380 | 0.855 | −0.157 |
| RW | AGGTGG | 1124.01 | 876 | 0.779 | −0.249 |
| RW | CGATGG | 615.40 | 466 | 0.757 | −0.278 |
| RW | AGATGG | 1144.93 | 804 | 0.702 | −0.353 |
| RW | CGGTGG | 1135.26 | 777 | 0.684 | −0.379 |
| RY | CGCTAC | 1173.12 | 2612 | 2.227 | 0.800 |
| RY | CGCTAT | 953.25 | 1198 | 1.257 | 0.229 |
| RY | CGTTAC | 502.25 | 565 | 1.125 | 0.118 |
| RY | CGTTAT | 408.12 | 459 | 1.125 | 0.117 |
| RY | AGATAT | 1051.45 | 1018 | 0.968 | −0.032 |
| RY | AGATAC | 1293.97 | 1239 | 0.958 | −0.043 |
| RY | CGATAT | 565.15 | 509 | 0.901 | −0.105 |
| RY | CGATAC | 695.51 | 584 | 0.840 | −0.175 |
| RY | AGGTAC | 1270.33 | 1007 | 0.793 | −0.232 |
| RY | AGGTAT | 1032.24 | 769 | 0.745 | −0.294 |
| RY | CGGTAC | 1283.04 | 856 | 0.667 | −0.405 |
| RY | CGGTAT | 1042.57 | 455 | 0.436 | −0.829 |
| SA | TCGGCG | 241.39 | 778 | 3.223 | 1.170 |
| SA | TCGGCC | 892.76 | 1976 | 2.213 | 0.795 |
| SA | TCAGCA | 1366.87 | 2526 | 1.848 | 0.614 |
| SA | TCTGCA | 1690.75 | 3035 | 1.795 | 0.585 |
| SA | TCTGCT | 1931.41 | 3350 | 1.734 | 0.551 |
| SA | TCAGCT | 1561.43 | 2630 | 1.684 | 0.521 |
| SA | AGTGCT | 1587.01 | 2487 | 1.567 | 0.449 |
| SA | AGTGCA | 1389.27 | 2040 | 1.468 | 0.384 |
| SA | AGTGCC | 2413.15 | 3437 | 1.424 | 0.354 |
| SA | TCAGCC | 2374.25 | 3294 | 1.387 | 0.327 |
| SA | TCGGCT | 587.12 | 808 | 1.376 | 0.319 |
| SA | TCTGCC | 2936.83 | 3480 | 1.185 | 0.170 |
| SA | TCGGCA | 513.97 | 598 | 1.163 | 0.151 |
| SA | TCTGCG | 794.06 | 745 | 0.938 | −0.064 |
| SA | TCAGCG | 641.95 | 584 | 0.910 | −0.095 |
| SA | AGTGCG | 652.47 | 532 | 0.815 | −0.204 |
| SA | AGCGCG | 1034.18 | 802 | 0.775 | −0.254 |
| SA | AGCGCC | 3824.90 | 2428 | 0.635 | −0.454 |
| SA | TCCGCG | 912.82 | 577 | 0.632 | −0.459 |
| SA | TCCGCC | 3376.05 | 1230 | 0.364 | −1.010 |
| SA | AGCGCT | 2515.45 | 709 | 0.282 | −1.266 |
| SA | AGCGCA | 2202.02 | 601 | 0.273 | −1.299 |
| SA | TCCGCA | 1943.61 | 476 | 0.245 | −1.407 |
| SA | TCCGCT | 2220.26 | 481 | 0.217 | −1.530 |
| SC | TCCTGC | 1640.34 | 2828 | 1.724 | 0.545 |
| SC | AGCTGC | 1858.43 | 3034 | 1.633 | 0.490 |
| SC | TCCTGT | 1381.63 | 1779 | 1.288 | 0.253 |
| SC | AGCTGT | 1565.33 | 1922 | 1.228 | 0.205 |
| SC | TCGTGC | 433.77 | 361 | 0.832 | −0.184 |
| SC | TCTTGT | 1201.89 | 941 | 0.783 | −0.245 |
| SC | AGTTGT | 987.57 | 698 | 0.707 | −0.347 |
| SC | TCGTGT | 365.36 | 225 | 0.616 | −0.485 |
| SC | TCATGT | 971.65 | 584 | 0.601 | −0.509 |
| SC | TCTTGC | 1426.94 | 758 | 0.531 | −0.633 |
| SC | TCATGC | 1153.59 | 525 | 0.455 | −0.787 |
| SC | AGTTGC | 1172.49 | 504 | 0.430 | −0.844 |
| SD | TCAGAT | 1978.63 | 3706 | 1.873 | 0.628 |
| SD | AGTGAT | 2011.05 | 3683 | 1.831 | 0.605 |
| SD | AGTGAC | 2271.71 | 4040 | 1.778 | 0.576 |
| SD | TCGGAC | 840.43 | 1438 | 1.711 | 0.537 |
| SD | TCTGAT | 2447.46 | 3578 | 1.462 | 0.380 |
| SD | TCAGAC | 2235.09 | 2906 | 1.300 | 0.262 |
| SD | TCGGAT | 744.00 | 840 | 1.129 | 0.121 |
| SD | TCTGAC | 2764.69 | 2949 | 1.067 | 0.065 |
| SD | AGCGAC | 3600.71 | 2017 | 0.560 | −0.580 |
| SD | TCCGAC | 3178.17 | 1336 | 0.420 | −0.867 |
| SD | AGCGAT | 3187.56 | 920 | 0.289 | −1.243 |
| SD | TCCGAT | 2813.50 | 660 | 0.235 | −1.450 |
| SE | TCAGAA | 2420.84 | 4815 | 1.989 | 0.688 |
| SE | AGTGAA | 2460.50 | 4686 | 1.904 | 0.644 |
| SE | TCGGAG | 1217.33 | 2184 | 1.794 | 0.584 |
| SE | TCTGAA | 2994.45 | 4621 | 1.543 | 0.434 |
| SE | TCAGAG | 3237.43 | 4683 | 1.447 | 0.369 |
| SE | AGTGAG | 3290.47 | 4410 | 1.340 | 0.293 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| SE | TCTGAG | 4004.54 | 4891 | 1.221 | 0.200 |
| SE | TCGGAA | 910.28 | 879 | 0.966 | -0.035 |
| SE | AGCGAG | 5215.47 | 2961 | 0.568 | -0.566 |
| SE | TCCGAG | 4603.44 | 2005 | 0.436 | -0.831 |
| SE | AGCGAA | 3899.95 | 847 | 0.217 | -1.527 |
| SE | TCCGAA | 3442.29 | 715 | 0.208 | -1.572 |
| SF | TCCTTC | 2645.79 | 4407 | 1.666 | 0.510 |
| SF | AGCTTC | 2997.56 | 3942 | 1.315 | 0.274 |
| SF | TCATTT | 1625.65 | 1773 | 1.091 | 0.087 |
| SF | TCCTTT | 2311.58 | 2487 | 1.076 | 0.073 |
| SF | AGTTTT | 1652.29 | 1695 | 1.026 | 0.026 |
| SF | AGCTTT | 2618.91 | 2370 | 0.905 | -0.100 |
| SF | TCTTTT | 2010.85 | 1809 | 0.900 | -0.106 |
| SF | TCTTTC | 2301.58 | 1728 | 0.751 | -0.287 |
| SF | AGTTTC | 1891.18 | 1353 | 0.715 | -0.335 |
| SF | TCGTTT | 611.27 | 342 | 0.559 | -0.581 |
| SF | TCATTC | 1860.69 | 991 | 0.533 | -0.630 |
| SF | TCGTTC | 699.65 | 330 | 0.472 | -0.751 |
| SG | AGTGGT | 1051.00 | 2094 | 1.992 | 0.689 |
| SG | TCGGGG | 586.31 | 1117 | 1.905 | 0.645 |
| SG | TCGGGC | 814.29 | 1487 | 1.826 | 0.602 |
| SG | AGTGGA | 1623.36 | 2932 | 1.806 | 0.591 |
| SG | TCAGGA | 1597.19 | 2760 | 1.728 | 0.547 |
| SG | TCTGGA | 1975.64 | 3391 | 1.716 | 0.540 |
| SG | AGTGGG | 1584.81 | 2584 | 1.630 | 0.489 |
| SG | TCTGGG | 1928.73 | 2974 | 1.542 | 0.433 |
| SG | AGTGGC | 2201.05 | 3314 | 1.506 | 0.409 |
| SG | TCTGGT | 1279.07 | 1902 | 1.487 | 0.397 |
| SG | TCAGGG | 1559.26 | 2161 | 1.386 | 0.326 |
| SG | TCAGGT | 1034.06 | 1351 | 1.307 | 0.267 |
| SG | TCGGGA | 600.57 | 684 | 1.139 | 0.130 |
| SG | TCGGGT | 388.82 | 410 | 1.054 | 0.053 |
| SG | TCTGGC | 2678.70 | 2734 | 1.021 | 0.020 |
| SG | TCAGGC | 2165.57 | 2114 | 0.976 | -0.024 |
| SG | AGCGGC | 3488.72 | 2475 | 0.709 | -0.343 |
| SG | AGCGGG | 2511.96 | 1464 | 0.583 | -0.540 |
| SG | TCCGGG | 2217.18 | 1117 | 0.504 | -0.686 |
| SG | TCCGGC | 3079.31 | 1163 | 0.378 | -0.974 |
| SG | AGCGGT | 1665.85 | 536 | 0.322 | -1.134 |
| SG | AGCGGA | 2573.06 | 663 | 0.258 | -1.356 |
| SG | TCCGGA | 2271.11 | 560 | 0.247 | -1.400 |
| SG | TCCGGT | 1470.37 | 359 | 0.244 | -1.410 |
| SH | AGCCAC | 2202.27 | 3210 | 1.458 | 0.377 |
| SH | TCTCAT | 1226.22 | 1426 | 1.163 | 0.151 |
| SH | TCCCAC | 1943.83 | 2233 | 1.149 | 0.139 |
| SH | AGTCAT | 1007.57 | 1082 | 1.074 | 0.071 |
| SH | AGCCAT | 1597.01 | 1606 | 1.006 | 0.006 |
| SH | TCGCAC | 514.03 | 512 | 0.996 | -0.004 |
| SH | TCCCAT | 1409.60 | 1349 | 0.957 | -0.044 |
| SH | TCACAT | 991.32 | 929 | 0.937 | -0.065 |
| SH | AGTCAC | 1389.42 | 1077 | 0.775 | -0.255 |
| SH | TCACAC | 1367.03 | 956 | 0.699 | -0.358 |
| SH | TCTCAC | 1690.94 | 1158 | 0.685 | -0.379 |
| SH | TCGCAT | 372.75 | 174 | 0.467 | -0.762 |
| SI | TCCATC | 2374.96 | 4526 | 1.906 | 0.645 |
| SI | AGCATC | 2690.72 | 4471 | 1.662 | 0.508 |
| SI | TCCATT | 1878.09 | 2383 | 1.269 | 0.238 |
| SI | AGCATT | 2127.79 | 2384 | 1.120 | 0.114 |
| SI | TCCATA | 863.76 | 963 | 1.115 | 0.109 |
| SI | AGTATA | 617.40 | 640 | 1.037 | 0.036 |
| SI | TCAATA | 607.45 | 618 | 1.017 | 0.017 |
| SI | AGTATT | 1342.43 | 1299 | 0.968 | -0.033 |
| SI | AGCATA | 978.60 | 943 | 0.964 | -0.037 |
| SI | TCTATA | 751.38 | 658 | 0.876 | -0.133 |
| SI | TCTATT | 1633.75 | 1215 | 0.744 | -0.296 |
| SI | TCAATT | 1320.79 | 957 | 0.725 | -0.322 |
| SI | AGTATC | 1697.59 | 924 | 0.544 | -0.608 |
| SI | TCGATA | 228.41 | 109 | 0.477 | -0.740 |
| SI | TCTATC | 2065.98 | 958 | 0.464 | -0.769 |
| SI | TCGATT | 496.64 | 185 | 0.373 | -0.988 |
| SI | TCAATC | 1670.22 | 557 | 0.333 | -1.098 |
| SI | TCGATC | 628.03 | 184 | 0.293 | -1.228 |
| SK | TCCAAG | 3563.99 | 5021 | 1.409 | 0.343 |
| SK | TCCAAA | 2751.88 | 3634 | 1.321 | 0.278 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| SK | AGCAAG | 4037.83 | 5128 | 1.270 | 0.239 |
| SK | AGCAAA | 3117.75 | 3736 | 1.198 | 0.181 |
| SK | TCAAAA | 1935.30 | 2282 | 1.179 | 0.165 |
| SK | AGTAAA | 1967.01 | 2149 | 1.093 | 0.088 |
| SK | TCAAAG | 2506.42 | 2082 | 0.831 | -0.186 |
| SK | TCTAAA | 2393.86 | 1838 | 0.768 | -0.264 |
| SK | TCGAAG | 942.46 | 522 | 0.554 | -0.591 |
| SK | AGTAAG | 2547.49 | 1300 | 0.510 | -0.673 |
| SK | TCTAAG | 3100.32 | 1569 | 0.506 | -0.681 |
| SK | TCGAAA | 727.71 | 331 | 0.455 | -0.788 |
| SL | AGTTTA | 709.05 | 1103 | 1.556 | 0.442 |
| SL | TCGCTG | 1355.42 | 2104 | 1.552 | 0.440 |
| SL | TCCTTG | 1666.44 | 2462 | 1.477 | 0.390 |
| SL | TCTTTA | 862.92 | 1267 | 1.468 | 0.384 |
| SL | AGCCTC | 2794.39 | 4013 | 1.436 | 0.362 |
| SL | TCTTTG | 1449.64 | 2009 | 1.386 | 0.326 |
| SL | TCATTA | 697.62 | 862 | 1.236 | 0.212 |
| SL | AGCCTG | 5807.08 | 7014 | 1.208 | 0.189 |
| SL | AGTTTG | 1191.15 | 1427 | 1.198 | 0.181 |
| SL | TCGCTC | 652.23 | 777 | 1.191 | 0.175 |
| SL | TCTCTA | 797.87 | 950 | 1.191 | 0.175 |
| SL | TCTCTT | 1479.47 | 1750 | 1.183 | 0.168 |
| SL | TCCCTG | 5125.62 | 6034 | 1.177 | 0.163 |
| SL | TCCCTC | 2466.46 | 2805 | 1.137 | 0.129 |
| SL | TCCTTA | 991.98 | 1076 | 1.085 | 0.081 |
| SL | AGTCTT | 1215.66 | 1242 | 1.022 | 0.021 |
| SL | AGCCTT | 1926.85 | 1959 | 1.017 | 0.017 |
| SL | TCACTA | 645.03 | 630 | 0.977 | -0.024 |
| SL | AGCTTG | 1888.00 | 1786 | 0.946 | -0.056 |
| SL | TCACTT | 1196.06 | 1111 | 0.929 | -0.074 |
| SL | TCCCTT | 1700.73 | 1545 | 0.908 | -0.096 |
| SL | TCCCTA | 917.19 | 810 | 0.883 | -0.124 |
| SL | AGTCTA | 655.60 | 569 | 0.868 | -0.142 |
| SL | TCATTG | 1171.95 | 1015 | 0.866 | -0.144 |
| SL | AGCCTA | 1039.14 | 875 | 0.842 | -0.172 |
| SL | TCTCTC | 2145.58 | 1760 | 0.820 | -0.198 |
| SL | TCTCTG | 4458.78 | 3418 | 0.767 | -0.266 |
| SL | AGCTTA | 1123.86 | 758 | 0.674 | -0.394 |
| SL | AGTCTC | 1763.00 | 1158 | 0.657 | -0.420 |
| SL | TCGTTG | 440.67 | 280 | 0.635 | -0.454 |
| SL | TCACTC | 1734.58 | 1100 | 0.634 | -0.455 |
| SL | TCACTG | 3604.66 | 2254 | 0.625 | -0.470 |
| SL | TCGCTT | 449.74 | 279 | 0.620 | -0.477 |
| SL | TCGCTA | 242.54 | 143 | 0.590 | -0.528 |
| SL | TCGTTA | 262.32 | 140 | 0.534 | -0.628 |
| SL | AGTCTG | 3663.72 | 1808 | 0.493 | -0.706 |
| SM | TCCATG | 2282.65 | 3908 | 1.712 | 0.538 |
| SM | AGCATG | 2586.13 | 3300 | 1.276 | 0.244 |
| SM | TCAATG | 1605.31 | 1129 | 0.703 | -0.352 |
| SM | TCGATG | 603.62 | 365 | 0.605 | -0.503 |
| SM | AGTATG | 1631.61 | 966 | 0.592 | -0.524 |
| SM | TCTATG | 1985.68 | 1027 | 0.517 | -0.659 |
| SN | AGCAAC | 2539.42 | 3717 | 1.464 | 0.381 |
| SN | TCCAAC | 2241.42 | 3216 | 1.435 | 0.361 |
| SN | TCAAAT | 1431.22 | 1883 | 1.316 | 0.274 |
| SN | AGCAAT | 2305.68 | 2513 | 1.090 | 0.086 |
| SN | TCCAAT | 2035.11 | 2000 | 0.983 | -0.017 |
| SN | AGTAAT | 1454.67 | 1425 | 0.980 | -0.021 |
| SN | AGTAAC | 1602.14 | 1339 | 0.836 | -0.179 |
| SN | TCAAAC | 1576.31 | 1194 | 0.757 | -0.278 |
| SN | TCTAAT | 1770.34 | 1297 | 0.733 | -0.311 |
| SN | TCTAAC | 1949.81 | 955 | 0.490 | -0.714 |
| SN | TCGAAT | 538.16 | 258 | 0.479 | -0.735 |
| SN | TCGAAC | 592.72 | 240 | 0.405 | -0.904 |
| SP | TCGCCG | 282.21 | 549 | 1.945 | 0.665 |
| SP | TCGCCC | 778.87 | 1221 | 1.568 | 0.450 |
| SP | TCCCCG | 1067.21 | 1621 | 1.519 | 0.418 |
| SP | TCTCCA | 2214.76 | 3119 | 1.408 | 0.342 |
| SP | AGCCCC | 3336.96 | 4654 | 1.395 | 0.333 |
| SP | TCTCCT | 2294.78 | 2888 | 1.259 | 0.230 |
| SP | AGCCCG | 1209.10 | 1432 | 1.184 | 0.169 |
| SP | TCCCCA | 2545.99 | 2968 | 1.166 | 0.153 |
| SP | TCACCA | 1790.50 | 1869 | 1.044 | 0.043 |
| SP | AGCCCT | 2988.71 | 3086 | 1.033 | 0.032 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| SP | AGTCCT | 1885.59 | 1904 | 1.010 | 0.010 |
| SP | TCACCT | 1855.20 | 1752 | 0.944 | -0.057 |
| SP | AGCCCA | 2884.48 | 2607 | 0.904 | -0.101 |
| SP | TCCCCT | 2637.98 | 2238 | 0.848 | -0.164 |
| SP | AGTCCA | 1819.84 | 1473 | 0.809 | -0.211 |
| SP | TCGCCT | 697.59 | 562 | 0.806 | -0.216 |
| SP | TCGCCA | 673.26 | 541 | 0.804 | -0.219 |
| SP | TCTCCC | 2562.18 | 2036 | 0.795 | -0.230 |
| SP | TCACCC | 2071.37 | 1568 | 0.757 | -0.278 |
| SP | AGTCCC | 2105.31 | 1534 | 0.729 | -0.317 |
| SP | TCTCCG | 928.37 | 664 | 0.715 | -0.335 |
| SP | TCCCCC | 2945.37 | 2058 | 0.699 | -0.358 |
| SP | TCACCG | 750.53 | 426 | 0.568 | -0.566 |
| SP | AGTCCG | 762.83 | 319 | 0.418 | -0.872 |
| SQ | TCCCAG | 4427.95 | 5592 | 1.263 | 0.233 |
| SQ | AGCCAG | 5016.65 | 6041 | 1.204 | 0.186 |
| SQ | TCTCAA | 1379.40 | 1644 | 1.192 | 0.175 |
| SQ | AGTCAA | 1133.44 | 1293 | 1.141 | 0.132 |
| SQ | TCACAA | 1115.16 | 1196 | 1.072 | 0.070 |
| SQ | AGCCAA | 1796.52 | 1819 | 1.013 | 0.012 |
| SQ | TCCCAA | 1585.70 | 1474 | 0.930 | -0.073 |
| SQ | TCTCAG | 3851.88 | 3430 | 0.890 | -0.116 |
| SQ | TCGCAG | 1170.92 | 1015 | 0.867 | -0.143 |
| SQ | TCACAG | 3114.02 | 2271 | 0.729 | -0.316 |
| SQ | AGTCAG | 3165.04 | 2215 | 0.700 | -0.357 |
| SQ | TCGCAA | 419.32 | 186 | 0.444 | -0.813 |
| SR | AGCCGC | 1540.23 | 2828 | 1.836 | 0.608 |
| SR | TCCAGG | 1472.14 | 2309 | 1.568 | 0.450 |
| SR | AGCCGG | 1684.56 | 2353 | 1.397 | 0.334 |
| SR | TCCCGG | 1486.87 | 1976 | 1.329 | 0.284 |
| SR | AGCAGG | 1667.87 | 2186 | 1.311 | 0.271 |
| SR | AGCCGT | 659.43 | 857 | 1.300 | 0.262 |
| SR | TCGCGC | 359.50 | 446 | 1.241 | 0.216 |
| SR | TCCAGA | 1499.54 | 1850 | 1.234 | 0.210 |
| SR | TCAAGA | 1054.57 | 1294 | 1.227 | 0.205 |
| SR | TCGCGG | 393.19 | 481 | 1.223 | 0.202 |
| SR | TCCCGC | 1359.49 | 1605 | 1.181 | 0.166 |
| SR | TCTCGA | 701.14 | 826 | 1.178 | 0.164 |
| SR | AGTCGT | 416.04 | 484 | 1.163 | 0.151 |
| SR | TCCCGA | 806.00 | 937 | 1.163 | 0.151 |
| SR | AGCAGA | 1698.90 | 1925 | 1.133 | 0.125 |
| SR | AGCCGA | 913.16 | 1020 | 1.117 | 0.111 |
| SR | TCTCGT | 506.32 | 493 | 0.974 | -0.027 |
| SR | AGTCGA | 576.12 | 553 | 0.960 | -0.041 |
| SR | TCCCGT | 582.04 | 553 | 0.950 | -0.051 |
| SR | TCAAGG | 1035.31 | 922 | 0.891 | -0.116 |
| SR | TCGAGG | 389.29 | 324 | 0.832 | -0.184 |
| SR | TCTCGG | 1293.43 | 1062 | 0.821 | -0.197 |
| SR | TCACGT | 409.33 | 323 | 0.789 | -0.237 |
| SR | AGTAGA | 1071.85 | 746 | 0.696 | -0.362 |
| SR | TCGCGT | 153.92 | 102 | 0.663 | -0.411 |
| SR | AGTCGG | 1062.80 | 675 | 0.635 | -0.454 |
| SR | AGTCGC | 971.74 | 591 | 0.608 | -0.497 |
| SR | TCACGA | 566.83 | 344 | 0.607 | -0.499 |
| SR | TCGAGA | 396.54 | 240 | 0.605 | -0.502 |
| SR | TCTAGA | 1304.45 | 750 | 0.575 | -0.553 |
| SR | TCGCGA | 213.14 | 115 | 0.540 | -0.617 |
| SR | TCTCGC | 1182.62 | 636 | 0.538 | -0.620 |
| SR | TCACGG | 1045.66 | 534 | 0.511 | -0.672 |
| SR | TCTAGG | 1280.62 | 574 | 0.448 | -0.802 |
| SR | TCACGC | 956.08 | 406 | 0.425 | -0.856 |
| SR | AGTAGG | 1052.27 | 443 | 0.421 | -0.865 |
| SS | AGCAGC | 3919.72 | 7160 | 1.827 | 0.602 |
| SS | TCGTCG | 213.54 | 376 | 1.761 | 0.566 |
| SS | TCCTCG | 807.53 | 1302 | 1.612 | 0.478 |
| SS | TCCAGC | 3459.74 | 4832 | 1.397 | 0.334 |
| SS | TCTTCA | 1868.19 | 2596 | 1.390 | 0.329 |
| SS | AGCAGT | 2472.97 | 3417 | 1.382 | 0.323 |
| SS | TCCTCC | 3053.74 | 4162 | 1.363 | 0.310 |
| SS | TCTTCT | 2310.85 | 2896 | 1.253 | 0.226 |
| SS | TCCAGT | 2182.77 | 2691 | 1.233 | 0.209 |
| SS | TCATCA | 1510.32 | 1795 | 1.188 | 0.173 |
| SS | AGCTCC | 3459.74 | 4024 | 1.163 | 0.151 |
| SS | TCATCT | 1868.19 | 2118 | 1.134 | 0.126 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| SS | TCCTCA | 2147.58 | 2413 | 1.124 | 0.117 |
| SS | AGCTCG | 914.89 | 1001 | 1.094 | 0.090 |
| SS | TCCTCT | 2656.45 | 2744 | 1.033 | 0.032 |
| SS | TCGTCC | 807.53 | 818 | 1.013 | 0.013 |
| SS | TCTTCC | 2656.45 | 2600 | 0.979 | -0.021 |
| SS | AGTTCT | 1898.79 | 1856 | 0.977 | -0.023 |
| SS | AGTTCA | 1535.06 | 1498 | 0.976 | -0.024 |
| SS | TCAAGT | 1535.06 | 1404 | 0.915 | -0.089 |
| SS | AGCTCA | 2433.11 | 2075 | 0.853 | -0.159 |
| SS | AGCTCT | 3009.63 | 2465 | 0.819 | -0.200 |
| SS | TCTTCG | 702.47 | 556 | 0.791 | -0.234 |
| SS | TCATCC | 2147.58 | 1632 | 0.760 | -0.275 |
| SS | AGTAGT | 1560.21 | 1030 | 0.660 | -0.415 |
| SS | AGTTCC | 2182.77 | 1405 | 0.644 | -0.441 |
| SS | TCGTCT | 702.47 | 434 | 0.618 | -0.482 |
| SS | TCATCG | 567.91 | 343 | 0.604 | -0.504 |
| SS | TCGTCA | 567.91 | 313 | 0.551 | -0.596 |
| SS | TCTAGT | 1898.79 | 957 | 0.504 | -0.685 |
| SS | TCGAGC | 914.89 | 440 | 0.481 | -0.732 |
| SS | AGTAGC | 2472.97 | 1158 | 0.468 | -0.759 |
| SS | TCAAGC | 2433.11 | 1117 | 0.459 | -0.779 |
| SS | TCGAGT | 577.21 | 259 | 0.449 | -0.801 |
| SS | AGTTCG | 577.21 | 251 | 0.435 | -0.833 |
| SS | TCTAGC | 3009.63 | 899 | 0.299 | -1.208 |
| ST | TCCACG | 785.52 | 1434 | 1.826 | 0.602 |
| ST | AGCACC | 2709.18 | 4149 | 1.531 | 0.426 |
| ST | TCCACC | 2391.25 | 3527 | 1.475 | 0.389 |
| ST | AGCACG | 889.95 | 1180 | 1.326 | 0.282 |
| ST | AGCACA | 2193.18 | 2692 | 1.227 | 0.205 |
| ST | TCCACA | 1935.81 | 2329 | 1.203 | 0.185 |
| ST | TCCACT | 1711.89 | 1937 | 1.131 | 0.124 |
| ST | AGCACT | 1939.49 | 2193 | 1.131 | 0.123 |
| ST | TCAACA | 1361.39 | 1485 | 1.091 | 0.087 |
| ST | TCAACT | 1203.91 | 1270 | 1.055 | 0.053 |
| ST | TCTACT | 1489.18 | 1390 | 0.933 | -0.069 |
| ST | TCTACA | 1683.97 | 1461 | 0.868 | -0.142 |
| ST | AGTACT | 1223.64 | 1036 | 0.847 | -0.166 |
| ST | AGTACA | 1383.69 | 1061 | 0.767 | -0.266 |
| ST | TCGACG | 207.72 | 145 | 0.698 | -0.359 |
| ST | TCTACC | 2080.15 | 1218 | 0.586 | -0.535 |
| ST | TCGACC | 632.34 | 365 | 0.577 | -0.550 |
| ST | AGTACC | 1709.24 | 976 | 0.571 | -0.560 |
| ST | TCGACT | 452.69 | 240 | 0.530 | -0.635 |
| ST | TCAACC | 1681.68 | 873 | 0.519 | -0.656 |
| ST | TCAACG | 552.43 | 275 | 0.498 | -0.698 |
| ST | TCGACA | 511.90 | 236 | 0.461 | -0.774 |
| ST | TCTACG | 683.32 | 302 | 0.442 | -0.817 |
| ST | AGTACG | 561.48 | 201 | 0.358 | -1.027 |
| SV | TCGGTG | 935.47 | 1822 | 1.948 | 0.667 |
| SV | TCTGTA | 788.92 | 1398 | 1.772 | 0.572 |
| SV | TCTGTT | 1214.96 | 2136 | 1.758 | 0.564 |
| SV | TCAGTA | 637.79 | 1121 | 1.758 | 0.564 |
| SV | AGTGTT | 998.32 | 1719 | 1.722 | 0.543 |
| SV | TCAGTT | 982.23 | 1591 | 1.620 | 0.482 |
| SV | TCTGTC | 1555.54 | 2367 | 1.522 | 0.420 |
| SV | AGTGTC | 1278.17 | 1943 | 1.520 | 0.419 |
| SV | TCTGTG | 3077.33 | 4672 | 1.518 | 0.418 |
| SV | AGTGTA | 648.24 | 976 | 1.506 | 0.409 |
| SV | TCGGTC | 472.87 | 683 | 1.444 | 0.368 |
| SV | TCAGTG | 2487.84 | 2925 | 1.176 | 0.162 |
| SV | AGTGTG | 2528.60 | 2901 | 1.147 | 0.137 |
| SV | TCAGTC | 1257.56 | 1351 | 1.074 | 0.072 |
| SV | TCGGTA | 239.82 | 231 | 0.963 | -0.037 |
| SV | TCGGTT | 369.33 | 266 | 0.720 | -0.328 |
| SV | AGCGTC | 2025.93 | 1298 | 0.641 | -0.445 |
| SV | TCCGTG | 3537.57 | 2065 | 0.584 | -0.538 |
| SV | AGCGTG | 4007.89 | 2221 | 0.554 | -0.590 |
| SV | TCCGTC | 1788.18 | 829 | 0.464 | -0.769 |
| SV | AGCGTT | 1582.36 | 446 | 0.282 | -1.266 |
| SV | TCCGTA | 906.91 | 239 | 0.264 | -1.334 |
| SV | TCCGTT | 1396.67 | 329 | 0.236 | -1.446 |
| SV | AGCGTA | 1027.48 | 217 | 0.211 | -1.555 |
| SW | TCCTGG | 1756.97 | 2825 | 1.608 | 0.475 |
| SW | AGCTGG | 1990.56 | 2404 | 1.208 | 0.189 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| SW | TCGTGG | 464.61 | 444 | 0.956 | -0.045 |
| SW | TCTTGG | 1528.39 | 1137 | 0.744 | -0.296 |
| SW | TCATGG | 1235.61 | 778 | 0.630 | -0.463 |
| SW | AGTTGG | 1255.86 | 644 | 0.513 | -0.668 |
| SY | TCCTAC | 1871.53 | 3038 | 1.623 | 0.484 |
| SY | AGCTAC | 2120.35 | 2864 | 1.351 | 0.301 |
| SY | TCCTAT | 1520.75 | 1869 | 1.229 | 0.206 |
| SY | AGCTAT | 1722.94 | 1609 | 0.934 | -0.068 |
| SY | AGTTAT | 1087.01 | 1010 | 0.929 | -0.073 |
| SY | AGTTAC | 1337.74 | 1153 | 0.862 | -0.149 |
| SY | TCATAT | 1069.49 | 897 | 0.839 | -0.176 |
| SY | TCTTAT | 1322.91 | 1100 | 0.832 | -0.185 |
| SY | TCTTAC | 1628.04 | 1204 | 0.740 | -0.302 |
| SY | TCGTAC | 494.91 | 304 | 0.614 | -0.487 |
| SY | TCGTAT | 402.15 | 204 | 0.507 | -0.679 |
| SY | TCATAC | 1316.18 | 642 | 0.488 | -0.718 |
| TA | ACGGCG | 348.71 | 734 | 2.105 | 0.744 |
| TA | ACAGCA | 1829.79 | 3283 | 1.794 | 0.585 |
| TA | ACGGCC | 1289.71 | 2090 | 1.621 | 0.483 |
| TA | ACTGCA | 1618.13 | 2557 | 1.580 | 0.458 |
| TA | ACAGCT | 2090.24 | 3295 | 1.576 | 0.455 |
| TA | ACTGCT | 1848.45 | 2764 | 1.495 | 0.402 |
| TA | ACAGCC | 3178.34 | 3912 | 1.231 | 0.208 |
| TA | ACGGCA | 742.49 | 804 | 1.083 | 0.080 |
| TA | ACTGCC | 2810.69 | 3015 | 1.073 | 0.070 |
| TA | ACGGCT | 848.18 | 804 | 0.948 | -0.053 |
| TA | ACAGCG | 859.36 | 803 | 0.934 | -0.068 |
| TA | ACTGCG | 759.96 | 623 | 0.820 | -0.199 |
| TA | ACCGCG | 1061.55 | 584 | 0.550 | -0.598 |
| TA | ACCGCC | 3926.11 | 1648 | 0.420 | -0.868 |
| TA | ACCGCA | 2260.29 | 561 | 0.248 | -1.394 |
| TA | ACCGCT | 2582.01 | 577 | 0.223 | -1.498 |
| TC | ACCTGC | 1892.82 | 3247 | 1.715 | 0.540 |
| TC | ACCTGT | 1594.30 | 1994 | 1.251 | 0.224 |
| TC | ACGTGC | 621.78 | 691 | 1.111 | 0.106 |
| TC | ACGTGT | 523.72 | 484 | 0.924 | -0.079 |
| TC | ACTTGT | 1141.35 | 1033 | 0.905 | -0.100 |
| TC | ACATGT | 1290.64 | 938 | 0.727 | -0.319 |
| TC | ACTTGC | 1355.07 | 815 | 0.601 | -0.508 |
| TC | ACATGC | 1532.31 | 750 | 0.489 | -0.714 |
| TD | ACAGAT | 2415.25 | 4195 | 1.737 | 0.552 |
| TD | ACAGAC | 2728.31 | 3765 | 1.380 | 0.322 |
| TD | ACTGAT | 2135.87 | 2913 | 1.364 | 0.310 |
| TD | ACGGAC | 1107.10 | 1446 | 1.306 | 0.267 |
| TD | ACTGAC | 2412.71 | 2615 | 1.084 | 0.081 |
| TD | ACGGAT | 980.07 | 922 | 0.941 | -0.061 |
| TD | ACCGAC | 3370.20 | 1547 | 0.459 | -0.779 |
| TD | ACCGAT | 2983.49 | 730 | 0.245 | -1.408 |
| TE | ACAGAA | 3127.33 | 5307 | 1.697 | 0.529 |
| TE | ACGGAG | 1697.07 | 2517 | 1.483 | 0.394 |
| TE | ACTGAA | 2765.58 | 4093 | 1.480 | 0.392 |
| TE | ACAGAG | 4182.23 | 5419 | 1.296 | 0.259 |
| TE | ACTGAG | 3698.46 | 4124 | 1.115 | 0.109 |
| TE | ACGGAA | 1269.01 | 1080 | 0.851 | -0.161 |
| TE | ACCGAG | 5166.20 | 2450 | 0.474 | -0.746 |
| TE | ACCGAA | 3863.10 | 779 | 0.202 | -1.601 |
| TF | ACCTTC | 3026.54 | 4955 | 1.637 | 0.493 |
| TF | ACATTT | 2140.61 | 2275 | 1.063 | 0.061 |
| TF | ACTTTT | 1893.00 | 1904 | 1.006 | 0.006 |
| TF | ACCTTT | 2644.23 | 2518 | 0.952 | -0.049 |
| TF | ACTTTC | 2166.69 | 1822 | 0.841 | -0.173 |
| TF | ACGTTT | 868.62 | 650 | 0.748 | -0.290 |
| TF | ACGTTC | 994.21 | 666 | 0.670 | -0.401 |
| TF | ACATTC | 2450.10 | 1394 | 0.569 | -0.564 |
| TG | ACTGGA | 1710.74 | 3660 | 2.139 | 0.761 |
| TG | ACTGGT | 1107.57 | 1887 | 1.704 | 0.533 |
| TG | ACAGGA | 1934.51 | 2970 | 1.535 | 0.429 |
| TG | ACGGGC | 1064.34 | 1583 | 1.487 | 0.397 |
| TG | ACTGGG | 1670.12 | 2322 | 1.390 | 0.330 |
| TG | ACGGGG | 766.35 | 1049 | 1.369 | 0.314 |
| TG | ACAGGT | 1252.44 | 1694 | 1.353 | 0.302 |
| TG | ACAGGG | 1888.57 | 2148 | 1.137 | 0.129 |
| TG | ACTGGC | 2319.53 | 2620 | 1.130 | 0.122 |
| TG | ACAGGC | 2622.93 | 2664 | 1.016 | 0.016 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| TG | ACGGGT | 508.22 | 484 | 0.952 | -0.049 |
| TG | ACGGGA | 784.99 | 710 | 0.904 | -0.100 |
| TG | ACCGGG | 2332.90 | 1093 | 0.469 | -0.758 |
| TG | ACCGGC | 3240.03 | 1373 | 0.424 | -0.859 |
| TG | ACCGGT | 1547.11 | 355 | 0.229 | -1.472 |
| TG | ACCGGA | 2389.65 | 528 | 0.221 | -1.510 |
| TH | ACTCAT | 1054.95 | 1291 | 1.224 | 0.202 |
| TH | ACCCAC | 2032.09 | 2408 | 1.185 | 0.170 |
| TH | ACGCAC | 667.53 | 764 | 1.145 | 0.135 |
| TH | ACACAT | 1192.94 | 1186 | 0.994 | -0.006 |
| TH | ACTCAC | 1454.76 | 1384 | 0.951 | -0.050 |
| TH | ACCCAT | 1473.60 | 1287 | 0.873 | -0.135 |
| TH | ACACAC | 1645.05 | 1383 | 0.841 | -0.174 |
| TH | ACGCAT | 484.07 | 302 | 0.624 | -0.472 |
| TI | ACCATC | 2842.70 | 5915 | 2.081 | 0.733 |
| TI | ACCATT | 2247.97 | 2878 | 1.280 | 0.247 |
| TI | ACAATA | 836.96 | 980 | 1.171 | 0.158 |
| TI | ACCATA | 1033.87 | 1137 | 1.100 | 0.095 |
| TI | ACAATT | 1819.82 | 1579 | 0.868 | -0.142 |
| TI | ACTATA | 740.14 | 642 | 0.867 | -0.142 |
| TI | ACTATT | 1609.31 | 1337 | 0.831 | -0.185 |
| TI | ACGATA | 339.62 | 190 | 0.559 | -0.581 |
| TI | ACGATT | 738.45 | 389 | 0.527 | -0.641 |
| TI | ACGATC | 933.81 | 463 | 0.496 | -0.702 |
| TI | ACTATC | 2035.08 | 942 | 0.463 | -0.770 |
| TI | ACAATC | 2301.27 | 1027 | 0.446 | -0.807 |
| TK | ACCAAG | 3878.56 | 6678 | 1.722 | 0.543 |
| TK | ACCAAA | 2994.77 | 3789 | 1.265 | 0.235 |
| TK | ACAAAA | 2424.38 | 2546 | 1.050 | 0.049 |
| TK | ACAAAG | 3139.84 | 2507 | 0.798 | -0.225 |
| TK | ACTAAA | 2143.95 | 1684 | 0.785 | -0.241 |
| TK | ACGAAG | 1274.09 | 708 | 0.556 | -0.588 |
| TK | ACGAAA | 983.77 | 511 | 0.519 | -0.655 |
| TK | ACTAAG | 2776.65 | 1193 | 0.430 | -0.845 |
| TL | ACGCTG | 1815.48 | 3357 | 1.849 | 0.615 |
| TL | ACTTTA | 765.72 | 1207 | 1.576 | 0.455 |
| TL | ACTTTG | 1286.34 | 1876 | 1.458 | 0.377 |
| TL | ACATTA | 865.87 | 1115 | 1.288 | 0.253 |
| TL | ACCTTG | 1796.82 | 2257 | 1.256 | 0.228 |
| TL | ACTCTA | 707.99 | 876 | 1.237 | 0.213 |
| TL | ACGCTC | 873.61 | 1057 | 1.210 | 0.191 |
| TL | ACCCTC | 2659.44 | 3133 | 1.178 | 0.164 |
| TL | ACCCTG | 5526.65 | 6354 | 1.150 | 0.140 |
| TL | ACTCTT | 1312.81 | 1469 | 1.119 | 0.112 |
| TL | ACACTA | 800.60 | 799 | 0.998 | -0.002 |
| TL | ACGCTA | 324.87 | 307 | 0.945 | -0.057 |
| TL | ACCTTA | 1069.59 | 957 | 0.895 | -0.111 |
| TL | ACACTT | 1484.53 | 1316 | 0.886 | -0.121 |
| TL | ACGTTG | 590.25 | 505 | 0.856 | -0.156 |
| TL | ACATTG | 1454.60 | 1210 | 0.832 | -0.184 |
| TL | ACCCTT | 1833.80 | 1515 | 0.826 | -0.191 |
| TL | ACCCTA | 988.95 | 802 | 0.811 | -0.210 |
| TL | ACTCTG | 3956.51 | 3120 | 0.789 | -0.238 |
| TL | ACGTTA | 351.36 | 262 | 0.746 | -0.293 |
| TL | ACTCTC | 1903.88 | 1391 | 0.731 | -0.314 |
| TL | ACGCTT | 602.39 | 427 | 0.709 | -0.344 |
| TL | ACACTG | 4474.03 | 3013 | 0.673 | -0.395 |
| TL | ACACTC | 2152.92 | 1274 | 0.592 | -0.525 |
| TM | ACCATG | 2733.42 | 4467 | 1.634 | 0.491 |
| TM | ACAATG | 2212.81 | 1641 | 0.742 | -0.299 |
| TM | ACGATG | 897.92 | 655 | 0.729 | -0.315 |
| TM | ACTATG | 1956.85 | 1038 | 0.530 | -0.634 |
| TN | ACCAAC | 2378.62 | 4300 | 1.808 | 0.592 |
| TN | ACAAAT | 1748.34 | 2194 | 1.255 | 0.227 |
| TN | ACCAAT | 2159.68 | 2454 | 1.136 | 0.128 |
| TN | ACAAAC | 1925.59 | 1486 | 0.772 | -0.259 |
| TN | ACTAAT | 1546.11 | 1077 | 0.697 | -0.362 |
| TN | ACGAAT | 709.45 | 336 | 0.474 | -0.747 |
| TN | ACTAAC | 1702.85 | 789 | 0.463 | -0.769 |
| TN | ACGAAC | 781.37 | 316 | 0.404 | -0.905 |
| TP | ACGCCG | 349.03 | 632 | 1.811 | 0.594 |
| TP | ACGCCC | 963.29 | 1491 | 1.548 | 0.437 |
| TP | ACTCCA | 1814.66 | 2359 | 1.300 | 0.262 |
| TP | ACCCCG | 1062.52 | 1331 | 1.253 | 0.225 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| TP | ACTCCT | 1880.23 | 2186 | 1.163 | 0.151 |
| TP | ACACCA | 2052.02 | 2361 | 1.151 | 0.140 |
| TP | ACCCCA | 2534.80 | 2784 | 1.098 | 0.094 |
| TP | ACACCT | 2126.17 | 2104 | 0.990 | −0.010 |
| TP | ACCCCT | 2626.39 | 2415 | 0.920 | −0.084 |
| TP | ACGCCA | 832.67 | 748 | 0.898 | −0.107 |
| TP | ACCCCC | 2932.43 | 2380 | 0.812 | −0.209 |
| TP | ACACCC | 2373.91 | 1922 | 0.810 | −0.211 |
| TP | ACGCCT | 862.76 | 697 | 0.808 | −0.213 |
| TP | ACTCCC | 2099.31 | 1649 | 0.785 | −0.241 |
| TP | ACTCCG | 760.66 | 538 | 0.707 | −0.346 |
| TP | ACACCG | 860.15 | 534 | 0.621 | −0.477 |
| TQ | ACTCAA | 1103.35 | 1368 | 1.240 | 0.215 |
| TQ | ACCCAG | 4303.71 | 5173 | 1.202 | 0.184 |
| TQ | ACGCAG | 1413.75 | 1518 | 1.074 | 0.071 |
| TQ | ACACAA | 1247.67 | 1328 | 1.064 | 0.062 |
| TQ | ACTCAG | 3081.01 | 2839 | 0.921 | −0.082 |
| TQ | ACCCAA | 1541.21 | 1410 | 0.915 | −0.089 |
| TQ | ACACAG | 3484.02 | 2765 | 0.794 | −0.231 |
| TQ | ACGCAA | 506.28 | 280 | 0.553 | −0.592 |
| TR | ACCAGG | 1331.08 | 2049 | 1.539 | 0.431 |
| TR | ACGCGC | 403.79 | 605 | 1.498 | 0.404 |
| TR | ACGCGG | 441.63 | 661 | 1.497 | 0.403 |
| TR | ACTCGA | 521.72 | 717 | 1.374 | 0.318 |
| TR | ACAAGA | 1097.61 | 1429 | 1.302 | 0.264 |
| TR | ACCCGC | 1229.22 | 1547 | 1.259 | 0.230 |
| TR | ACCCGG | 1344.40 | 1668 | 1.241 | 0.216 |
| TR | ACTCGT | 376.76 | 448 | 1.189 | 0.173 |
| TR | ACCAGA | 1355.85 | 1599 | 1.179 | 0.165 |
| TR | ACCCGA | 728.77 | 758 | 1.040 | 0.039 |
| TR | ACCCGT | 526.27 | 535 | 1.017 | 0.016 |
| TR | ACAAGG | 1077.56 | 1072 | 0.995 | −0.005 |
| TR | ACGAGG | 437.25 | 433 | 0.990 | −0.010 |
| TR | ACTCGG | 962.45 | 823 | 0.855 | −0.157 |
| TR | ACGCGT | 172.88 | 141 | 0.816 | −0.204 |
| TR | ACACGT | 426.04 | 329 | 0.772 | −0.258 |
| TR | ACGAGA | 445.39 | 331 | 0.743 | −0.297 |
| TR | ACACGA | 589.97 | 432 | 0.732 | −0.312 |
| TR | ACACGG | 1088.34 | 756 | 0.695 | −0.364 |
| TR | ACTCGC | 879.99 | 607 | 0.690 | −0.371 |
| TR | ACTAGA | 970.65 | 624 | 0.643 | −0.442 |
| TR | ACGCGA | 239.40 | 150 | 0.627 | −0.468 |
| TR | ACACGC | 995.10 | 498 | 0.500 | −0.692 |
| TR | ACTAGG | 952.91 | 383 | 0.402 | −0.911 |
| TS | ACCAGC | 2807.29 | 4575 | 1.630 | 0.488 |
| TS | ACCTCG | 655.24 | 1060 | 1.618 | 0.481 |
| TS | ACGTCG | 215.24 | 348 | 1.617 | 0.480 |
| TS | ACTTCA | 1247.51 | 1844 | 1.478 | 0.391 |
| TS | ACTTCT | 1543.11 | 1974 | 1.279 | 0.246 |
| TS | ACATCA | 1410.69 | 1754 | 1.243 | 0.218 |
| TS | ACCAGT | 1771.14 | 2194 | 1.239 | 0.214 |
| TS | ACCTCC | 2477.85 | 3050 | 1.231 | 0.208 |
| TS | ACCTCA | 1742.59 | 1938 | 1.112 | 0.106 |
| TS | ACATCT | 1744.95 | 1911 | 1.095 | 0.091 |
| TS | ACGTCC | 813.96 | 840 | 1.032 | 0.031 |
| TS | ACCTCT | 2155.49 | 2072 | 0.961 | −0.040 |
| TS | ACAAGT | 1433.80 | 1335 | 0.931 | −0.071 |
| TS | ACTTCC | 1773.89 | 1524 | 0.859 | −0.152 |
| TS | ACGTCA | 572.43 | 450 | 0.786 | −0.241 |
| TS | ACATCC | 2005.92 | 1570 | 0.783 | −0.245 |
| TS | ACTTCG | 469.09 | 353 | 0.753 | −0.284 |
| TS | ACGTCT | 708.07 | 527 | 0.744 | −0.295 |
| TS | ACATCG | 530.44 | 361 | 0.681 | −0.385 |
| TS | ACTAGT | 1267.95 | 725 | 0.572 | −0.559 |
| TS | ACAAGC | 2272.61 | 1275 | 0.561 | −0.578 |
| TS | ACGAGT | 581.81 | 297 | 0.510 | −0.672 |
| TS | ACGAGC | 922.18 | 469 | 0.509 | −0.676 |
| TS | ACTAGC | 2009.73 | 687 | 0.342 | −1.073 |
| TT | ACCACG | 875.88 | 1567 | 1.789 | 0.582 |
| TT | ACCACC | 2666.32 | 4767 | 1.788 | 0.581 |
| TT | ACCACA | 2158.49 | 2882 | 1.335 | 0.289 |
| TT | ACCACT | 1908.81 | 2309 | 1.210 | 0.190 |
| TT | ACAACA | 1747.38 | 1793 | 1.026 | 0.026 |
| TT | ACAACT | 1545.26 | 1567 | 1.014 | 0.014 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| TT | ACGACG | 287.72 | 252 | 0.876 | -0.133 |
| TT | ACTACT | 1366.51 | 1065 | 0.779 | -0.249 |
| TT | ACTACA | 1545.26 | 1196 | 0.774 | -0.256 |
| TT | ACGACC | 875.88 | 575 | 0.656 | -0.421 |
| TT | ACGACA | 709.06 | 437 | 0.616 | -0.484 |
| TT | ACAACC | 2158.49 | 1310 | 0.607 | -0.499 |
| TT | ACGACT | 627.04 | 357 | 0.569 | -0.563 |
| TT | ACTACC | 1908.81 | 992 | 0.520 | -0.655 |
| TT | ACAACG | 709.06 | 365 | 0.515 | -0.664 |
| TT | ACTACG | 627.04 | 283 | 0.451 | -0.796 |
| TV | ACTGTA | 845.20 | 1425 | 1.686 | 0.522 |
| TV | ACTGTT | 1301.64 | 2058 | 1.581 | 0.458 |
| TV | ACGGTG | 1512.80 | 2306 | 1.524 | 0.422 |
| TV | ACAGTA | 955.76 | 1371 | 1.434 | 0.361 |
| TV | ACTGTC | 1666.51 | 2289 | 1.374 | 0.317 |
| TV | ACAGTT | 1471.90 | 2019 | 1.372 | 0.316 |
| TV | ACTGTG | 3296.87 | 4505 | 1.366 | 0.312 |
| TV | ACGGTC | 764.70 | 911 | 1.191 | 0.175 |
| TV | ACAGTG | 3728.11 | 4108 | 1.102 | 0.097 |
| TV | ACAGTC | 1884.50 | 1933 | 1.026 | 0.025 |
| TV | ACGGTA | 387.83 | 286 | 0.737 | -0.305 |
| TV | ACGGTT | 597.27 | 415 | 0.695 | -0.364 |
| TV | ACCGTG | 4605.23 | 2640 | 0.573 | -0.556 |
| TV | ACCGTC | 2327.87 | 1285 | 0.552 | -0.594 |
| TV | ACCGTT | 1818.19 | 496 | 0.273 | -1.299 |
| TV | ACCGTA | 1180.62 | 298 | 0.252 | -1.377 |
| TW | ACGTGG | 606.25 | 837 | 1.381 | 0.323 |
| TW | ACCTGG | 1845.52 | 2403 | 1.302 | 0.264 |
| TW | ACATGG | 1494.02 | 1089 | 0.729 | -0.316 |
| TW | ACTTGG | 1321.21 | 938 | 0.710 | -0.343 |
| TY | ACCTAC | 2130.11 | 3648 | 1.713 | 0.538 |
| TY | ACCTAT | 1730.88 | 1778 | 1.027 | 0.027 |
| TY | ACTTAC | 1524.94 | 1383 | 0.907 | -0.098 |
| TY | ACGTAC | 699.73 | 621 | 0.887 | -0.119 |
| TY | ACATAT | 1401.21 | 1136 | 0.811 | -0.210 |
| TY | ACTTAT | 1239.13 | 907 | 0.732 | -0.312 |
| TY | ACGTAT | 568.59 | 408 | 0.718 | -0.332 |
| TY | ACATAC | 1724.41 | 1138 | 0.660 | -0.416 |
| VA | GTGGCC | 6082.92 | 9316 | 1.532 | 0.426 |
| VA | GTAGCA | 897.78 | 1347 | 1.500 | 0.406 |
| VA | GTTGCT | 1579.41 | 2217 | 1.404 | 0.339 |
| VA | GTAGCT | 1025.57 | 1407 | 1.372 | 0.316 |
| VA | GTGGCT | 4000.44 | 5252 | 1.313 | 0.272 |
| VA | GTGGCG | 1644.71 | 2099 | 1.276 | 0.244 |
| VA | GTTGCA | 1382.62 | 1728 | 1.250 | 0.223 |
| VA | GTGGCA | 3501.98 | 3859 | 1.102 | 0.097 |
| VA | GTAGCC | 1559.44 | 1363 | 0.874 | -0.135 |
| VA | GTTGCC | 2401.60 | 1808 | 0.753 | -0.284 |
| VA | GTAGCG | 421.64 | 216 | 0.512 | -0.669 |
| VA | GTTGCG | 649.35 | 234 | 0.360 | -1.021 |
| VA | GTCGCG | 831.37 | 284 | 0.342 | -1.074 |
| VA | GTCGCC | 3074.82 | 992 | 0.323 | -1.131 |
| VA | GTCGCT | 2022.16 | 406 | 0.201 | -1.606 |
| VA | GTCGCA | 1770.19 | 318 | 0.180 | -1.717 |
| VC | GTCTGC | 1410.66 | 2160 | 1.531 | 0.426 |
| VC | GTCTGT | 1188.18 | 1572 | 1.323 | 0.280 |
| VC | GTTTGT | 928.03 | 942 | 1.015 | 0.015 |
| VC | GTATGT | 602.60 | 594 | 0.986 | -0.014 |
| VC | GTGTGC | 2790.71 | 2583 | 0.926 | -0.077 |
| VC | GTGTGT | 2350.57 | 1996 | 0.849 | -0.164 |
| VC | GTTTGC | 1101.80 | 830 | 0.753 | -0.283 |
| VC | GTATGC | 715.44 | 411 | 0.574 | -0.554 |
| VD | GTAGAT | 1225.65 | 1924 | 1.570 | 0.451 |
| VD | GTGGAC | 5400.58 | 7734 | 1.432 | 0.359 |
| VD | GTTGAT | 1887.55 | 2389 | 1.266 | 0.236 |
| VD | GTGGAT | 4780.91 | 5727 | 1.198 | 0.181 |
| VD | GTAGAC | 1384.52 | 1346 | 0.972 | -0.028 |
| VD | GTTGAC | 2132.21 | 1791 | 0.840 | -0.174 |
| VD | GTCGAC | 2729.91 | 602 | 0.221 | -1.512 |
| VD | GTCGAT | 2416.67 | 445 | 0.184 | -1.692 |
| VE | GTAGAA | 1456.83 | 2855 | 1.960 | 0.673 |
| VE | GTGGAG | 7599.48 | 11579 | 1.524 | 0.421 |
| VE | GTTGAA | 2243.56 | 2905 | 1.295 | 0.258 |
| VE | GTGGAA | 5682.64 | 6229 | 1.096 | 0.092 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| VE | GTAGAG | 1948.24 | 2002 | 1.028 | 0.027 |
| VE | GTTGAG | 3000.36 | 1987 | 0.662 | -0.412 |
| VE | GTCGAG | 3841.42 | 721 | 0.188 | -1.673 |
| VE | GTCGAA | 2872.48 | 367 | 0.128 | -2.058 |
| VF | GTCTTC | 2309.08 | 4216 | 1.826 | 0.602 |
| VF | GTATTT | 1023.16 | 1512 | 1.478 | 0.391 |
| VF | GTCTTT | 2017.40 | 2238 | 1.109 | 0.104 |
| VF | GTTTTT | 1575.70 | 1706 | 1.083 | 0.079 |
| VF | GTTTTC | 1803.52 | 1604 | 0.889 | -0.117 |
| VF | GTGTTT | 3991.02 | 3257 | 0.816 | -0.203 |
| VF | GTGTTC | 4568.05 | 3205 | 0.702 | -0.354 |
| VF | GTATTC | 1171.09 | 721 | 0.616 | -0.485 |
| VG | GTTGGT | 779.74 | 1617 | 2.074 | 0.729 |
| VG | GTTGGA | 1204.37 | 2315 | 1.922 | 0.653 |
| VG | GTGGGC | 4136.07 | 5977 | 1.445 | 0.368 |
| VG | GTAGGA | 782.04 | 1089 | 1.393 | 0.331 |
| VG | GTTGGG | 1175.77 | 1510 | 1.284 | 0.250 |
| VG | GTTGGC | 1632.96 | 1794 | 1.099 | 0.094 |
| VG | GTAGGT | 506.31 | 554 | 1.094 | 0.090 |
| VG | GTGGGG | 2978.07 | 3255 | 1.093 | 0.089 |
| VG | GTGGGT | 1974.96 | 2009 | 1.017 | 0.017 |
| VG | GTAGGG | 763.47 | 683 | 0.895 | -0.111 |
| VG | GTGGGA | 3050.51 | 2599 | 0.852 | -0.160 |
| VG | GTAGGC | 1060.34 | 676 | 0.638 | -0.450 |
| VG | GTCGGG | 1505.36 | 734 | 0.488 | -0.718 |
| VG | GTCGGC | 2090.72 | 734 | 0.351 | -1.047 |
| VG | GTCGGT | 998.31 | 292 | 0.292 | -1.229 |
| VG | GTCGGA | 1541.98 | 343 | 0.222 | -1.503 |
| VH | GTTCAT | 911.79 | 1418 | 1.555 | 0.442 |
| VH | GTACAT | 592.06 | 773 | 1.306 | 0.267 |
| VH | GTCCAC | 1609.82 | 2085 | 1.295 | 0.259 |
| VH | GTCCAT | 1167.39 | 1313 | 1.125 | 0.118 |
| VH | GTTCAC | 1257.35 | 1319 | 1.049 | 0.048 |
| VH | GTGCAC | 3184.70 | 2856 | 0.897 | -0.109 |
| VH | GTACAC | 816.44 | 613 | 0.751 | -0.287 |
| VH | GTGCAT | 2309.44 | 1472 | 0.637 | -0.450 |
| VI | GTCATC | 2367.78 | 5207 | 2.199 | 0.788 |
| VI | GTCATT | 1872.41 | 2827 | 1.510 | 0.412 |
| VI | GTAATA | 436.74 | 614 | 1.406 | 0.341 |
| VI | GTAATT | 949.63 | 1074 | 1.131 | 0.123 |
| VI | GTTATT | 1462.46 | 1595 | 1.091 | 0.087 |
| VI | GTCATA | 861.15 | 904 | 1.050 | 0.049 |
| VI | GTTATA | 672.60 | 702 | 1.044 | 0.043 |
| VI | GTGATT | 3704.20 | 2742 | 0.740 | -0.301 |
| VI | GTGATC | 4684.19 | 3353 | 0.716 | -0.334 |
| VI | GTGATA | 1703.61 | 1117 | 0.656 | -0.422 |
| VI | GTTATC | 1849.37 | 1053 | 0.569 | -0.563 |
| VI | GTAATC | 1200.86 | 577 | 0.480 | -0.733 |
| VK | GTAAAA | 1288.46 | 1945 | 1.510 | 0.412 |
| VK | GTCAAG | 3290.24 | 3982 | 1.210 | 0.191 |
| VK | GTGAAG | 6509.08 | 7513 | 1.154 | 0.143 |
| VK | GTAAAG | 1668.70 | 1704 | 1.021 | 0.021 |
| VK | GTCAAA | 2540.51 | 2376 | 0.935 | -0.067 |
| VK | GTTAAA | 1984.27 | 1777 | 0.896 | -0.110 |
| VK | GTGAAA | 5025.89 | 4409 | 0.877 | -0.131 |
| VK | GTTAAG | 2569.85 | 1171 | 0.456 | -0.786 |
| VL | GTTTTA | 668.83 | 1311 | 1.960 | 0.673 |
| VL | GTTCTT | 1146.70 | 1859 | 1.621 | 0.483 |
| VL | GTTTTG | 1123.58 | 1737 | 1.546 | 0.436 |
| VL | GTATTA | 434.30 | 646 | 1.487 | 0.397 |
| VL | GTCCTC | 2129.16 | 3019 | 1.418 | 0.349 |
| VL | GTTCTA | 618.41 | 832 | 1.345 | 0.297 |
| VL | GTCCTG | 4424.65 | 5574 | 1.260 | 0.231 |
| VL | GTCCTT | 1468.14 | 1722 | 1.173 | 0.159 |
| VL | GTGCTG | 8753.31 | 10107 | 1.155 | 0.144 |
| VL | GTCTTG | 1438.54 | 1628 | 1.132 | 0.124 |
| VL | GTACTA | 401.55 | 447 | 1.113 | 0.107 |
| VL | GTCCTA | 791.76 | 874 | 1.104 | 0.099 |
| VL | GTCTTA | 856.32 | 863 | 1.008 | 0.008 |
| VL | GTATTG | 729.58 | 711 | 0.975 | -0.026 |
| VL | GTACTT | 744.59 | 693 | 0.931 | -0.072 |
| VL | GTTCTC | 1662.99 | 1501 | 0.903 | -0.102 |
| VL | GTGCTC | 4212.12 | 3765 | 0.894 | -0.112 |
| VL | GTGCTA | 1566.34 | 1286 | 0.821 | -0.197 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| VL | GTTCTG | 3455.90 | 2350 | 0.680 | -0.386 |
| VL | GTGTTG | 2845.87 | 1910 | 0.671 | -0.399 |
| VL | GTGCTT | 2904.43 | 1933 | 0.666 | -0.407 |
| VL | GTGTTA | 1694.06 | 965 | 0.570 | -0.563 |
| VL | GTACTC | 1079.84 | 541 | 0.501 | -0.691 |
| VL | GTACTG | 2244.04 | 1121 | 0.500 | -0.694 |
| VM | GTCATG | 2149.52 | 3308 | 1.539 | 0.431 |
| VM | GTGATG | 4252.41 | 3872 | 0.911 | -0.094 |
| VM | GTAATG | 1090.17 | 935 | 0.858 | -0.154 |
| VM | GTTATG | 1678.90 | 1056 | 0.629 | -0.464 |
| VN | GTCAAC | 2052.00 | 3311 | 1.614 | 0.478 |
| VN | GTAAAT | 944.92 | 1518 | 1.606 | 0.474 |
| VN | GTCAAT | 1863.13 | 2155 | 1.157 | 0.146 |
| VN | GTTAAT | 1455.20 | 1325 | 0.911 | -0.094 |
| VN | GTGAAC | 4059.49 | 3551 | 0.875 | -0.134 |
| VN | GTGAAT | 3685.83 | 3110 | 0.844 | -0.170 |
| VN | GTAAAC | 1040.71 | 854 | 0.821 | -0.198 |
| VN | GTTAAC | 1602.73 | 880 | 0.549 | -0.600 |
| VP | GTTCCT | 1434.04 | 2257 | 1.574 | 0.454 |
| VP | GTTCCA | 1384.03 | 1911 | 1.381 | 0.323 |
| VP | GTGCCC | 4055.45 | 4998 | 1.232 | 0.209 |
| VP | GTACCT | 931.17 | 1048 | 1.125 | 0.118 |
| VP | GTCCCC | 2049.96 | 2260 | 1.102 | 0.098 |
| VP | GTCCCT | 1836.02 | 2014 | 1.097 | 0.093 |
| VP | GTACCA | 898.70 | 963 | 1.072 | 0.069 |
| VP | GTCCCG | 742.77 | 786 | 1.058 | 0.057 |
| VP | GTTCCC | 1601.13 | 1506 | 0.941 | -0.061 |
| VP | GTCCCA | 1772.00 | 1596 | 0.901 | -0.105 |
| VP | GTGCCT | 3632.21 | 3062 | 0.843 | -0.171 |
| VP | GTGCCG | 1469.43 | 1228 | 0.836 | -0.179 |
| VP | GTACCC | 1039.67 | 809 | 0.778 | -0.251 |
| VP | GTGCCA | 3505.55 | 2431 | 0.693 | -0.366 |
| VP | GTTCCG | 580.15 | 279 | 0.481 | -0.732 |
| VP | GTACCG | 376.71 | 161 | 0.427 | -0.850 |
| VQ | GTACAA | 633.37 | 1049 | 1.656 | 0.505 |
| VQ | GTTCAA | 975.42 | 1485 | 1.522 | 0.420 |
| VQ | GTCCAG | 3487.32 | 3907 | 1.120 | 0.114 |
| VQ | GTACAG | 1768.65 | 1752 | 0.991 | -0.009 |
| VQ | GTTCAG | 2723.79 | 2689 | 0.987 | -0.013 |
| VQ | GTGCAG | 6898.98 | 6734 | 0.976 | -0.024 |
| VQ | GTCCAA | 1248.85 | 1067 | 0.854 | -0.157 |
| VQ | GTGCAA | 2470.60 | 1524 | 0.617 | -0.483 |
| VR | GTTCGA | 463.33 | 867 | 1.871 | 0.627 |
| VR | GTTCGT | 334.59 | 580 | 1.733 | 0.550 |
| VR | GTCCGA | 593.21 | 805 | 1.357 | 0.305 |
| VR | GTCCGC | 1000.57 | 1332 | 1.331 | 0.286 |
| VR | GTGCGC | 1979.43 | 2543 | 1.285 | 0.251 |
| VR | GTCCGT | 428.38 | 549 | 1.282 | 0.248 |
| VR | GTCCGG | 1094.32 | 1346 | 1.230 | 0.207 |
| VR | GTACGA | 300.86 | 361 | 1.200 | 0.182 |
| VR | GTAAGA | 559.73 | 660 | 1.179 | 0.165 |
| VR | GTGCGG | 2164.91 | 2552 | 1.179 | 0.164 |
| VR | GTCAGA | 1103.65 | 1291 | 1.170 | 0.157 |
| VR | GTACGT | 217.26 | 253 | 1.165 | 0.152 |
| VR | GTCAGG | 1083.48 | 1238 | 1.143 | 0.133 |
| VR | GTGAGG | 2143.46 | 1986 | 0.927 | -0.076 |
| VR | GTGCGT | 847.46 | 761 | 0.898 | -0.108 |
| VR | GTAAGG | 549.51 | 444 | 0.808 | -0.213 |
| VR | GTTCGG | 854.73 | 650 | 0.760 | -0.274 |
| VR | GTGCGA | 1173.55 | 826 | 0.704 | -0.351 |
| VR | GTTCGC | 781.50 | 545 | 0.697 | -0.360 |
| VR | GTGAGA | 2183.35 | 1511 | 0.692 | -0.368 |
| VR | GTACGG | 555.00 | 377 | 0.679 | -0.387 |
| VR | GTTAGA | 862.01 | 556 | 0.645 | -0.438 |
| VR | GTACGC | 507.46 | 286 | 0.564 | -0.573 |
| VR | GTTAGG | 846.26 | 309 | 0.365 | -1.007 |
| VS | GTTTCT | 1206.81 | 2161 | 1.791 | 0.583 |
| VS | GTCTCC | 1776.18 | 2936 | 1.653 | 0.503 |
| VS | GTCAGC | 2012.32 | 3223 | 1.602 | 0.471 |
| VS | GTTTCA | 975.63 | 1465 | 1.502 | 0.407 |
| VS | GTCAGT | 1269.59 | 1841 | 1.450 | 0.372 |
| VS | GTATCT | 783.62 | 1093 | 1.395 | 0.333 |
| VS | GTATCA | 633.51 | 806 | 1.272 | 0.241 |
| VS | GTCTCT | 1545.10 | 1847 | 1.195 | 0.178 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| VS | GTTTCC | 1387.29 | 1604 | 1.156 | 0.145 |
| VS | GTCTCG | 469.69 | 542 | 1.154 | 0.143 |
| VS | GTCTCA | 1249.12 | 1333 | 1.067 | 0.065 |
| VS | GTGTCC | 3513.81 | 3722 | 1.059 | 0.058 |
| VS | GTGTCG | 929.19 | 860 | 0.926 | -0.077 |
| VS | GTGTCT | 3056.67 | 2784 | 0.911 | -0.093 |
| VS | GTATCC | 900.82 | 763 | 0.847 | -0.166 |
| VS | GTAAGT | 643.89 | 499 | 0.775 | -0.255 |
| VS | GTGAGC | 3980.98 | 2901 | 0.729 | -0.316 |
| VS | GTGTCA | 2471.14 | 1710 | 0.692 | -0.368 |
| VS | GTTAGT | 991.62 | 640 | 0.645 | -0.438 |
| VS | GTATCG | 238.21 | 138 | 0.579 | -0.546 |
| VS | GTTTCG | 366.85 | 202 | 0.551 | -0.597 |
| VS | GTGAGT | 2511.63 | 1371 | 0.546 | -0.605 |
| VS | GTAAGC | 1020.58 | 514 | 0.504 | -0.686 |
| VS | GTTAGC | 1571.73 | 551 | 0.351 | -1.048 |
| VT | GTCACC | 2294.69 | 4477 | 1.951 | 0.668 |
| VT | GTCACT | 1642.76 | 2452 | 1.493 | 0.401 |
| VT | GTCACG | 753.80 | 997 | 1.323 | 0.280 |
| VT | GTAACT | 833.15 | 1046 | 1.255 | 0.228 |
| VT | GTCACA | 1857.64 | 2207 | 1.188 | 0.172 |
| VT | GTAACA | 942.13 | 1096 | 1.163 | 0.151 |
| VT | GTTACT | 1283.09 | 1208 | 0.941 | -0.060 |
| VT | GTGACC | 4539.59 | 4223 | 0.930 | -0.072 |
| VT | GTGACG | 1491.24 | 1318 | 0.884 | -0.123 |
| VT | GTGACT | 3249.88 | 2758 | 0.849 | -0.164 |
| VT | GTGACA | 3674.98 | 2947 | 0.802 | -0.221 |
| VT | GTTACA | 1450.92 | 1111 | 0.766 | -0.267 |
| VT | GTAACC | 1163.79 | 758 | 0.651 | -0.429 |
| VT | GTTACC | 1792.28 | 969 | 0.541 | -0.615 |
| VT | GTAACG | 382.30 | 191 | 0.500 | -0.694 |
| VT | GTTACG | 588.76 | 183 | 0.311 | -1.169 |
| VV | GTTGTA | 655.54 | 1109 | 1.692 | 0.526 |
| VV | GTTGTT | 1009.55 | 1701 | 1.685 | 0.522 |
| VV | GTAGTA | 425.66 | 698 | 1.640 | 0.495 |
| VV | GTGGTG | 6476.64 | 9025 | 1.393 | 0.332 |
| VV | GTGGTC | 3273.84 | 4256 | 1.300 | 0.262 |
| VV | GTAGTT | 655.54 | 800 | 1.220 | 0.199 |
| VV | GTTGTC | 1292.55 | 1561 | 1.208 | 0.189 |
| VV | GTGGTA | 1660.38 | 1777 | 1.070 | 0.068 |
| VV | GTGGTT | 2557.05 | 2613 | 1.022 | 0.022 |
| VV | GTTGTG | 2557.05 | 2261 | 0.884 | -0.123 |
| VV | GTAGTG | 1660.38 | 1161 | 0.699 | -0.358 |
| VV | GTAGTC | 839.30 | 553 | 0.659 | -0.417 |
| VV | GTCGTC | 1654.87 | 858 | 0.518 | -0.657 |
| VV | GTCGTG | 3273.84 | 1250 | 0.382 | -0.963 |
| VV | GTCGTA | 839.30 | 213 | 0.254 | -1.371 |
| VV | GTCGTT | 1292.55 | 288 | 0.223 | -1.501 |
| VW | GTCTGG | 1316.29 | 1763 | 1.339 | 0.292 |
| VW | GTGTGG | 2604.03 | 2451 | 0.941 | -0.061 |
| VW | GTATGG | 667.58 | 578 | 0.866 | -0.144 |
| VW | GTTTGG | 1028.10 | 824 | 0.801 | -0.221 |
| VY | GTCTAC | 1602.79 | 2490 | 1.554 | 0.441 |
| VY | GTTTAT | 1017.23 | 1438 | 1.414 | 0.346 |
| VY | GTATAT | 660.53 | 875 | 1.325 | 0.281 |
| VY | GTCTAT | 1302.39 | 1544 | 1.186 | 0.170 |
| VY | GTGTAC | 3170.80 | 2654 | 0.837 | -0.178 |
| VY | GTTTAC | 1251.87 | 1008 | 0.805 | -0.217 |
| VY | GTATAC | 812.88 | 582 | 0.716 | -0.334 |
| VY | GTGTAT | 2576.51 | 1804 | 0.700 | -0.356 |
| WA | TGGGCA | 1469.77 | 1535 | 1.044 | 0.043 |
| WA | TGGGCG | 690.28 | 695 | 1.007 | 0.007 |
| WA | TGGGCT | 1678.97 | 1664 | 0.991 | -0.009 |
| WA | TGGGCC | 2552.98 | 2498 | 0.978 | -0.022 |
| WC | TGGTGC | 1057.38 | 1066 | 1.008 | 0.008 |
| WC | TGGTGT | 890.62 | 882 | 0.990 | -0.010 |
| WD | TGGGAC | 2699.37 | 2807 | 1.040 | 0.039 |
| WD | TGGGAT | 2389.63 | 2282 | 0.955 | -0.046 |
| WE | TGGGAG | 3580.00 | 3650 | 1.020 | 0.019 |
| WE | TGGGAA | 2677.00 | 2607 | 0.974 | -0.026 |
| WF | TGGTTT | 1639.95 | 1735 | 1.058 | 0.056 |
| WF | TGGTTC | 1877.05 | 1782 | 0.949 | -0.052 |
| WG | TGGGGT | 955.95 | 1064 | 1.113 | 0.107 |
| WG | TGGGGC | 2002.00 | 2179 | 1.088 | 0.085 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| WG | TGGGGA | 1476.56 | 1454 | 0.985 | -0.015 |
| WG | TGGGGG | 1441.49 | 1179 | 0.818 | -0.201 |
| WH | TGGCAT | 971.42 | 1000 | 1.029 | 0.029 |
| WH | TGGCAC | 1339.58 | 1311 | 0.979 | -0.022 |
| WI | TGGATT | 1537.91 | 1627 | 1.058 | 0.056 |
| WI | TGGATA | 707.30 | 714 | 1.009 | 0.009 |
| WI | TGGATC | 1944.78 | 1849 | 0.951 | -0.051 |
| WK | TGGAAG | 3491.83 | 3645 | 1.044 | 0.043 |
| WK | TGGAAA | 2696.17 | 2543 | 0.943 | -0.058 |
| WL | TGGCTA | 683.88 | 798 | 1.167 | 0.154 |
| WL | TGGCTG | 3821.78 | 4228 | 1.106 | 0.101 |
| WL | TGGCTT | 1268.11 | 1334 | 1.052 | 0.051 |
| WL | TGGCTC | 1839.05 | 1879 | 1.022 | 0.021 |
| WL | TGGTTG | 1242.54 | 855 | 0.688 | -0.374 |
| WL | TGGTTA | 739.64 | 501 | 0.677 | -0.390 |
| WM | TGGATG | 2335.00 | 2335 | 1.000 | 0.000 |
| WN | TGGAAT | 1978.70 | 2005 | 1.013 | 0.013 |
| WN | TGGAAC | 2179.30 | 2153 | 0.988 | -0.012 |
| WP | TGGCCC | 1302.21 | 1381 | 1.061 | 0.059 |
| WP | TGGCCG | 471.84 | 486 | 1.030 | 0.030 |
| WP | TGGCCA | 1125.64 | 1123 | 0.998 | -0.002 |
| WP | TGGCCT | 1166.31 | 1076 | 0.923 | -0.081 |
| WQ | TGGCAG | 2983.56 | 2997 | 1.005 | 0.004 |
| WQ | TGGCAA | 1068.44 | 1055 | 0.987 | -0.013 |
| WR | TGGAGG | 1198.99 | 1665 | 1.389 | 0.328 |
| WR | TGGAGA | 1221.30 | 1472 | 1.205 | 0.187 |
| WR | TGGCGG | 1210.98 | 979 | 0.808 | -0.213 |
| WR | TGGCGC | 1107.23 | 895 | 0.808 | -0.213 |
| WR | TGGCGT | 474.05 | 377 | 0.795 | -0.229 |
| WR | TGGCGA | 656.45 | 481 | 0.733 | -0.311 |
| WS | TGGAGT | 1031.75 | 1239 | 1.201 | 0.183 |
| WS | TGGAGC | 1635.35 | 1956 | 1.196 | 0.179 |
| WS | TGGTCA | 1015.12 | 898 | 0.885 | -0.123 |
| WS | TGGTCC | 1443.44 | 1271 | 0.881 | -0.127 |
| WS | TGGTCT | 1255.65 | 1076 | 0.857 | -0.154 |
| WS | TGGTCG | 381.70 | 323 | 0.846 | -0.167 |
| WT | TGGACG | 598.07 | 674 | 1.127 | 0.120 |
| WT | TGGACA | 1473.88 | 1559 | 1.058 | 0.056 |
| WT | TGGACT | 1303.39 | 1240 | 0.951 | -0.050 |
| WT | TGGACC | 1820.65 | 1723 | 0.946 | -0.055 |
| WV | TGGGTC | 1318.64 | 1378 | 1.045 | 0.044 |
| WV | TGGGTG | 2608.66 | 2633 | 1.009 | 0.009 |
| WV | TGGGTA | 668.77 | 665 | 0.994 | -0.006 |
| WV | TGGGTT | 1029.93 | 950 | 0.922 | -0.081 |
| WW | TGGTGG | 1559.00 | 1559 | 1.000 | 0.000 |
| WY | TGGTAC | 1444.91 | 1520 | 1.052 | 0.051 |
| WY | TGGTAT | 1174.09 | 1099 | 0.936 | -0.066 |
| YA | TATGCA | 1120.39 | 2249 | 2.007 | 0.697 |
| YA | TATGCT | 1279.86 | 2296 | 1.794 | 0.584 |
| YA | TATGCC | 1946.11 | 2862 | 1.471 | 0.386 |
| YA | TACGCG | 647.56 | 622 | 0.961 | -0.040 |
| YA | TATGCG | 526.19 | 482 | 0.916 | -0.088 |
| YA | TACGCC | 2395.00 | 1402 | 0.585 | -0.535 |
| YA | TACGCA | 1378.81 | 512 | 0.371 | -0.991 |
| YA | TACGCT | 1575.07 | 444 | 0.282 | -1.266 |
| YC | TACTGC | 1588.07 | 2411 | 1.518 | 0.418 |
| YC | TACTGT | 1337.61 | 1587 | 1.186 | 0.171 |
| YC | TATTGT | 1086.90 | 659 | 0.606 | -0.500 |
| YC | TATTGC | 1290.42 | 646 | 0.501 | -0.692 |
| YD | TATGAT | 2091.17 | 3707 | 1.773 | 0.572 |
| YD | TATGAC | 2362.22 | 3731 | 1.579 | 0.457 |
| YD | TACGAC | 2907.08 | 1653 | 0.569 | -0.565 |
| YD | TACGAT | 2573.52 | 843 | 0.328 | -1.116 |
| YE | TATGAA | 2515.85 | 5225 | 2.077 | 0.731 |
| YE | TATGAG | 3364.48 | 4722 | 1.403 | 0.339 |
| YE | TACGAG | 4140.53 | 2309 | 0.558 | -0.584 |
| YE | TACGAA | 3096.14 | 861 | 0.278 | -1.280 |
| YF | TACTTC | 2766.63 | 3380 | 1.222 | 0.200 |
| YF | TATTTT | 1964.12 | 2124 | 1.081 | 0.078 |
| YF | TACTTT | 2417.16 | 2201 | 0.911 | -0.094 |
| YF | TATTTC | 2248.09 | 1691 | 0.752 | -0.285 |
| YG | TATGGA | 1472.35 | 2874 | 1.952 | 0.669 |
| YG | TATGGT | 953.23 | 1665 | 1.747 | 0.558 |
| YG | TATGGG | 1437.38 | 2129 | 1.481 | 0.393 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| YG | TATGGC | 1996.30 | 2749 | 1.377 | 0.320 |
| YG | TACGGG | 1768.93 | 1088 | 0.615 | -0.486 |
| YG | TACGGC | 2456.76 | 1484 | 0.604 | -0.504 |
| YG | TACGGT | 1173.10 | 448 | 0.382 | -0.963 |
| YG | TACGGA | 1811.96 | 633 | 0.349 | -1.052 |
| YH | TACCAC | 1862.81 | 2378 | 1.277 | 0.244 |
| YH | TACCAT | 1350.85 | 1420 | 1.051 | 0.050 |
| YH | TATCAT | 1097.67 | 1021 | 0.930 | -0.072 |
| YH | TATCAC | 1513.67 | 1006 | 0.665 | -0.409 |
| YI | TACATC | 2684.66 | 3935 | 1.466 | 0.382 |
| YI | TACATT | 2122.99 | 2162 | 1.018 | 0.018 |
| YI | TATATT | 1725.09 | 1554 | 0.901 | -0.104 |
| YI | TACATA | 976.39 | 846 | 0.866 | -0.143 |
| YI | TATATA | 793.39 | 648 | 0.817 | -0.202 |
| YI | TATATC | 2181.48 | 1339 | 0.614 | -0.488 |
| YK | TACAAG | 3508.58 | 4372 | 1.246 | 0.220 |
| YK | TACAAA | 2709.10 | 2847 | 1.051 | 0.050 |
| YK | TATAAA | 2201.34 | 2262 | 1.028 | 0.027 |
| YK | TATAAG | 2850.98 | 1789 | 0.628 | -0.466 |
| YL | TACCTG | 4522.42 | 6324 | 1.398 | 0.335 |
| YL | TATTTA | 711.20 | 966 | 1.358 | 0.306 |
| YL | TACCTC | 2176.20 | 2598 | 1.194 | 0.177 |
| YL | TACTTG | 1470.33 | 1701 | 1.157 | 0.146 |
| YL | TATTTG | 1194.75 | 1358 | 1.137 | 0.128 |
| YL | TACCTA | 809.25 | 876 | 1.082 | 0.079 |
| YL | TACCTT | 1500.58 | 1449 | 0.966 | -0.035 |
| YL | TATCTT | 1219.33 | 1166 | 0.956 | -0.045 |
| YL | TACTTA | 875.24 | 763 | 0.872 | -0.137 |
| YL | TATCTA | 657.58 | 541 | 0.823 | -0.195 |
| YL | TATCTC | 1768.32 | 1087 | 0.615 | -0.487 |
| YL | TATCTG | 3674.80 | 1751 | 0.476 | -0.741 |
| YM | TACATG | 2325.97 | 3055 | 1.313 | 0.273 |
| YM | TATATG | 1890.03 | 1161 | 0.614 | -0.487 |
| YN | TACAAC | 2442.24 | 3341 | 1.368 | 0.313 |
| YN | TACAAT | 2217.44 | 2200 | 0.992 | -0.008 |
| YN | TATAAT | 1801.83 | 1629 | 0.904 | -0.101 |
| YN | TATAAC | 1984.50 | 1276 | 0.643 | -0.442 |
| YP | TACCCG | 668.65 | 1004 | 1.502 | 0.406 |
| YP | TACCCA | 1595.15 | 1925 | 1.207 | 0.188 |
| YP | TATCCA | 1296.18 | 1438 | 1.109 | 0.104 |
| YP | TACCCC | 1845.38 | 1961 | 1.063 | 0.061 |
| YP | TATCCT | 1343.02 | 1379 | 1.027 | 0.026 |
| YP | TACCCT | 1652.79 | 1558 | 0.943 | -0.059 |
| YP | TATCCC | 1499.51 | 937 | 0.625 | -0.470 |
| YP | TATCCG | 543.32 | 242 | 0.445 | -0.809 |
| YQ | TACCAG | 3987.12 | 5013 | 1.257 | 0.229 |
| YQ | TATCAA | 1160.22 | 1179 | 1.016 | 0.016 |
| YQ | TACCAA | 1427.83 | 1397 | 0.978 | -0.022 |
| YQ | TATCAG | 3239.83 | 2226 | 0.687 | -0.375 |
| YR | TACCGC | 1307.70 | 2153 | 1.646 | 0.499 |
| YR | TACCGA | 775.30 | 990 | 1.277 | 0.244 |
| YR | TACAGA | 1442.41 | 1834 | 1.271 | 0.240 |
| YR | TACCGG | 1430.23 | 1796 | 1.256 | 0.228 |
| YR | TACAGG | 1416.06 | 1671 | 1.180 | 0.166 |
| YR | TACCGT | 559.87 | 642 | 1.147 | 0.137 |
| YR | TATCGA | 629.99 | 570 | 0.905 | -0.100 |
| YR | TATCGT | 454.94 | 383 | 0.842 | -0.172 |
| YR | TATAGA | 1172.07 | 827 | 0.706 | -0.349 |
| YR | TATCGG | 1162.17 | 629 | 0.541 | -0.614 |
| YR | TATAGG | 1150.66 | 560 | 0.487 | -0.720 |
| YR | TATCGC | 1062.60 | 509 | 0.479 | -0.736 |
| YS | TACAGC | 2204.13 | 3590 | 1.629 | 0.488 |
| YS | TACTCG | 514.46 | 783 | 1.522 | 0.420 |
| YS | TACAGT | 1390.60 | 1887 | 1.357 | 0.305 |
| YS | TATTCA | 1111.75 | 1210 | 1.088 | 0.085 |
| YS | TACTCC | 1945.47 | 2088 | 1.073 | 0.071 |
| YS | TATTCT | 1375.18 | 1466 | 1.066 | 0.064 |
| YS | TACTCA | 1368.18 | 1188 | 0.868 | -0.141 |
| YS | TATTCC | 1580.84 | 1306 | 0.826 | -0.191 |
| YS | TACTCT | 1692.37 | 1173 | 0.693 | -0.367 |
| YS | TATAGT | 1129.96 | 728 | 0.644 | -0.440 |
| YS | TATTCG | 418.04 | 229 | 0.548 | -0.602 |
| YS | TATAGC | 1791.02 | 874 | 0.488 | -0.717 |
| YT | TACACG | 697.26 | 1311 | 1.880 | 0.631 |

SUPPLEMENTAL TABLE 1-continued

Expected and Observed Codon Pair Frequencies and Codon Pair Scores for 14,795 Human Genes

| amino acid pair | codon pair | expected | observed | observed / expected | CPS |
|---|---|---|---|---|---|
| YT | TACACC | 2122.58 | 2696 | 1.270 | 0.239 |
| YT | TACACA | 1718.31 | 2158 | 1.256 | 0.228 |
| YT | TACACT | 1519.54 | 1409 | 0.927 | -0.076 |
| YT | TATACT | 1234.74 | 1049 | 0.850 | -0.163 |
| YT | TATACA | 1396.25 | 1049 | 0.751 | -0.286 |
| YT | TATACC | 1724.75 | 1063 | 0.616 | -0.484 |
| YT | TATACG | 566.57 | 245 | 0.432 | -0.838 |
| YV | TATGTT | 986.79 | 1723 | 1.746 | 0.557 |
| YV | TATGTA | 640.76 | 1113 | 1.737 | 0.552 |
| YV | TATGTC | 1263.40 | 1862 | 1.474 | 0.388 |
| YV | TATGTG | 2499.39 | 3382 | 1.353 | 0.302 |
| YV | TACGTG | 3075.90 | 2279 | 0.741 | -0.300 |
| YV | TACGTC | 1554.82 | 991 | 0.637 | -0.450 |
| YV | TACGTA | 788.55 | 284 | 0.360 | -1.021 |
| YV | TACGTT | 1214.40 | 390 | 0.321 | -1.136 |
| YW | TACTGG | 1609.87 | 2212 | 1.374 | 0.318 |
| YW | TATTGG | 1308.13 | 706 | 0.540 | -0.617 |
| YY | TACTAC | 2256.03 | 2854 | 1.265 | 0.235 |
| YY | TATTAT | 1489.60 | 1459 | 0.979 | -0.021 |
| YY | TACTAT | 1833.19 | 1760 | 0.960 | -0.041 |
| YY | TATTAC | 1833.19 | 1339 | 0.730 | -0.314 |

We claim:

1. A modified influenza virus genome having a recoded hemagglutinin (HA) protein-encoding sequence and a recoded neuraminidase (NA) protein-encoding sequence, wherein the other influenza protein-encoding sequences are not recoded, wherein:
   (a) the HA protein-encoding sequence, the NA protein-encoding sequence, or both are recoded by:
      (i) lowering the codon pair bias of the protein-encoding sequence as compared to the parent HA protein-encoding sequence, the parent NA protein-encoding sequence, or both, wherein the codon pair bias is calculated relative to an influenza host; or
      (ii) lowering the codon bias of the protein-encoding sequence as compared to the parent HA protein-encoding sequence, the parent NA protein-encoding sequence, or both, wherein the codon bias is calculated relative to the influenza host; and
   (b) the recoded sequence encodes the same protein as the parent protein-encoding sequence.

2. The modified influenza virus genome of claim 1, wherein reducing the codon pair bias comprises identifying a codon pair in the parent protein-encoding sequence having a codon pair score that can be reduced, and reducing the codon pair bias by substituting the codon pair with a codon pair that encodes the same amino acid pair and has a lower codon pair score.

3. The modified influenza virus genome of claim 1, wherein reducing the codon pair bias comprises rearranging the codons of a parent protein-encoding sequence.

4. The modified influenza virus genome of claim 2, wherein each of the recoded HA protein-encoding sequence and the recoded NA protein-encoding sequence have a codon pair bias less than −0.1, or less than −0.2, or less than −0.3, or less than −0.4.

5. The modified influenza virus genome of claim 1, wherein the HA protein-encoding sequence, the NA protein-encoding sequence, or both are recoded by replacing one or more codons with synonymous codons that are less frequent in an influenza host, wherein the influenza host is a human.

6. The modified influenza virus genome of claim 1, the HA protein-encoding sequence, the NA protein-encoding sequence, or both are further recoded by modifying the CG dinucleotide content, the TA dinucleotide content, or both.

7. A modified influenza virus comprising the modified influenza virus genome of claim 1.

8. The modified influenza virus of claim 7, wherein the expression of the recoded HA-encoding nucleotide sequence and expression of the recoded NA-encoding nucleotide sequence is reduced compared to the parent virus.

9. A vaccine composition comprising a modified influenza virus comprising the modified influenza virus genome of claim 3 for inducing a protective immune response in a subject.

10. The vaccine composition of claim 9, further comprising at least one adjuvant.

11. The modified influenza virus genome of claim 1, wherein the influenza host is a human.

* * * * *

UNITED STATES PATENT AND TRADEMARK OFFICE
CERTIFICATE OF CORRECTION

PATENT NO. : 11,549,101 B2
APPLICATION NO. : 16/436475
DATED : January 10, 2023
INVENTOR(S) : Steffen Mueller et al.

It is certified that error appears in the above-identified patent and that said Letters Patent is hereby corrected as shown below:

On the Title Page

(73) Assignee should read: The Research Foundation for The State University of New York Signed and Sealed this
Eleventh Day of April, 2023

Katherine Kelly Vidal
*Director of the United States Patent and Trademark Office*